United States Patent
Deng et al.

(10) Patent No.: US 10,508,118 B2
(45) Date of Patent: Dec. 17, 2019

(54) PYRIMIDOPYRROLE COMPOUNDS, METHOD FOR PREPARING THE SAME, PHARMACEUTICAL COMPOSITIONS COMPRISING THE SAME AND USES THEREOF

(71) Applicant: Xiamen University, Fujian (CN)

(72) Inventors: Xianming Deng, Fujian (CN); Zhongji Zhuang, Fujian (CN); Zhou Deng, Fujian (CN); Xiaoxing Huang, Fujian (CN); Yan Liu, Fujian (CN); Ting Zhang, Fujian (CN); Wei Huang, Fujian (CN); Qingyan Xu, Fujian (CN); Zhiyu Hu, Fujian (CN)

(73) Assignee: Xiamen University, Fujian (CN)

( * ) Notice: Subject to any disclaimer, the term of this patent is extended or adjusted under 35 U.S.C. 154(b) by 0 days.

(21) Appl. No.: 15/570,119

(22) PCT Filed: Apr. 25, 2016

(86) PCT No.: PCT/CN2016/080127
§ 371 (c)(1),
(2) Date: Oct. 27, 2017

(87) PCT Pub. No.: WO2016/173477
PCT Pub. Date: Nov. 3, 2016

(65) Prior Publication Data
US 2018/0312508 A1 Nov. 1, 2018

(30) Foreign Application Priority Data
Apr. 29, 2015 (CN) .......................... 2015 1 0210380

(51) Int. Cl.
| | |
|---|---|
| *C07D 487/04* | (2006.01) |
| *A61K 31/519* | (2006.01) |
| *A61K 31/5377* | (2006.01) |
| *A61P 35/00* | (2006.01) |
| *A61K 31/675* | (2006.01) |
| *C07F 9/6561* | (2006.01) |
| *A61P 35/02* | (2006.01) |

(52) U.S. Cl.
CPC .......... *C07D 487/04* (2013.01); *A61K 31/519* (2013.01); *A61K 31/5377* (2013.01); *A61K 31/675* (2013.01); *A61P 35/00* (2018.01); *A61P 35/02* (2018.01); *C07F 9/6561* (2013.01)

(58) Field of Classification Search
CPC ...... C07D 487/04; A61K 31/519; A61P 35/00
USPC ........................................ 544/280; 514/265.1
See application file for complete search history.

(56) References Cited

U.S. PATENT DOCUMENTS

| | | | | |
|---|---|---|---|---|
| 6,040,310 A | * | 3/2000 | Dow .................... | A61K 31/519 514/234.5 |
| 8,207,178 B2 | * | 6/2012 | Shaginian ............ | C07D 487/04 514/261.1 |
| 2014/0303188 A1 | | 10/2014 | Gangjee | |

FOREIGN PATENT DOCUMENTS

| | | |
|---|---|---|
| CN | 104177363 A | 12/2014 |
| CN | 104311573 A | 1/2015 |
| WO | 2015180642 A1 | 12/2015 |

OTHER PUBLICATIONS

Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Cecil Textbook of Medicine, edited by Bennet, J.C., and Plum F., 20th edition, vol. 1, 1004-1010, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
Zhao et al., Cancer Biology & Therapy 16:12, 1691-1701, 2015.*
Modnikova et al. Khimiko-Farmatsevticheskii Zhurnal (1988), 22(2), 185-91; CA 109:242,1988.CAPLUS abstract provided.*

* cited by examiner

*Primary Examiner* — Venkataraman Balasubramanian
(74) *Attorney, Agent, or Firm* — Fox Rothschild LLP

(57) ABSTRACT

The present invention relates to a compound of formula I, a stereoisomer, a prodrug, a pharmaceutically acceptable salt thereof or a pharmaceutically acceptable solvate thereof, and a process for preparing the same, a pharmaceutical composition comprising the same, and use of the compound in the preparation of medicine preventing and treating tumors, wherein the substituents are as defined in the specification.

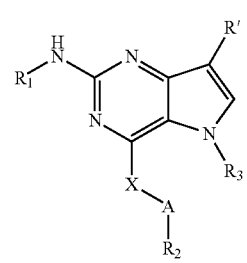

15 Claims, No Drawings

PYRIMIDOPYRROLE COMPOUNDS, METHOD FOR PREPARING THE SAME, PHARMACEUTICAL COMPOSITIONS COMPRISING THE SAME AND USES THEREOF

TECHNICAL FIELD

The present invention relates to pharmacochemical field, particular to compounds having ALK and/or c-Met selective inhibition activity, a method for preparing the same, a pharmaceutical composition comprising the same, and use of said compounds in the preparation of medicine for preventing or treating diseases associated with Anaplastic Lymphoma Kinase (ALK) in living organisms, and the use in the preparation of medicine for preventing or treating diseases associated with angiogenesis or cancer metastasis.

BACKGROUND OF THE INVENTION

Anaplastic Lymphoma Kinase (ALK) is a receptor tyrosine kinase, being in insulin receptor superfamily. Protein structure, from N terminal to C terminal, is successively: extracellular domain, transmembrane domain and intracellular tyrosine kinase domain. Normal ALK protein is mainly expressed in the central nervous system and the peripheral nervous system. The expression level of ALK gene in human body decreases with the development of brain, especially in mature brain tissue. However, in other systems especially in hematopoietic system the expression of ALK has not yet been found. This shows that the expression and distribution thereof have certain regional characteristics.

Normally, human ALK gene encodes 1602 amino acids and 200 kDa type I transmembrane protein ALK, but the gene is usually dormant. In the case of fusion with other genes, ALK gene can become a very powerful oncogene. At present, it has been found that genes that can fuses ALK gene include nuclear phosphoprotein (NPM, anaplastic large cell lymphoma ALCL), echinoderm microtubule associated protein-like 4 genes (EML4, non-small cell lung cancer NSCLC), tropomyosin 3 gene (TPM3, inflammatory myofibroblastic tumor IMT) and so on (*Nat. Rev. Cancer*, 2008, 8, 11-23; *Nat. Rev. Cancer*, 2013, 13, 685-700; *Expert Opin. Ther. Pat.*, 2014. 24(4): p. 417-42).

In non-small cell lung cancer, the fusion with EML4 mainly occurs. The incidence rate of fused gene (EML4-ALK) in NSCLC is 4%-7%. With the deepening of research on non-small cell lung cancer (NSCLC) in molecular biology, personalized treatment based on molecular marker (biomarker) has been from the laboratory to the clinic, and has made great progress in the clinical treatment of patients with advanced non-small cell lung cancer. This means that besides traditional histopathological classification, NSCLC can be subjected to the molecular phenotype classification according to different expression level of different biomarkers in specific patients. NSCLC patients are tested for relevant biomarkers prior to treatment. In clinical practice, doctors can conduct targeted therapies based on the phenotypic characteristics of tumor molecules to thereby enhance therapeutic efficiency. In this context, research and development of new drugs have become the focus of anticancer drug research with driving genes associated with tumorigenesis and development of tumors or coding proteins thereof as targets.

At present, the U.S. Food and Drug Administration (FDA) has approved small molecule inhibitors Crizotlnib (J. Thorac. Oncol., 2010.5 (12): p. 2044-6) developed by Pfizer, Ceritinib (J. Med. Chem., 2013.56 (14): p. 5675-90) developed by Novartis for listing. Alectinib (Cancer Lett., 2014.351 (2): P. 215-21) developed by Chugai Pharmaceutlcal has been approved for listing in Japan. However, clinical studies show that some patients have been resistant to Crizotinib, and the bioavailability of Crizotinib remains to be improved. Ceritinib can target patients with Crizotinib resistance or intolerance, while Alectinib is only marketed in Japan and is still in clinical trials in Europe and the United states. As a result, alternative compounds are needed in clinical practice.

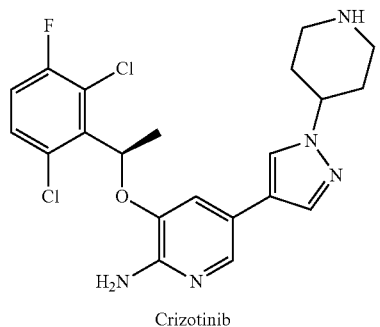

Crizotinib

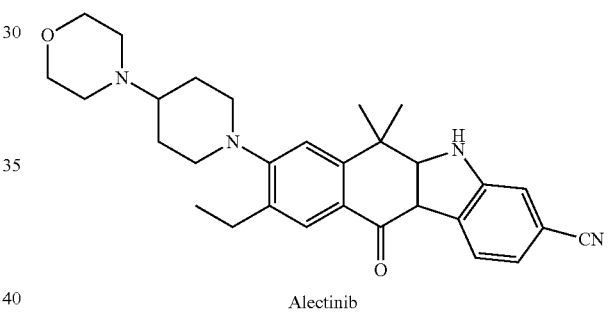

Alectinib

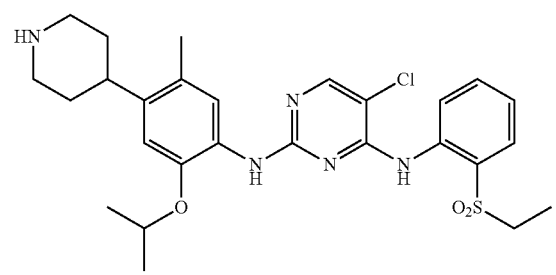

Ceritinib

SUMMARY OF THE INVENTION

The inventor of the present invention has, after extensive research, designed and synthesized a series of polysubstituted pyrimidopyrrole (pyrrole[3,2-d] pyrimidine) derivatives having novel structure, high safety, and having high activity to a variety of tyrosine kinases (EGFR, PDGFR, c-Met etc.) especially to ALK in order to seek novel ALK inhibitors, and has studied the antitumor activity of the novel derivatives.

The compound has a formula:

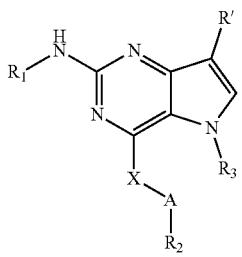

The definition on the substituents and the symbols in the formula are described following in details.

An object of the present invention is to provide a compound having ALK and/or c-Met selective inhibition activity and a pharmaceutically acceptable salt thereof or a pharmaceutically acceptable solvate.

Another object of the present invention is to provide a method for the preparation of the compound.

Another object of the present invention is to provide a pharmaceutical composition comprising the compound.

Another object of the present invention is to provide use of the compound in the preparation of medicine for preventing or treating diseases associated with anaplastic lymphoma enzyme in the organisms, accompanied by abnormal cell proliferation, morphological changes, and hyperfunction of motion, and the use of the compound in the preparation of medicine for preventing or treating diseases associated with angiogenesis or cancer metastasis, particularly the use of the compound in the preparation of medicine for preventing or treating tumor growth and metastasis.

The present invention is achieved through following technical solutions.

At one aspect, the present invention provides a compound of formula I:

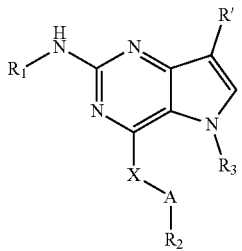

wherein R' is hydrogen, chlorine or bromine;
$R_1$ is optionally selected from the group consisting of:
1) C1-C6 alkyl, 2-N,N-dimethylaminoethyl, 2-hydroxyethyl, 2-N,N-diethylaminoethyl, 2-N,N-diisopropylaminoethyl, 2-morpholinoethyl, 2-(4-N-methyl piperazine) ethyl, 3-N,N-dimethylaminopropyl, 3-N,N-diethylaminopropyl, 3-N,N-diisopropylaminopropyl, 3-morpholinopropyl, 3-(4-N-methylpiperazine)propyl, 4-N,N-dimethylaminocyclohexyl, 4-N,N-diethylaminocyclohexyl, N-methyl-4-piperidyl, N-ethyl-4-piperidyl, N-isopropyl-4-piperidyl, 1,3-dimethyl-5-pyrazolyl, 1-methyl-4-pyrazolyl, 3-methyl-5-isooxazolinyl, 1-(N-methyl-4-piperidyl)-4-pyrazolyl, 1-(N-tert-butoxyformyl-4-piperidyl)-4-pyrazolyl;

1)

wherein $Z_1$, $Z_2$, $Z_3$, $Z_4$, $Z_5$ are independently selected from the group consisting of:
(1) H, F, Cl, Br, I, nitro, cyano;
(2) C1-C6 alkyl, C1-C6 alkoxy, C1-C6 oxyalkyl, C1-C6 fluoroalkyl, C1-C6 fluoroalkoxy, N-methyl-4-piperidyl;
(3) N,N-dimethylamino, N,N-diethylamino, N,N-diisopropylamino, 2-N,N-dimethylaminoethylamino, 2-morpholinoethylamino, 2-(4-N-methylpiperazinyl)ethylamino, 3-N,N-dimethylaminopropylamino, 3-N,N-diethylaminopropylamino, 3-N,N-diisopropylaminopropylamino, 3-morpholinopropylamino, 3-(4-N-methylpiperazinyl)propylamino, N-methylpiperidin-4-ylamino, N-ethylpiperidin-4-ylamino, N-isopropylpiperidin-4-ylamino;
(4) 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinoethoxy, 2-thiomorpholinoethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinopropoxy, 3-thiomorpholinoethoxy, 3-piperidylpropoxy, 2-pyridylpropoxy, 3-pyridylmethoxy, 4-pyridylmethoxy, phenylmethoxy, monohalogen-substituted phenyl methoxy, gem-dihalogen substituted phenyl methoxy, hetero-dihalogen substituted phenyl methoxy;
(5) piperidyl, 4-N,N-dimethylaminopiperidyl, 4-N,N-diethylaminopiperidyl, 4-N,N-diisopropylaminopiperidyl, 4-hydroxypiperidyl, morpholino, 3,5-dimethylmorpholino, thiomorpholino, pyrrolidinyl, 3-N,N-dimethylpyrrolidinyl, 3-N,N-diethylpyrrolidinyl, N-methylpiperazinyl, N-ethylpiperazinyl, N-ispropylpiperazinyl, N-acetylpiperazinyl, N-tert-butoxyformylpiperazinyl, N-methylsulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, imidazolyl, 4-methylimidazolyl;
(6) 4-(N-methylpiperazinyl)piperidyl, 4-(N-ethylpiperazinyl)piperidyl, 4-(N-isopropylpiperazinyl)piperidyl, 4-(N-acetylpiperazinyl)piperidyl, 4-(N-tert-butoxyformyl)piperazinyl)piperidyl, 4-(N-methylsulfonylpiperazinyl)piperidyl, 4-(N-(2-hydroxyethyl)piperazinyl)piperidyl, 4-(N-(2-cyanoethyl)piperazinyl)piperidyl, 4-(N-(3-hydroxypropyl)piperazinyl)piperidyl, 4-(N-(2-N,N-dimethylethyl)piperazinyl)piperidyl, 4-(N-(2-N,N-diethylethyl)piperazinyl)piperidyl, 4-(N-(3-N,N-dimethylpropyl)piperazinyl)piperidyl, 4-(N-(3-N,N-diethylpropyl)piperazinyl)piperidyl, 4-(pyrrolidinyl)

piperidyl, 4-(3-N,N-dimethylpyrrolidinyl)piperidyl, N—(N-methyl-4-piperidyl)piperazinyl, N—(N-ethyl-4-piperidyl)piperazinyl;

(7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylpiperidin-1-ylsulfonyl, 4-N,N-diethylpiperidin-1-ylsulfonyl, pyrrolidin-1-ylsulfonyl, 3-N,N-dimethylpyrrolidin-1-ylsulfonyl, 3-N,N-diethylpyrrolidin-1-ylsulfonyl, N-methylpiperazin-1-ylsulfonyl, N-ethylpiperazin-1-ylsulfonyl, N-acetylpiperazin-1-ylsulfonyl, N-tert-butoxyformylpiperazin-1-ylsulfonyl, N-(2-hydroxyethyl)piperazin-1-ylsulfonyl, N-(2-cyanoethyl)piperazin-1-ylsulfonyl, N-(2-N,N-dimethylethyl)piperazin-1-ylsulfonyl, N-(2-N,N-diethylethyl)piperazin-1-ylsulfonyl, N-(3-hydroxypropyl)piperazin-1-ylsulfonyl, (3-N,N-dimethyl propyl)piperazin-1-ylsulfonyl, (3-N,N-diethylpropyl)piperazin-1-ylsulfonyl, morpholino-1-sulfonyl, 3,5-dimethylmorpholino-1-sulfonyl 4-(N-methyl-1-piperazinyl)piperidin-1-ylsulfonyl, 4-(N-ethyl-1-piperazinyl)piperidin-1-ylsulfonyl, 4-(N-acetyl-1-piperazinyl)piperidin-1-ylsulfonyl, N—(N-methyl-4-piperidyl)piperazin-1-ylsulfonyl;

(8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidin-1-ylcarbonyl, 4-hydroxypiperidin-1-ylcarbonyl, 4-N,N-dimethylpiperidin-1-ylcarbonyl, 4-N,N-diethylpiperidin-1-ylcarbonyl, pyrrolidin-1-ylcarbonyl, 3-N,N-dimethyl pyrrolidin-1-ylcarbonyl, 3-N,N-diethylpyrrolidin-1-ylcarbonyl, N-methylpiperazin-1-ylcarbonyl, N-ethylpiperazin-1-ylcarbonyl, N-acetylpiperazin-1-ylcarbonyl, N-tert-butoxycarbonylpiperazin-1-ylcarbonyl, N-(2-hydroxyethyl)piperazin-1-ylcarbonyl, N-(2-cyanoethyl)piperazin-1-ylcarbonyl, N-(2-N,N-dimethylethyl)piperazin-1-ylcarbonyl, N-(2-N,N-diethylethyl)piperazin-1-ylcarbonyl, N-(3-hydroxypropyl)piperazin-1-ylcarbonyl, N-(3-N,N-dimethylpropyl)piperazin-1-ylcarbonyl, N-(3-N,N-diethylpropyl)piperazin-1-ylcarbonyl, morpholino-1-carbonyl, 3,5-dimethylmorpholino-1-carbonyl 4-(N-methyl-1-piperazinyl)piperidin-1-ylcarbonyl, 4-(N-ethyl-1-piperazinyl)piperidin-1-ylcarbonyl, 4-(N-acetyl-1-piperazinyl)piperidin-1-ylcarbonyl, N—(N-methyl-4-piperidyl)piperazin-1-ylcarbonyl;

(9) methoxycarbonyl, ethoxycarbonyl, propoxycarbonyl, isopropoxycarbonyl, n-butoxycarbonyl, isobutoxycarbonyl, tert-butoxycarbonyl;

(10) aminoformamido, methylaminoformamido, ethylaminoformamido, propylaminoformamido, isopropylaminoformamido, cyclopropylaminoformamido, cyclobutylaminoformamido, cyclopentylaminoformamido, piperidin-1-ylformamido, 4-hydroxypiperidin-1-ylformamido, 4-N,N-dimethylpiperidin-1-ylformamido, 4-N,N-diethylpiperidin-1-ylformamido, pyrrolidin-1-ylformamido, 3-N,N-dimethylpyrrolidin-1-ylformamido, 3-N,N-diethylpyrrolidin-1-ylformamido, N-methylpiperazin-1-ylformamido, N-ethylpiperazin-1-ylformamido, N-acetylpiperazin-1-ylformamido, N-tert-butoxycarbonylpiperazin-1-ylformamido, N-(2-hydroxyethyl)piperazin-1-ylformamido, N-(2-cyanoethyl)piperazin-1-ylformamido, N-(2-N,N-dimethylethyl)piperazin-1-ylformamido, N-(2-N,N-diethylethyl)piperazin-1-ylformamido, N-(3-hydroxypropyl)piperazin-1-ylformamido, N-(3-N,N-dimethylpropyl)piperazin-1-ylformamido, N-(3-N,N-diethylpropyl)piperazin-1-ylformamido, morpholino-1-formamido, 3,5-dimethylmorpholino-1-formamido 4-(N-methyl-1-piperazinyl)piperidin-1-ylformamido, 4-(N-ethyl-1-piperazinyl)piperidin-1-ylformamido, 4-(N-acetyl-1-piperazinyl)piperidin-1-ylformamido, N—(N-methyl-4-piperidyl)piperazin-1-ylformamido;

(11) (11) aminoacetamido, N-tert-butoxycarbonylacetamido, N-acetylaminoacetamido, acrylamido, cyclopropionamido, chloroacetamido, piperidylacetamido, 4-hydroxypiperidylacetamido, 4-N,N-dimethyl piperidylacetamido, 4-N,N-diethylpiperidylacetamido, pyrrolidinylacetamido, 3-N,N-dimethylpyrrolidinylacetamido, 3-N,N-diethylpyrrolidinylacetamido, N-methylpiperazinylacetamido, N-ethylpiperazinylacetamido, N-acetylpiperazinylacetamido, N-tert-butoxycarbonylpiperazinylacetamido, N-(2-hydroxyethyl)piperazinylacetamido, N-(2-cyanoethyl)piperazinylacetamido, N-(2-N,N-dimethylethyl)piperazinylacetamido, N-(2-N,N-diethylethyl)piperazinylacetamido, N-(3-hydroxypropyl)piperazinylacetamido, N-(3-N,N-dimethylpropyl)piperazinylacetamido, N-(3-N,N-diethylpropyl)piperazinylacetamido, morpholino-1-acetamido, 3,5-dimethylmorpholinoacetamido 4-(N-methyl-1-piperazinyl)piperidylacetamido, 4-(N-ethyl-1-piperazinyl)piperidylacetamido, 4-(N-acetyl-1-piperazinyl)piperidylacetamido, N—(N-methyl-4-piperidyl)piperazinylacetamido; 4-(pyrrolidin-1-yl)piperidylacetamido, 2-methylaminoacetamido, 2-(1-methylethyl)aminoacetamido; N-benzyloxycarbonyl-2-methylaminoacetamido;

(12) $Z_2$ and $Z_3$ can form substituted or unsubstituted 5- or 6-membered oxygen-containing ring; the substituents may be selected from the same substituents for $Z_1$;

(13) $Z_2$ and $Z_3$ can form substituted or unsubstituted 5- or 6-membered nitrogen-containing ring; the substituents may be selected from the same substituents for $Z_1$;

3)

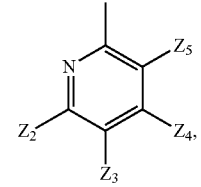

wherein $Z_2$, $Z_3$, $Z_4$, $Z_5$ are as defined in item 2);

4)

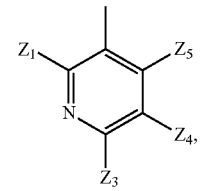

wherein $Z_1$, $Z_3$, $Z_4$, $Z_5$ are as defined in item 2);
A is a direct bond or methylene;
X is a direct bond, NH, S or O;

R₂ is optionally selected from the group consisting of:
1) C1-C6 alkyl, C2-C6 alkenyl, C2-C6 alkynyl, C3-C6 cycloalky;
2)

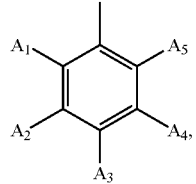

wherein A₁, A₂, A₃, A₄, A₅ are independently selected from the group consisting of:
(1) H, F, Cl, Br, I, cyano, trifluoromethyl, trifluoromethoxy, nitro;
(2) methylthio, ethylthio, isopropylthio, methylsulfinyl, ethylsulfinyl, isopropylsulfinyl, methylsulfonyl, ethylsulfonyl, isopropylsulfonyl, methylsulfonylamino, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl;
3)

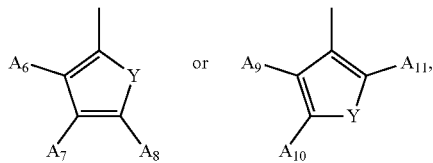

Wherein Y is NH, S or O,
A₆, A₇, A₈, A₉, A₁₀, A₁₁ are independently selected from the group consisting of:
(1) H, F, Cl, Br, I, cyano, trifluoromethyl, trifluoromethoxy, nitro;
(2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl;
4)

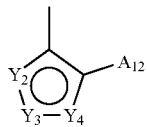

wherein A₁₂ is optionally selected from the group consisting of:
(1) H, F, Cl, Br, I, cyano, trifluoromethyl, trifluoromethoxy, nitro,
(2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, methylsulfinyl, ethylsulfinyl, isopropylsulfinyl, methylsulfonyl, ethylsulfonyl, isopropylsulfonyl;
$Y_2$, $Y_3$, $Y_4$ are selected from the group consisting of:
$Y_2$ is N, $Y_3$ is N-$A_{13}$, $Y_4$ is CH or N;
$Y_2$ is N, $Y_3$ is C-$A_{13}$, $Y_4$ is N, O or S;
$Y_2$ is O or S, $Y_3$ is N-$A_{13}$, $Y_4$ is CH;
$Y_2$ is O or S, $Y_3$ is C-$A_{13}$, $Y_4$ is N;
$Y_2$ is C, $Y_3$ is N-$A_{13}$, $Y_4$ is O or S;
wherein $A_{13}$ is H, C1-C6 alky, C2-C6 alkenyl, C2-C6 alkynyl, C3-C6 cycloalky;
5) piperidyl, 4-N,N-dimethylaminopiperidyl, 4-N,N-diethylaminopiperidyl, 4-N,N-diisopropylaminopiperidyl, 4-hydroxypiperidyl, morpholino, 3,5-dimethylmorpholino, thiomorpholino, pyrrolidinyl, 3-N,N-dimethylpyrrolidyl, 3-N,N-diethylpyrrolidyl, N-methylpiperazinyl, N-ethylpiperazinyl, N-isopropylpiperazinyl, N-acetylpiperazinyl, N-tert-butoxycarbonylpiperazinyl, N-methylsulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, 4-(2-N,N-diethylethyl)piperazinyl, N-(3-N,N-dimethylpropyl)piperazinyl, N-(3-N,N-diethylpropyl)piperazinyl;
R₃ is H, C1-C6 alky, C2-C6 alkenyl, C2-C6 alkynyl, C3-C6 cycloalky, a stereoisomer, a prodrug, a pharmaceutically acceptable salt or a pharmaceutically acceptable solvate thereof.
Unless specified, above groups and substituents have general meanings in pharmacochemical field. It should be noted that an oxygen-containing alkyl means there are one or more 0-substituted groups inside the keleton of alkyl group, such as, methoxyethyl, methoxyethoxymethyl.
According to one embodiment of the present invention, the present invention provides a compound of formula II:

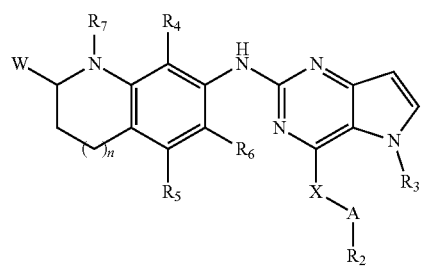

wherein,
W is oxo, thio, or H;
n=0 or 1;
R₄, R₅, R₆ are independently selected from the group consisting of:
(1) H, F, Cl, Br, I, nitro, cyano;
(2) C1-C6 alky, C1-C6 alkoxy, C1-C6 oxyalkyl, C1-C6 fluoroalky, C1-C6 fluoroalkoxy;
R₇ is independently selected from the group consisting of:
(1) H, C1-C6 alkyl, acetyl, propionyl, butyryl, isobutyryl;
(2) glycyl, 2-N,N-dimethylacetyl, 2-N,N-diethylacetyl, 2-N,N-diisopropylacetyl, piperidylacetyl, 4-hydroxypiperidylacetyl, 4-N,N-dimethylpiperidylacetyl, 4-N,N-diethylpiperidylacetyl, pyrrolidinylacetyl, 3-N,N-dimethylpyrrolidinylacetyl, 3-N,N-diethylpyrrolidinylacetyl, N-methylpiperazinylacetyl, N-ethylpiperazinylacetyl, N-acetylpiperazinylacetyl, N-tert-butoxycarbonylpiperazinylacetyl, N-(2-hydroxyethyl) piperazinylacetyl, N-(2-cyanoethyl)piperazinylacetyl, N-(2-N,N-dimethylethyl)piperazinylacetyl, N-(2-N,N-diethylethyl)piperazinylacetyl, N-(3-hydroxypropyl)piperazinylacetyl, N-(3-N,N-dimethylpropyl)piperazinylacetyl, N-(3-N,N-diethylpropyl)piperazinylacetyl, morpholinoacetyl, 3,5-dimethylmorpholinoacetyl, 4-(N-methyl-1-piperazinyl) piperidylacetyl, 4-(N-ethyl-1-piperazinyl) piperidylacetyl, 4-(N-acetyl-1-piperazinyl) piperidylacetyl, N—(N-methyl-4-piperidyl) piperazinylacetyl;

A, X, $R_2$, $R_3$ are as defined in the above technical solution; a stereoisomer, a prodrug, a pharmaceutically acceptable salt, or a pharmaceutically acceptable solvate thereof.

According to one embodiment of the present invention, the present invention provides a compound of formula III:

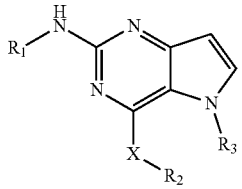

III wherein,

X, $R_1$, $R_2$, $R_3$ are as defined in the compound of formula I, corresponding to A being a direct bond, $R_1$ being hydrogen in the compound of formula I, or a stereoisomer, prodrug, a pharmaceutically acceptable salt, and a pharmaceutically acceptable solvate thereof.

According to one embodiment of the present invention, the present invention provides a compound of formula IV:

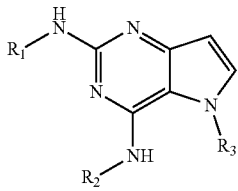

IV wherein, $R_1$, $R_3$ are as defined in the compound of formula I,
$R_2$ is optionally selected from the group consisting of:
1) C1-C6 alky, C2-C6 alkenyl, C2-C6 alkynyl, C3-C6 cycloalky;
2)

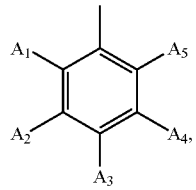

wherein $A_1$, $A_2$, $A_3$, $A_4$, $A_5$ are independently selected from the group consisting of:
(1) H, F, Cl, Br, I, cyano, trifluoromethyl, trifluoromethoxy, nitro;
(2) methylthio, ethylthio, isopropylthio, methylsulfinyl, ethylsulfinyl, isopropylsulfinyl, methylsulfonyl, ethylsulfonyl, isopropylsulfonyl, methylsulfonylamino, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl;
3)

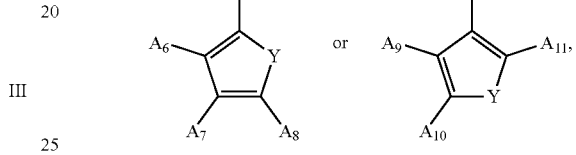

wherein
$A_6$, $A_7$, $A_8$, $A_9$, $A_{10}$, $A_{11}$ are independently selected from the group consisting of:
(1) H, F, Cl, Br, I, cyano, trifluormethyl, trifluoromethoxy, nitro;
(2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl; or a stereoisomer, prodrug, a pharmaceutically acceptable salt, and a pharmaceutically acceptable solvate thereof.

According to one embodiment of the present invention, the present invention provides a compound, a stereoisomer, prodrug, a pharmaceutically acceptable salts, or a pharmaceutically acceptable solvate thereof, which are preferably selected from at least one of the group consisting of:
(1) in $R_1$, $Z_1$ is independently selected from methoxy, ethoxy, isopropoxy or trifluoromethoxy, and/or $Z_3$ is independently selected from 4-N,N-dimethylaminopiperidyl, 4-hydroxypiperidyl, morpholino, pyrrolidinyl, 3-N,N-dimethylpyrrolidyl, N-methylpiperazinyl, N-ethylpiperazinyl, N-acetylpiperazinyl, N-(2-hydroxyethyl)piperazinyl, N-(2-cyanoethyl)piperazinyl, N-(3-hydroxypropyl)piperazinyl, 4-(N-methylpiperazinyl)piperidyl, 4-(N-ethyl piperazinyl)piperidyl, 4-(N-acetylpiperazinyl)piperidyl, 4-(N-tert-butoxycarbonylpiperazinyl)piperidyl, 4-(N-(2-hydroxyethyl) piperazinyl)piperidyl, 4-(N-(2-cyanoethyl)piperazinyl) piperidyl, 4-pyrrolidylpiperidyl, N—(N-methyl-4-piperidyl)piperazinyl, N—(N-ethyl-4-piperidyl) piperazinyl, aminosulfonyl, methaminosulfonyl, cyclopropaminosulfonyl, piperidin-1-ylsulfonyl, 4-hydroxypiperidin-1-ylsulfonyl, 4-N,N-dimethylpiperidin-1-ylsulfonyl, pyrrolidin-1-ylsulfonyl, 3-N,N-dimethylpyrrolidin-1-ylsulfonyl, 4-methylpiperazin-1-ylsulfonyl, 4-ethylpiperazin-1-ylsulfonyl, morpholino-1-sulfonyl, hydroxycarbonyl, aminocarbonyl, methylaminocarbonyl, ethylaminocarbonyl, isopropylaminocarbonyl, cyclopropylaminocarbonyl, piperidin-1-ylcarbonyl, 4-hydroxypiperidin-1-ylcarbonyl, 4-N,N-dimethylpiperidin-1-ylcarbonyl, pyrrolidin-1-ylcarbonyl, 3-N,N-dimethylpyrrolidin-1-ylcarbonyl, N-methylpiperazin-1-ylcarbonyl, N-ethylpiperazin-1-ylcarbonyl, N-acetylpiperazin-1-ylcarbonyl, morpholino-1-carbonyl, 4-(N-methyl-1-piperazinyl)piperidin-1-ylcarbonyl, 4-(N-ethyl-1-piperazinyl)piperidin-1-ylcarbonyl, 4-(N-acetyl-1-piperazinyl)piperidin-1-ylcarbonyl, N—(N-methyl-4-piperidyl)piperazin-1-ylcarbonyl;
(2) $R_2$ is selected from 2-methylsulfonylphenzyl, 2-ethylsulfonylphenzyl, 2-isopropylsulfonylphenzyl, 2-methylsulfoamidophenyl or 2-dimethylphosphinylphenyl;
(3) $R_3$ is selected from H and methyl;
(4) the compound is a pharmaceutically acceptable salt, wherein the pharmaceutically acceptable salt is a salt of an inorganic or organic acid, wherein the salt of inorganic acid is the salt of hydrochloric, hydrobromic, nitric, sulfuric and phosphoric acid; the salt of organic acid is the salt of formic acid, acetic acid, propionic acid, benzoic acid, maleic acid, fumaric acid, succinic acid, tartaric acid, citric acid, alkylsulfonic acid or arylsulfonic acid; preferably, the salt of alkylsulfonic acid is the salt of methylsulfonic acid and ethylsulfonic acid; the salt of arylsulfonic acid is the salt of benzenesulfonic acid and p-methylbenzenesulfonic acid.

According to one embodiment of the present invention, the invention provides a compound of the formula, a stereoisomer, a prodrug, a pharmaceutically acceptable salt, a pharmaceutically acceptable solvate thereof, wherein the compound is one of the compounds in the following examples.

In another aspect, the present invention provides a pharmaceutical composition comprising the compound according to any of the above technical solutions, a stereoisomer, a prodrug, a pharmaceutically acceptable salt, a pharmaceutically acceptable solvate thereof, and a pharmaceutically acceptable carrier, a diluent or an excipient.

In another aspect, the present invention provides a process for preparing the compound according to any of the above technical solutions, comprising the steps of:

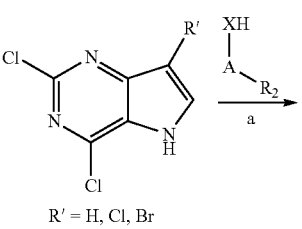

The starting materials for the reaction are commercially available.

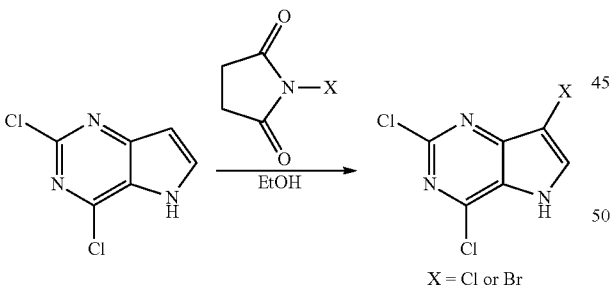

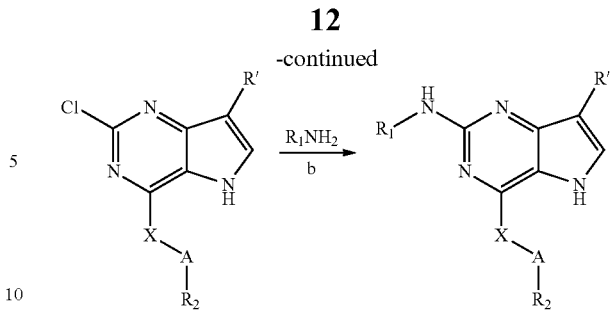

Reaction conditions: (a) substitution reaction under basic condition (e.g. diisopropylethylamine, trimethylamine, potassium carbonate, etc.) or acidic condition (trifluoroacetic acid, hydrochloric acid, etc.); (b) amination reaction under acidic condition (trifluoroacetic acid, hydrochloric acid, etc.) or in the presence of palladium catalyst; or

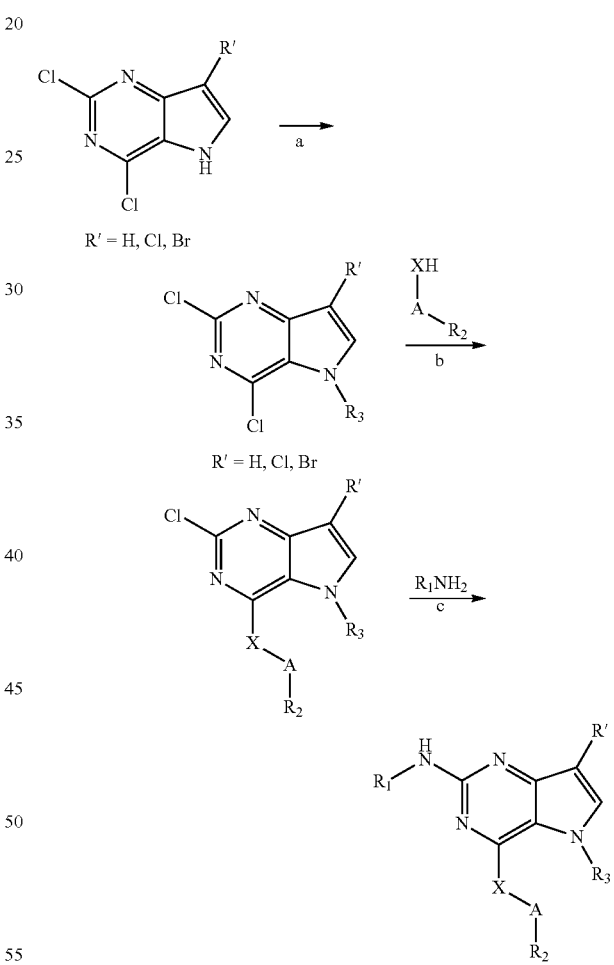

Reaction conditions: (a) substitution reaction with alkyl halide under basic condition (NaH, etc.) or methylation with dimethyl sulfate; (b) substitution reaction under basic condition (e.g. diisopropylethylamine, trimethylamine, potassium carbonate, etc.) or acidic condition (trifluoroacetic acid, hydrochloric acid, etc.); (c) amination reaction under acidic condition (trifluoroacetic acid, hydrochloric acid, etc.) or in the presence of palladium catalyst.

In another aspect, the present invention also provides use of a compound according to any of the above technical solutions, a stereoisomer, a prodrug, a pharmaceutically acceptable salt, a pharmaceutically acceptable solvate thereof in the preparation of medicine for preventing or treating tumors. Preferably, the tumors include anaplastic large cell lymphoma (ALCL), inflammatory myofibroblastic tumor (IMT), non-small cell lung cancer (NSCLC), neuroblastoma, small cell lung cancer, lung adenocarcinoma, pancreatic cancer, breast cancer, prostate cancer, liver cancer, skin cancer, squamous cell cancer, gastrointestinal stromal tumors (GIST), leukemia, histocytic lymphoma, nasopharyngeal carcinoma (NPC); more preferably, the tumors include anaplastic large cell lymphoma (ALCL), inflammatory myofibroblastic tumor (IMT), non-small cell lung cancer (NSCLC), and neuroblastoma.

EMBODIMENTS

The embodiments of the present invention are described following in details through specific examples, but in any case, they cannot be interpreted as limits to the invention.

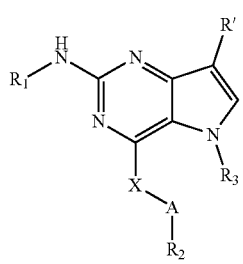

The compounds of the formula are prepared by following synthesis processes.

The Formula of Compound I

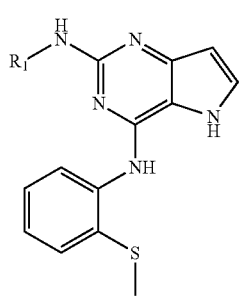

IA

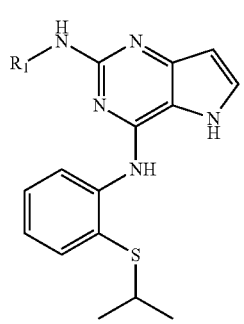

IB

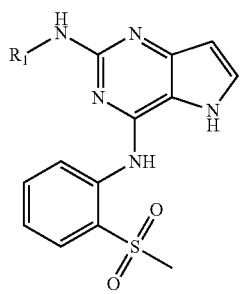

IC

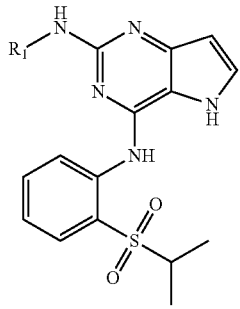

ID

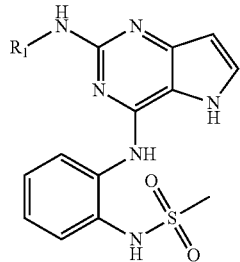

IE

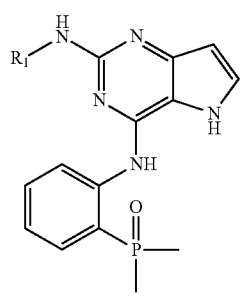

IF

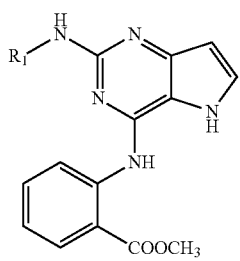

IG

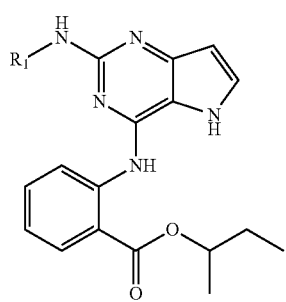 IH
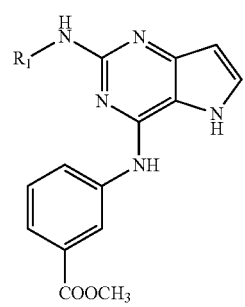 II
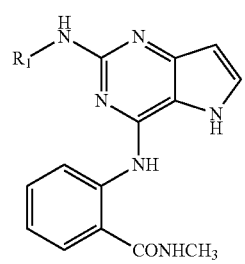 IJ
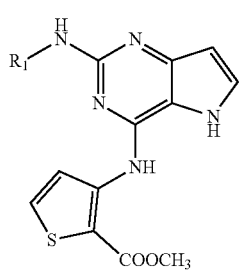 IK
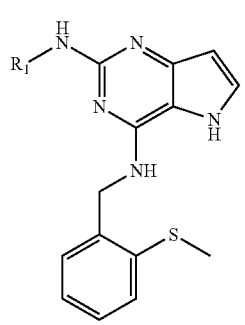 IL
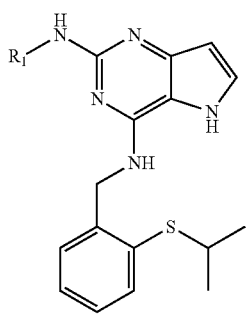 IM
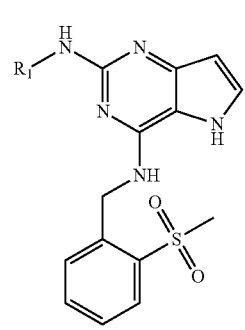 IN
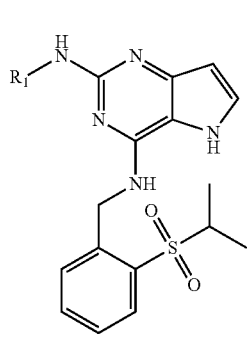 IO
 IP
 IQ -continued
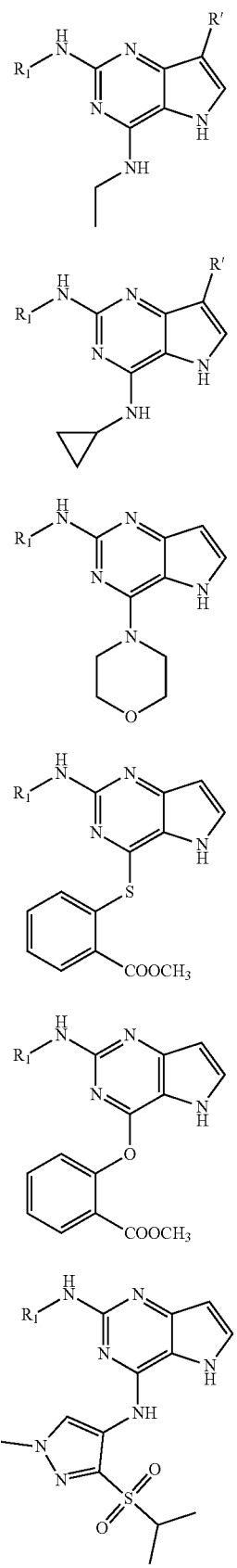
Example 1
Synthesis Scheme of Compound IA
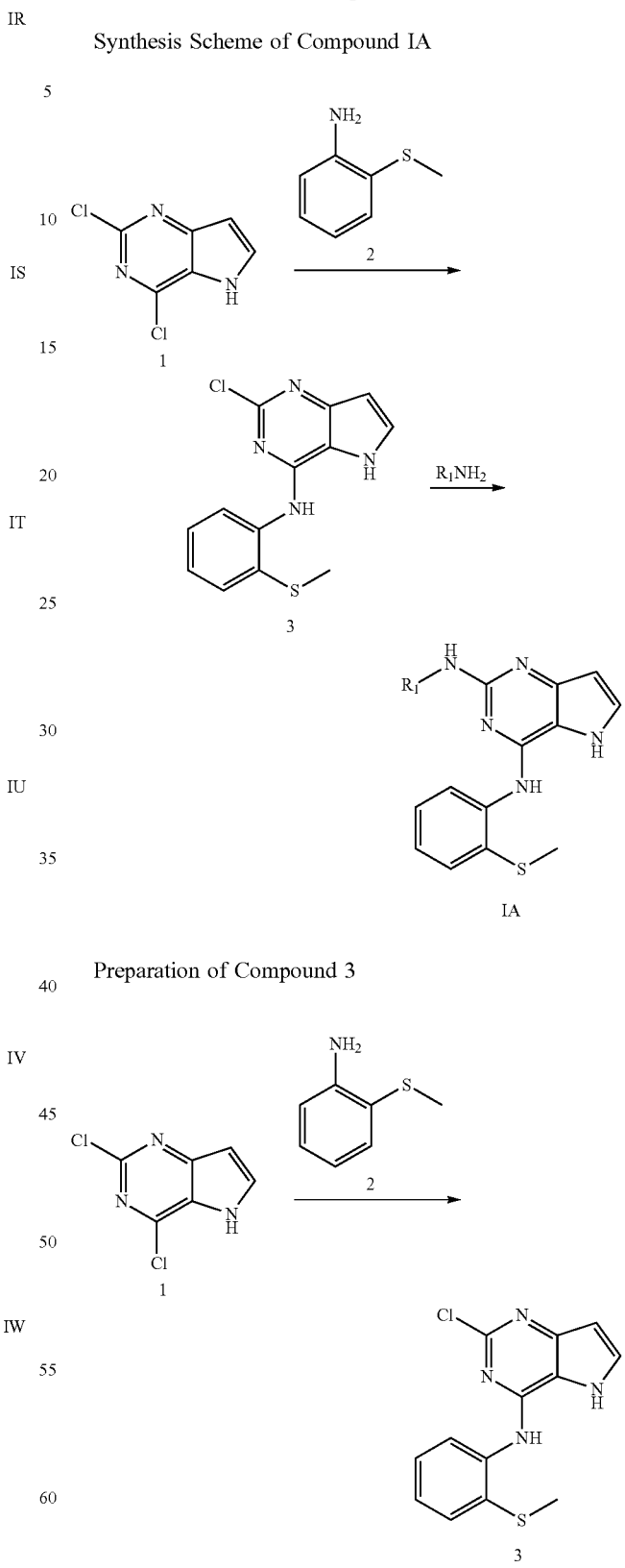
Preparation of Compound 3
Compound 1 (200 mg, 1.06 mmol), compound 2 (163 mg, 1.17 mmol) were dissolved in 10 mL tert-butanol. To the solution was added trifluoroacetic acid (0.393 mL, 5.3 mmol). The resulting reaction liquid was heated in 100° C. oil bath with stirring until compound 1 was reacted completely (LC-MS and TLC tracking). The reaction was stopped. To the reaction liquid was added saturated sodium bicarbonate solution, and the liquid was separated. The organic phase was washed twice with saturated sodium chloride solution, dried over anhydride sodium sulfate, concentrated and purified by silica-gel column chromatography (petroleum ether/ethyl acetate=1/2) to yield compound 3 (white solid, 147.3 mg, yield 47.8%), which was used directly for the reaction in next step.

MS (ESI) m/z: 291 [M+H]$^+$.

Preparation of Compound IA

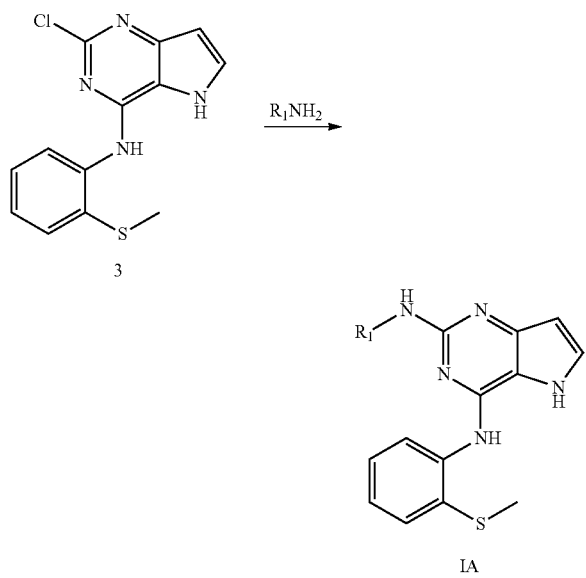

Process A:

Compound 3 (18.3 mg, 0.063 mmol), aniline (0.044 mmol) were dissolved in 1 mL tert-butanol. To the solution was added trifluoroacetic acid (23.4 μL, 0.32 mmol). The resulting reaction liquid was heated in 110° C. oil bath with stirring until aniline was reacted completely (LC-MS and TLC tracking). The reaction was stopped. To the reaction liquid was added saturated sodium bicarbonate solution, and the liquid was separated. The organic phase was washed twice with saturated sodium chloride solution, dried over anhydride sodium sulfate, concentrated and purified by silica-gel column chromatography (dichloromethane/methanol) to yield compound IA.

Process B:

Compound 3 (18.3 mg, 0.063 mmol), aniline (0.044 mmol) were dissolved in 1 mL tert-butanol. To the solution was added trifluoroacetic acid (23.4 μL, 0.32 mmol). The resulting reaction solution was heated in 110° C. oil bath with stirring until aniline was reacted completely (LC-MS and TLC tracking). The reaction was stopped. The reaction solution was concentrated, purified by reversed-phase preparative HPLC (with 0.35% trifluoroacetic acid aqueous solution and methanol as mobile phase), and concentrated in vacuum to yield compound IA.

Compounds IB, IC, ID, IE, IF were synthesized using similar processes.

Following table lists the specific compounds and data of their structure identification.

TABLE 1

Structure and identification of compounds IA-IF

| ID | Structure | NMR and/or MS data |
|---|---|---|
| IA-1 | (TFA salt) | $^1$H NMR (600 MHz, Methanol-d$_4$) δ 7.53-7.48 (m, 2H), 7.45 (dd, J = 8.0, 1.4 Hz, 1H), 7.41-7.3411 (m, 2H), 7.25 (td, J = 7.6, 1.4 Hz, 1H), 6.67 (d, J = 2.4 Hz, 1H), 6.40-6.34 (m, 1H), 6.32 (d, J = 3.0 Hz, 1H), 3.84 (s, 3H), 3.79 (d, J = 13.2 Hz, 2H), 3.62 (d, J = 11.3 Hz, 2H), 3.25 (t, J = 11.8 Hz, 2H), 3.07 (t, J = 13.4 Hz, 2H), 2.96 (s, 3H), 2.42 (s, 3H). MS (ESI) m/z: 476 [M + H]$^+$. |

TABLE 1-continued

Structure and identification of compounds IA-IF

| ID | Structure | NMR and/or MS data |
|---|---|---|
| IA-2 | 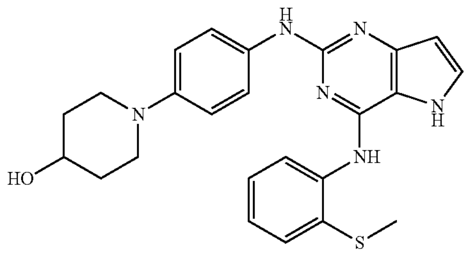 | $^1$H NMR (600 MHz, Methanol-d$_4$) δ 7.83 (dd, J = 7.8, 1.5 Hz, 1H), 7.45 (dd, J = 7.7, 1.6 Hz, 1H), 7.40-7.34 (m, 2H), 7.34 (d, J = 3.0 Hz, 1H), 7.24 (td, J = 7.6, 1.6 Hz, 1H), 7.20 (td, J = 7.6, 1.6 Hz, 1H), 6.89-6.83 (m, 2H), 6.24 (d, J = 3.0 Hz, 1H), 3.71 (hept, J = 8.9, 4.1 Hz, 1H), 3.39 (dt, J = 12.1, 4.3 Hz, 2H), 2.77 (ddd, J = 12.6, 10.3, 2.9 Hz, 2H), 2.40 (s, 3H), 1.99-1.93 (m, 2H), 1.6727 (dtd, J = 13.2, 9.7, 3.8 Hz, 2H). MS (ESI) m/z: 447 [M + H]$^+$. |
| IA-3 | 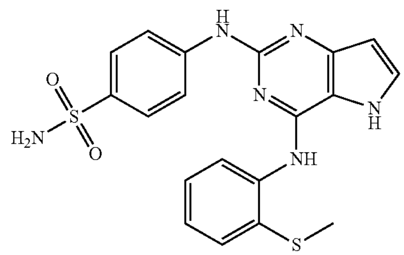 [SMILES: CSc1ccccc1Nc1nc(Nc2ccc(S(N)(=O)=O)cc2)nc2cc[nH]c12] | $^1$H NMR (600 MHz, DMSO-d$_6$) δ 11.01 (d, J = 3.1 Hz, 1H), 9.09 (s, 1H), 8.6210 (s, 1H), 7.85-7.74 (m, 2H), 7.62 (dd, J = 7.8, 1.7 Hz, 1H), 7.53 (t, J = 2.9 Hz, 1H), 7.51-7.46 (m, 2H), 7.41 (dd, J = 7.7, 1.6 Hz, 1H), 7.34-7.25 (m, 2H), 7.04 (s, 2H), 6.27 (t, J = 2.4 Hz, 1H), 2.43 (s, 3H). MS (ESI) m/z: 427 [M + H]$^+$. |
| IB-1 | TFA salt | $^1$H NMR (600 MHz, DMSO-d$_6$) δ 12.13 (s, 1H), 10.15 (s, 1H), 9.20 (s, 1H), 7.66 (t, J = 3.0 Hz, 1H), 7.57 (d, J = 2.1 Hz, 1H), 7.55 (d, J = 2.5 Hz, 1H), 7.37-7.31 (m, 2H), 7.28 (d, J = 8.4 Hz, 1H), 6.69 (d, J = 2.6 Hz, 1H), 6.37-6.32 (m, 2H), 3.82 (d, J = 13.0 Hz, 2H), 3.78 (s, 3H), 3.54 (s, 2H), 3.45 (hept, J = 6.6 Hz, 1H), 3.22-3.12 (m, 2H), 2.97 (s, 2H), 2.88 (s, 3H), 1.18 (d, J = 6.6 Hz, 6H). MS (ESI) m/z: 504 [M + H]$^+$. |
| IB-2 | 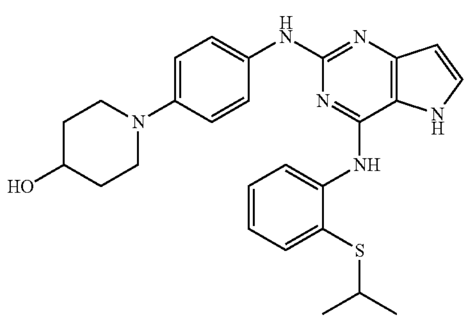 [SMILES: CC(C)Sc1ccccc1Nc1nc(Nc2ccc(N3CCC(O)CC3)cc2)nc2cc[nH]c12] | $^1$H NMR (600 MHz, DMSO-d$_6$) δ 11.23 (s, 1H), 8.42 (s, 1H), 8.30 (s, 1H), 8.13-7.96 (m, 1H), 7.60-7.55 (m, 2H), 7.52 (dd, J = 7.7, 1.5 Hz, 1H), 7.48-7.44 (m, 1H), 7.34 (td, J = 7.6, 1.6 Hz, 1H), 7.15 (td, J = 7.5, 1.4 Hz, 1H), 6.79-6.74 (m, 2H), 6.23-6.18 (m, 1H), 4.64 (d, J = 3.9 Hz, 1H), 3.57 (dt, J = 8.8, 4.9 Hz, 1H), 3.17 (d, J = 3.9 Hz, 2H), 2.69 (ddd, J = 12.4, 10.4, 3.0 Hz, 2H), 1.82 (dt, J = 12.8, 4.0 Hz, 2H), 1.50 (dtd, J = 13.0, 9.5, 3.8 Hz, 2H), 1.19 (d, J = 6.8 Hz, 6H). MS (ESI) m/z: 475 [M + H]$^+$. |
| IB-3 | 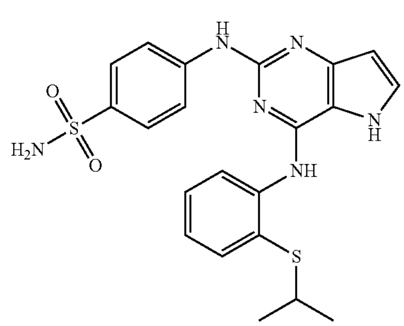 [SMILES: CC(C)Sc1ccccc1Nc1nc(Nc2ccc(S(N)(=O)=O)cc2)nc2cc[nH]c12] | $^1$H NMR (600 MHz, DMSO-d$_6$) δ 11.30-11.21 (m, 1H), 9.15 (s, 1H), 8.64 (s, 1H), 7.88 (dd, J = 8.0, 1.3 Hz, 1H), 7.86-7.82 (m, 2H), 7.57-7.54 (m, 2H), 7.54-7.51 (m, 2H), 7.37 (td, J = 7.7, 1.5 Hz, 1H), 7.24 (td, J = 7.6, 1.4 Hz, 1H), 7.05 (s, 2H), 6.29 (dd, J = 2.9, 2.0 Hz, 1H), 3.42-3.35 (m, 1H), 1.18 (d, J = 6.6 Hz, 6H). MS (ESI) m/z: 455 [M + H]$^+$. |

TABLE 1-continued

Structure and identification of compounds IA-IF

| ID | Structure | NMR and/or MS data |
|---|---|---|
| IC-1 | 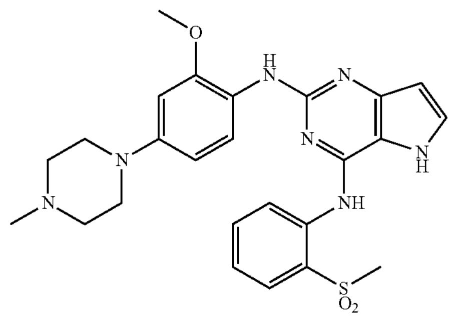 | $^1$H NMR (600 MHz, DMSO-d$_6$) δ 11.32 (s, 1H), 8.75 (s, 1H), 8.07 (d, J = 8.8 Hz, 1H), 7.99-7.92 (m, 2H), 7.81-7.72 (m, 1H), 7.51 (s, 1H), 7.44 (t, J = 7.7 Hz, 1H), 7.04 (s, 1H), 6.59 (d, J = 2.6 Hz, 1H), 6.36 (dd, J = 8.8, 2.5 Hz, 1H), 6.25 (d, J = 2.9 Hz, 1H), 3.80 (s, 3H), 3.15 (s, 3H), 3.08 (t, J = 5.0 Hz, 4H), 2.56-2.53 (m, 4H), 2.29 (s, 3H). MS (ESI) m/z: 508 [M + H]$^+$. |
| IC-2 | TFA salt | $^1$H NMR (600 MHz, Methanol-d$_4$) δ 8.10 (dd, J = 8.0, 1.5 Hz, 1H), 7.92 (d, J = 8.0 Hz, 1H), 7.80 (td, J = 7.8, 1.6 Hz, 1H), 7.65-7.57 (m, 2H), 7.42-7.36 (m, 1H), 6.91 (d, J = 2.1 Hz, 1H), 6.63 (dd, J = 8.7, 2.5 Hz, 1H), 6.40 (d, J = 3.0 Hz, 1H), 3.87 (s, 3H), 3.81 (d, J = 12.6 Hz, 2H), 3.40 (s, 4H), 3.22 (s, 4H), 3.12 (d, J = 13.6 Hz, 2H), 3.08 (s, 3H), 3.07-3.02 (m, 1H), 2.90 (s, 3H), 2.66 (s, 1H), 2.22-2.13 (m, 2H), 1.91 (qd, J = 12.2, 3.9 Hz, 2H). MS (ESI) m/z: 591 [M + H]$^+$. |
| IC-3 | 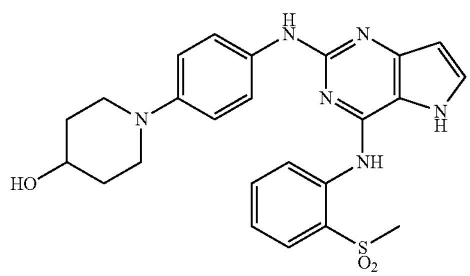 [SMILES: CS(=O)(=O)c1ccccc1Nc1nc(Nc2ccc(N3CCC(O)CC3)cc2)nc2cc[nH]c12] | $^1$H NMR (600 MHz, Methanol-d$_4$) δ 8.08 (dd, J = 8.0, 1.5 Hz, 1H), 7.88 (d, J = 8.0 Hz, 1H), 7.78 (td, J = 7.7, 1.5 Hz, 1H), 7.63-7.57 (m, 2H), 7.23 (d, J = 9.0 Hz, 2H), 6.98 (d, J = 8.4 Hz, 2H), 6.41 (d, J = 2.9 Hz, 1H), 3.83 (tt, J = 8.0, 3.7 Hz, 1H), 3.56 (dt, J = 11.0, 4.7 Hz, 2H), 3.06 (s, 3H), 2.99 (td, J = 10.5, 9.5, 4.5 Hz, 2H), 2.01 (dq, J = 13.1, 4.1 Hz, 2H), 1.72 (ddt, J = 14.0, 9.3, 4.6 Hz, 2H). MS (ESI) m/z: 479 [M + H]$^+$. |
| IC-4 | 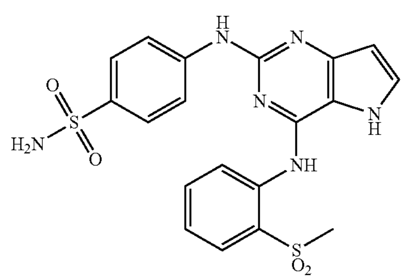 [SMILES: CS(=O)(=O)c1ccccc1Nc1nc(Nc2ccc(S(N)(=O)=O)cc2)nc2cc[nH]c12] | $^1$H NMR (600 MHz, DMSO-d$_6$) δ 11.43 (s, 1H), 9.24 (s, 1H), 8.85 (s, 1H), 8.02-7.92 (m, 2H), 7.80 (ddd, J = 11.3, 6.9, 1.8 Hz, 3H), 7.60 (q, J = 2.4 Hz, 1H), 7.52 (dd, J = 9.0, 7.2 Hz, 3H), 7.07 (s, 2H), 6.34 (dt, J = 2.9, 1.8 Hz, 1H), 3.15 (d, J = 1.8 Hz, 3H). MS (ESI) m/z: 459 [M + H]$^+$. |
| IC-5 | 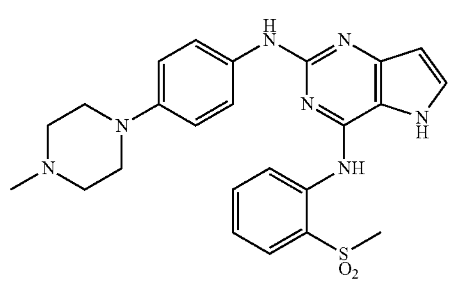 [SMILES: CN1CCN(c2ccc(Nc3nc(Nc4ccccc4S(C)(=O)=O)c4[nH]ccc4n3)cc2)CC1] | $^1$H NMR (600 MHz, DMSO-d$_6$) δ 11.26 (s, 1H), 8.67 (s, 1H), 8.40 (s, 1H), 8.02 (d, J = 8.2 Hz, 1H), 7.95 (dd, J = 7.9, 1.6 Hz, 1H), 7.76 (ddd, J = 8.5, 7.5, 1.6 Hz, 1H), 7.57-7.52 (m, 2H), 7.50 (t, J = 3.0 Hz, 1H), 7.42 (t, J = 7.4 Hz, 1H), 6.76-6.74 (m, 2H), 6.24 (dd, J = 2.8, 1.6 Hz, 1H), 3.15 (s, 3H), 3.01-2.99 (m, 4H), 2.44 (t, J = 4.9 Hz, 4H), 2.21 (s, 3H). MS (ESI) m/z: 478 [M + H]$^+$. |

TABLE 1-continued

Structure and identification of compounds IA-IF

| ID | Structure | NMR and/or MS data |
|---|---|---|
| ID-1 | <br>TFA salt | $^1$H NMR (600 MHz, DMSO-d$_6$) δ 12.23 (s, 1H), 10.26 (s, 1H), 9.23 (s, 1H), 7.92 (dd, J = 8.0, 1.6 Hz, 1H), 7.80 (td, J = 7.7, 1.6 Hz, 1H), 7.71 (d, J = 8.0 Hz, 1H), 7.66 (t, J = 3.0 Hz, 1H), 7.60 (td, J = 7.7, 1.3 Hz, 1H), 7.11 (d, J = 8.7 Hz 1H), 6.62 (d, J = 2.6 Hz, 1H), 6.35-6.29 (m, 1H), 6.22 (s, 1H), 3.78 (d, J = 12.5 Hz, 2H), 3.74 (s, 3H), 3.51 (d, J = 11.9 Hz, 2H), 3.30 (hept, J = 13.9, 7.0 Hz, 1H), 3.12 (d, J = 8.1 Hz, 2H), 2.91 (s, 2H), 2.84 (s, 3H), 1.00 (d, J = 6.7 Hz, 6H). MS (ESI) m/z: 536 [M + H]$^+$. |
| ID-2 | 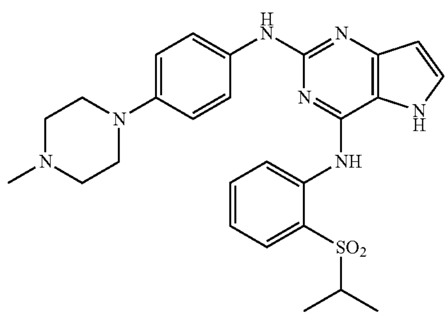 [SMILES: CC(C)S(=O)(=O)c1ccccc1Nc1nc(Nc2ccc(N3CCN(C)CC3)cc2)nc2cc[nH]c12] | $^1$H NMR (600 MHz, Methanol-d$_4$) δ 8.24 (d, J = 8.3 Hz, 1H), 7.88 (dd, J = 8.0, 1.6 Hz, 1H), 7.69-7.61 (m, 1H), 7.41-7.40 (m, 1H), 7.39-7.35 (m, 2H), 7.35-7.31 (m, 1H), 6.83 (d, J = 9.0 Hz, 2H), 6.28 (d, J = 3.0 Hz, 1H), 3.24 (hept, J = 6.9 Hz, 1H), 3.12-3.07 (m, 4H), 2.66-2.59 (m, 4H), 2.34 (s, 3H), 1.16 (d, J = 6.8 Hz, 6H). MS (ESI) m/z: 506 [M + H]$^+$. |
| ID-3 | <br>TFA salt | $^1$H NMR (600 MHz, DMSO-d$_6$) δ 12.27 (s, 1H), 10.31 (s, 1H), 9.25 (s, 1H), 7.97 (d, J = 7.9 Hz, 1H), 7.84 (t, J = 7.8 Hz, 1H), 7.76 (d, J = 8.0 Hz, 1H), 7.70 (d, J = 3.9 Hz, 1H), 7.65 (t, J = 7.7 Hz, 1H), 7.15 (d, J = 8.7 Hz, 1H), 6.71 (s, 1H), 6.36 (s, 1H), 6.31 (d, J = 8.7 Hz, 1H), 3.82 (d, J = 12.2 Hz, 2H), 3.78 (s, 3H), 3.60 (s, 4H), 3.45-3.32 (m, 5H), 2.90 (s, 3H), 2.77 (t, J = 12.2 Hz, 2H), 2.59-2.51 (m, 1H), 2.16 (d, J = 11.6 Hz, 2H), 1.78-1.69 (m, 2H), 1.05 (d, J = 6.8 Hz, 6H). MS (ESI) m/z: 619 [M + H]$^+$. |
| ID-4 | <br>TFA salt | $^1$H NMR (600 MHz, Methanol-d$_4$) δ 8.04 (dd, J = 8.0, 1.5 Hz, 1H), 7.90 (d, J = 7.9 Hz, 1H), 7.85 (td, J = 7.7, 1.5 Hz, 1H), 7.69-7.63 (m, 2H), 7.46 (d, J = 8.9 Hz, 2H), 7.33-7.27 (m, 2H), 6.48 (d, J = 3.0 Hz, 1H), 4.01 (hept, J = 7.3, 3.5 Hz, 1H), 3.70 (ddd, J = 11.8, 7.6, 3.6 Hz, 2H), 3.38 (ddd, J = 12.0, 8.0, 3.6 Hz, 2H), 3.24 (hept, J = 6.9 Hz, 1H), 2.17 (ddt, J = 14.5, 7.5, 3.6 Hz, 2H), 1.92 (dtd, J = 14.9, 7.7, 3.6 Hz, 2H), 1.12 (d, J = 6.8 Hz, 6H). MS (ESI) m/z: 507 [M + H]$^+$. |

TABLE 1-continued

Structure and identification of compounds IA-IF

| ID | Structure | NMR and/or MS data |
|---|---|---|
| ID-5 | 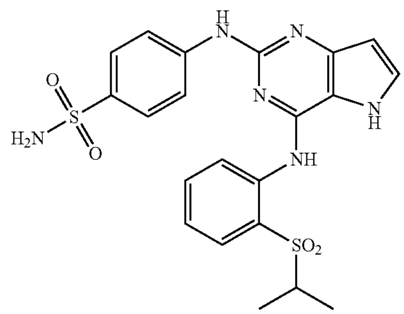 [SMILES: CC(C)S(=O)(=O)c1ccccc1Nc1nc(Nc2ccc(S(N)(=O)=O)cc2)nc2cc[nH]c12] | $^1$H NMR (600 MHz, DMSO-d$_6$) δ 12.05 (s, 1H), 10.56 (s, 1H), 10.21 (s, 1H), 8.03 (dd, J = 7.9, 1.5 Hz, 1H), 7.92 (td, J = 7.7, 1.6 Hz, 1H), 7.87 (dd, J = 8.1, 1.3 Hz, 1H), 7.78 (t, J = 3.0 Hz, 1H), 7.74-7.68 (m, 1H), 7.51-7.43 (m, 4H), 7.22 (s, 2H), 6.43 (dd, J = 3.0, 1.9 Hz, 1H), 3.30 (hept, J = 6.7 Hz, 1H), 1.03 (d, J = 6.8 Hz, 6H). MS (ESI) m/z: 487 [M + H]$^+$. |
| ID-6 | 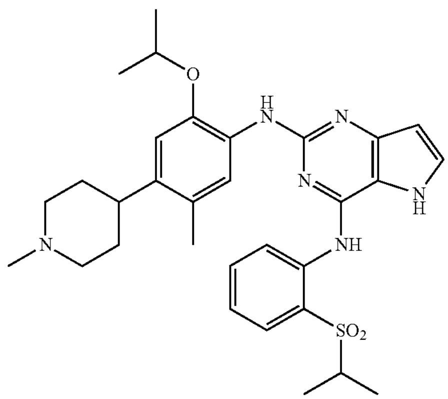 [SMILES: Cc1cc(Nc2nc(Nc3ccccc3S(=O)(=O)C(C)C)c3[nH]ccc3n2)c(OC(C)C)cc1C1CCN(C)CC1] | $^1$H NMR (600 MHz, Methanol-d$_4$) δ 8.02 (dd, J = 8.0, 1.6 Hz, 1H), 7.94 (d, J = 8.0 Hz, 1H), 7.78 (td, J = 7.8, 1.6 Hz, 1H), 7.63 (d, J = 3.0 Hz, 1H), 7.59 (td, J = 7.7, 1.2 Hz, 1H), 7.34 (s, 1H), 6.85 (s, 1H), 6.40 (d, J = 3.0 Hz, 1H), 4.62 (hept, J = 5.9 Hz, 1H), 3.61 (d, J = 12.8 Hz, 2H), 3.32-3.24 (m, 1H), 3.17 (td, J = 12.1, 4.6 Hz, 2H), 3.05 (hept, J = 10.5, 5.0 Hz, 1H), 2.91 (s, 3H), 2.0718 (s, 3H), 2.02-1.94 (m, 4H), 1.27 (d, J = 6.0 Hz, 6H), 1.15 (d, J = 6.8 Hz, 6H). MS (ESI) m/z: 577 [M + H]$^+$. |
| ID-7 | 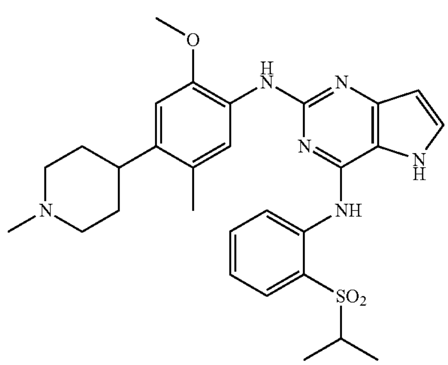 [SMILES: COc1cc(C2CCN(C)CC2)c(C)cc1Nc1nc(Nc2ccccc2S(=O)(=O)C(C)C)c2[nH]ccc2n1] | $^1$H NMR (600 MHz, Methanol-d$_4$) δ 8.02 (dd, J = 7.9, 1.5 Hz, 1H), 7.92 (d, J = 8.0 Hz, 1H), 7.77 (td, J = 7.8, 1.6 Hz, 1H), 7.63 (d, J = 2.9 Hz, 1H), 7.59 (td, J = 7.7, 1.2 Hz, 1H), 7.32 (s, 1H), 6.84 (s, 1H), 6.41 (d, J = 3.0 Hz, 1H), 3.85 (s, 3H), 3.63 (dq, J = 10.5, 1.9 Hz, 2H), 3.27 (q, J =6.8 Hz, 1H), 3.18 (td, J = 12.5, 3.4 Hz, 2H), 3.07 (tt, J = 11.8, 4.1 Hz, 1H), 2.93 (s, 3H), 2.08 (s, 3H), 2.06-1.95 (m, 4H), 1.15 (d, J = 6.8 Hz, 6H). MS (ESI) m/z: 549 [M + H]$^+$. |
| ID-8 | 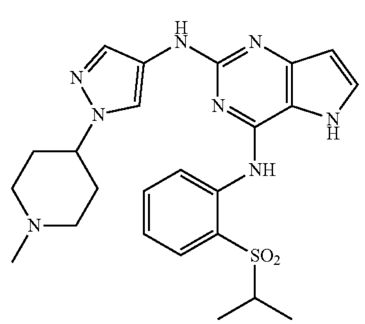 [SMILES: CC(C)S(=O)(=O)c1ccccc1Nc1nc(Nc2cnn(C3CCN(C)CC3)c2)nc2cc[nH]c12] | $^1$H NMR (600 MHz, Methanol-d$_4$) δ 8.16 (d, J = 8.3 Hz, 1H), 7.95 (dd, J = 7.9, 1.6 Hz, 1H), 7.79-7.72 (m, 1H), 7.70 (s, 1H), 7.45 (s, 1H), 7.44-7.38 (m, 2H), 6.28 (d, J = 3.0 Hz, 1H), 4.03 (dq, J = 10.8, 5.6, 4.5 Hz, 1H), 3.32-3.24 (m, 1H), 3.10 (d, J = 12.1 Hz, 2H), 2.45 (s, 3H), 2.42-2.37 (m, 2H), 2.09-1.97 (m, 4H), 1.19 (d, J = 6.8 Hz, 6H). MS (ESI) m/z: 495 [M + H]$^+$. |

TABLE 1-continued

Structure and identification of compounds IA-IF

| ID | Structure | NMR and/or MS data |
|---|---|---|
| ID-9 | 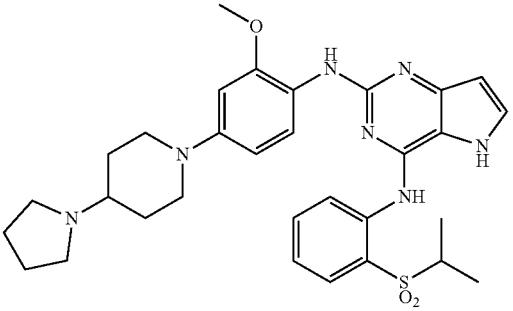 [SMILES: COc1cc(N2CCC(N3CCCC3)CC2)ccc1Nc1nc(Nc2ccccc2S(=O)(=O)C(C)C)c2[nH]ccc2n1] | $^1$H NMR (600 MHz, DMSO-$d_6$) δ 11.35 (s, 1H), 8.97-8.67 (m, 1H), 8.02 (dd, J = 19.5, 8.5 Hz, 2H), 7.89 (dd, J = 8.0, 1.6 Hz, 1H), 7.79-7.73 (m, 1H), 7.51 (d, J = 3.3 Hz, 1H), 7.43 (t, J = 7.7 Hz, 1H), 7.02 (s, 1H), 6.59 (d, J = 2.6 Hz, 1H), 6.31 (dd, J = 8.7, 2.6 Hz, 1H), 6.24 (d, J = 2.9 Hz, 1H), 4.58 (s, 2H), 3.80 (s, 3H), 3.57-3.52 (m, 2H), 3.34-3.28 (m, 1H), 2.75-2.66 (m, 2H), 2.61 (td, J = 12.2, 2.5 Hz, 2H), 1.96 (d, J = 12.2 Hz, 2H), 1.74 (s, 4H), 1.60-1.52 (m, 2H), 1.10 (d, J = 6.8 Hz, 6H). MS (ESI) m/z: 590 [M + H]$^+$. |
| ID-10 | 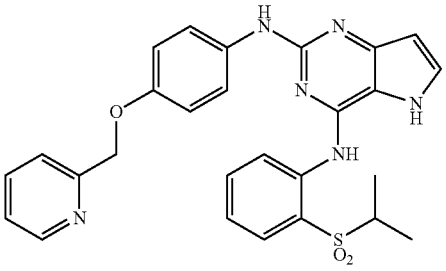 [SMILES: CC(C)S(=O)(=O)c1ccccc1Nc1nc(Nc2ccc(OCc3ccccn3)cc2)nc2cc[nH]c12] | $^1$H NMR (600 MHz, DMSO-$d_6$) δ 11.39 (s, 1H), 8.95 (s, 1H), 8.66 (s, 1H), 8.58 (ddd, J = 4.8, 1.8, 0.9 Hz, 1H), 8.01 (d, J = 8.2 Hz, 1H), 7.88 (dd, J = 8.0, 1.6 Hz, 1H), 7.83 (td, J = 7.7, 1.8 Hz, 1H), 7.74 (ddd, J = 8.4, 7.3, 1.6 Hz, 1H), 7.56-7.51 (m, 3H), 7.49 (dt, J = 7.8, 1.0 Hz, 1H), 7.45-7.41 (m, 1H), 7.34 (ddd, J = 7.5, 4.8, 1.1 Hz, 1H), 6.81-6.76 (m, 2H), 6.25 (dd, J = 2.9, 1.7 Hz, 1H), 5.09 (s, 2H), 1.09 (d, J = 6.8 Hz, 6H). MS (ESI) m/z: 515 [M + H]$^+$. |
| ID-11 | 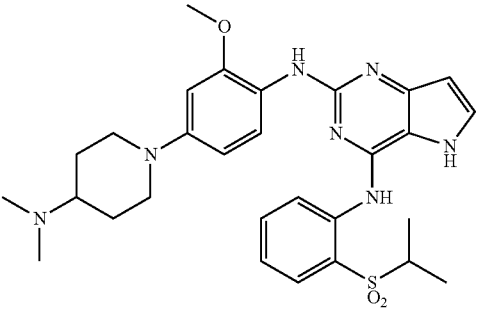 [SMILES: COc1cc(N2CCC(N(C)C)CC2)ccc1Nc1nc(Nc2ccccc2S(=O)(=O)C(C)C)c2[nH]ccc2n1] | $^1$H NMR (600 MHz, DMSO-$d_6$) δ 11.34 (s, 1H), 8.85 (s, 1H), 8.01 (dd, J = 12.9, 8.4 Hz, 2H), 7.88 (dd, J = 8.0, 1.6 Hz, 1H), 7.81-7.69 (m, 1H), 7.51 (s, 1H), 7.43 (t, J = 7.7 Hz, 1H), 7.07-6.98 (m, 1H), 6.58 (d, J = 2.5 Hz, 1H), 6.31 (dd, J = 8.8, 2.6 Hz, 1H), 6.27-6.21 (m, 1H), 3.80 (s, 3H), 3.79-3.74 (m, 1H), 3.61-3.55 (m, 2H), 2.57 (td, J = 12.2, 2.5 Hz, 2H), 2.23 (s, 6H), 1.87-1.81 (m, 2H), 1.50 (qd, J = 12.0, 4.0 Hz, 2H), 1.10 (d, J = 6.8 Hz, 6H). MS (ESI) m/z: 564 [M + H]$^+$. |
| ID-12 | 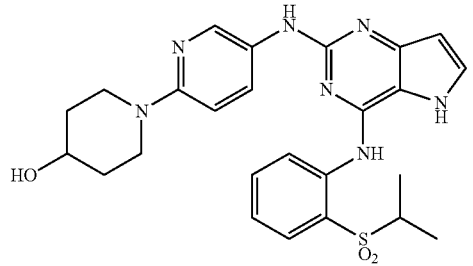 [SMILES: CC(C)S(=O)(=O)c1ccccc1Nc1nc(Nc2ccc(N3CCC(O)CC3)nc2)nc2cc[nH]c12] | $^1$H NMR (600 MHz, Methanol-$d_4$) δ 7.99-7.96 (m, 2H), 7.85 (d, J = 8.1 Hz, 1H), 7.77 (td, J = 7.7, 1.5 Hz, 1H), 7.62 (dd, J = 7.6, 2.8 Hz, 2H), 7.57 (td, J = 7.7, 1.2 Hz, 1H), 6.85 (d, J = 9.3 Hz, 1H), 6.43 (d, J = 3.0 Hz, 1H), 4.00 (dt, J = 13.7, 4.6 Hz, 2H), 3.90 (hept, J = 8.5, 4.0 Hz, 1H), 3.24 (ddd, J = 11.8, 4.9, 2.6 Hz, 2H), 1.98-1.92 (m, 2H), 1.55 (dtd, J = 13.1, 9.3, 3.8 Hz, 2H), 1.12 (d, J = 6.8 Hz, 6H). MS (ESI) m/z: 508 [M + H]$^+$. |
| ID-13 | 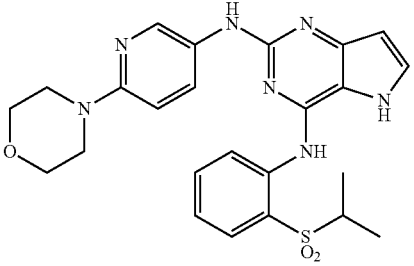 [SMILES: CC(C)S(=O)(=O)c1ccccc1Nc1nc(Nc2ccc(N3CCOCC3)nc2)nc2cc[nH]c12] | $^1$H NMR (600 MHz, DMSO-$d_6$) δ 11.34 (d, J = 3.1 Hz, 1H), 8.82 (s, 1H), 8.51 (s, 1H), 8.43 (d, J = 2.7 Hz, 1H), 8.06 (dd, J = 8.2, 1.1 Hz, 1H), 7.96 (dd, J = 9.1, 2.7 Hz, 1H), 7.87 (dd, J = 8.0, 1.6 Hz, 1H), 7.76 (ddd, J = 8.5, 7.3, 1.6 Hz, 1H), 7.50 (t, J = 2.8 Hz, 1H), 7.40 (ddd, J = 8.2, 7.3, 1.2 Hz, 1H), 6.66 (d, J = 9.1 Hz, 1H), 6.24 (dd, J = 3.0, 1.5 Hz, 1H), 3.72-3.68 (m, 4H), 3.30-3.26 (m, 4H), 1.11 (d, J = 6.8 Hz, 6H). MS (ESI) m/z: 494 [M + H]$^+$. |

TABLE 1-continued

Structure and identification of compounds IA-IF

| ID | Structure | NMR and/or MS data |
|---|---|---|
| ID-14 | 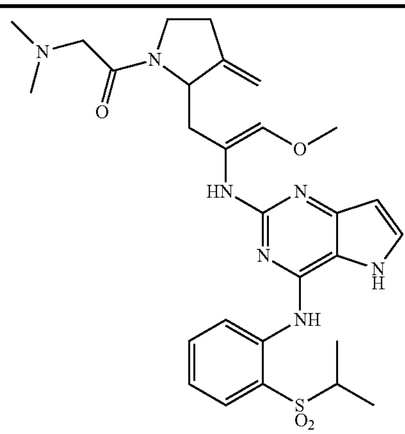 | $^1$H NMR (600 MHz, DMSO-d$_6$) δ 11.40 (s, 1H), 9.03 (s, 1H), 8.89 (s, 1H), 8.10 (d, J = 8.3 Hz, 1H), 7.85 (d, J = 7.9 Hz, 1H), 7.66 (t, J = 7.8 Hz, 1H), 7.55-7.52 (m, 1H), 7.36 (t, J = 7.6 Hz, 1H), 7.19 (s, 1H), 6.91 (s, 1H), 6.24 (d, J = 3.0 Hz, 1H), 4.15 (t, J = 8.3 Hz, 2H), 3.79 (s, 3H), 3.33-3.32 (m, 1H), 3.26 (s, 2H), 3.09 (t, J = 8.3 Hz, 2H), 2.32 (s, 6H), 1.15 (d, J = 6.8 Hz, 6H). MS (ESI) m/z: 564 [M + H]$^+$. |
| ID-15 | 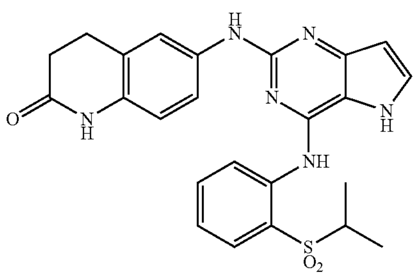 [SMILES: CC(C)S(=O)(=O)c1ccccc1Nc1nc(Nc2ccc3c(c2)CCC(=O)N3)nc2cc[nH]c12] | $^1$H NMR (600 MHz, DMSO-d$_6$) δ 11.40-11.29 (m, 1H), 9.80 (s, 1H), 8.83 (s, 1H), 8.62 (s, 1H), 7.99 (dd, J = 8.3, 1.2 Hz, 1H), 7.89 (dd, J = 8.0, 1.6 Hz, 1H), 7.78-7.71 (m, 1H), 7.52 (t, J = 2.9 Hz, 1H), 7.48 (d, J = 2.4 Hz, 1H), 7.47-7.41 (m, 1H), 7.33 (dd, J = 8.6, 2.4 Hz, 1H), 6.60 (d, J = 8.6 Hz, 1H), 6.23 (dd, J = 2.9, 1.8 Hz, 1H), 3.32 (p, J = 6.8 Hz, 1H), 2.61 (t, J = 7.5 Hz, 2H), 2.36 (dd, J = 8.5, 6.5 Hz, 2H), 1.10 (d, J = 6.8 Hz, 6H). MS (ESI) m/z: 477 [M + H]$^+$ |
| ID-16 | TFA salt | $^1$H NMR (600 MHz, DMSO-d$_6$) δ 12.30-12.17 (m, 1H), 10.49 (s, 1H), 9.33 (s, 1H), 7.99 (dd, J = 7.9, 1.5 Hz, 1H), 7.89 (td, J = 7.7, 1.6 Hz, 1H), 7.81-7.77 (m, 2H), 7.70 (td, J = 7.6, 1.2 Hz, 1H), 7.44 (d, J = 8.2 Hz, 1H), 7.00 (d, J = 1.7 Hz, 1H), 6.51 (dd, J = 8.2, 1.7 Hz, 1H), 6.48 (dd, J = 2.9, 2.0 Hz, 1H), 4.53 (s, 2H), 3.84 (s, 3H), 3.53 (d, J = 49.5 Hz, 4H), 3.29 (p, J = 6.8 Hz, 1H), 3.11 (d, J = 70.3 Hz, 6H), 2.84 (s, 3H), 2.54 (s, 1H), 1.93 (d, J = 45.7 Hz, 2H), 1.51 (s, 2H), 1.00 (d, J = 6.7 Hz, 6H). MS (ESI) m/z: 647 [M + H]$^+$. |
| ID-17 | 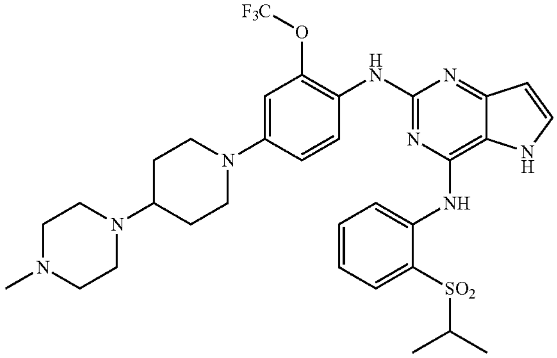 [SMILES: CC(C)S(=O)(=O)c1ccccc1Nc1nc(Nc2ccc(N3CCC(N4CCN(C)CC4)CC3)cc2OC(F)(F)F)nc2cc[nH]c12] | $^1$H NMR (600 MHz, DMSO-d$_6$) δ 11.46 (s, 1H), 8.96 (s, 1H), 8.38 (d, J = 9.0 Hz, 1H), 7.95 (d, J = 8.2 Hz, 1H), 7.92 (dd, J = 8.0, 1.6 Hz, 1H), 7.79-7.75 (m, 1H), 7.62 (s, 1H), 7.59 (d, J = 3.0 Hz, 1H), 7.47 (t, J = 7.9 Hz, 1H), 7.02 (d, J = 2.8 Hz, 1H), 6.90-6.87 (m, 1H), 6.34 (d, J = 3.0 Hz, 1H), 3.31-3.27 (m, 1H), 2.96 (d, J = 11.4 Hz, 2H), 2.64 (dd, J = 12.5, 10.3 Hz, 2H), 2.5517 (s, 1H), 2.48 (s, 4H), 2.4105-2.2923 (m, 4H), 2.19 (s, 3H), 1.83 (d, J = 12.2 Hz, 2H), 1.55-1.46 (m, 2H), 1.09 (d, J = 6.8 Hz, 6H). MS (ESI) m/z: 673 [M + H]$^+$ |

TABLE 1-continued

Structure and identification of compounds IA-IF

| ID | Structure | NMR and/or MS data |
| --- | --- | --- |
| ID-18 | TFA salt | $^1$H NMR (600 MHz, Methanol-d$_4$) δ 8.01-7.93 (m, 2H), 7.86 (s, 1H), 7.72 (t, J = 7.1 Hz, 1H), 7.67 (d, J = 2.8 Hz, 1H) 7.54 (t J = 7.3 Hz 1H) 7.24 (dd, J = 13.4, 5.6 Hz, 1H), 7.13 (d, J = 7.4 Hz, 1H), 6.47 (d, J = 2.9 Hz, 1H), 6.44 (d, J = 10.0 Hz, 1H), 6.39 (d, J = 1.6 Hz, 1H), 5.82 (dd, J = 10.0, 1.7 Hz, 1H), 3.28-3.21 (m, 1H), 1.28 (d, J = 6.8 Hz, 1H), 1.16 (d, J = 6.8 Hz, 6H). MS (ESI) m/z: 477 [M + H]$^+$. |
| ID-19 | 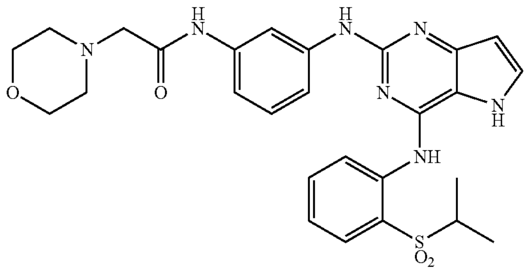 [SMILES: CC(C)S(=O)(=O)c1ccccc1Nc1nc(Nc2cccc(NC(=O)CN3CCOCC3)c2)nc2cc[nH]c12] | $^1$H NMR (600 MHz, DMSO-d$_6$) δ 11.39 (s, 1H), 9.49 (s, 1H), 8.89 (s, 1H), 8.77 (s, 1H), 8.15 (d, J = 8.2 Hz, 1H), 7.89 (dd, J = 8.0, 1.6 Hz, 1H), 7.80 (t, J = 1.8 Hz, 1H), 7.78-7.73 (m, 1H), 7.56-7.50 (m, 2H), 7.43-7.39 (m, 1H), 7.12 (d, J = 8.8 Hz, 1H), 7.03 (t, J = 8.1 Hz, 1H), 6.29 (dd, J = 2.8, 1.7 Hz, 1H), 4.04 (q, J = 7.1 Hz, 1H), 3.67-3.61 (m, 4H), 3.12 (s, 2H), 2.00 (s, 2H), 1.18 (d, J = 7.1 Hz, 1H), 1.14 (d, J = 6.8 Hz, 6H). MS (ESI) m/z: 550 [M + H]$^+$. |
| ID-20 | 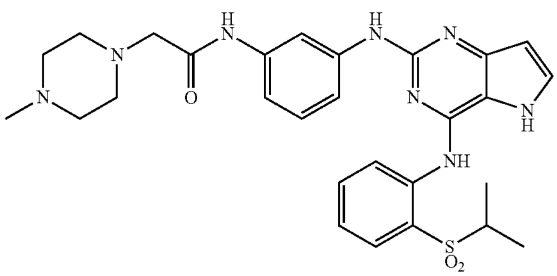 [SMILES: CC(C)S(=O)(=O)c1ccccc1Nc1nc(Nc2cccc(NC(=O)CN3CCN(C)CC3)c2)nc2cc[nH]c12] | $^1$H NMR (600 MHz, DMSO-d$_6$) δ 9.52 (s, 1H), 8.78 (s, 1H), 8.13 (d, J = 8.1 Hz, 1H), 7.96 (s, 2H), 7.89 (dd, J = 8.0, 1.6 Hz, 1H), 7.79 (t, J = 1.8 Hz, 1H), 7.77-7.73 (m, 1H), 7.55 (s, 1H), 7.51 (dd, J = 8.2, 1.1 Hz, 1H), 7.44-7.39 (m, 1H), 7.15-7.11 (m, 1H), 7.03 (t, J = 8.1 Hz, 1H), 6.29 (d, J = 2.8 Hz, 1H), 3.16 (s, 2H), 2.89 (s, 4H), 2.74 (d, J = 0.5 Hz, 4H), 2.40 (s, 3H), 1.23 (s, 1H), 1.13 (d, J = 6.8 Hz, 6H). MS (ESI) m/z: 563 [M + H]$^+$. |
| ID-21 | 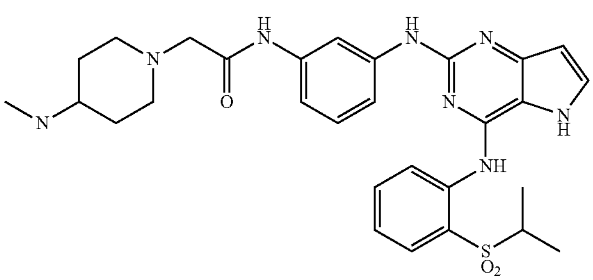 | $^1$H NMR (600 MHz, DMSO-d$_6$) δ 11.41 (s, 1H), 9.42 (s, 1H), 8.90 (s, 1H), 8.75 (s, 1H), 8.13 (d, J = 8.2 Hz, 1H), 7.88 (dd, J = 8.0, 1.6 Hz, 1H), 7.79-7.70 (m, 2H), 7.54 (s, 1H), 7.51 (dd, J = 8.2, 1.0 Hz, 1H), 7.43-7.39 (m, 1H), 7.15-7.11 (m, 1H), 7.03 (t, J = 8.1 Hz, 1H), 6.28 (d, J = 2.9 Hz, 1H), 3.08 (s, 2H), 2.27 (s, 8H), 1.77 (s, 1H), 1.23 (s, 6H), 1.19-1.15 (m, 1H), 1.13 (d, J = 6.8 Hz, 6H). MS (ESI) m/z: 591 [M + H]$^+$. |
| ID-22 | 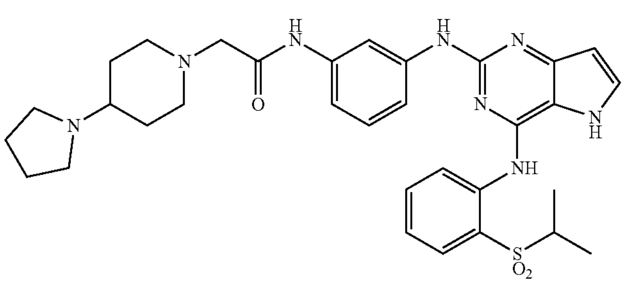 [SMILES: CC(C)S(=O)(=O)c1ccccc1Nc1nc(Nc2cccc(NC(=O)CN3CCC(N4CCCC4)CC3)c2)nc2cc[nH]c12] | $^1$H NMR (600 MHz, DMSO-d$_6$) δ 11.44 (s, 1H), 9.53 (s, 1H), 8.94 (s, 1H), 8.74 (s, 1H), 8.12 (d, J = 8.2 Hz, 1H), 7.89 (dd, J = 8.0, 1.5 Hz, 1H), 7.78 (s, 1H), 7.77-7.72 (m, 1H), 7.54 (t, J = 2.6 Hz, 1H), 7.51 (d, J = 8.1 Hz, 1H), 7.42 (t, J = 7.7 Hz, 1H), 7.10 (d, J = 8.0 Hz, 1H), 7.02 (t, J = 8.1 Hz, 1H), 6.29 (s, 1H), 4.12 (s, 1H), 3.17 (d, J = 17.1 Hz, 8H), 2.55 (s, 1H), 2.21 (dd, J = 19.8, 8.5 Hz, 2H), 1.99 (d, J = 10.4 Hz, 2H), 1.91 (d, J = 18.0 Hz, 4H), 1.76 (d, J = 9.9 Hz, 2H), 1.14 (d, J = 6.8 Hz, 6H). MS (ESI) m/z: 617 [M + H]$^+$. |

TABLE 1-continued

Structure and identification of compounds IA-IF

| ID | Structure | NMR and/or MS data |
|---|---|---|
| ID-23 | 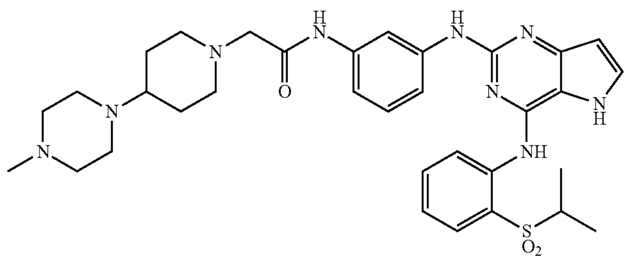 [SMILES: CC(C)S(=O)(=O)c1ccccc1Nc1nc(Nc2cccc(NC(=O)CN3CCC(N4CCN(C)CC4)CC3)c2)nc2cc[nH]c12] | $^1$H NMR (600 MHz, DMSO-d$_6$) δ 12.10 (s, 1H), 10.59 (s, 1H), 10.29 (s, 1H), 9.87 (s, 1H), 7.98 (d, J = 8.2 Hz, 1H), 7.91-7.82 (m, 2H), 7.77 (s, 1H), 7.68 (d, J = 7.6 Hz, 1H), 7.39 (s, 1H), 7.23 (d, J = 8.0 Hz, 2H), 6.93 (t, J = 8.0 Hz, 1H), 6.40 (s, 1H), 3.18 (s, 2H), 2.79 (s, 3H), 2.54-2.48 (m, 12H), 1.99 (d, J = 11.7 Hz, 2H), 1.75 (d, J = 12.2 Hz, 2H), 1.24 (s, 1H), 1.02 (d, J = 6.7 Hz, 6H). MS (ESI) m/z: 646 [M + H]$^+$. |
| ID-24 | TFA salt | $^1$H NMR (600 MHz, DMSO-d$_6$) δ 11.39 (s, 1H), 10.01 (s, 1H), 8.89 (s, 1H), 8.76 (s, 1H), 8.14 (d, J = 8.1 Hz, 1H), 7.88 (dd, J = 8.0, 1.5 Hz, 1H), 7.75 (dd, J = 12.0, 5.0 Hz, 2H), 7.55 (t, J = 2.9 Hz, 1H), 7.45 (d, J = 8.2 Hz, 1H), 7.43-7.38 (m, 1H), 7.11 (d, J = 8.0 Hz, 1H), 7.00 (t, J = 8.1 Hz, 1H), 6.30 (dd, J = 2.9, 1.9 Hz, 1H), 4.38 (d, J = 4.2 Hz, 1H), 3.78 (dtd, J = 12.2, 6.1, 4.2 Hz, 1H), 1.13 (d, J = 6.8 Hz, 6H), 0.81-0.74 (m, 4H). MS (ESI) m/z: 491 [M + H]$^+$. |
| ID-25 | 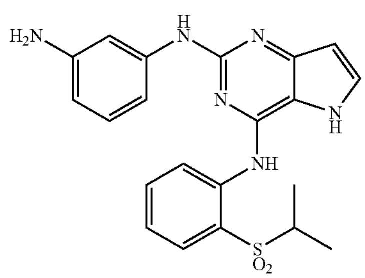 [SMILES: CC(C)S(=O)(=O)c1ccccc1Nc1nc(Nc2cccc(N)c2)nc2cc[nH]c12] | $^1$H NMR (600 MHz, DMSO-d$_6$) δ 11.80 (s, 1H), 9.71 (s, 1H), 9.46 (s, 1H), 7.96-7.92 (m, 2H), 7.85 (td, J = 7.8, 1.5 Hz, 1H), 7.65 (s, 1H), 7.57 (t, J = 7.6 Hz, 1H), 6.75 (t, J = 7.9 Hz, 1H), 6.68-6.60 (m, 2H), 6.33 (d, J = 2.5 Hz, 1H), 6.21 (dd, J = 7.9, 1.1 Hz, 1H), 3.31-3.28 (m, 1H), 1.07 (d, J = 6.8 Hz, 6H). MS (ESI) m/z: 423 [M + H]$^+$. |
| ID-26 | 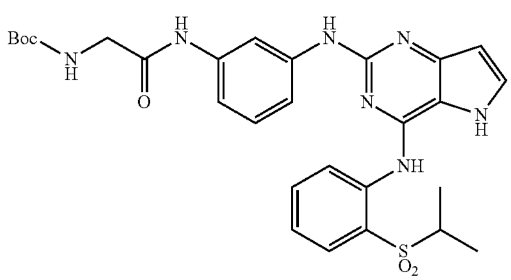 [SMILES: CC(C)S(=O)(=O)c1ccccc1Nc1nc(Nc2cccc(NC(=O)CNC(=O)OC(C)(C)C)c2)nc2cc[nH]c12] | $^1$H NMR (600 MHz, DMSO-d$_6$) δ 11.36 (s, 1H), 9.72 (s, 1H), 8.84 (s, 1H), 8.77 (s, 1H), 8.11 (d, J = 8.3 Hz, 1H), 7.87 (d, J = 8.0 Hz, 1H), 7.75 (dd, J = 15.4, 7.0 Hz, 2H), 7.53 (t, J = 2.9 Hz, 1H), 7.45 (d, J = 0.6 Hz, 1H), 7.40 (t, J = 7.7 Hz, 1H), 7.08 (d, J = 8.8 Hz, 1H), 7.04-6.96 (m, 2H), 6.28 (s, 1H), 3.70 (d, J = 6.1 Hz, 2H), 3.31 (d, J = 6.3 Hz, 1H), 1.39 (s, 9H), 1.12 (d, J = 6.8 Hz, 6H). MS (ESI) m/z: 580 [M + H]$^+$. |
| ID-27 | 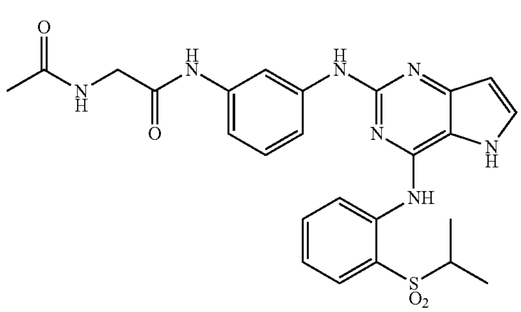 [SMILES: CC(=O)NCC(=O)Nc1cccc(Nc2nc(Nc3ccccc3S(=O)(=O)C(C)C)c3[nH]ccc3n2)c1] | $^1$H NMR (600 MHz, DMSO-d$_6$) δ 11.37 (s, 1H), 9.78 (s, 1H), 8.86 (s, 1H), 8.76 (s, 1H), 8.17 (t, J = 5.7 Hz, 1H), 8.11 (d, J = 7.9 Hz, 1H), 7.87 (dd, J = 8.0, 1.4 Hz, 1H), 7.77-7.72 (m, 2H), 7.53 (t, J = 2.9 Hz, 1H), 7.46 (d, J = 7.4 Hz, 1H), 7.40 (t, J = 7.2 Hz, 1H), 7.10 (d, J = 7.9 Hz, 1H), 7.00 (t, J = 8.1 Hz, 1H), 6.30-6.26 (m, 1H), 4.36 (d, J = 4.2 Hz, 1H), 3.85 (d, J = 5.9 Hz, 2H), 1.88 (s, 3H), 1.12 (d, J = 6.8 Hz, 6H). MS (ESI) m/z: 522 [M + H]$^+$. |

TABLE 1-continued

Structure and identification of compounds IA-IF

| ID | Structure | NMR and/or MS data |
| --- | --- | --- |
| ID-28 | 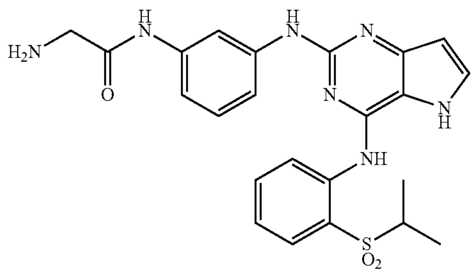 [SMILES: CC(C)S(=O)(=O)c1ccccc1Nc1nc(Nc2cccc(NC(=O)CN)c2)nc2cc[nH]c12] | ¹H NMR (600 MHz, DMSO-d₆) δ 11.39 (s, 1H), 9.82 (s, 1H), 8.79 (s, 2H), 8.10 (d, J = 8.2 Hz, 1H), 7.88 (d, J = 7.9 Hz, 1H), 7.76 (dd, J = 17.6, 9.8 Hz, 2H), 7.54 (d, J = 2.8 Hz, 1H), 7.47 (d, J = 8.1 Hz, 1H), 7.41 (t, J = 7.6 Hz, 1H), 7.15 (d, J = 7.7 Hz, 1H), 7.02 (t, J = 8.1 Hz, 1H), 6.27 (d, J = 2.9 Hz, 1H), 3.41 (s, 2H), 3.32-3.31 (m, 1H), 1.12 (d, J = 6.8 Hz, 6H). MS (ESI) m/z: 480 [M + H]⁺. |
| ID-29 | 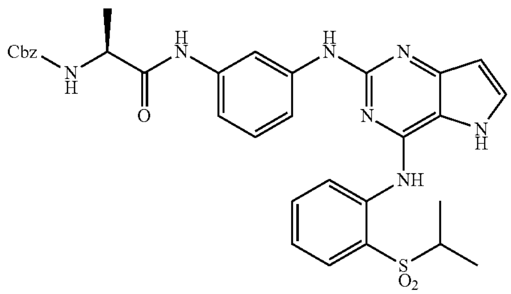 [SMILES: CC(C)S(=O)(=O)c1ccccc1Nc1nc(Nc2cccc(NC(=O)[C@H](C)NC(=O)OCc3ccccc3)c2)nc2cc[nH]c12] | ¹H NMR (600 MHz, DMSO-d₆) δ 11.35 (s, 1H), 9.79 (s, 1H), 8.87 (s, 1H), 8.72 (s, 1H), 8.14 (d, J = 8.4 Hz, 1H), 7.88-7.84 (m, 1H), 7.76 (d, J = 15.1 Hz, 2H), 7.53 (dd, J = 6.7, 4.0 Hz, 2H), 7.47 (d, J = 8.3 Hz, 1H), 7.39 (t, J = 7.8 Hz, 1H), 7.36 (d, J = 4.3 Hz, 3H), 7.31 (dd, J = 8.8, 4.5 Hz, 1H), 7.11 (d, J = 8.1 Hz, 1H), 7.00 (t, J = 8.1 Hz, 1H), 6.28 (s, 1H), 5.06-4.97 (m, 2H), 4.38 (d, J = 4.2 Hz, 1H), 4.22 (t, J = 7.2 Hz, 1H), 3.33-3.28 (m, 1H), 1.28 (d, J = 7.1 Hz, 3H), 1.12 (d, J = 6.8 Hz, 6H). MS (ESI) m/z: 628 [M + H]⁺. |
| ID-30 | 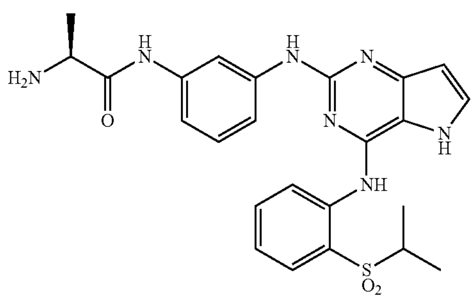 [SMILES: CC(C)S(=O)(=O)c1ccccc1Nc1nc(Nc2cccc(NC(=O)[C@H](C)N)c2)nc2cc[nH]c12] | ¹H NMR (600 MHz, DMSO-d₆) δ 11.38 (s, 1H), 9.63 (s, 1H), 8.79 (d, J = 79.9 Hz, 2H), 8.12 (d, J = 8.0 Hz, 1H), 7.88 (dd, J = 8.0, 1.6 Hz, 1H), 7.76-7.74 (m, 2H), 7.53 (d, J = 3.0 Hz, 1H), 7.47 (dd, J = 8.3, 1.2 Hz, 1H), 7.42-7.39 (m, 1H), 7.18-7.15 (m, 1H), 7.01 (t, J = 8.1 Hz, 1H), 6.28 (d, J = 2.9 Hz, 1H), 3.77 (dt, J = 12.2, 6.1 Hz, 1H), 3.46-3.43 (m, 1H), 1.22 (d, J = 6.9 Hz, 3H), 1.12 (d, J = 6.8 Hz, 6H). MS (ESI) m/z: 494 [M + H]⁺. |
| ID-31 | 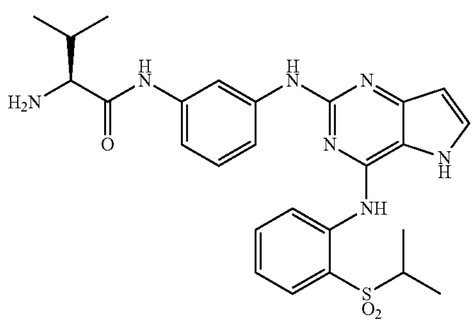 [SMILES: CC(C)[C@H](N)C(=O)Nc1cccc(Nc2nc(Nc3ccccc3S(=O)(=O)C(C)C)c3[nH]ccc3n2)c1] | MS (ESI) m/z: 522 [M + H]⁺. |
| IE-1 | 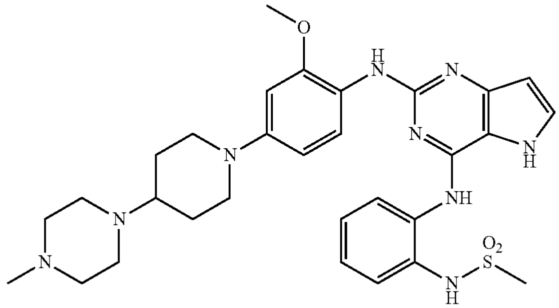 [SMILES: COc1cc(N2CCC(N3CCN(C)CC3)CC2)ccc1Nc1nc(Nc2ccccc2NS(C)(=O)=O)c2[nH]ccc2n1] | MS (ESI) m/z: 606 [M + H]⁺. |

TABLE 1-continued

Structure and identification of compounds IA-IF

| ID | Structure | NMR and/or MS data |
|---|---|---|
| IE-2 | 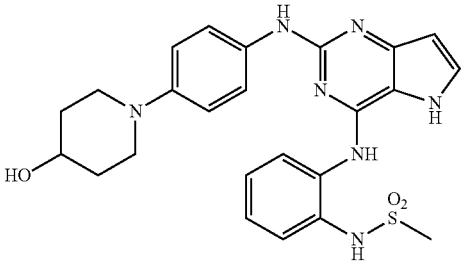 TFA salt | $^1$H NMR (600 MHz; Methanol-d$_4$): δ 8.41 (d, J = 8.4 Hz, 1H), 7.87 (d, J = 7.9 Hz, 1H), 7.71-7.68 (m, 1H), 7.64 (tt, J = 4.2, 2.1 Hz, 2H), 7.56 (d, J = 9.0 Hz, 2H), 7.49 (td, J = 7.8, 1.5 Hz, 1H), 7.42-7.39 (m, 2H), 6.55 (d, J = 2.9 Hz, 1H), 6.47 (d, J = 3.0 Hz, 1H), 4.08 (t, J = 3.5 Hz, 1H), 3.78-3.74 (m, 2H), 3.52-3.49 (m, 2H), 2.95 (s, 3H), 2.25-2.21 (m, 2H), 2.02-1.99 (m, 2H). MS (ESI) m/z: 494 [M + H]$^+$. |
| IE-3 | 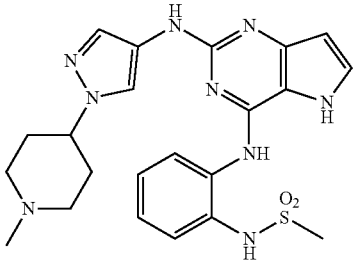 [SMILES: CN1CCC(n2cc(Nc3nc(Nc4ccccc4NS(C)(=O)=O)c4[nH]ccc4n3)cn2)CC1] | MS (ESI) m/z: 482 [M + H]$^+$. |
| IE-4 | 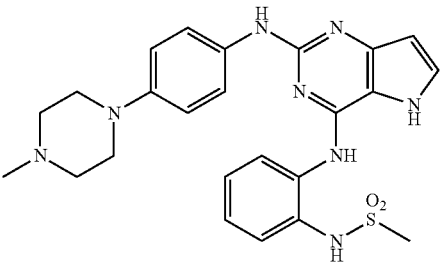 [SMILES: CN1CCN(c2ccc(Nc3nc(Nc4ccccc4NS(C)(=O)=O)c4[nH]ccc4n3)cc2)CC1] | $^1$H NMR (600 MHz, DMSO-d$_6$) δ 10.99 (d, J = 4.0 Hz, 1H), 8.61 (s, 1H), 8.37 (s, 1H), 7.85 (dd, J = 8.0, 1.5 Hz, 1H), 7.61-7.55 (m, 2H), 7.47 (d, J = 2.9 Hz, 1H), 7.44 (dd, J = 8.0, 1.5 Hz, 1H), 7.29 (td, J = 7.7, 1.6 Hz, 1H), 7.21 (td, J = 7.7, 1.5 Hz, 1H), 6.81-6.75 (m, 2H), 6.21 (d, J = 2.9 Hz, 1H), 3.17 (s, 1H), 3.04-2.99 (m, 4H), 2.93 (s, 3H), 2.47 (t, J = 5.0 Hz, 4H), 2.23 (s, 3H). MS (ESI) m/z: 493 [M + H]$^+$. |
| IE-5 | 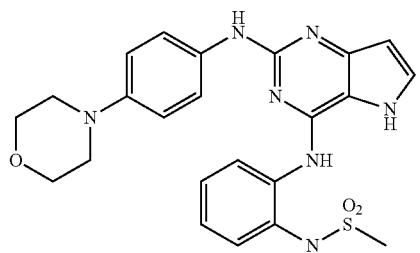 TFA salt | $^1$H-NMR (600 MHz; Methanol-d$_4$): δ 7.72 (dd, J = 7.9, 1.4 Hz, 1H), 7.62-7.60 (m, 1H), 7.59-7.57 (m, 1H), 7.44 (td, J = 7.8, 1.5 Hz, 1H), 7.37 (ddt, J = 7.3, 4.1, 1.9 Hz, 3H), 7.15-7.13 (m, 1H), 7.12 (d, J = 4.8 Hz, 1H), 6.41 (d, J = 3.0 Hz, 1H), 3.94 (dd, J = 5.7, 3.9 Hz, 4H), 3.89 (t, J = 4.8 Hz, 2H), 3.27-3.25 (m, 2H), 2.95 (s, 3H). MS (ESI) m/z: 480 [M + H]$^+$. |
| IE-6 | 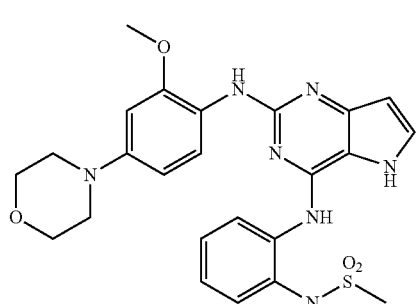 TFA salt | $^1$H-NMR (600 MHz; Methanol-d$_4$): δ 7.76 (dd, J = 7.9, 1.4 Hz, 1H), 7.58-7.56 (m, 2H), 7.41 (td, J = 7.7, 1.6 Hz, 1H), 7.38-7.35 (m, 2H), 6.79 (d, J = 2.5 Hz, 1H), 6.56 (dd, J = 8.7, 2.5 Hz, 1H), 6.36 (d, J = 3.0 Hz, 1H), 3.91 (t, J = 4.8 Hz, 4H), 3.86 (s, 3H), 3.28-3.27 (m, 4H), 2.98 (s, 3H). MS (ESI) m/z: 510 [M + H]$^+$. |

TABLE 1-continued

Structure and identification of compounds IA-IF

| ID | Structure | NMR and/or MS data |
| --- | --- | --- |
| IF-1 | 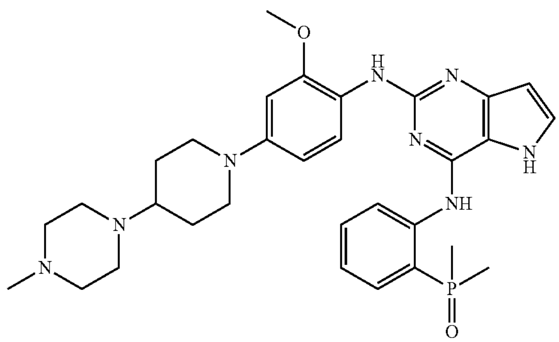 [SMILES: COc1cc(N2CCC(N3CCN(C)CC3)CC2)ccc1Nc1nc(Nc2ccccc2P(C)(C)=O)c2[nH]ccc2n1] | $^1$H NMR (600 MHz, DMSO-d$_6$) δ 10.80 (s, 1H), 10.73 (s, 1H), 8.35 (dd, J = 8.4, 4.0 Hz, 1H), 8.11 (d, J = 8.7 Hz, 1H), 7.62 (ddd, J = 13.9, 7.8, 1.7 Hz, 1H), 7.53 (t, J = 7.8 Hz, 1H), 7.41-7.37 (m, 1H), 7.16 (t, J = 7.2 Hz, 1H), 7.07 (s, 1H), 6.60 (d, J = 2.5 Hz, 1H), 6.44 (dd, J = 8.8, 2.5 Hz, 1H) 6.21 (d, J = 2.8 Hz, 1H), 3.82 (s, 3H), 3.76 (d, J = 6.3 Hz, 1H), 3.65-3.56 (m, 2H), 2.59 (td, J = 12.3, 2.5 Hz, 2H), 2.37-2.22 (m, 4H), 2.14 (s, 3H), 1.83 (d, J = 13.2 Hz, 2H), 1.80 (d, J = 13.5 Hz, 6H), 1.52 (qd, J = 12.0, 3.9 Hz, 2H), 1.27-1.12 (m, 2H), 1.04 (d, J = 6.1 Hz, 2H). MS (ESI) m/z: 589 [M + H]$^+$. |
| IF-2 | 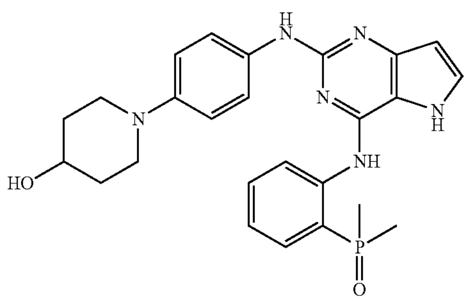 [SMILES: CP(C)(=O)c1ccccc1Nc1nc(Nc2ccc(N3CCC(O)CC3)cc2)nc2cc[nH]c12] | $^1$H NMR (600 MHz, DMSO-d$_6$) δ 10.91 (s, 1H), 10.61 (s, 1H), 8.52 (dd, J = 8.5, 4.0 Hz, 1H), 8.46 (s, 1H), 7.62 (dd, J = 22.4, 8.2 Hz, 3H), 7.55 (t, J = 7.9 Hz, 1H), 7.39 (t, J = 2.7 Hz, 1H), 7.16 (t, J = 7.5 Hz, 1H), 6.84 (d, J = 8.5 Hz, 2H), 6.24-6.20 (m, 1H), 3.59 (tt, J = 9.0, 4.2 Hz, 1H), 3.43-3.38 (m, 2H), 2.77-2.69 (m, 2H), 1.85 (d, J = 5.0 Hz, 2H), 1.82 (d, J = 13.4 Hz, 6H), 1.55-1.48 (m, 2H). MS (ESI) m/z: 477 [M + H]$^+$. |
| IF-3 | 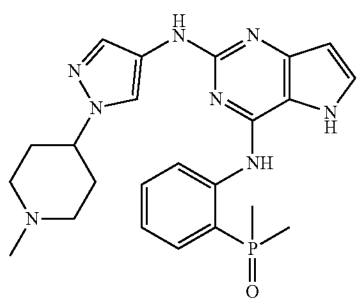 [SMILES: CN1CCC(n2cc(Nc3nc(Nc4ccccc4P(C)(C)=O)c4[nH]ccc4n3)cn2)CC1] | $^1$H NMR (600 MHz, DMSO-d$_6$) δ 10.61 (d, J = 62.9 Hz, 2H), 8.48 (s, 1H), 8.34 (s, 1H), 7.81 (d, J = 14.9 Hz, 1H), 7.70-7.63 (m, 1H), 7.56 (t, J = 7.8 Hz, 1H), 7.42-7.35 (m, 2H), 7.20 (t, J = 7.4 Hz, 1H), 6.19 (d, J = 2.9 Hz, 1H), 3.77 (p, J = 6.1 Hz, 1H), 2.90 (d, J = 11.4 Hz, 2H), 2.25 (s, 3H), 2.15-2.08 (m, 2H), 1.94-1.85 (m, 4H), 1.78 (d, J = 13.3 Hz, 6H). MS (ESI) m/z: 465 [M + H]$^+$. |
| IF-4 | 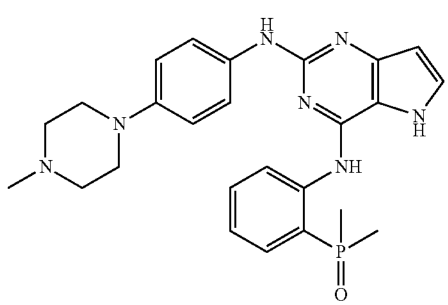 [SMILES: CN1CCN(c2ccc(Nc3nc(Nc4ccccc4P(C)(C)=O)c4[nH]ccc4n3)cc2)CC1] | $^1$H NMR (600 MHz, DMSO-d$_6$) δ 10.90 (s, 1H), 10.59 (s, 1H), 8.56-8.50 (m, 1H), 8.45 (s, 1H), 7.66-7.57 (m, 3H), 7.54 (ddt, J = 8.6, 7.3, 1.2 Hz, 1H), 7.38 (dd, J = 2.9, 1.4 Hz, 1H), 7.18-7.12 (m, 1H), 6.85-6.79 (m, 2H), 6.21 (d, J = 2.9 Hz, 1H), 3.05-3.00 (m, 4H), 2.47 (t, J = 5.0 Hz, 4H), 2.23 (s, 3H), 1.81 (d, J = 13.4 Hz, 6H). MS (ESI) m/z: 476 [M + H]$^+$. |

TABLE 1-continued

Structure and identification of compounds IA-IF

| ID | Structure | NMR and/or MS data |
|---|---|---|
| IF-5 | 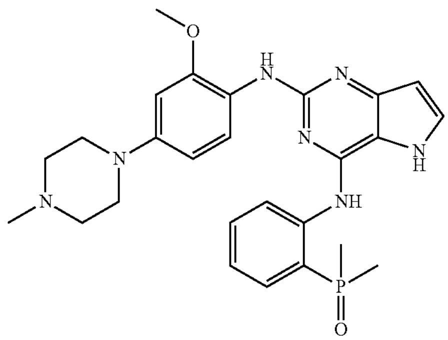 [SMILES: COc1cc(N2CCN(C)CC2)ccc1Nc1nc(Nc2ccccc2P(C)(C)=O)c2[nH]ccc2n1] | $^1$H NMR (600 MHz, DMSO-d$_6$) δ 10.84 (s, 1H), 10.71 (s, 1H), 8.34 (dd, J = 8.4, 4.0 Hz, 1H), 8.12 (d, J = 8.7 Hz, 1H), 7.68-7.57 (m, 1H), 7.54 (t, J = 7.9 Hz, 1H), 7.39 (t, J = 2.7 Hz, 1H), 7.19-7.13 (m, 1H), 7.09 (s, 1H), 6.62 (d, J = 2.6 Hz, 1H), 6.44 (dd, J = 8.7, 2.6 Hz, 1H), 6.21 (d, J = 2.9 Hz, 1H), 3.83 (s, 3H), 3.33 (s, 4H), 3.14-3.04 (m, 4H), 2.25 (s, 3H), 1.80 (d, J = 13.4 Hz, 6H). MS (ESI) m/z: 506 [M + H]$^+$. |
| IF-6 | 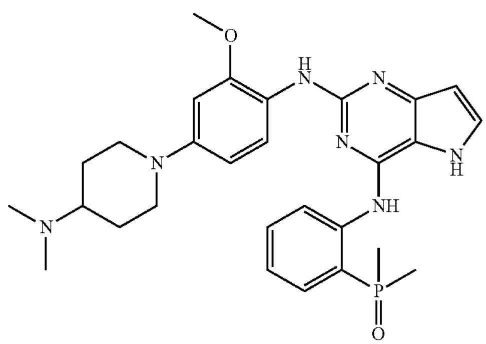 [SMILES: COc1cc(N2CCC(N(C)C)CC2)ccc1Nc1nc(Nc2ccccc2P(C)(C)=O)c2[nH]ccc2n1] | $^1$H NMR (600 MHz, DMSO-d$_6$) δ 10.82 (s, 1H), 10.70 (s, 1H), 8.34 (dd, J = 8.5, 4.1 Hz, 1H), 8.11 (d, J = 8.7 Hz, 1H), 7.65-7.60 (m, 1H), 7.54 (t, J = 7.8 Hz, 1H), 7.39 (t, J = 2.8 Hz, 1H), 7.16 (td, J = 7.7, 6.6, 1.9 Hz, 1H), 7.06 (s, 1H), 6.62 (d, J = 2.5 Hz, 1H), 6.45 (dd, J = 8.8, 2.5 Hz, 1H), 6.23-6.19 (m, 1H), 3.83 (s, 3H), 3.67-3.58 (m, 2H), 2.61 (td, J = 12.1, 2.4 Hz, 2H), 2.51 (s, 1H), 2.26 (s, 6H), 1.86 (d, J = 12.3 Hz, 2H), 1.80 (d, J = 13.4 Hz, 6H), 1.53 (qd, J = 12.2, 4.1 Hz, 2H). MS (ESI) m/z: 534 [M + H]$^+$. |

Example 2

Synthesis Scheme of Compound IG

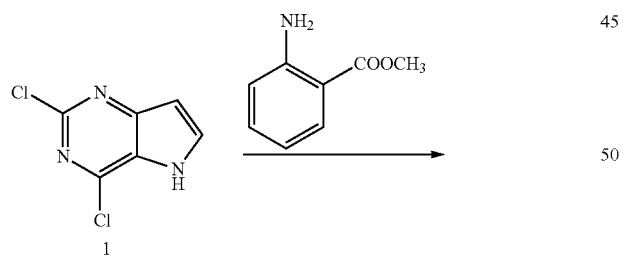

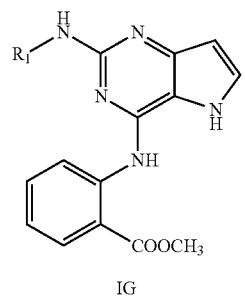

Preparation of Compound 4

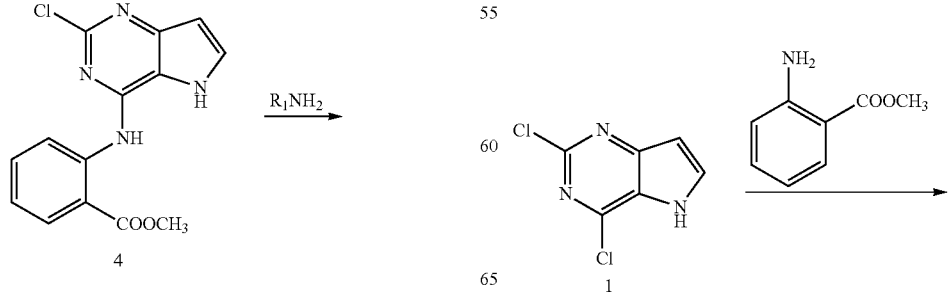

45
-continued

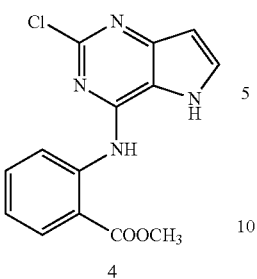

4

46
-continued

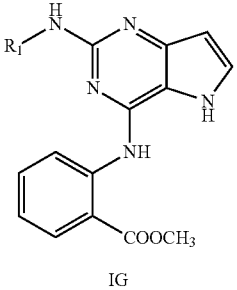

IG

Compound 1 (435 mg, 2.3 mmol), methyl o-aminobenzoate (419 mg, 2.7 mmol) were dissolved in 10 mL tert-butanol. To the solution was added trifluoroacetic acid (0.256 mL, 3.45 mmol). The resulting reaction liquid was heated in 85° C. oil bath with stirring until compound 1 was reacted completely (LC-MS tracking). The reaction was stopped. To the reaction liquid was added 40 mL of saturated sodium bicarbonate solution, and the liquid was separated. The organic phase was washed twice with saturated sodium chloride solution, dried over anhydride sodium sulfate, concentrated and purified by silica-gel column chromatography (dichloromethane/methanol) to yield compound 4 (white solid, 424 mg, yield 61%), which was used directly for the reaction in next step.

MS (ESI) m/z: 303 [m+H]$^+$.

Preparation of Compound IG

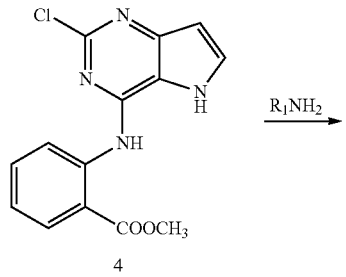

Process A:

Compound 4 (30.3 mg, 0.1 mmol), aniline (0.1 mmol) were dissolved in 1 mL tert-butanol. To the solution was added trifluoroacetic acid (45 μL, 0.6 mmol). The resulting reaction liquid was heated in 110° C. oil bath with stirring until aniline was reacted completely (LC-MS tracking). The reaction was stopped. To the reaction liquid was added 10 mL of saturated sodium bicarbonate solution, and the liquid was separated. The organic phase was washed twice with saturated sodium chloride solution, dried over anhydride sodium sulfate, concentrated and purified by silica-gel column chromatography (dichloromethane/methanol) to yield compound IH.

Process B:

Compound 3 (10.0 mg, 0.03 mmol), aniline (0.03 mmol) were dissolved in 1 mL tert-butanol. To the solution was added 4N hydrochloric acid (16.5 μL). The resulting reaction solution was heated in 110° C. oil bath with stirring until aniline was reacted completely (LC-MS tracking). The reaction was stopped. The reaction solution was concentrated, purified by reversed-phase preparative HPLC (with 0.35% trifluoroacetic acid aqueous solution and methanol as mobile phase), and concentrated in vaccum to yield compound IH.

Process C:

Compound 4 (25.0 mg, 0.08 mmol), aniline (0.08 mmol) were dissolved in 1 mL tert-butanol. To the solution was added trifluoroacetic acid (36.8 μL, 0.24 mmol). The resulting reaction solution was heated in 110° C. oil bath with stirring until aniline was reacted completely (LC-MS tracking). The reaction was stopped. The reaction solution was concentrated, purified by reversed-phase preparative HPLC (with 0.35% trifluoroacetic acid aqueous solution and methanol as mobile phase), and concentrated in vaccum to yield compound IH.

Compounds IH, II, IJ, IK were synthesized using similar processes.

TABLE 2

Structure and identification of compounds IG-IK

| ID | Structure | NMR and/or MS data |
|---|---|---|
| IG-1 | 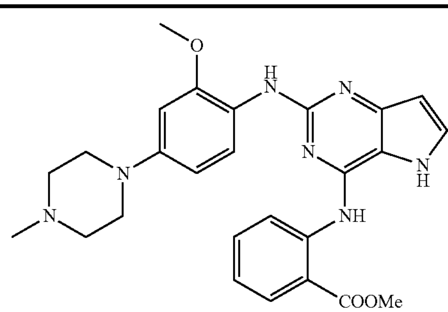 | MS (ESI) m/z: 488 [M + H]$^+$. |

TABLE 2-continued

Structure and identification of compounds IG-IK

| ID | Structure | NMR and/or MS data |
| --- | --- | --- |
| IG-2 | 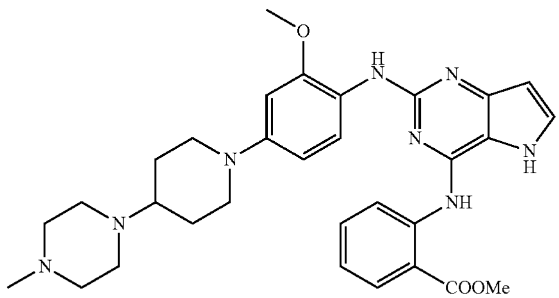 [SMILES: COC(=O)c1ccccc1Nc1nc(Nc2ccc(N3CCC(N4CCN(C)CC4)CC3)cc2OC)nc2cc[nH]c12] | $^1$H-NMR (600 MHz; Methanol-$d_4$): δ 8.63 (d, J = 8.4 Hz, 1H) 8.05-8.04 (m, 1H), 7.90 (d, J = 8.6 Hz, 1H), 7.52-7.49 (m, 1H), 7.42 (d, J = 3.0 Hz, 1H), 7.10-7.07 (m, 1H), 6.64 (d, J = 2.3 Hz, 1H), 6.49 (dd, J = 8.8, 2.1 Hz, 1H), 6.29 (d, J = 3.0 Hz, 1H), 3.95 (s, 3H), 3.86 (d, J = 3.7 Hz, 3H), 3.63-3.61 (m, 2H), 3.46-3.42 (m, 1H), 2.65-2.61 (m, 10H), 2.33 (s, 3H), 1.96 (d, J = 12.1 Hz, 2H), 1.66-1.62 (m, 2H). MS (ESI) m/z: 571 [M + H]$^+$. |
| IG-3 | 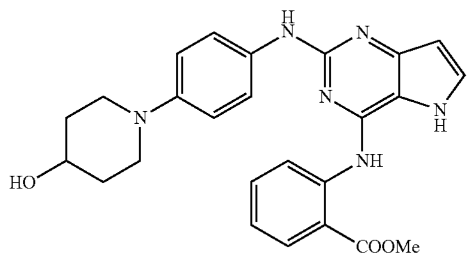 [SMILES: COC(=O)c1ccccc1Nc1nc(Nc2ccc(N3CCC(O)CC3)cc2)nc2cc[nH]c12] | $^1$H-NMR (600 MHz; Methanol-$d_4$): δ 8.76 (d, J = 8.5 Hz, 1H), 8.05 (dd, J = 8.0, 1.6 Hz, 1H), 7.50 (td, J = 7.9, 1.4 Hz, 1H), 7.45 (d, J = 8.8 Hz, 2H), 7.41 (d, J = 3.0 Hz, 1H), 7.09-7.06 (m, 1H), 6.98 (d, J = 8.5 Hz, 2H), 6.30 (d, J = 3.0 Hz, 1H), 3.97 (s, 3H), 3.76 (dt, J = 8.9, 4.6 Hz, 1H), 3.50-3.46 (m, 2H), 2.87-2.84 (m, 2H), 2.02-1.99 (m, 2H), 1.72 (dtd, J = 12.9, 9.7, 3.3 Hz, 2H). MS (ESI) m/z: 459 [M + H]$^+$. |
| IG-4 | <br>TFA salt | $^1$H-NMR (600 MHz; Methanol-$d_4$): δ 8.17-8.13 (m, 2H), 7.86-7.80 (m, 3H), 7.68-7.62 (m, 3H), 7.40 (dd, J = 8.2, 0.8 Hz, 1H), 6.49-6.48 (m, 1H), 3.91 (s, 3H). MS (ESI) m/z: 439 [M + H]$^+$. |
| IG-5 | 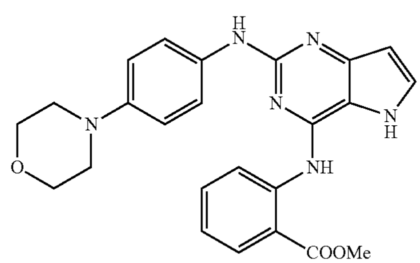 [SMILES: COC(=O)c1ccccc1Nc1nc(Nc2ccc(N3CCOCC3)cc2)nc2cc[nH]c12] | $^1$H-NMR (600 MHz, Acetone-$d_6$): δ 8.99 (m, 1H), 8.06-8.00 (m, 2H), 7.77-7.75 (m, 2H), 7.53 (d, J = 41.2 Hz, 2H), 7.09-7.08 (m, 1H), 6.93-6.91 (m, 1H), 6.33 (m, 1H), 3.95 (s, 2H), 3.78 (s, 3H), 3.07-3.06 (m, 2H), 1.96 (s, 2H), 1.29-1.28 (m, 2H). MS (ESI) m/z: 445 [M + H]$^+$. |
| IG-6 | 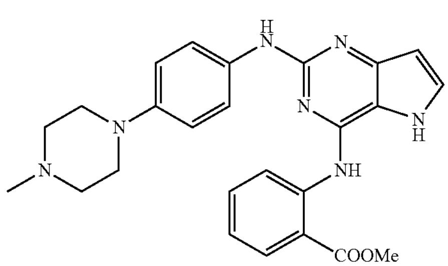 [SMILES: COC(=O)c1ccccc1Nc1nc(Nc2ccc(N3CCN(C)CC3)cc2)nc2cc[nH]c12] | MS (ESI) m/z: 458 [M + H]$^+$. |

TABLE 2-continued

Structure and identification of compounds IG-IK

| ID | Structure | NMR and/or MS data |
| --- | --- | --- |
| IG-7 | 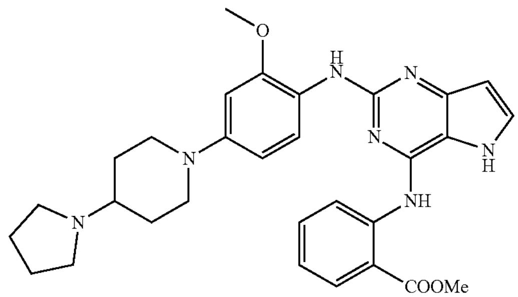 [SMILES: COC(=O)c1ccccc1Nc1nc(Nc2ccc(N3CCC(N4CCCC4)CC3)cc2OC)nc2cc[nH]c12] | ¹H-NMR (600 MHz; Methanol-d₄): δ 8.65 (d, J = 8.5 Hz, 1H), 8.07 (dd, J = 8.0, 1.4 Hz, 1H), 7.98 (d, J = 8.7 Hz, 1H), 7.53 (d, J = 1.3 Hz, 1H), 7.43 (d, J = 3.0 Hz, 1H), 7.11-7.10 (m, 1H), 6.66 (d, J = 2.2 Hz, 1H), 6.51-6.50 (m, 1H), 6.30 (d, J = 3.0 Hz, 1H), 3.97 (s, 3H), 3.88 (s, 3H), 3.60-3.58 (m, 2H), 2.70 (d, J = 3.4 Hz, 3H), 2.05-2.03 (m, 2H), 1.84 (d, J = 2.9 Hz, 4H), 1.69-1.67 (m, 2H). MS (ESI) m/z: 542 [M + H]⁺. |
| IG-8 | 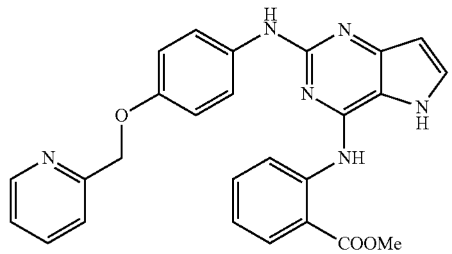 [SMILES: COC(=O)c1ccccc1Nc1nc(Nc2ccc(OCc3ccccn3)cc2)nc2cc[nH]c12] | ¹H-NMR (600 MHz; Methanol-d₄): δ 8.73 (d, J = 8.5 Hz, 1H), 8.56 (d, J = 4.9 Hz, 1H), 8.02 (d, J = 8.0 Hz, 1H), 7.87 (d, J = 1.4 Hz, 1H), 7.62 (d, J = 7.8 Hz, 1H), 7.48-7.46 (m, 2H), 7.39-7.38 (m, 3H), 7.04 (d, J = 7.3 Hz, 1H), 6.95-6.93 (m, 2H), 6.29 (t, J = 2.6 Hz, 1H), 5.17 (s, 2H), 3.95 (s, 3H). MS (ESI) m/z: 467 [M + H]⁺. |
| IG-9 | 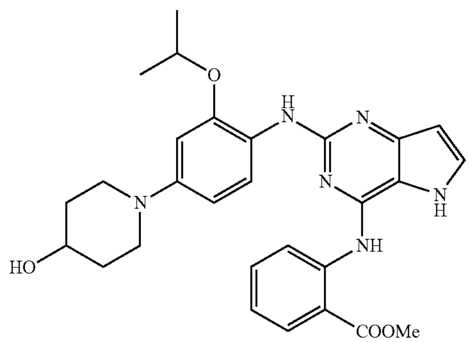 [SMILES: COC(=O)c1ccccc1Nc1nc(Nc2ccc(N3CCC(O)CC3)cc2OC(C)C)nc2cc[nH]c12] | ¹H-NMR (600 MHz; Methanol-d₄): δ 8.25-8.24 (m, 1H), 8.14 (d, J = 7.8 Hz, 1H), 7.70-7.65 (m, 3H), 7.41-7.38 (m, 1H), 7.13 (t, J = 0.6 Hz, 1H), 6.92-6.90 (m, 1H), 6.44 (d, J = 2.8 Hz, 1H), 4.76-4.74 (m, 1H), 4.03-4.00 (m, 1H), 3.94-3.93 (m, 3H), 3.79-3.75 (m, 2H), 3.41-3.35 (m, 2H), 2.20-2.16 (m, 2H), 1.93-1.90 (m, 2H), 1.33-1.31 (m, 6H). MS (ESI) m/z: 517 [M + H]⁺. |
| IG-10 | 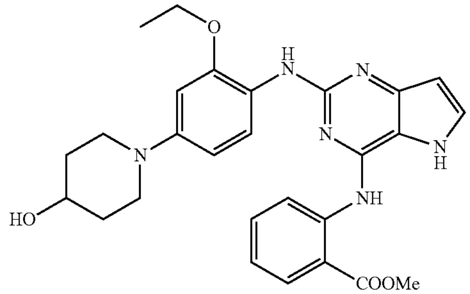 [SMILES: CCOc1cc(N2CCC(O)CC2)ccc1Nc1nc(Nc2ccccc2C(=O)OC)c2[nH]ccc2n1] | ¹H-NMR (600 MHz; Methanol-d₄): δ 8.26-8.25 (m, 1H), 8.14 (dd, J = 8.0, 1.5 Hz, 1H), 7.67-7.62 (m, 3H), 7.38 (t, J = 7.7 Hz, 1H), 7.06 (d, J = 0.5 Hz, 1H), 6.89-6.87 (m, 1H), 6.43 (d, J = 2.9 Hz, 1H), 4.16 (q, J = 7.0 Hz, 2H), 4.00-3.98 (m, 1H), 3.98-3.94 (m, 3H), 3.78-3.74 (m, 2H), 3.37-3.35 (m, 2H), 2.18-2.14 (m, 2H), 1.91-1.86 (m, 2H), 1.37 (t, J = 7.0 Hz, 3H). MS (ESI) m/z: 503 [M + H]⁺. |
| IG-11 | TFA salt | ¹H-NMR (600 MHz; Methanol-d₄): δ 8.09-8.05 (m, 2H), 7.92 (d, J = 8.8 Hz, 1H), 7.80 (d, J = 8.8 Hz, 1H), 7.67 (t, J = 4.3 Hz, 1H), 7.60 (d, J = 8.7 Hz, 2H), 7.39 (d, J = 7.6 Hz, 1H), 6.50 (d, J = 2.9 Hz, 1H), 3.88 (s, 3H), 3.67 (d, J = 3.9 Hz, 1H), 3.35 (d, J = 3.6 Hz, 2H), 2.80 (dd, J = 9.9, 6.7 Hz, 2H), 1.90 (ddd, J = 9.6, 6.3, 3.3 Hz, 2H), 1.61 (dt, J = 8.6, 4.2 Hz, 2H). MS (ESI) m/z: 523 [M + H]⁺. |

TABLE 2-continued

Structure and identification of compounds IG-IK

| ID | Structure | NMR and/or MS data |
| --- | --- | --- |
| IG-12 | 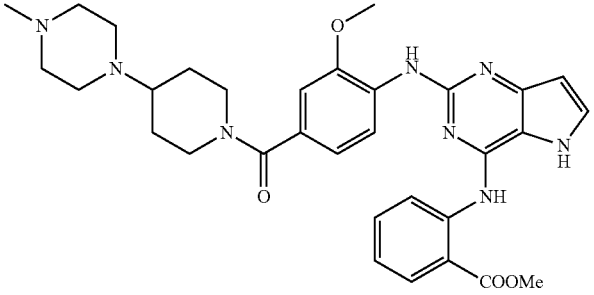<br>TFA salt | ¹H-NMR (600 MHz; Methanol-d₄): δ 8.16-8.11 (m, 2H), 7.78 (d, J = 8.1 Hz, 1H), 7.67-7.64 (m, 2H), 7.40-7.37 (m, 1H), 7.15 (d, J = 1.6 Hz, 1H), 6.91 (dd, J = 8.1, 1.6 Hz, 1H), 6.46 (d, J = 3.0 Hz, 1H), 3.93 (s, 3H), 3.91 (s, 3H), 3.37-3.35 (m, 2H), 3.13-2.98 (m, 7H), 2.90 (s, 3H), 2.12-1.96 (m, 2H), 1.62 (dtd, J = 3.0, 1.5, 0.9 Hz, 2H). MS (ESI) m/z: 599 [M + H]⁺. |
| IG-13 | 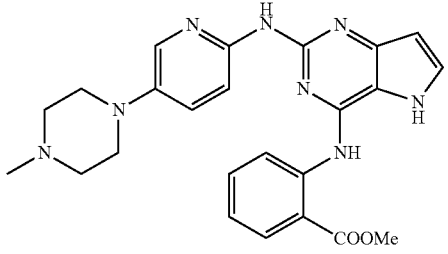<br>TFA salt | ¹H-NMR (600 MHz; Methanol-d₄): δ 8.23 (dd, J = 8.3, 0.7 Hz, 1H), 8.15 (dd, J = 7.9, 1.6 Hz, 1H), 7.88 (dd, J = 9.7, 2.7 Hz, 1H), 7.83 (d, J = 3.1 Hz, 1H), 7.74 (ddd, J = 8.4, 7.2, 1.4 Hz, 1H), 7.33-7.30 (m, 2H), 6.97 (d, J = 9.8 Hz, 1H), 6.77-6.72 (m, 1H), 3.98 (t, J = 0.6 Hz, 2H), 3.98-3.95 (m, 3H), 3.91 (s, 1H), 3.69-3.66 (m, 1H), 3.57 (m, 3H), 3.16-3.14 (m, 2H), 3.00-2.97 (m, 1H), 2.71 (m, 1H). MS (ESI) m/z: 459 [M + H]⁺. |
| IG-14 | 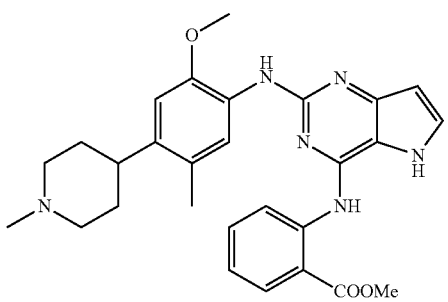<br>TFA salt | ¹H-NMR (600 MHz; Methanol-d₄): δ 8.24 (dd, J = 3.9, 3.2 Hz, 1H), 8.09 (d, J = 7.6 Hz, 1H), 7.60-7.54 (m, 2H), 7.41 (s, 1H), 7.33-7.30 (m, 1H), 6.91 (s, 1H), 6.40 (s, 1H), 3.92 (s, 3H), 3.87 (s, 3H), 3.67 (d, J = 11.8 Hz, 2H), 3.25-3.22 (m, 2H), 3.15 (s, 1H), 2.96 (s, 3H), 2.23 (s, 3H), 2.11-2.07 (m, 4H). MS (ESI) m/z: 501 [M + H]⁺. |
| IG-15 | 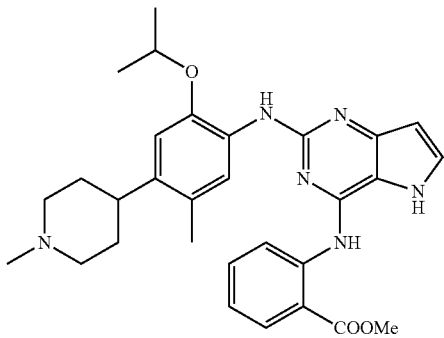<br>TFA salt | ¹H-NMR (600 MHz; Methanol-d₄): δ 8.27 (d, J = 8.2 Hz, 1H), 8.11 (d, J = 7.9 Hz, 1H), 7.62-7.58 (m, 2H), 7.43 (s, 1H), 7.34 (t, J = 7.6 Hz, 1H), 6.92 (s, 1H), 6.41 (d, J = 2.8 Hz, 1H), 4.65 (t, J = 6.1 Hz, 1H), 3.93 (s, 3H), 3.67 (d, J = 12.2 Hz, 2H), 3.24-3.22 (m, 2H), 3.15 (s, 1H), 2.96 (s, 3H), 2.06 (d, J = 2.4 Hz, 4H), 2.03 (s, 3H), 1.28 (dd, J = 5.8, 2.0 Hz, 6H). MS (ESI) m/z: 528 [M + H]⁺. |

TABLE 2-continued

Structure and identification of compounds IG-IK

| ID | Structure | NMR and/or MS data |
| --- | --- | --- |
| IG-16 | 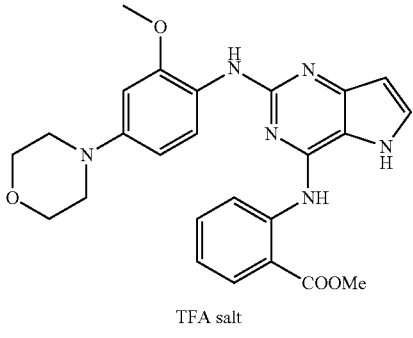 [SMILES: COC(=O)c1ccccc1Nc1nc(Nc2ccc(N3CCOCC3)cc2OC)nc2cc[nH]c12] TFA salt | ¹H-NMR (600 MHz; Methanol-d₄): δ 8.39-8.37 (m, 1H), 8.10-8.09 (m, 1H), 7.56 (d, J = 2.9 Hz, 2H), 7.30 (dt, J = 14.8, 7.7 Hz, 2H), 6.73 (d, J = 2.3 Hz, 1H), 6.60-6.58 (m, 1H), 6.37 (d, J = 2.9 Hz, 1H), 3.96 (s, 3H), 3.89 (s, 4H), 3.84 (s, 3H), 3.23 (d, J = 4.8 Hz, 4H). MS (ESI) m/z: 475 [M + H]⁺. |
| IG-17 | 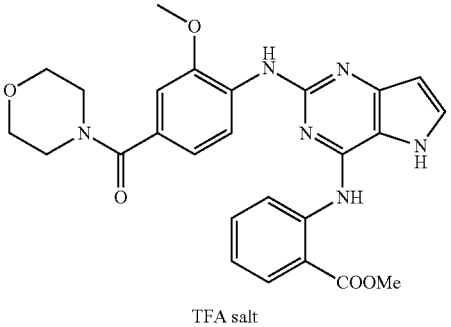 [SMILES: COC(=O)c1ccccc1Nc1nc(Nc2ccc(C(=O)N3CCOCC3)cc2OC)nc2cc[nH]c12] TFA salt | ¹H-NMR (600 MHz; Methanol-d₄): δ 8.12 (dd, J = 15.7, 8.0 Hz, 2H), 7.77 (d, J = 8.2 Hz, 1H), 7.66-7.63 (m, 2H), 7.39 (t, J = 7.7 Hz, 1H), 7.16 (s, 1H), 6.91 (d, J = 8.2 Hz, 1H), 6.45 (d, J = 2.9 Hz, 1H), 3.96 (s, 1H), 3.94 (s, 3H), 3.91 (s, 3H), 3.81-3.76 (m, 4H), 3.56-3.51 (m, 4H). MS (ESI) m/z: 503 [M + H]⁺. |
| IG-18 | 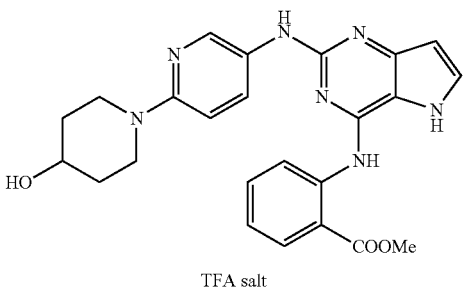 [SMILES: COC(=O)c1ccccc1Nc1nc(Nc2ccc(N3CCC(O)CC3)nc2)nc2cc[nH]c12] TFA salt | ¹H-NMR (600 MHz; Methanol-d₄): δ 8.20-8.08 (m, 3H), 7.80 (ddd, J = 18.6, 9.3, 2.6 Hz, 1H), 7.62 (dd, J = 13.9, 3.0 Hz, 1H), 7.59-7.51 (m, 1H), 7.34-7.27 (m, 1H), 7.09 (dd, J = 18.2, 9.4 Hz, 1H), 6.44 (dd, J = 4.0, 3.0 Hz, 1H), 4.09-4.07 (m, 1H), 3.93 (s, 3H), 3.38-3.34 (m, 2H), 2.03-2.00 (m, 2H), 1.63 (dq, J = 12.7, 4.1 Hz, 2H). MS (ESI) m/z: 460 [M + H]⁺. |
| IG-19 | 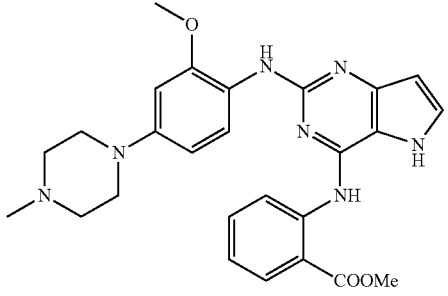 TFA salt | ¹H-NMR (600 MHz; Methanol-d₄): δ 8.34-8.33 (m, 1H), 8.11 (dd, J = 8.0, 1.5 Hz, 1H), 7.59-7.56 (m, 2H), 7.40 (d, J = 8.5 Hz, 1H), 7.32-7.29 (m, 1H), 6.76 (d, J = 2.5 Hz, 1H), 6.62 (dd, J = 8.6, 2.4 Hz, 1H), 6.39 (d, J = 2.9 Hz, 1H), 4.10 (q, J = 7.0 Hz, 2H), 3.96 (s, 3H), 3.92-3.89 (m, 2H), 3.68-3.65 (m, 2H), 3.32-3.30 (m, 2H), 3.16-3.13 (m, 2H), 3.01 (s, 3H), 1.30 (t, J = 7.0 Hz, 3H). MS (ESI) m/z: 502 [M + H]⁺. |

TABLE 2-continued

Structure and identification of compounds IG-IK

| ID | Structure | NMR and/or MS data |
| --- | --- | --- |
| IH-1 | 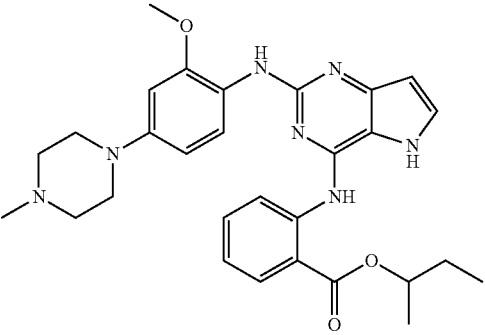<br>TFA salt | ¹H-NMR (600 MHz; Methanol-d₄): δ 8.30-8.28 (m, 1H), 8.12 (d, J = 8.0 Hz, 1H), 7.58 (s, 2H), 7.40-7.39 (m, 1H), 7.34 (t, J = 7.6 Hz, 1H), 6.81-6.80 (m, 1H), 6.63-6.61 (m, 1H), 6.39 (d, J = 2.8 Hz, 1H), 5.14 (dq, J = 12.4, 6.3 Hz, 1H), 3.97-3.91 (m, 2H), 3.90 (s, 3H), 3.68-3.62 (m, 2H), 3.17-3.12 (m, 2H), 3.02 (s, 3H), 2.68 (s, 2H), 1.75-1.66 (m, 2H), 1.32 (d, J = 6.2 Hz, 3H), 0.97 (t, J = 7.4 Hz, 3H). MS (ESI) m/z: 530 [M + H]⁺. |
| IH-2 | 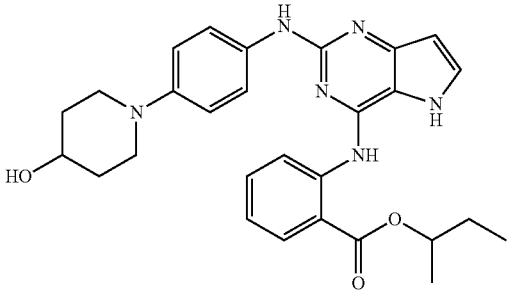<br>TFA salt | ¹H-NMR (600 MHz; Methanol-d₄): δ 8.23-8.22 (m, 1H), 8.13 (d, J = 8.0 Hz, 1H), 7.64-7.60 (m, 2H), 7.50 (d, J = 8.6 Hz, 1H), 7.37 (m, 1H), 6.96 (s, 1H), 6.77-6.75 (m, 1H), 6.41-6.40 (m, 1H), 5.11 (m, 1H), 3.90-3.87 (m, 5H), 3.47-3.38 (m, 3H), 3.17-3.13 (m, 8H), 2.92 (s, 3H), 2.22-2.19 (m, 2H), 1.98-1.91 (m, 2H), 1.72-1.63 (m, 2H), 1.30 (d, J = 6.3 Hz, 3H), 0.95 (t, J = 7.4 Hz, 3H). MS (ESI) m/z: 501 [M + H]⁺. |
| IH-3 | 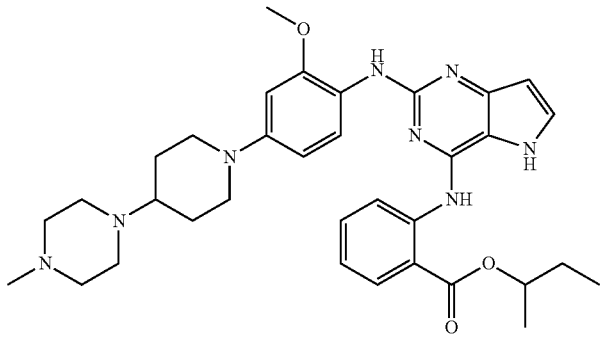<br>TFA salt | ¹H-NMR (600 MHz; Methanol-d₄): δ 8.23-8.22 (m, 1H), 8.13 (d, J = 8.0 Hz, 1H), 7.64-7.60 (m, 2H), 7.50 (d, J = 8.6 Hz, 1H), 7.37 (m, 1H), 6.96 (s, 1H), 6.77-6.75 (m, 1H), 6.41-6.40 (m, 1H), 5.11 (qd, J = 6.2, 0.4 Hz, 1H), 3.90-3.87 (m, 5H), 3.47-3.38 (m, 3H), 3.17-3.13 (m, 8H), 2.92 (s, 3H), 2.22-2.19 (m, 2H), 1.98-1.91 (m, 2H), 1.72-1.63 (m, 2H), 1.30 (d, J = 6.3 Hz, 3H), 0.95 (t, J = 7.4 Hz, 3H). MS (ESI) m/z: 613 [M + H]⁺. |
| IH-4 | 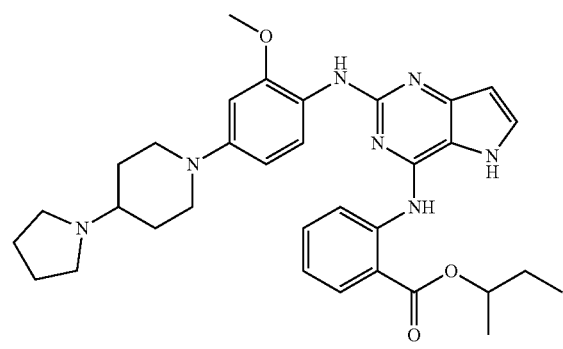<br>TFA salt | ¹H-NMR (600 MHz; Methanol-d₄): δ 8.13-8.12 (m, 1H), 7.68-7.57 (m, 4H), 7.34-7.32 (m, 2H), 6.77 (m, 1H), 6.63-6.62 (m, 1H), 6.38 (m, 1H), 5.16-5.13 (m, 1H), 3.98 (s, 1H), 3.95-3.92 (m, 2H), 3.86 (s, 3H), 3.74-3.71 (m, 2H), 3.21 (m, 2H), 2.91-2.86 (m, 2H), 2.32-2.29 (m, 2H), 2.22-2.20 (m, 2H), 2.08-2.04 (m, 2H), 1.92-1.85 (m, 2H), 1.76-1.67 (m, 2H), 1.33 (d, J = 6.3 Hz, 3H), 0.98 (t, J = 7.5 Hz, 3H). MS (ESI) m/z: 613 [M + H]⁺. |

TABLE 2-continued

Structure and identification of compounds IG-IK

| ID | Structure | NMR and/or MS data |
|---|---|---|
| II-1 | 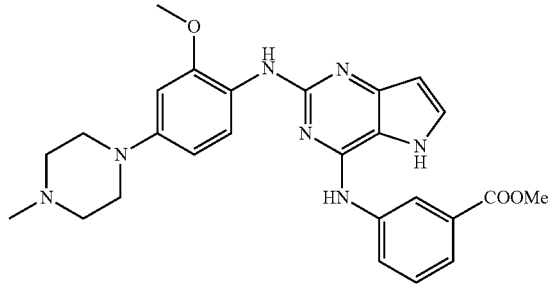<br>TFA salt | ¹H-NMR (600 MHz; Methanol-d₄): δ 8.32 (s, 1H), 8.08-8.07 (m, 1H), 7.85 (d, J = 7.8 Hz, 1H), 7.57 (d, J = 3.0 Hz, 1H), 7.49-7.44 (m, 2H), 6.80 (d, J = 2.5 Hz, 1H), 6.61-6.59 (m, 1H), 6.36 (d, J = 2.9 Hz, 1H), 3.93 (s, 3H), 3.88 (s, 3H), 3.69-3.66 (m, 2H), 3.17-3.12 (m, 2H), 3.02 (s, 3H). MS (ESI) m/z: 488 [M + H]⁺. |
| II-2 | 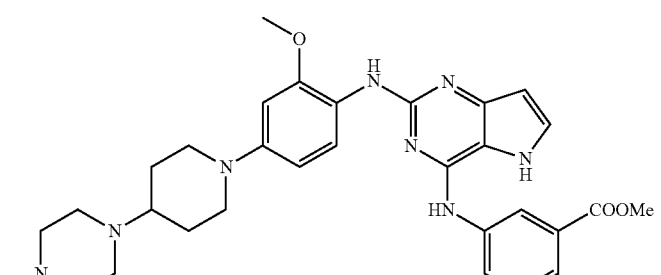<br>TFA salt | ¹H-NMR (600 MHz; Methanol-d₄): δ 8.29 (s, 1H), 8.03 (dd, J = 8.2, 1.0 Hz, 1H), 7.86 (d, J = 7.8 Hz, 1H), 7.62 (d, J = 8.6 Hz, 1H), 7.61-7.58 (m, 1H), 7.49 (t, J = 7.9 Hz, 1H), 7.02 (d, J = 2.0 Hz, 1H), 6.78 (dd, J = 8.7, 2.4 Hz, 1H), 6.38 (d, J = 3.0 Hz, 1H), 3.92 (s, 3H), 3.91 (s, 3H), 3.90-3.88 (m, 2H), 3.55 (d, J = 0.5 Hz, 4H), 3.41-3.37 (m, 4H), 3.23 (dd, J = 21.4, 9.6 Hz, 3H), 2.98 (s, 3H), 2.27 (dd, J = 12.3, 0.5 Hz, 2H), 2.03 (tt, J = 12.1, 6.1 Hz, 2H). MS (ESI) m/z: 571 [M + H]⁺. |
| II-3 | 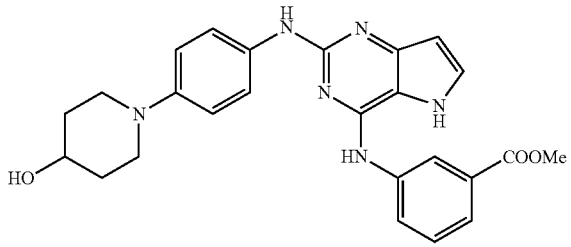<br>TFA salt | ¹H-NMR (600 MHz; Methanol-d₄): δ 8.31 (s, 1H), 7.97 (dd, J = 8.1, 0.4 Hz, 1H), 7.93-7.92 (m, 1H), 7.65 (t, J = 3.9 Hz, 3H), 7.55 (t, J = 7.9 Hz, 1H), 7.46-7.44 (m, 2H), 6.47 (d, J = 2.9 Hz, 1H), 4.07-4.06 (m, 1H), 3.93 (s, 3H), 3.79-3.78 (m, 2H), 3.48-3.44 (m, 2H), 2.23-2.18 (m, 2H), 1.99-1.95 (m, 2H). MS (ESI) m/z: 459 [M + H]⁺. |
| II-4 | 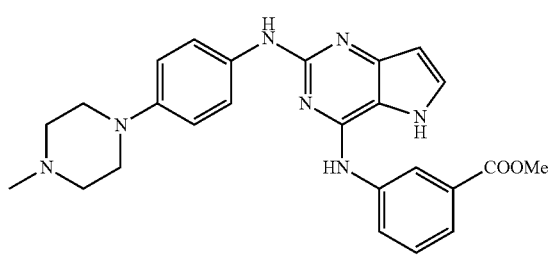<br>TFA salt | ¹H-NMR (600 MHz; Methanol-d₄): δ 8.29 (s, 1H), 8.04-8.03 (m, 1H), 7.85 (d, J = 7.7 Hz, 1H), 7.58 (d, J = 3.0 Hz, 1H), 7.47 (t, J = 7.9 Hz, 1H), 7.41-7.39 (m, 2H), 7.05 (d, J = 8.9 Hz, 2H), 6.40 (d, J = 3.0 Hz, 1H), 3.91-3.87 (m, 5H), 3.67-3.64 (m, 2H), 3.13-3.11 (m, 2H), 3.01 (s, 3H). MS (ESI) m/z: 459 [M + H]⁺. |
| II-5 | 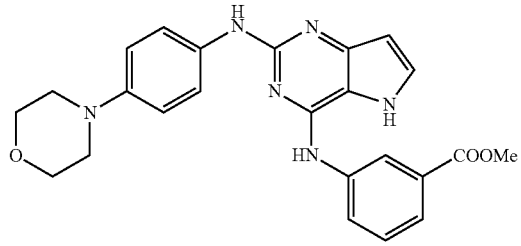<br>TFA salt | ¹H-NMR (600 MHz; Methanol-d₄): δ 8.29 (s, 1H), 8.04 (dt, J = 8.1, 0.5 Hz, 1H), 7.84 (d, J = 7.7 Hz, 1H), 7.57 (d, J = 2.9 Hz, 1H), 7.46 (t, J = 7.9 Hz, 1H), 7.40 (d, J = 8.9 Hz, 2H), 7.10 (d, J = 8.8 Hz, 2H), 6.38 (d, J = 2.9 Hz, 1H), 3.91 (t, J = 4.7 Hz, 7H), 3.27 (t, J = 4.6 Hz, 4H). MS (ESI) m/z: 445 [M + H]⁺. |

TABLE 2-continued

Structure and identification of compounds IG-IK

| ID | Structure | NMR and/or MS data |
|---|---|---|
| II-6 | 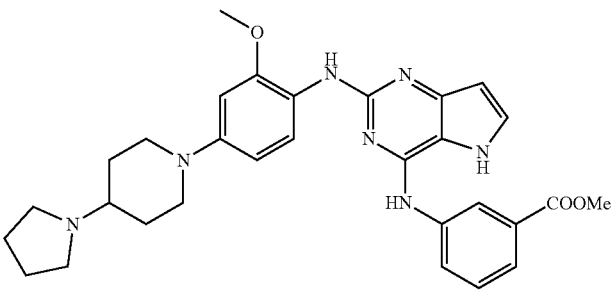 TFA salt | ¹H-NMR (600 MHz; Methanol-d₄): δ 8.29 (s, 1H), 7.85 (dt, J = 7.8, 1.2 Hz, 1H), 7.58 (d, J = 3.0 Hz, 1H), 7.47 (t, J = 8.0 Hz, 1H), 7.41-7.39 (m, 1H), 7.05 (d, J = 8.9 Hz, 2H), 6.40 (d, J = 3.0 Hz, 1H), 3.91 (d, J = 20.2 Hz, 5H), 3.67-3.66 (m, 2H), 3.11-3.10 (m, 2H), 3.01 (s, 3H). MS (ESI) m/z: 542 [M + H]⁺. |
| II-7 | 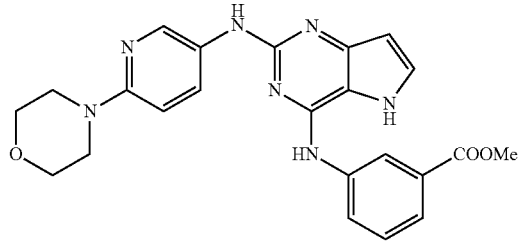 TFA salt | ¹H-NMR (600 MHz; Methanol-d4): δ 8.33 (d, J = 1.2 Hz, 1H), 8.20 (d, J = 2.5 Hz, 1H), 7.91-7.90 (m, 1H), 7.87-7.85 (m, 1H), 7.81-7.79 (m, 1H), 7.62 (d, J = 3.0 Hz, 1H), 7.49 (t, J = 7.9 Hz, 1H), 7.00 (d, J = 9.2 Hz, 1H), 6.42 (d, J = 3.0 Hz, 1H), 3.92 (s, 3H), 3.86 (t, J = 4.9 Hz, 4H), 3.57 (t, J = 4.9 Hz, 4H). MS (ESI) m/z: 446 [M + H]⁺. |
| II-8 | 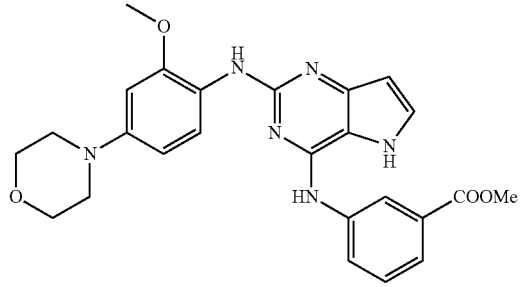 TFA salt | ¹H-NMR (600 MHz; Methanol-d4): δ 8.32 (d, J = 4.0 Hz, 1H), 8.11-8.10 (m, 1H), 7.83 (d, J = 7.7 Hz, 1H), 7.54 (d, J = 2.9 Hz, 1H), 7.47 (t, J = 8.0 Hz, 1H), 7.36-7.34 (m, 1H), 6.72 (s, 1H), 6.57-6.55 (m, 1H), 6.33 (d, J = 2.9 Hz, 1H), 3.93 (s, 3H), 3.88 (t, J = 4.8 Hz, 4H), 3.85 (s, 3H), 3.22 (t, J = 4.7 Hz, 4H). MS (ESI) m/z: 475 [M + H]⁺. |
| IJ-1 | 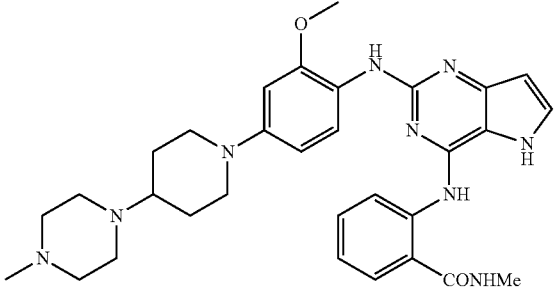 | MS (ESI) m/z: 570 [M + H]⁺. |
| IJ-2 | 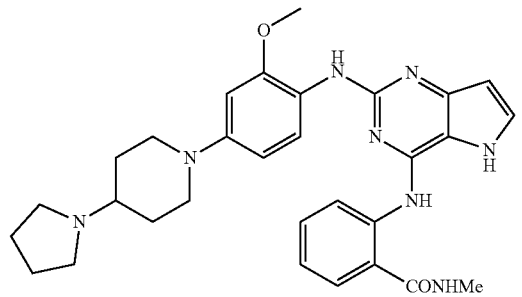 | ¹H-NMR (600 MHz; Methanol-d₄): δ 8.51 (dd, J = 8.4, 0.6 Hz, 1H), 7.99 (d, J = 8.7 Hz, 1H), 7.67 (dd, J = 7.9, 1.4 Hz, 1H), 7.48 (ddd, J = 8.4, 7.3, 1.3 Hz, 1H), 7.41 (t, J = 1.5 Hz, 1H), 7.15-7.13 (m, 1H), 6.65 (d, J = 2.5 Hz, 1H), 6.47 (dd, J = 8.8, 2.5 Hz, 1H), 3.88 (s, 3H), 3.57 (d, J = 12.7 Hz, 2H), 2.94 (s, 3H), 2.74 (t, J = 5.5 Hz, 4H), 2.62 (td, J = 12.2, 1.7 Hz, 2H), 2.28 (s, 1H), 2.04-2.02 (m, 2H), 1.84 (dt, J = 6.6, 3.3 Hz, 4H), 1.67 (dt, J = 11.9, 6.0 Hz, 2H). MS (ESI) m/z: 541 [M + H]⁺. |

TABLE 2-continued

Structure and identification of compounds IG-IK

| ID | Structure | NMR and/or MS data |
|---|---|---|
| IJ-3 | 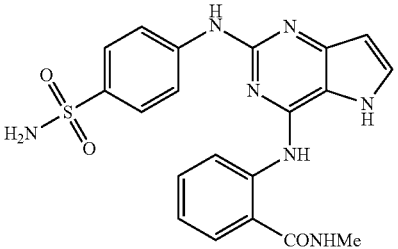<br>TFA salt | ¹H-NMR (600 MHz; Methanol-d₄): δ 8.13-8.11 (m, 1H), 7.82-7.80 (m, 2H), 7.75 (d, J = 7.7 Hz, 1H), 7.68-7.65 (m, 3H), 7.57 (s, 1H), 7.39 (s, 1H), 6.49 (d, J = 2.7 Hz, 1H), 2.92 (s, 3H). MS (ESI) m/z: 438 [M + H]⁺. |
| IK-1 | 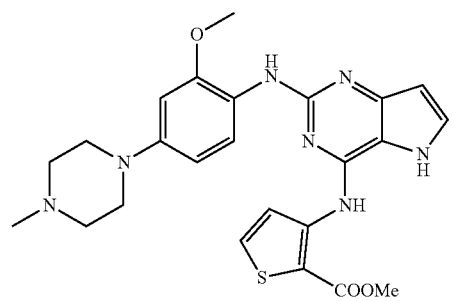<br>TFA salt | ¹H-NMR (600 MHz; Aceton-d₆): δ 7.64-7.56 (m, 3H), 7.35 (d, J = 8.6 Hz 1H) 6.78 (d, J = 2.4 Hz, 1H), 6.61 (dd, J = 8.6, 2.5 Hz, 1H), 6.37 (d, J = 2.9 Hz, 1H), 3.98-3.90 (m, 2H), 3.86 (s, 3H), 3.75 (s, 3H), 3.74-3.68 (m, 2H), 3.39-3.33 (m, 4H), 3.00 (s, 3H). MS (ESI) m/z: 494 [M + H]⁺. |
| IK-2 | 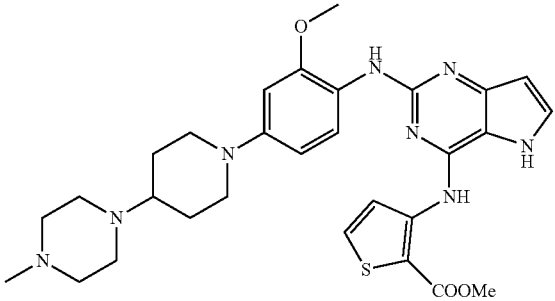<br>TFA salt | ¹H-NMR (600 MHz; Aceton-d₆): δ 7.78-7.76 (m, 1H), 7.69 (d, J = 2.9 Hz, 1H), 7.61 (d, J = 5.3 Hz, 1H), 7.36 (t, J = 4.3 Hz, 1H), 6.87 (s, 1H), 6.68 (dd, J = 8.6, 2.3 Hz, 1H), 6.41 (d, J = 2.8 Hz, 1H), 4.01 (d, J = 12.7 Hz, 2H), 3.92-3.89 (m, 4H), 3.89-3.81 (m, 9H), 3.80 (s, 3H), 3.54-3.50 (m, 1H), 3.03 (d, J = 5.9 Hz, 3H), 2.99-2.95 (m, 2H), 2.36 (dd, J = 11.4, 0.5 Hz, 2H). MS (ESI) m/z: 577 [M + H]⁺. |
| IK-3 | 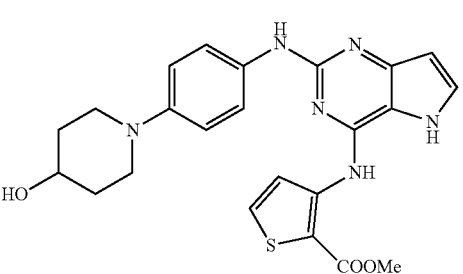<br>TFA salt | ¹H-NMR (600 MHz; Methanol-d₄): δ 7.88 (d, J = 5.4 Hz, 1H), 7.71 (d, J = 5.4 Hz, 1H), 7.65 (dd, J = 6.0, 3.0 Hz, 3H), 7.58-7.57 (m, 2H), 6.48 (d, J = 3.0 Hz, 1H), 4.08 (qt, J = 7.1, 3.5 Hz, 1H), 3.94 (s, 3H), 3.83 (ddd, J = 11.9, 8.0, 3.6 Hz, 2H), 3.53 (ddd, J = 12.0, 8.0, 3.7 Hz, 2H), 2.24 (ddt, J = 13.9, 7.6, 3.5 Hz, 2H), 2.00 (dtd, J = 14.3, 7.3, 3.6 Hz, 2H). MS (ESI) m/z: 465 [M + H]⁺. |

TABLE 2-continued

Structure and identification of compounds IG-IK

| ID | Structure | NMR and/or MS data |
| --- | --- | --- |
| IK-4 | 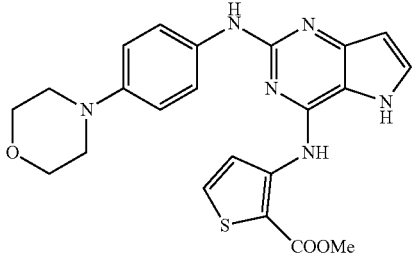<br>TFA salt | 1H-NMR (600 MHz; Methanol-$d_4$): δ 7.79-7.76 (m, 1H), 7.65-7.64 (m, 1H), 7.60 (d, J = 2.9 Hz, 1H), 7.35-7.33 (m, 2H), 7.10 (d, J = 8.9 Hz, 2H), 6.41-6.40 (m, 1H), 3.96 (s, 3H), 3.89 (t, J = 4.8 Hz, 5H), 3.22 (t, J = 4.8 Hz, 4H). MS (ESI) m/z: 451 [M + H]$^+$. |
| IK-5 | 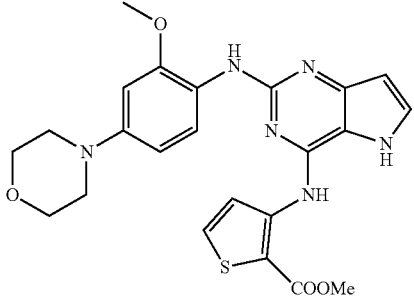<br>TFA salt | MS (ESI) m/z: 481 [M + H]$^+$. |
| IK-6 | 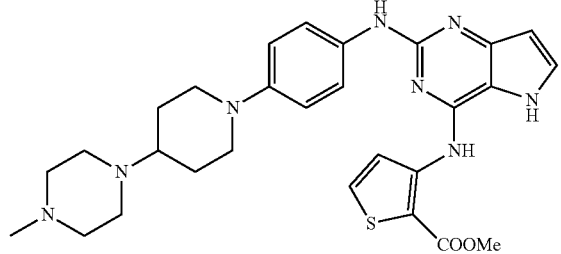<br>TFA salt | $^1$H-NMR (600 MHz; Methanol-$d_4$): δ 7.96 (d, J = 5.2 Hz, 1H), 7.65 (d, J = 5.5 Hz, 1H), 7.61 (d, J = 2.9 Hz, 1H), 7.47 (d, J = 8.9 Hz, 2H), 7.31 (d, J = 9.0 Hz, 2H), 6.44 (d, J = 2.9 Hz, 1H), 3.94 (s, 3H), 3.87 (d, J = 12.7 Hz, 2H), 3.49-3.46 (m, 4H), 3.19-3.14 (m, 3H), 2.94 (d, J = 8.0 Hz, 3H), 2.67 (s, 6H), 2.24-2.22 (m, 2H), 2.02-1.95 (m, 2H). MS (ESI) m/z: 547 [M + H]$^+$. |
| IK-7 | 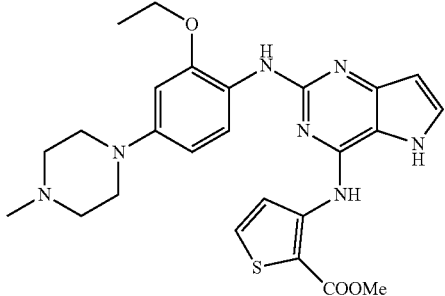<br>TFA salt | $^1$H-NMR (600 MHz; Methanol-$d_4$): δ 8.07-8.06 (m, 1H), 7.61 (dd, J = 29.9, 4.1 Hz, 2H), 7.37 (d, J = 8.5 Hz, 1H), 6.79 (d, J = 2.5 Hz, 1H), 6.68 (dd, J = 8.6, 2.5 Hz, 1H), 6.40 (d, J = 2.9 Hz, 1H), 4.10 (q, J = 7.0 Hz, 2H), 3.95 (s, 3H), 3.01 (s, 3H), 1.26 (t, J = 7.0 Hz, 3H). MS (ESI) m/z: 508 [M + H]$^+$. |

TABLE 2-continued
Structure and identification of compounds IG-IK
| ID | Structure | NMR and/or MS data |
|---|---|---|
| IK-8 | 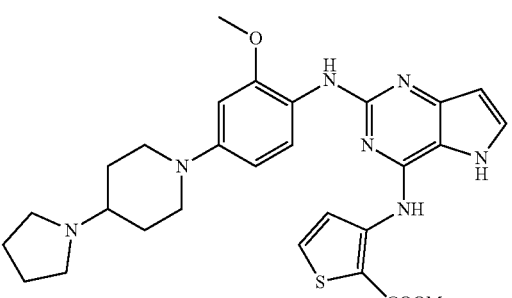 TFA salt | MS (ESI) m/z: 548 [M + H]$^+$. |
| IK-9 | 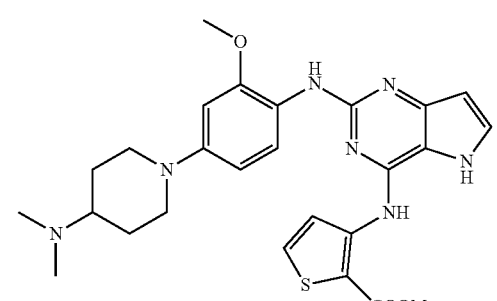 TFA salt | $^1$H-NMR (600 MHz; Methanol-d$_4$): δ 8.10-8.08 (m, 1H), 7.63 (d, J = 5.1 Hz, 1H), 7.57 (d, J = 2.9 Hz, 1H), 7.31-7.30 (m, 1H), 6.77 (d, J = 2.5 Hz, 1H), 6.67 (dd, J = 8.7, 2.5 Hz, 1H), 6.38 (d, J = 2.9 Hz, 1H), 3.98 (dd, J = 10.9, 1.9 Hz, 2H), 3.95 (s, 3H), 3.84 (s, 3H), 3.41 (tt, J = 8.1, 4.0 Hz, 1H), 2.94 (s, 6H), 2.90 (td, J = 12.5, 1.8 Hz, 2H), 2.25-2.23 (m, 2H), 1.94-1.87 (m, 2H). MS (ESI) m/z: 522 [M + H]$^+$. |
| IK-10 | 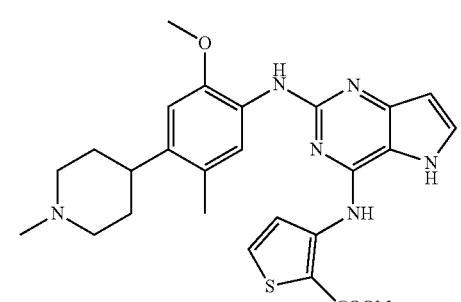 TFA salt | MS (ESI) m/z: 507 [M + H]$^+$. |
| IK-11 | 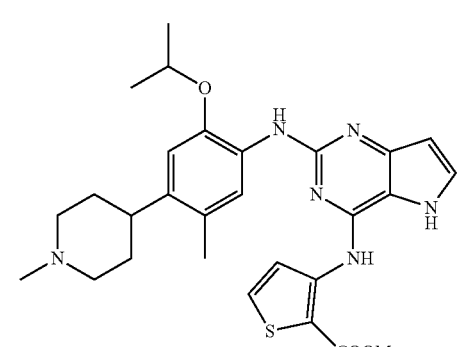 TFA salt | MS (ESI) m/z: 535 [M + H]$^+$. |

TABLE 2-continued

Structure and identification of compounds IG-IK

| ID | Structure | NMR and/or MS data |
|---|---|---|
| IK-12 | 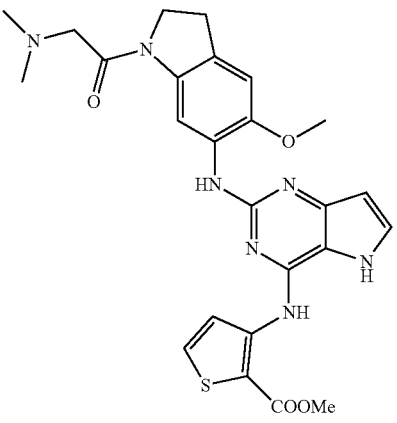<br>TFA salt | $^1$H-NMR (600 MHz; Methanol-$d_4$): δ 8.26 (s, 1H), 8.05-8.04 (m, 1H), 7.62 (d, J = 3.0 Hz, 2H), 7.19 (s, 1H), 6.42 (d, J = 3.0 Hz, 1H), 4.35 (s, 2H), 4.18 (t, J = 8.4 Hz, 2H), 3.96 (s, 3H), 3.85 (s, 3H), 3.40 (t, J = 8.3 Hz, 2H), 3.01 (s, 6H). MS (ESI) m/z: 522 [M + H]$^+$. |
| IW-1 | 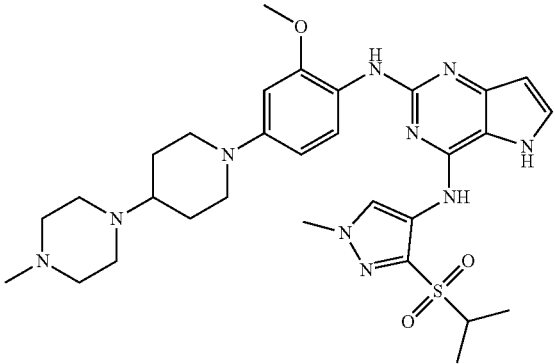 | $^1$H-NMR (600 MHz, DMSO-d6) δ 11.50 (s, 1H), 8.82 (s, 1H), 8.55 (s, 1H), 8.20 (s, 1H), 7.45 (dd, J = 6.0, 3.1 Hz, 2H), 6.95 (s, 1H), 6.24-6.08 (m, 1H), 4.16 (t, J = 8.3 Hz, 2H), 3.88 (s, 3H), 3.79 (s, 3H), 3.46-3.40 (m, 1H), 3.20 (s, 2H), 3.11 (t, J = 8.4 Hz, 2H), 2.26 (s, 6H), 1.23 (d, J = 6.7 Hz, 6H). MS (ESI) m/z: 568 [M + H]$^+$. |
| IW-2 | 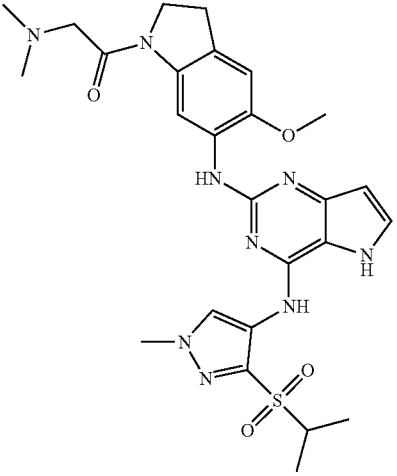 | $^1$H-NMR (600 MHz, DMSO-d6) δ 11.4520 (s, 1H), 8.51 (s, 1H), 8.21 (s, 1H), 7.89 (d, J = 8.7 Hz, 1H), 7.42 (d, J = 2.9 Hz, 1H), 7.34 (s, 1H), 6.62 (d, J = 2.5 Hz, 1H), 6.50 (dd, J = 8.7, 2.5 Hz, 1H), 6.18 (d, J = 2.9 Hz, 1H), 3.95 (s, 3H), 3.80 (s, 3H), 3.78-3.75 (m, 1H), 3.67 (d, J = 12.6 Hz, 2H), 3.49 (t, J = 5.3 Hz, 2H), 2.63 (td, J = 12.3, 2.4 Hz, 8H), 2.38 (s, 2H), 2.30 (s, 3H), 1.86 (d, J = 11.5 Hz, 2H), 1.53 (qd, J = 12.0, 3.9 Hz, 2H), 1.23 (d, J = 6.7 Hz, 6H). MS (ESI) m/z: 623 [M + H]$^+$. |

TABLE 2-continued
Structure and identification of compounds IG-IK
| ID | Structure | NMR and/or MS data |
|---|---|---|
| IW-3 | 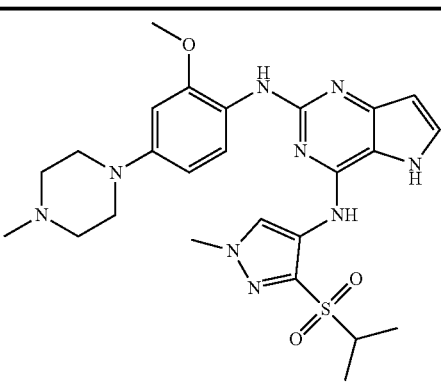 | MS (ESI) m/z: 540 [M + H]+ |
| IW-4 | 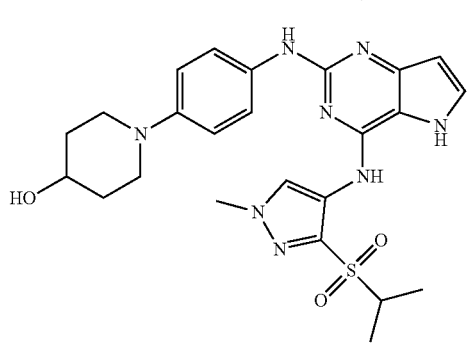 [SMILES: CC(C)S(=O)(=O)c1nn(C)cc1Nc1nc(Nc2ccc(N3CCC(O)CC3)cc2)nc2cc[nH]c12] | MS (ESI) m/z: 511 [M + H]+ |
Example 3
Synthesis Scheme of Compound IL
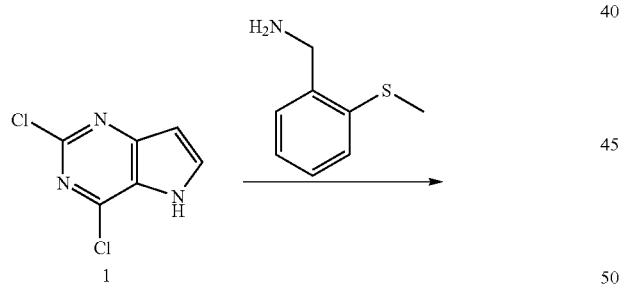
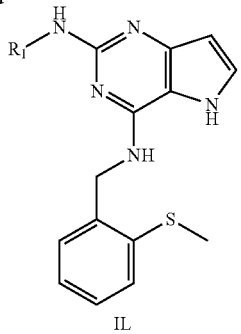
Preparation of Compound 5
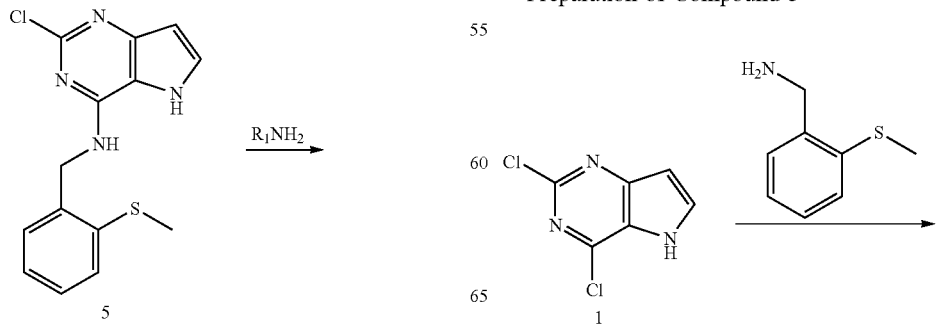

-continued

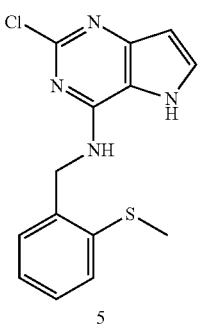

5

Compound 1 (170 mg, 1.11 mmol), 2-methylthiobenzylamine (224 mg, 1.11 mmol) were dissolved in 10 mL tert-butanol. To the solution was added N,N-diisopropylethylamine (0.55 mL, 3.33 mmol). The resulting reaction liquid was heated in 120° C. oil bath with stirring until compound 1 was reacted completely (LC-MS tracking). The reaction was stopped. The reaction liquid was concentrated and purified by silica-gel column chromatography (ethyl acetate/petroleum ether=2/5) to yield compound 5 (white solid, 238 mg, yield 70%), which was used directly for the reaction in next step.

MS (ESI) m/z: 305 [M+H]$^+$.

Preparation of Compound IL

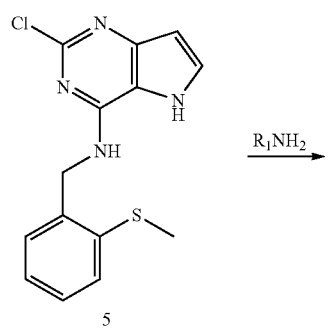

5

$R_1NH_2$ →

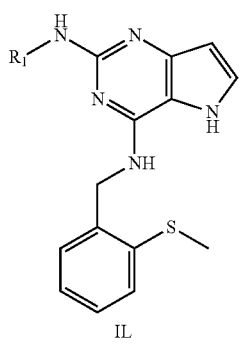

IL

Process A:

Compound 5 (45 mg, 0.15 mmol), aniline (0.12 mmol) were dissolved in 2 mL sec-butanol. To the solution was added trifluoroacetic acid (56 µL, 0.75 mmol). The resulting reaction liquid was heated in 120° C. oil bath with stirring until compound 5 was reacted completely (LC-MS tracking). The reaction was stopped. To the reaction liquid was added 10 mL of saturated sodium bicarbonate solution and 50 mL of dichloromethane, and the liquid was separated. The organic phase was washed twice with saturated sodium chloride solution, dried over anhydride sodium sulfate, concentrated and purified by silica-gel column chromatography (dichloromethane/methanol=5/2) to yield compound IL.

Process B:

Compound 5 (59 mg, 0.19 mmol), aniline (0.15 mmol) were dissolved in 2 mL sec-butanol. To the solution was added trifluoroacetic acid (70 µL, 0.95 mmol). The resulting reaction liquid was placed in a microwave reactor and reacted at 120° C. for 2 hours. The reaction was stopped. To the reaction liquid was added 10 mL of saturated sodium bicarbonate solution and 50 mL of dichloromethane, and the liquid was separated. The organic phase was washed twice with saturated sodium chloride solution, dried over anhydride sodium sulfate, concentrated and purified by reversed-phase preparative HPLC (with 0.35% trifluoroacetic acid aqueous solution and methanol as mobile phase), and concentrated in vacuum to yield compound IL.

Process C:

Compound 5 (45 mg, 0.15 mmol), aniline (0.12 mmol) were dissolved in 2 mL sec-butanol. To the solution was added trifluoroacetic acid (56 µL, 0.75 mmol). The resulting reaction solution was heated in 120° C. oil bath with stirring until compound 2 was reacted completely (LC-MS tracking). The reaction was stopped. To the reaction liquid was added 10 mL of saturated sodium bicarbonate solution and 50 mL of dichloromethane, and the liquid was separated. The organic phase was washed twice with saturated sodium chloride solution, dried over anhydride sodium sulfate, concentrated and purified by reversed-phase preparative HPLC (with 0.35% trifluoroacetic acid aqueous solution and methanol as mobile phase), and concentrated in vaccum to yield compound IL.

Compounds IM, IN, IO, IP were synthesized using similar processes.

TABLE 3

Structure and identification of compounds IL-IP

| ID | Structure | NMR and/or MS data |
| --- | --- | --- |
| IL-1 | 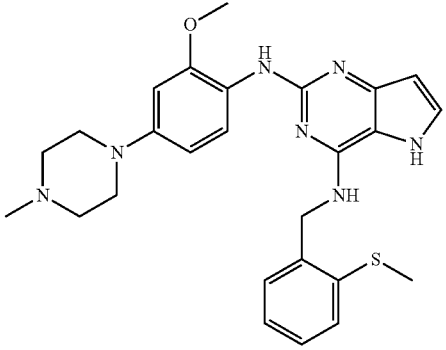 | $^1$H NMR (600 MHz, DMSO-d$_6$) δ 10.66 (s, 1H), 8.28 (s, 1H), 7.38-7.27 (m, 5H), 7.16 (t, J = 7.4 Hz, 1H), 7.06-6.87 (m, 1H), 6.60 (d, J = 2.7 Hz, 1H), 6.40 (dd, J = 8.7, 2.6 Hz, 1H), 6.16-6.11 (m, 1H), 4.70 (d, J = 5.3 Hz, 2H), 3.84 (s, 3H), 3.05 (d, J = 4.9 Hz, 4H), 2.52 (s, 3H), 2.47 (s, 4H), 2.23 (s, 3H). MS (ESI) m/z: 490 [M + H]$^+$. |
| IL-2 | 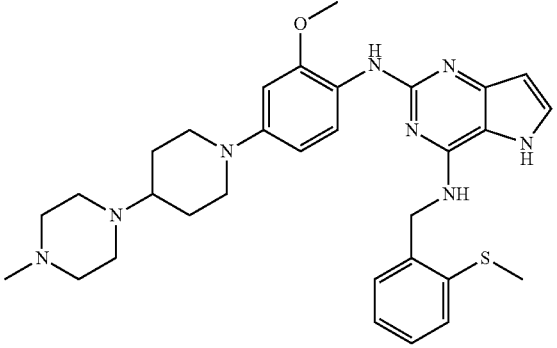<br>TFA salt | MS (ESI) m/z: 573 [M + H]$^+$. |
| IL-3 | 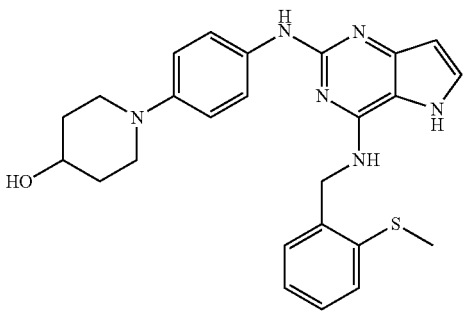 [SMILES: CSc1ccccc1CNc1nc(Nc2ccc(N3CCC(O)CC3)cc2)nc2cc[nH]c12] | $^1$H NMR (600 MHz, DMSO-d$_6$) δ 10.62 (s, 1H), 8.25 (s, 1H), 7.60 (d, J = 9.0 Hz, 2H), 7.40-7.37 (m, 1H), 7.36-7.29 (m, 3H), 7.21 (t, J = 5.4 Hz, 1H), 7.15 (td, J = 7.3, 1.6 Hz, 1H), 6.77 (d, J = 9.0 Hz, 2H), 6.12 (dd, J = 2.7, 2.2 Hz, 1H), 4.74 (d, J = 5.4 Hz, 2H), 4.64 (d, J = 2.8 Hz, 1H), 3.57 (s, 1H), 3.34 (s, 2H), 2.72-2.65 (m, 2H), 2.51 (s, 3H), 1.85-1.78 (m, 2H), 1.53-1.45 (m, 2H). MS (ESI) m/z: 461 [M + H]$^+$. |
| IL-4 | 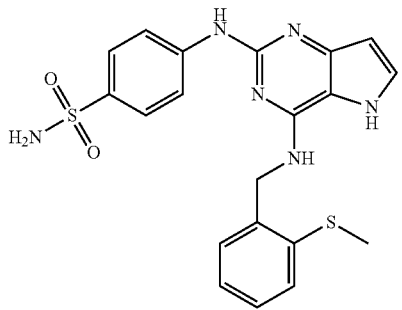<br>TFA salt | $^1$H NMR (600 MHz, DMSO-d$_6$) δ 11.78 (s, 1H), 10.76 (s, 1H), 9.17 (s, 1H), 7.69 (d, J = 8.8 Hz, 2H), 7.63 (d, J = 8.5 Hz, 3H), 7.41-7.32 (m, 3H), 7.27 (s, 2H), 7.19-7.15 (m, 1H), 6.35 (t, J = 2.3 Hz, 1H), 4.80 (d, J = 5.3 Hz, 2H), 2.53 (s, 3H). MS (ESI) m/z: 441 [M + H]$^+$. |

TABLE 3-continued

Structure and identification of compounds IL-IP

| ID | Structure | NMR and/or MS data |
| --- | --- | --- |
| IM-1 | 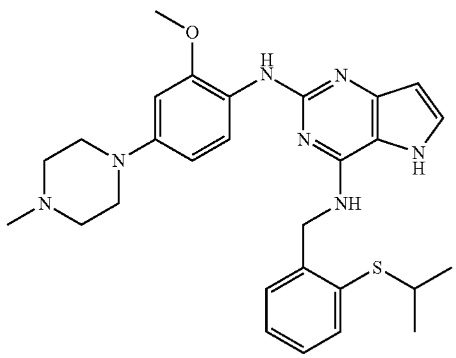 [SMILES: COc1cc(N2CCN(C)CC2)ccc1Nc1nc(NCc2ccccc2SC(C)C)c2[nH]ccc2n1] | ¹H NMR (600 MHz, Methanol-d₄) δ 8.07 (d, J = 8.8 Hz, 1H), 7.51 (dd, J = 7.7, 1.3 Hz, 1H), 7.41 (dd, J = 7.5, 1.5 Hz, 1H), 7.28-7.22 (m, 2H), 7.21 (td, J = 7.5, 1.5 Hz, 1H), 6.62 (d, J = 2.5 Hz, 1H), 6.43 (dd, J = 8.8, 2.6 Hz, 1H), 6.17 (d, J = 3.0 Hz, 1H), 4.93 (s, 2H), 3.86 (s, 3H), 3.42 (hept, J = 6.7 Hz, 1H), 3.11 (t, J = 5.1 Hz, 4H), 2.60 (t, J = 5.0 Hz, 4H), 2.32 (s, 3H), 1.28 (d, J = 6.7 Hz, 6H). MS (ESI) m/z: 518 [M + H]⁺. |
| IM-2 | 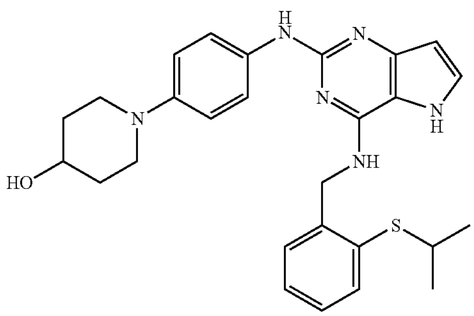 [SMILES: CC(C)Sc1ccccc1CNc1nc(Nc2ccc(N3CCC(O)CC3)cc2)nc2cc[nH]c12] | ¹H NMR (600 MHz, Methanol-d₄) δ 7.51 (dd, J = 7.7, 1.3 Hz, 1H), 7.39 (dd, J = 7.6, 1.5 Hz, 1H), 7.38-7.34 (m, 2H), 7.28-7.25 (m, 2H), 7.21 (td, J = 7.5, 1.4 Hz, 1H), 6.90 (d, J = 8.4 Hz, 2H), 6.19 (d, J = 3.0 Hz, 1H), 4.91 (s, 2H), 3.72 (hept, J = 8.9, 4.1 Hz, 1H), 3.42 (dq, J = 13.3, 6.5 Hz, 3H), 2.83-2.77 (m, 2H), 1.95 (ddd, J = 12.5, 6.2, 2.9 Hz, 2H), 1.66 (dtd, J = 13.1, 9.8, 3.8 Hz, 2H), 1.28 (s, 3H), 1.27 (s, 3H). MS (ESI) m/z: 489 [M + H]⁺ |
| IM-3 | 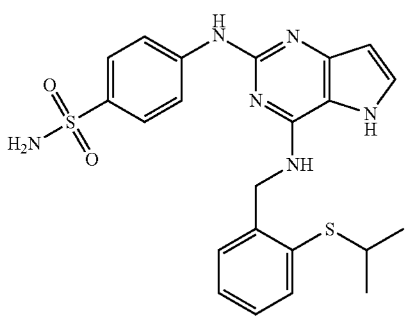 [SMILES: CC(C)Sc1ccccc1CNc1nc(Nc2ccc(S(N)(=O)=O)cc2)nc2cc[nH]c12] | ¹H NMR (600 MHz, Methanol-d₄) δ 7.75-7.72 (m, 1H), 7.70-7.67 (m, 1H), 7.51 (dd, J = 7.7, 1.3 Hz, 0H), 7.44-7.41 (m, 0H), 7.30 (d, J = 3.0 Hz, 0H), 7.25 (td, J = 7.5, 1.6 Hz, 1H), 7.21 (td, J = 7.4, 1.4 Hz, 1H), 6.26 (d, J = 3.0 Hz, 0H), 4.94 (s, 1H), 3.43 (hept, J = 7.2 Hz, 1H), 1.28 (d, J = 6.7 Hz, 3H). MS (ESI) m/z: 469 [M + H]⁺ |
| IN-1 | 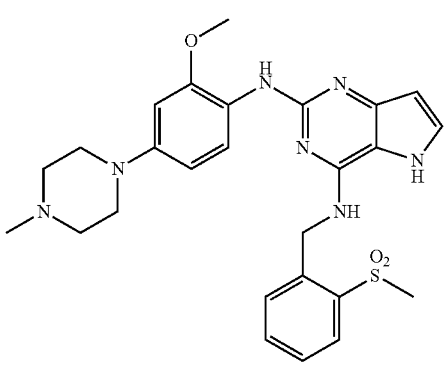 [SMILES: COc1cc(N2CCN(C)CC2)ccc1Nc1nc(NCc2ccccc2S(C)(=O)=O)c2[nH]ccc2n1] | ¹H NMR (600 MHz, CDCl₃) δ 7.93 (dd, J = 7.6, 1.7 Hz, 1H), 7.79 (d, J = 8.7 Hz, 1H), 7.55-7.51 (m, 1H), 7.37-7.30 (m, 2H), 7.04-7.02 (m, 1H), 6.91 (d, J = 14.0 Hz, 1H), 6.41 (d, J = 2.5 Hz, 1H), 6.24 (dd, J = 8.7, 2.3 Hz, 1H), 6.15 (d, J = 3.0 Hz, 1H), 4.97 (s, 2H), 3.69 (s, 3H), 3.02 (d, J = 13.5 Hz, 7H), 2.56-2.52 (m, 4H), 2.31 (s, 3H). MS (ESI) m/z: 522 [M + H]⁺. |

TABLE 3-continued

Structure and identification of compounds IL-IP

| ID | Structure | NMR and/or MS data |
| --- | --- | --- |
| IN-2 | 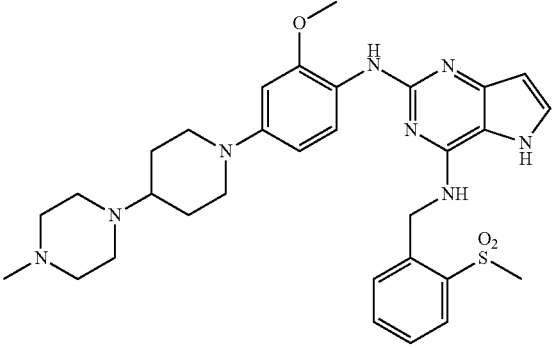 TFA salt | $^1$H NMR (600 MHz, DMSO-d$_6$) δ 11.98 (s, 1H), 9.25 (s, 1H), 9.11 (t, J = 5.8 Hz, 1H), 7.99 (dd, J = 7.9, 1.3 Hz, 1H), 7.69 (td, J = 7.6, 1.4 Hz, 1H), 7.59 (td, J = 7.7, 1.3 Hz, 1H), 7.56 (dd, J = 6.6, 3.5 Hz, 2H), 7.23 (d, J = 8.6 Hz, 1H), 6.73 (d, J = 2.5 Hz, 1H), 6.48 (q, J = 2.4 Hz, 1H), 6.26 (t, J = 2.4 Hz, 1H), 5.14 (d, J = 5.7 Hz, 2H), 3.91-3.85 (m, 2H), 3.77 (d, J = 4.4 Hz, 3H), 3.71-3.34 (m, 8H), 3.22 (s, 3H), 2.89 (s, 3H), 2.77 (t, J = 12.2 Hz, 2H), 2.18-2.11 (m, 2H), 1.77-1.68 (m, 2H). MS (ESI) m/z: 605[M + H]$^+$. |
| IN-3 | 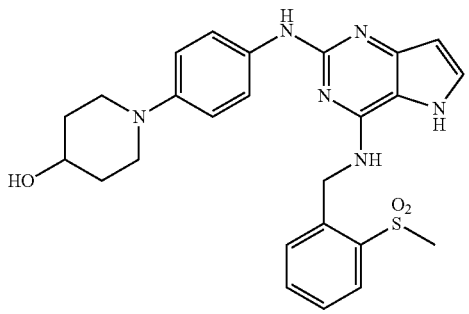 TFA salt | $^1$H NMR (600 MHz, DMSO-d$_6$) δ 11.80 (s, 1H), 10.25 (s, 1H), 9.08 (s, 1H), 8.03 (dd, J = 7.9, 1.2 Hz, 1H), 7.71 (dd, J = 10.8, 4.4 Hz, 1H), 7.64-7.57 (m, 3H), 7.35 (d, J = 8.4 Hz, 2H), 7.19 (d, J = 8.5 Hz, 2H), 6.34-6.29 (m, 1H), 5.19 (d, J = 5.5 Hz, 2H), 3.56-3.51 (m, 2H), 3.23 (s, 3H), 3.16 (d, J = 6.9 Hz, 2H), 1.93 (s, 2H), 1.65 (s, 2H). MS (ESI) m/z: 493 [M + H]$^+$. |
| IN-4 | 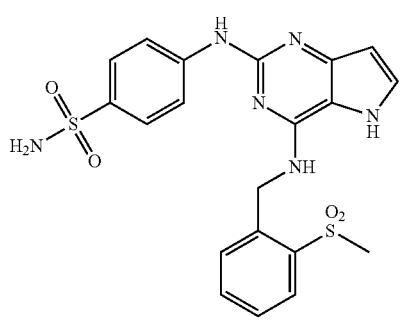 [SMILES: CS(=O)(=O)c1ccccc1CNc1nc(Nc2ccc(S(N)(=O)=O)cc2)nc2cc[nH]c12] | $^1$H NMR (600 MHz, DMSO-d$_6$) δ 11.76 (s, 1H), 10.46 (s, 1H), 9.07 (s, 1H), 8.04 (dd, J = 8.2, 1.3 Hz, 1H), 7.75-7.70 (m, 1H), 7.68 (s, 1H), 7.67-7.65 (m, 2H), 7.63 (t, J = 7.0 Hz, 2H), 7.60 (d, J = 8.8 Hz, 2H), 7.27 (s, 2H), 6.41-6.36 (m, 1H), 5.23 (d, J = 5.5 Hz, 2H), 3.23 (s, 3H). MS (ESI) m/z: 473[M + H]$^+$. |
| IN-5 | 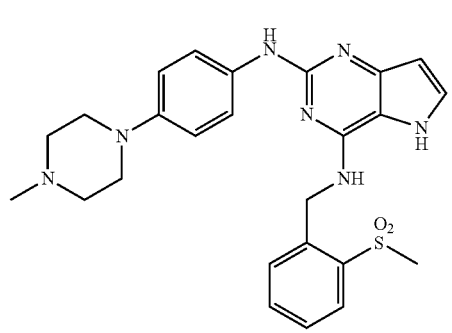 [SMILES: CN1CCN(c2ccc(Nc3nc(NCc4ccccc4S(C)(=O)=O)c4[nH]ccc4n3)cc2)CC1] | $^1$H NMR (600 MHz, CDCl$_3$) δ 7.95 (dd, J = 7.8, 1.4 Hz, 1H), 7.49 (dd, J = 4.8, 3.9 Hz, 1H), 7.44 (td, J = 7.5, 1.4 Hz, 1H), 7.40 (td, J = 7.6, 1.4 Hz, 1H), 7.18-7.13 (m, 2H), 7.04 (d, J = 2.9 Hz, 1H), 6.69-6.64 (m, 2H), 6.08 (d, J = 2.9 Hz, 1H), 4.99 (s, 2H), 3.06-3.00 (m, 4H), 2.96 (s, 3H), 2.57-2.51 (m, 4H), 2.32 (s, 3H). MS (ESI) m/z: 492 [M + H]$^+$. |

TABLE 3-continued

Structure and identification of compounds IL-IP

| ID | Structure | NMR and/or MS data |
|---|---|---|
| IO-1 | 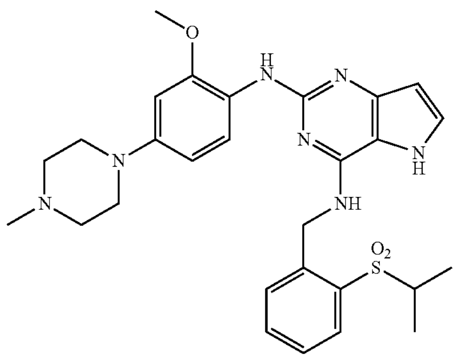 [SMILES: COc1cc(N2CCN(C)CC2)ccc1Nc1nc(NCc2ccccc2S(=O)(=O)C(C)C)c2[nH]ccc2n1] | $^1$H NMR (600 MHz, Methanol-d$_4$) δ 7.97 (dd, J = 7.9, 1.3 Hz, 1H), 7.92 (d, J = 8.7 Hz, 1H), 7.72-7.67 (m, 1H), 7.61 (td, J = 7.6, 1.4 Hz, 1H), 7.51 (td, J = 7.5, 1.3 Hz, 1H), 7.28 (d, J = 2.9 Hz, 1H), 6.62 (d, J = 2.5 Hz, 1H), 6.43 (dd, J = 8.9, 2.5 Hz, 1H), 6.19 (d, J = 3.0 Hz, 1H), 5.1921 (s, 2H), 3.85 (s, 3H), 3.49 (hept, J = 6.7 Hz, 1H), 3.12 (t, 4H), 2.60 (t, J = 5.0 Hz, 4H), 2.33 (s, 3H), 1.27 (s, 3H), 1.26 (s, 3H). MS (ESI) m/z: 550 [M + H]$^+$. |
| IO-2 | 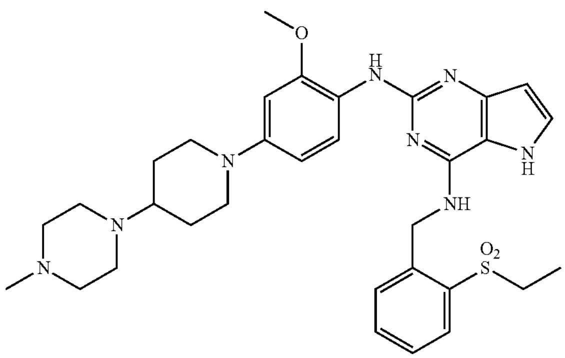 | $^1$H NMR (600 MHz, DMSO-d$_6$) δ 10.75 (s, 1H), 8.30 (d, J = 8.8 Hz, 1H), 7.91 (dd, J = 7.9, 1.3 Hz, 1H), 7.71 (dd, J = 7.8, 1.3 Hz, 1H), 7.67 (dd, J = 7.9, 1.5 Hz, 1H), 7.58 (t, J = 5.9 Hz, 1H), 7.55 (ddd, J = 8.2, 7.2, 1.7 Hz, 1H), 7.36 (t, J = 2.9 Hz, 1H), 6.77 (s, 1H), 6.58 (d, J = 2.5 Hz, 1H), 6.40 (dd, J = 8.9, 2.5 Hz, 1H), 6.19-6.15 (m, 1H), 5.06 (d, J = 5.8 Hz, 2H), 3.81 (s, 3H), 3.75 (hept, J = 7.7, 7.0 Hz, 1H), 3.57 (d, J = 12.2 Hz, 2H), 2.60-2.52 (m, 4H), 2.54-2.50 (m, 1H), 2.35-2.30 (m, 2H), 2.28-2.22 (m, 2H), 2.15 (s, 3H), 1.82 (d, J = 11.3 Hz, 2H), 1.50 (qd, J = 12.4, 4.3 Hz, 2H), 1.27 (d, J = 6.8 Hz, 6H), 1.04 (d, J = 6.1 Hz, 2H). MS (ESI) m/z: 633 [M + H]$^+$. |
| IO-3 | 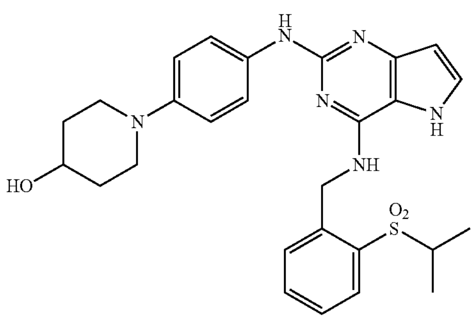 [SMILES: CC(C)S(=O)(=O)c1ccccc1CNc1nc(Nc2ccc(N3CCC(O)CC3)cc2)nc2cc[nH]c12] | $^1$H NMR (600 MHz, DMSO-d$_6$) δ 10.73 (s, 1H), 8.20 (s, 1H), 7.95-7.88 (m, 1H), 7.74-7.67 (m, 2H), 7.56 (ddd, J = 8.3, 6.2, 2.5 Hz, 1H), 7.52 (d, J = 9.0 Hz, 2H), 7.38 (s, 1H), 7.34 (t, J = 2.9 Hz, 1H), 6.79-6.73 (m, 2H), 6.13 (t, J = 2.4 Hz, 1H), 5.13 (d, J = 5.7 Hz, 2H), 3.60-3.49 (m, 3H), 2.68 (ddd, J = 12.7, 10.3, 2.9 Hz, 2H), 2.54-2.50 (m, 1H), 1.80 (dq, J = 13.2, 3.7 Hz, 2H), 1.48 (dtd, J = 12.9, 9.6, 3.7 Hz, 2H), 1.20 (d, J = 6.7 Hz, 6H). MS (ESI) m/z: 521 [M + H]$^+$. |
| IO-4 | 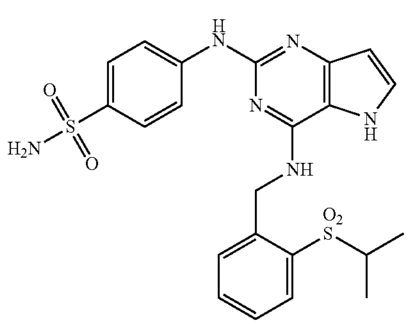 [SMILES: CC(C)S(=O)(=O)c1ccccc1CNc1nc(Nc2ccc(S(N)(=O)=O)cc2)nc2cc[nH]c12] | $^1$H NMR (600 MHz, Methanol-d$_4$) δ 7.98 (dd, J = 7.9, 1.3 Hz, 1H), 7.75 (dd, J = 7.8, 1.2 Hz, 1H), 7.66 (s, 4H), 7.64 (dd, J = 7.6, 1.4 Hz, 1H), 7.52 (td, J = 7.7, 1.3 Hz, 1H), 7.33 (d, J = 3.0 Hz, 1H), 6.2715 (d, J = 3.0 Hz, 1H), 5.23 (s, 2H), 3.49-3.39 (m, 1H), 1.24 (d, J = 6.8 Hz, 6H). MS (ESI) m/z: 501 [M + H]$^+$. |

TABLE 3-continued

Structure and identification of compounds IL-IP

| ID | Structure | NMR and/or MS data |
| --- | --- | --- |
| IO-5 | 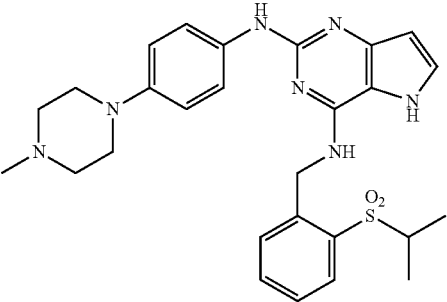 [SMILES: CC(C)S(=O)(=O)c1ccccc1CNc1nc(Nc2ccc(N3CCN(C)CC3)cc2)nc2cc[nH]c12] | $^1$H NMR (600 MHz, Methanol-d$_4$) δ 7.95 (dd, J = 7.9, 1.4 Hz, 1H), 7.69 (dd, J = 7.8, 1.2 Hz, 1H), 7.60 (td, J = 7.6, 1.4 Hz, 1H), 7.50 (td, J = 7.6, 1.3 Hz, 1H), 7.38-7.32 (m, 2H), 7.26 (d, J = 3.0 Hz, 1H), 6.87-6.80 (m, 2H), 6.19 (d, J = 3.0 Hz, 1H), 5.17 (s, 2H), 3.41 (hept, J = 6.8 Hz, 1H), 3.08 (t, J = 4.9 Hz, 4H), 2.59 (t, J = 4.9 Hz, 4H), 2.32 (s, 3H), 1.23 (d, J = 6.8 Hz, 6H). MS (ESI) m/z: 520 [M + H]$^+$. |
| IP-1 | 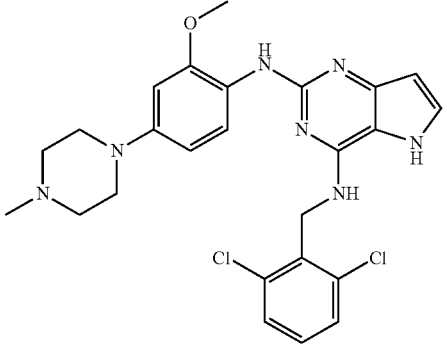 [SMILES: COc1cc(N2CCN(C)CC2)ccc1Nc1nc(NCc2c(Cl)cccc2Cl)c2[nH]ccc2n1] | $^1$H NMR (600 MHz, DMSO-d$_6$) δ 11.63 (s, 1H), 9.43 (s, 1H), 8.62 (s, 1H), 7.59 (d, J = 8.1 Hz, 3H), 7.51 (s, 1H), 7.47 (t, J = 8.1 Hz, 1H), 6.78 (s, 1H), 6.65 (d, J = 8.5 Hz, 1H), 6.24 (s, 1H), 4.94 (d, J = 3.8 Hz, 2H), 3.83 (s, 3H), 2.87 (s, 3H). MS (ESI) m/z: 513 [M + H]$^+$. |
| IP-2 | 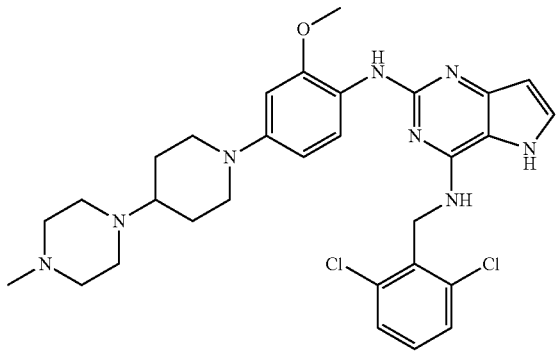 [SMILES: COc1cc(N2CCC(N3CCN(C)CC3)CC2)ccc1Nc1nc(NCc2c(Cl)cccc2Cl)c2[nH]ccc2n1] | $^1$H NMR (600 MHz, DMSO-d$_6$) δ 10.60 (s, 1H), 8.44 (d, J = 8.8 Hz, 1H), 7.57 (d, J = 8.1 Hz, 2H), 7.43 (dd, J = 8.4, 7.8 Hz, 1H), 7.31 (t, J = 2.9 Hz, 1H), 7.14 (t, J = 4.4 Hz, 1H), 7.09 (s, 1H), 6.63 (d, J = 2.5 Hz, 1H), 6.50 (dd, J = 8.9, 2.5 Hz, 1H), 6.16 (dd, J = 2.8, 2.1 Hz, 1H), 4.87 (d, J = 4.6 Hz, 2H), 4.60 (s, 1H), 3.88 (s, 3H), 3.61 (d, J = 12.3 Hz, 2H), 3.50 (d, J = 5.4 Hz, 2H), 3.43 (dd, J = 7.8, 2.9 Hz,2H), 2.58 (dd, J = 12.0, 10.1 Hz, 2H), 2.35 (s, 2H), 2.27 (ddd, J = 11.2, 7.8, 3.5 Hz, 2H), 2.17 (s, 3H), 1.84 (d, J = 11.8 Hz, 2H), 1.52 (qd, J = 12.2, 3.8 Hz, 2H). MS (ESI) m/z: 596 [M + H]$^+$. |
| IP-3 | 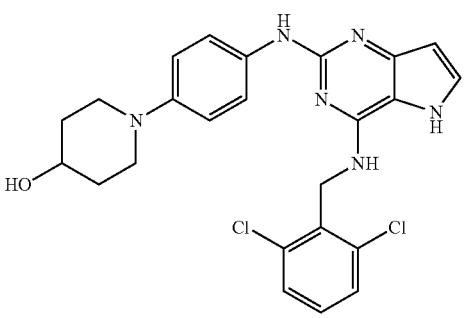 [SMILES: OC1CCN(c2ccc(Nc3nc(NCc4c(Cl)cccc4Cl)c4[nH]ccc4n3)cc2)CC1] | $^1$H NMR (600 MHz, DMSO-d$_6$) δ 10.50 (s, 1H), 8.32 (s, 1H), 7.70 (d, J = 9.0 Hz, 2H), 7.60 (d, J = 8.1 Hz, 2H), 7.46 (t, J = 8.1 Hz, 1H), 7.29 (t, J = 2.8 Hz, 1H), 6.95 (s, 1H), 6.85 (d, J = 9.0 Hz, 2H), 6.13 (t, J = 2.4 Hz, 1H), 4.91 (d, J = 4.2 Hz, 2H), 4.68 (d, J = 2.9 Hz, 1H), 3.57 (s, 2H), 2.75-2.66 (m, 2H), 1.88-1.76 (m, 2H), 1.56-1.43 (m, 2H). MS (ESI) m/z: 484 [M + H]$^+$. |

TABLE 3-continued

Structure and identification of compounds IL-IP

| ID | Structure | NMR and/or MS data |
|---|---|---|
| IP-4 | 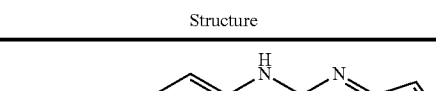 | $^1$H NMR (600 MHz, DMSO-$d_6$) δ 10.03 (s, 1H), 7.87 (s, 1H), 7.53 (t, J = 7.3 Hz, 2H), 7.47 (d, J = 2.8 Hz, 1H), 7.45-7.40 (m, 1H), 7.36 (d, J = 7.9 Hz, 1H), 7.29 (s, 1H), 7.20 (s, 1H), 7.12 (s, 1H), 7.01 (d, J = 7.9 Hz, 1H), 6.16 (t, J = 39.9 Hz, 1H), 5.01 (d, J = 4.6 Hz, 2H), 3.89 (d, J = 75.0 Hz, 3H), 2.86 (d, J = 13.7 Hz, 2H), 1.83 (d, J = 9.2 Hz, 2H), 1.58-1.38 (m, 2H). MS (ESI) m/z: 483 [M + H]$^+$. |

Example 4

Synthesis Scheme of Compound IQ

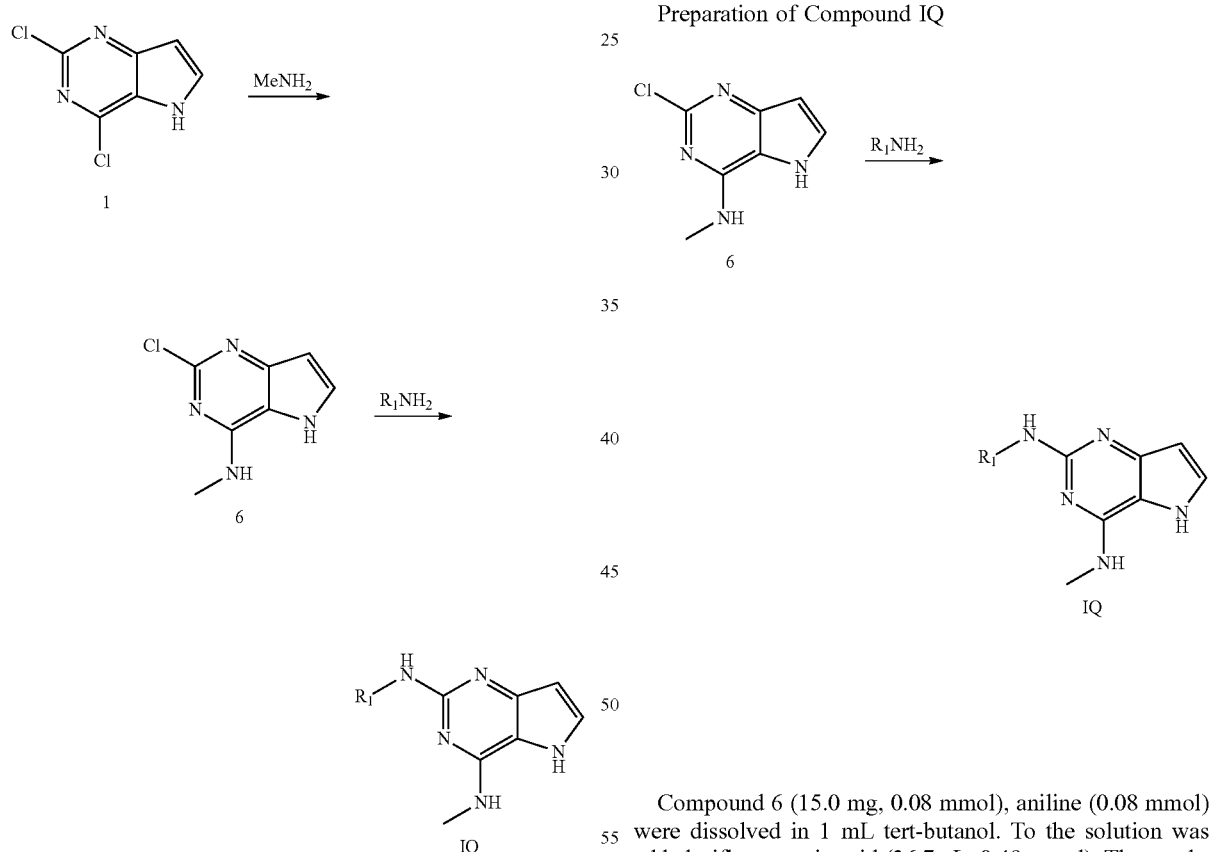

Preparation of Compound 6

Compound 1 (200 mg, 1.06 mmol), methylamine (33% wt 1N EtoH, 2.34 mmol) were dissolved in 4 mL tert-butanol. The resulting reaction liquid was heated in 45° C. oil bath with stirring until compound 1 was reacted completely (LC-MS tracking), concentrated and purified by silica-gel column chromatography (dichloromethane/methanol=50/1) to yield compound 6 (yellow solid, 165 mg, yield 85.2%), which was used directly for the reaction in next step.

MS (ESI) m/z: 183 [M+H]$^+$.

Preparation of Compound IQ

Compound 6 (15.0 mg, 0.08 mmol), aniline (0.08 mmol) were dissolved in 1 mL tert-butanol. To the solution was added trifluoroacetic acid (36.7 μL, 0.49 mmol). The resulting reaction liquid was heated in 110° C. oil bath with stirring until aniline was reacted completely (LC-MS tracking). The reaction was stopped. To the reaction liquid was added 10 mL of saturated sodium bicarbonate solution and 50 mL of dichloromethane, and the liquid was separated. The organic phase was washed twice with saturated sodium chloride solution, dried over anhydride sodium sulfate, concentrated and purified by silica-gel column chromatography (dichloromethane/methanol) to yield compound IQ.

Compounds IR, IS, IT were synthesized using similar processes.

TABLE 4

Structure and identification of compounds IQ-IT

| ID | Structure | NMR and/or MS data |
|---|---|---|
| IQ-1 | 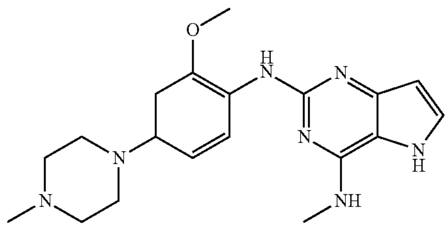 [SMILES: CNc1nc(NC2=C(OC)CC(N3CCN(C)CC3)C=C2)nc2cc[nH]c12] | ¹H-NMR (600 MHz; Methanol-d₄): δ 8.02 (dd, J = 8.7, 2.1 Hz, 1H), 7.28 (t, J = 1.5 Hz, 1H), 6.69 (d, J = 2.5 Hz, 1H), 6.60 (dd, J = 8.8, 2.4 Hz, 1H), 6.19 (d, J = 3.0 Hz, 1H), 3.90 (s, 3H), 3.20 (d, J = 3.9 Hz, 4H), 3.15 (s, 3H), 2.66 (t, J = 4.9 Hz, 4H), 2.38 (s, 3H). MS (ESI) m/z: 368 [M + H]⁺. |
| IQ-2 | 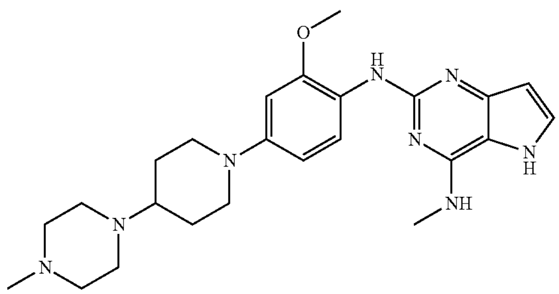 [SMILES: CNc1nc(Nc2ccc(N3CCC(N4CCN(C)CC4)CC3)cc2OC)nc2cc[nH]c12] | ¹H-NMR (600 MHz; Methanol-d₄): δ 8.19 (d, J = 8.7 Hz, 1H), 7.26 (s, 1H), 6.66 (s, 1H), 6.57-6.56 (m, 1H), 6.19-6.18 (m, 1H), 3.89 (s, 3H), 3.61 (d, J = 11.6 Hz, 2H), 3.14 (s, 3H), 2.64-2.61 (m, 6H), 2.29 (s, 5H), 1.96 (d, J = 12.1 Hz, 2H), 1.62 (dd, J = 11.9, 2.8 Hz, 2H). MS (ESI) m/z: 451 [M + H]⁺. |
| IQ-3 | 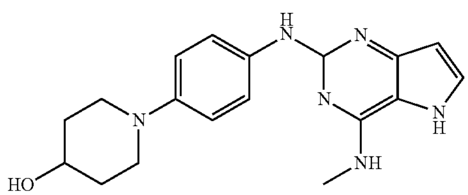 [SMILES: CNC1=c2[nH]ccc2=NC(Nc2ccc(N3CCC(O)CC3)cc2)N1] | ¹H-NMR (600 MHz; Methanol-d₄): δ 7.44 (d, J = 8.5 Hz, 2H), 7.37 (d, J = 2.5 Hz, 1H), 7.13 (d, J = 8.7 Hz, 2H), 6.27 (d, J = 2.5 Hz, 1H), 3.83 (t, J = 4.2 Hz, 1H), 3.64-3.60 (m, 2H), 3.16 (s, 3H), 3.02-2.98 (m, 2H), 2.04-2.02 (m, 2H), 1.73 (td, J = 8.8, 4.9 Hz, 2H). MS (ESI) m/z: 339 [M + H]⁺. |
| IQ-4 | 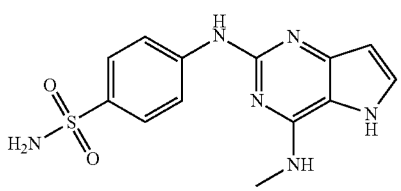 [SMILES: CNc1nc(Nc2ccc(S(N)(=O)=O)cc2)nc2cc[nH]c12] | ¹H-NMR (600 MHz; Methanol-d₄): δ 7.88 (q, J = 11.4 Hz, 4H), 7.44 (d, J = 3.0 Hz, 1H), 6.35 (d, J = 3.0 Hz, 1H), 3.21 (s, 3H). MS (ESI) m/z: 319 [M + H]⁺. |
| IQ-5 | 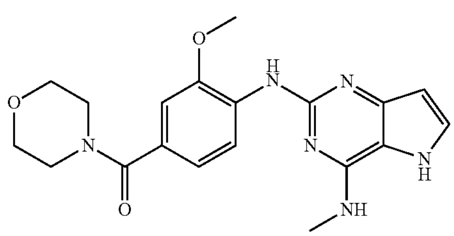 [SMILES: CNc1nc(Nc2ccc(C(=O)N3CCOCC3)cc2OC)nc2cc[nH]c12] | MS (ESI) m/z: 383 [M + H]⁺. |
| IQ-6 | 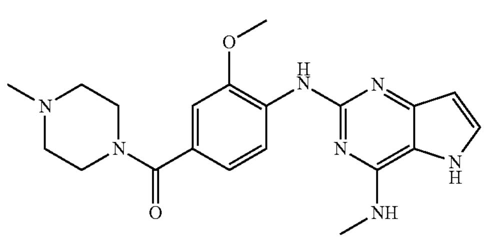 [SMILES: CNc1nc(Nc2ccc(C(=O)N3CCN(C)CC3)cc2OC)nc2cc[nH]c12] | ¹H-NMR (600 MHz; Methanol-d₄): δ 8.71 (d, J = 8.1 Hz, 1H), 7.32-7.31 (m, 1H), 7.07-7.06 (m, 2H), 6.25 (d, J = 3.0 Hz, 1H), 4.00 (s, 3H), 3.73-3.66 (m, 4H), 3.18 (s, 3H), 2.52 (dd, J = 1.4, 0.9 Hz, 4H), 2.36 (s, 4H). MS (ESI) m/z: 396 [M + H]⁺. |

TABLE 4-continued

Structure and identification of compounds IQ-IT

| ID | Structure | NMR and/or MS data |
|---|---|---|
| IQ-7 | 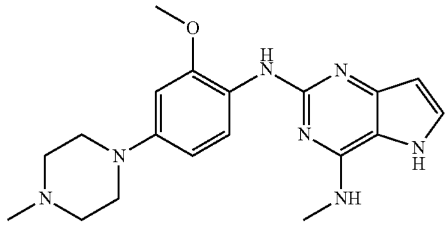 [SMILES: CNc1nc(Nc2ccc(N3CCN(C)CC3)cc2OC)nc2cc[nH]c12] | ¹H-NMR (600 MHz; Methanol-d₄): δ 8.12 (d, J = 8.6 Hz, 1H), 7.42 (s, 1H), 6.67 (d, J = 0.2 Hz, 1H), 6.58-6.57 (m, 1H), 3.93 (s, 3H), 3.16 (s, 3H), 3.00 (s, 3H). MS (ESI) m/z: 402 [M + H]⁺. |
| IQ-8 | 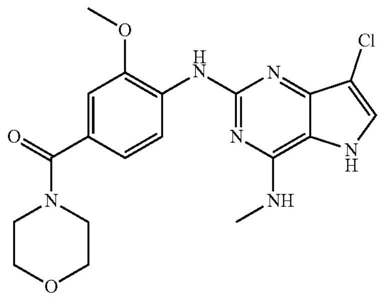 [SMILES: CNc1nc(Nc2ccc(C(=O)N3CCOCC3)cc2OC)nc2c(Cl)c[nH]c12] | ¹H-NMR (600 MHz; Methanol-d₄): δ 8.50 (d, J = 8.2 Hz, 1H), 7.49 (s, 1H), 7.14 (s, 1H), 7.10 (d, J = 8.2 Hz, 1H), 4.00 (s, 3H), 3.21 (s, 3H). MS (ESI) m/z: 417 [M + H]⁺. |
| IR-1 | 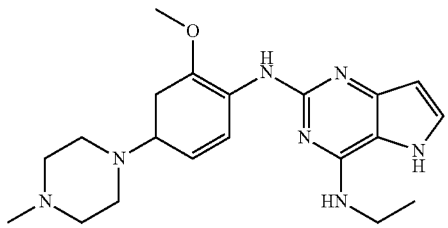 [SMILES: CCNc1nc(NC2=C(OC)CC(N3CCN(C)CC3)C=C2)nc2cc[nH]c12] | ¹H-NMR (600 MHz; Methanol-d₄): δ 7.60 (d, J = 3.1 Hz, 1H), 7.39 (d, J = 2.8 Hz, 1H), 6.77 (d, J = 2.4 Hz, 1H), 6.56 (d, J = 3.1 Hz, 1H), 6.23 (d, J = 2.9 Hz, 1H), 3.90 (d, J = 34.2 Hz, 5H), 3.68 (dd, J = 12.9, 7.2 Hz, 3H), 3.55 (s, 2H), 3.24-3.22 (m, 2H), 1.39 (t, J = 7.3 Hz, 3H). MS (ESI) m/z: 382 [M + H]⁺. |
| IR-2 | 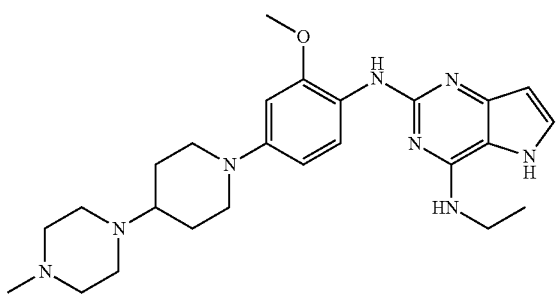 [SMILES: CCNc1nc(Nc2ccc(N3CCC(N4CCN(C)CC4)CC3)cc2OC)nc2cc[nH]c12] | ¹H-NMR (600 MHz; Methanol-d₄): δ 7.55-7.53 (m, 1H), 7.37 (d, J = 2.8 Hz, 1H), 6.72 (d, J = 2.3 Hz, 1H), 6.63 (dd, J = 8.7, 2.4 Hz, 1H), 6.23 (d, J = 2.9 Hz, 1H), 3.88 (s, 3H), 3.83 (d, J = 12.4 Hz, 2H), 3.66 (d, J = 7.3 Hz, 2H), 3.18-3.16 (m, 5H), 2.78 (td, J = 25.0, 9.8 Hz, 6H), 2.07 (d, J = 11.2 Hz, 2H), 1.74 (dd, J = 11.8, 2.8 Hz, 2H), 1.34 (t, J = 7.3 Hz, 3H). MS (ESI) m/z: 465 [M + H]⁺. |
| IR-3 | 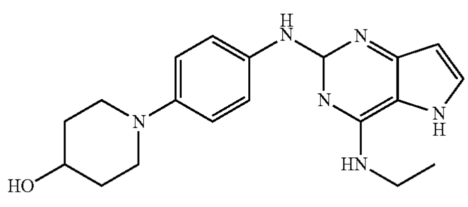 [SMILES: CCNC1=c2[nH]ccc2=NC(Nc2ccc(N3CCC(O)CC3)cc2)N1] | ¹H-NMR (600 MHz; Methanol-d₄): δ 7.38-7.35 (m, 3H), 7.04 (d, J = 8.9 Hz, 2H), 6.25 (d, J = 3.0 Hz, 1H), 3.78 (dd, J = 8.9, 4.6 Hz, 1H), 3.65 (q, J = 7.3 Hz, 2H), 3.58-3.55 (m, 2H), 2.92-2.88 (m, 2H), 2.01-1.97 (m, 2H), 1.71-1.66 (m, 2H), 1.33 (t, J = 7.3 Hz, 3H). MS (ESI) m/z: 353 [M + H]⁺. |
| IR-4 | 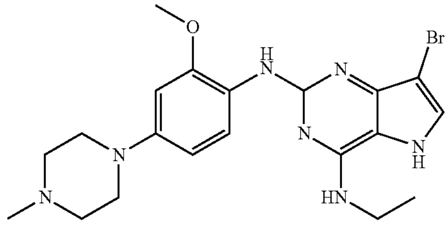 [SMILES: CCNC1=c2[nH]cc(Br)c2=NC(Nc2ccc(N3CCN(C)CC3)cc2OC)N1] | MS (ESI) m/z: 460 [M + H]⁺. |

TABLE 4-continued

Structure and identification of compounds IQ-IT

| ID | Structure | NMR and/or MS data |
|---|---|---|
| IR-5 | 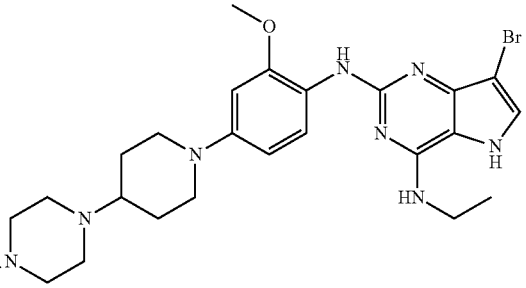 | ¹H-NMR (600 MHz, DMSO-d₆) δ 12.44 (d, J = 3.2 Hz, 1H), 9.11 (t, J = 5.3 Hz, 1H), 8.96 (s, 1H), 8.03 (d, J = 8.8 Hz, 1H), 7.73 (d, J = 3.1 Hz, 1H), 6.78 (d, J = 2.6 Hz, 1H), 6.64 (dd, J = 9.0, 2.5 Hz, 1H), 3.90 (s, 3H), 3.89-3.84 (m, 2H), 3.65-3.33 (m, 8H), 3.61-3.51 (m, 2H), 3.42-3.31 (m, 1H), 2.88 (s, 3H), 2.78 (t, J = 12.2 Hz, 2H), 2.14 (d, J = 11.8 Hz, 2H), 1.79-1.70 (m, 2H), 1.25 (t, J = 7.3 Hz, 3H). MS (ESI) m/z: 543 [M + H]⁺. |
| IR-6 | 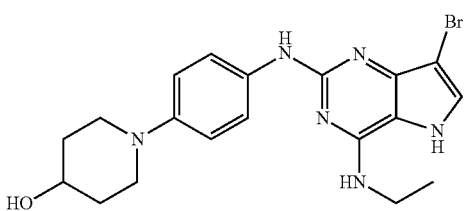 [SMILES: CCNc1nc(Nc2ccc(N3CCC(O)CC3)cc2)nc2c(Br)c[nH]c12] | MS (ESI) m/z: 431 [M + H]⁺. |
| IR-7 | 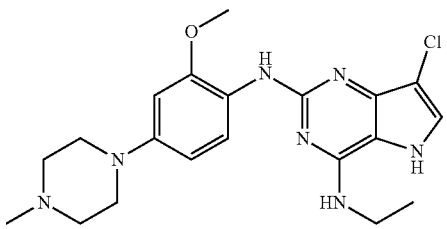 [SMILES: CCNc1nc(Nc2ccc(N3CCN(C)CC3)cc2OC)nc2c(Cl)c[nH]c12] | MS (ESI) m/z: 417 [M + H]⁺. |
| IR-8 | 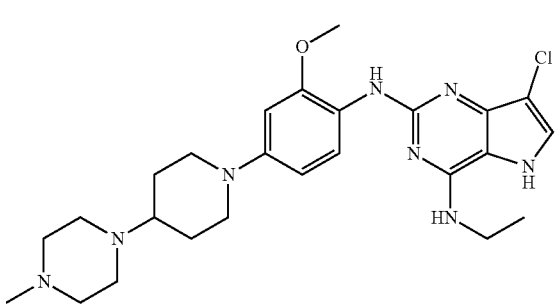 [SMILES: CCNc1nc(Nc2ccc(N3CCC(N4CCN(C)CC4)CC3)cc2OC)nc2c(Cl)c[nH]c12] | ¹H-NMR (600 MHz, DMSO-d₆) δ 10.84-10.79 (m, 1H), 8.48 (d, J = 8.7 Hz, 1H), 7.44 (d, J = 2.2 Hz, 1H), 7.04 (d, J = 5.6 Hz, 2H), 6.62 (d, J = 2.5 Hz, 1H), 6.48 (dd, J = 8.9, 2.5 Hz, 1H), 3.87 (s, 3H), 3.65-3.58 (m, 2H), 3.53-3.46 (m, 2H), 2.58 (td, J = 12.1, 2.3 Hz, 2H), 2.53-2.47 (m, 4H), 2.40-2.21 (m, 5H), 2.15 (s, 3H), 1.83 (d, J = 11.8 Hz, 2H), 1.52 (qd, J = 12.1, 3.9 Hz, 2H), 1.24 (t, J = 7.2 Hz, 3H). MS (ESI) m/z: 499 [M + H]⁺. |
| IR-9 | 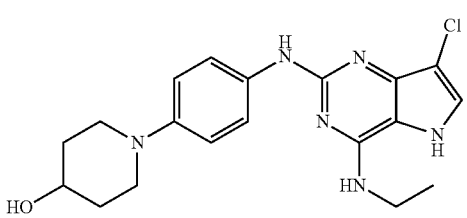 | MS (ESI) m/z: 388 [M + H]⁺. |
| IS-1 | 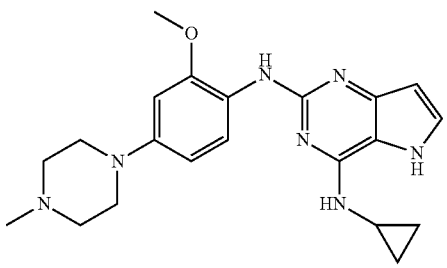

TFA salt | ¹H-NMR (600 MHz; Methanol-d₄): δ 7.94-7.93 (m, 1H), 7.39 (s, 1H), 6.75 (d, J = 2.4 Hz, 1H), 6.64 (dd, J = 8.7, 2.4 Hz, 1H), 6.24 (d, J = 0.5 Hz, 1H), 3.91 (s, 5H), 3.55-3.42 (m, 4H), 3.11 (s, 2H), 3.00 (s, 4H), 2.68 (s, 2H), 0.95 (d, J = 5.9 Hz, 2H), 0.74 (s, 2H). MS (ESI) m/z: 394 [M + H]⁺. |

TABLE 4-continued

Structure and identification of compounds IQ-IT

| ID | Structure | NMR and/or MS data |
|---|---|---|
| IS-2 | 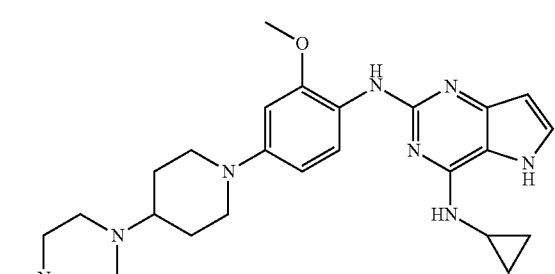 TFA salt | ¹H-NMR (600 MHz; Methanol-d₄): δ 8.27-8.26 (m, 1H), 7.44 (s, 1H), 7.06 (s, 1H), 6.98-6.97 (m, 1H), 6.29 (s, 1H), 3.97 (s, 3H), 3.85 (d, J = 12.3 Hz, 2H), 3.45-3.44 (m, 2H), 3.28-3.24 (m, 3H), 3.11-3.09 (m, 2H), 2.93 (s, 3H), 2.68 (s, 3H), 2.22 (d, J = 12.4 Hz, 2H), 2.02-2.00 (m, 2H), 0.98 (d, J = 6.4 Hz, 2H), 0.76 (s, 2H). MS (ESI) m/z: 477 [M + H]⁺. |
| IS-3 | 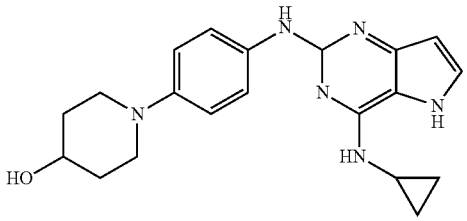 TFA salt | ¹H-NMR (600 MHz; Methanol-d₄): δ 7.99 (d, J = 8.6 Hz, 2H), 7.60-7.58 (m, 2H), 7.46 (d, J = 2.4 Hz, 1H), 6.36 (d, J = 2.5 Hz, 1H), 4.08 (t, J = 3.5 Hz, 1H), 3.80 (dd, J = 13.9, 5.7 Hz, 2H), 3.55-3.52 (m, 2H), 3.10 (ddd, J = 11.2, 7.3, 3.7 Hz, 1H), 2.24 (dq, J = 10.3, 3.8 Hz, 2H), 2.01 (dq, J = 10.6, 3.6 Hz, 2H), 1.00 (d, J = 6.2 Hz, 2H), 0.77 (s, 2H). MS (ESI) m/z: 365 [M + H]⁺. |
| IS-4 | 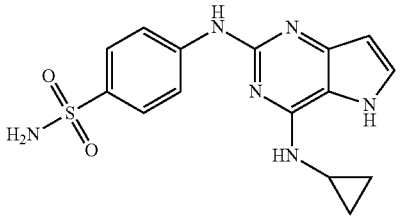 [SMILES: NS(=O)(=O)c1ccc(Nc2nc(NC3CC3)c3[nH]ccc3n2)cc1] | MS (ESI) m/z: 345 [M + H]⁺. |
| IS-5 | 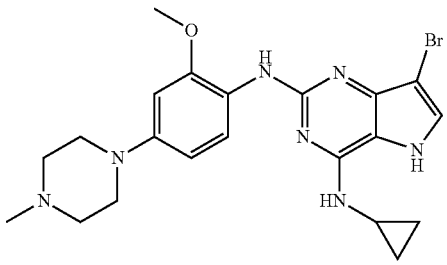 [SMILES: COc1cc(N2CCN(C)CC2)ccc1Nc1nc(NC2CC2)c2[nH]cc(Br)c2n1] | MS (ESI) m/z: 472 [M + H]⁺. |
| IS-6 | 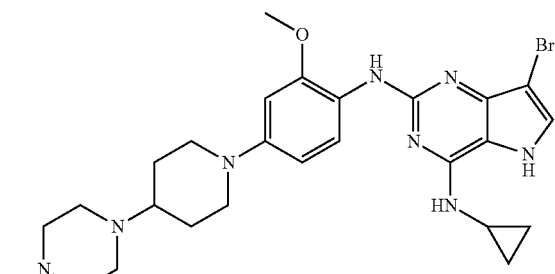 | ¹H NMR (600 MHz, DMSO-d₆) δ 10.95 (s, 1H), 8.63 (d, J = 8.8 Hz, 1H), 7.48 (s, 1H), 7.41 (d, J = 3.1 Hz, 1H), 7.10 (s, 1H), 6.64 (d, J = 2.5 Hz, 1H), 6.50 (dd, J = 8.9, 2.5 Hz, 1H), 3.89 (s, 3H), 3.65 (d, J = 12.0 Hz, 2H), 3.40-3.21 (m, 4H), 2.93 (dq, J = 7.0, 3.4 Hz, 1H), 2.87-2.67 (m, 5H), 2.61 (td, J = 12.2, 2.3 Hz, 2H), 2.46 (s, 3H), 1.92-1.84 (m, 2H), 1.56 (d, J = 11.8 Hz, 2H), 0.86-0.81 (m, 2H), 0.58-0.53 (m, 2H). MS (ESI) m/z: 555 [M + H]⁺. |

TABLE 4-continued
Structure and identification of compounds IQ-IT
| ID | Structure | NMR and/or MS data |
|---|---|---|
| IS-7 | 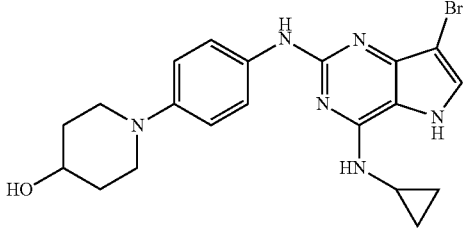 [SMILES: OC1CCN(c2ccc(Nc3nc(NC4CC4)c4[nH]cc(Br)c4n3)cc2)CC1] | MS (ESI) m/z: 443 [M + H]$^+$. |
| IS-8 | 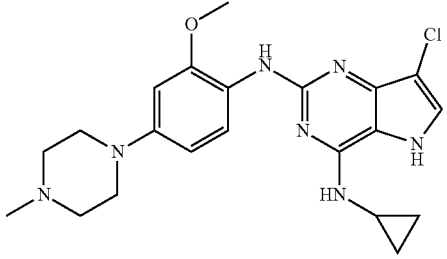 [SMILES: COc1cc(N2CCN(C)CC2)ccc1Nc1nc(NC2CC2)c2[nH]cc(Cl)c2n1] | MS (ESI) m/z: 429 [M + H]$^+$. |
| IS-9 | 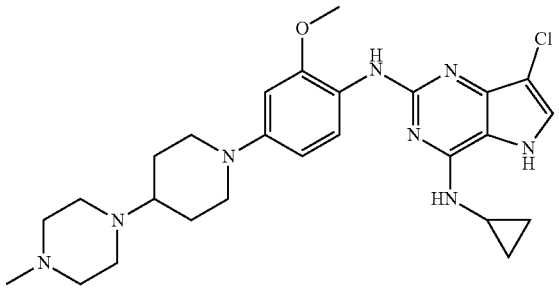 [SMILES: COc1cc(N2CCC(N3CCN(C)CC3)CC2)ccc1Nc1nc(NC2CC2)c2[nH]cc(Cl)c2n1] | $^1$H NMR (600 MHz, DMSO-d$_6$) δ 10.69 (d, J = 3.0 Hz, 1H), 8.59 (d, J = 8.8 Hz, 1H), 7.45 (d, J = 2.4 Hz, 1H), 7.30 (d, J = 3.2 Hz, 1H), 7.07 (s, 1H), 6.63 (d, J = 2.5 Hz, 1H), 6.49 (dd, J = 8.9, 2.5 Hz, 1H), 3.88 (s, 3H), 3.64-3.58 (m, 2H), 2.93 (dq, J = 7.0, 3.5 Hz, 1H), 2.59 (td, J = 12.1, 2.3 Hz, 2H), 2.55-2.43 (m, 4H), 2.38-2.21 (m, 5H), 2.15 (s, 3H), 1.83 (d, J = 12.2 Hz, 2H), 1.52 (qd, J = 12.1, 3.9 Hz, 2H), 0.84 (td, J = 6.7, 4.8 Hz, 2H), 0.58-0.51 (m, 2H). MS (ESI) m/z: 511 [M + H]$^+$. |
| IS-10 | 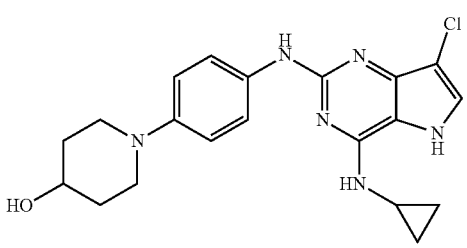 [SMILES: OC1CCN(c2ccc(Nc3nc(NC4CC4)c4[nH]cc(Cl)c4n3)cc2)CC1] | MS (ESI) m/z: 400 [M + H]$^+$. |
| IT-1 | 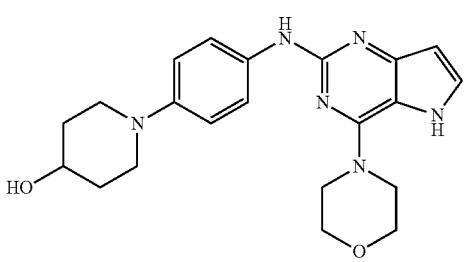 [SMILES: OC1CCN(c2ccc(Nc3nc(N4CCOCC4)c4[nH]ccc4n3)cc2)CC1] | MS (ESI) m/z: 395 [M + H]$^+$. |

Example 5

Synthesis Scheme of Compound IU

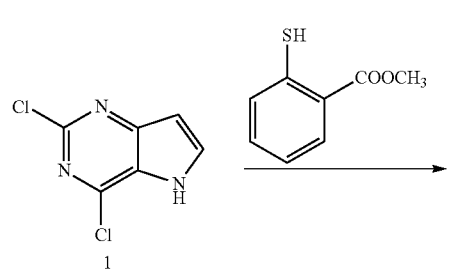

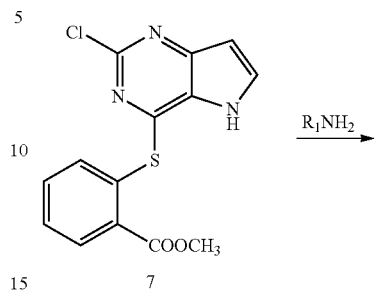

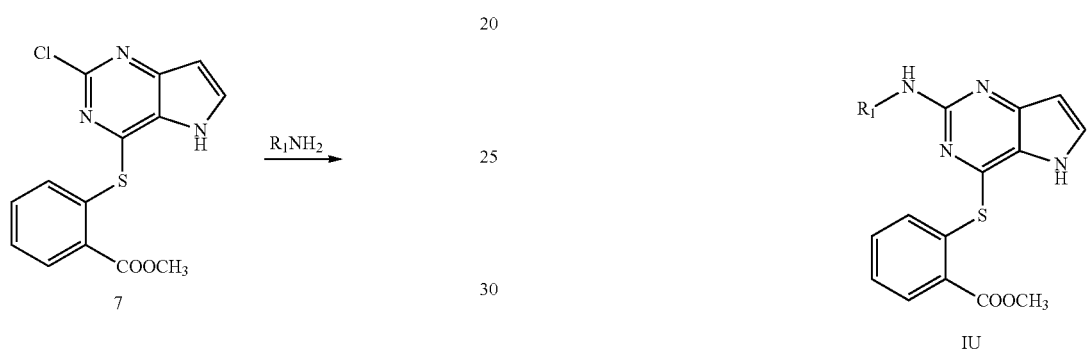

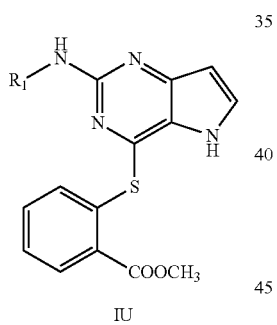

Preparation of Compound 7

Compound 1 (200 mg, 1.06 mmol), methyl thiosalicylate (179 mg, 1.06 mmol) were dissolved in 4 mL 1,4-dioxane. To the solution was added N,N-diisopropylethylamine (0.35 mL, 2.12 mmol). The resulting reaction liquid was heated in 50° C. oil bath with stirring and reacted for 10 hours. The reaction was stopped. To the reaction liquid was added 40 mL of saturated sodium chloride solution, and the liquid was separated. The organic phase was washed twice with saturated sodium chloride solution, dried over anhydride sodium sulfate, concentrated and purified by silica-gel column chromatography (dichloromethane/methanol=5/1) to yield compound 7 (yellow solid, 299.6 mg, yield 88.4%), which was used directly for the reaction in next step.

MS (ESI) m/z: 320 [M+H]$^+$.

Preparation of Compound IU

Process A:

Compound 7 (20.0 mg, 0.06 mmol), aniline (0.06 mmol) were dissolved in 1 mL tert-butanol. To the solution was added trifluoroacetic acid (14 μL, 0.18 mmol). The resulting reaction liquid was heated in 110° C. oil bath with stirring, reacted for 36 hours. The reaction was stopped. To the reaction liquid was added 10 mL of saturated sodium bicarbonate solution, and the liquid was separated. The organic phase was washed twice with saturated sodium chloride solution, dried over anhydride sodium sulfate, concentrated and purified by silica-gel column chromatography (dichloromethane/methanol) to yield compound IU.

Process B:

Compound 7 (20.0 mg, 0.06 mmol), aniline (0.06 mmol) were dissolved in 1 mL tert-butanol. To the solution was added trifluoroacetic acid (14 μL, 0.18 mmol). The resulting reaction liquid was heated in 110° C. oil bath with stirring and reacted for 36 hours. The reaction was stopped. The reaction liquid was concentrated and purified by reversed-phase preparative HPLC (with 0.35% trifluoroacetic acid aqueous solution and methanol as mobile phase), and concentrated in vacuum to yield compound IU.

TABLE 5

Structure and identification of compound IU

| ID | Structure | NMR and/or MS data |
|---|---|---|
| IU-1 | 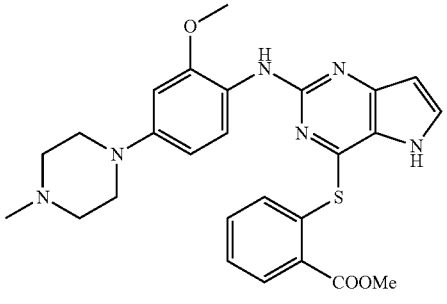<br>TFA salt | $^1$H-NMR (600 MHz; Methanol-d$_4$): δ 8.03-8.01 (m, 1H), 7.78 (s, 1H), 7.74 (d, J = 2.9 Hz, 1H), 7.67-7.66 (m, 2H), 7.07-7.06 (m, 1H), 6.68-6.67 (m, 1H), 6.43 (d, J = 2.9 Hz, 1H), 3.93-3.85 (m, 2H), 3.81 (s, 3H), 3.78 (s, 3H), 3.66-3.64 (m, 2H), 3.24 (dd, J = 1.2, 0.4 Hz, 2H), 3.12-3.06 (m, 2H), 3.00 (s, 3H). MS (ESI) m/z: 505 [M + H]$^+$. |
| IU-2 | 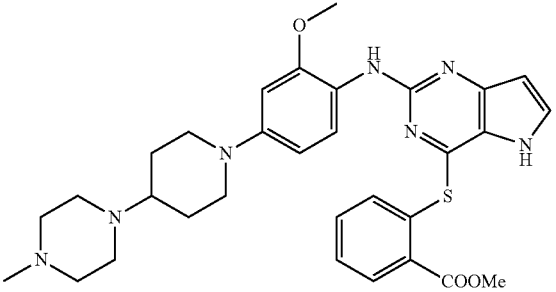 [SMILES: COC(=O)c1ccccc1Sc1nc(Nc2ccc(N3CCC(N4CCN(C)CC4)CC3)cc2OC)nc2cc[nH]c12] | $^1$H-NMR (600 MHz; Methanol-d$_4$): δ 8.01-8.00 (m, 1H), 7.67-7.66 (m, 1H), 7.61-7.58 (m, 3H), 7.55-7.54 (m, 1H), 6.62 (d, J = 2.5 Hz, 1H), 6.34 (d, J = 3.1 Hz, 1H), 6.25 (dd, J = 8.8, 2.5 Hz, 1H), 3.87 (d, J = 5.8 Hz, 3H), 3.76 (s, 3H), 3.59 (d, J = 12.4 Hz, 2H), 2.67-2.62 (m, 9H), 2.33-2.32 (m, 5H), 2.02-2.00 (m, 2H), 1.68-1.66 (m, 2H). MS (ESI) m/z: 588 [M + H]$^+$. |
| IU-3 | 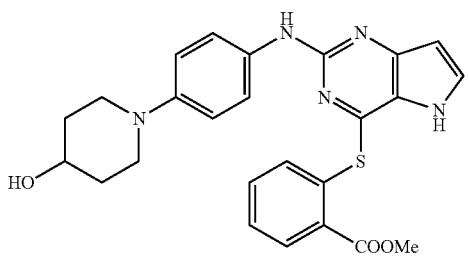<br>TFA salt | $^1$H-NMR (600 MHz; Methanol-d$_4$): δ 8.07 (dd, J = 7.7, 1.5 Hz, 1H), 7.82-7.70 (m, 4H), 7.33 (d, J = 8.9 Hz, 2H), 7.24 (d, J = 9.0 Hz, 2H), 6.53 (d, J = 3.0 Hz, 1H), 4.07-4.06 (m, 1H), 3.77 (s, 3H), 3.76-3.73 (m, 2H), 3.46-3.42 (m, 2H), 2.23-2.19 (m, 2H), 1.99-1.96 (m, 2H). MS (ESI) m/z: 476 [M + H]$^+$. |
| IU-4 | 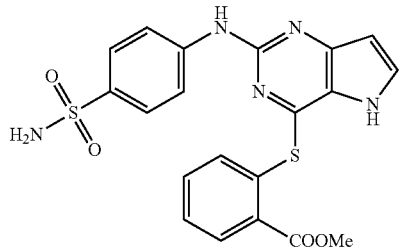<br>TFA salt | $^1$H-NMR (600 MHz; Methanol-d$_4$): δ 8.06-8.04 (m, 1H), 7.92-7.90 (m, 1H), 7.79-7.76 (m, 3H), 7.71-7.69 (m, 1H), 7.59-7.58 (m, 1H), 7.35-7.33 (m, 1H), 7.11-7.10 (m, 1H), 6.53 (dd, J = 1.7, 1.2 Hz, 1H), 3.75 (s, 3H). MS (ESI) m/z: 456 [M + H]$^+$. |
| IU-5 | 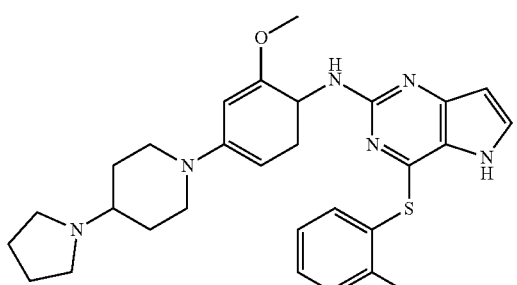 | $^1$H-NMR (600 MHz; Methanol-d$_4$): δ 8.02-8.00 (m, 1H), 7.67-7.66 (m, 1H), 7.63 (d, J = 8.8 Hz, 1H), 7.60-7.59 (m, 2H), 7.56 (d, J = 3.1 Hz, 1H), 6.62 (d, J = 2.5 Hz, 1H), 6.35 (d, J = 3.0 Hz, 1H), 6.26 (dd, J = 8.8, 2.5 Hz, 1H), 3.88 (s, 4H), 3.76 (s, 3H), 3.63-3.60 (m, 2H), 3.11-3.07 (m, 4H), 2.71-2.67 (m, 2H), 2.18-2.15 (m, 2H), 2.00-1.97 (m, 4H), 1.79-1.76 (m, 2H). MS (ESI) m/z: 559 [M + H]$^+$. |

Example 6

Synthesis Scheme of Compound IV

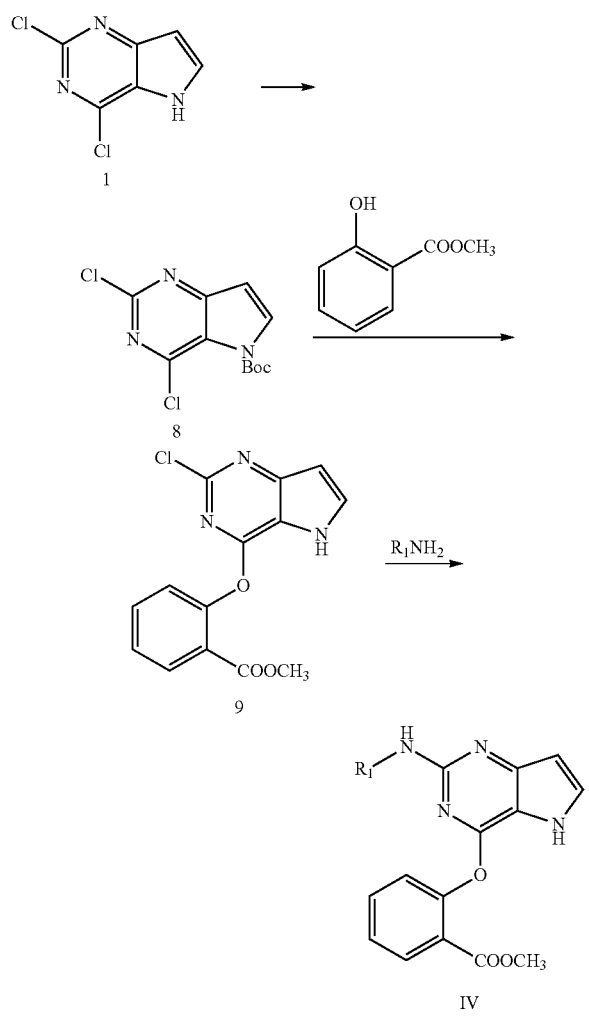

Preparation of Compound 8

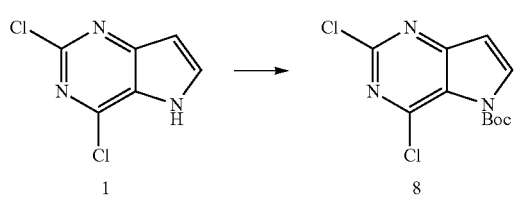 [SMILES: Clc1nc(Cl)c2[nH]ccc2n1 ; CC(C)(C)OC(=O)n1ccc2nc(Cl)nc(Cl)c21]

NaH (480 mg, 20 mmol, 60%), compound 1 (940 mg, 5 mmol) were added to 10 mL of dried dichloromethane in ice bath with stirring for 30 minutes. To the resulting reaction liquid was added (Boc)$_2$O (1.29 mL, 6 mmol). The resulting reaction liquid was stirred in ice bath, and the temperature was slowly elevated to room temperature, the reaction liquid was reacted for 4 hours. The reaction was stopped. To the reaction liquid was added 40 mL of saturated ammonium chloride solution and 20 mL of dichloromethane solution, and the liquid was separated. The organic phase was washed twice with saturated sodium chloride solution, dried over anhydride sodium sulfate, concentrated to yield compound 8 (yellow solid, 1.41 mg, yield 97.9%), which was used directly for the reaction in next step.

MS (ESI) m/z: 289 [M+H]$^+$.

Preparation of Compound 9

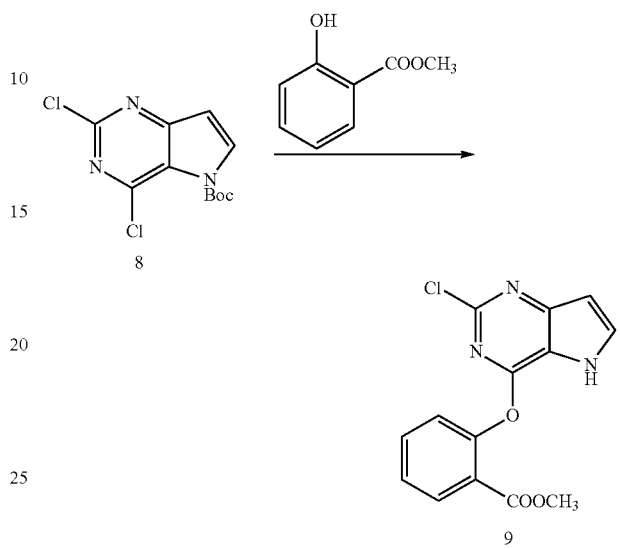

Compound 8 (300 mg, 1.04 mmol), methyl salicylate (237.6 mg, 1.56 mmol) were dissolved in 5 ml DMF. To the solution was added cesium carbonate (1.02 g, 3.12 mmol). The resulting reaction liquid was heated in 60° C. oil bath with stirring, reacted for 16 hours. The reaction was stopped. To the reaction liquid was added 40 mL of saturated sodium chloride solution and 20 mL of ethyl acetate, and the liquid was separated. The organic phase was washed twice with saturated sodium chloride solution, dried over anhydride sodium sulfate, concentrated and purified by silica-gel column chromatography (dichloromethane/methanol=50/1) to yield compound 9 (yellow solid, 65 mg, yield 20.5%), which was used directly for the reaction in next step.

MS (ESI) m/z: 304 [M+H]$^+$.

Preparation of Compound IV

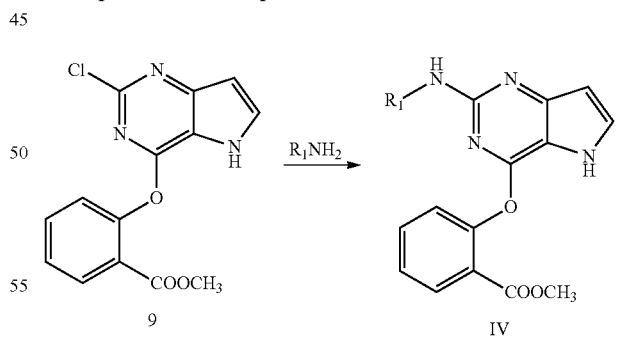

Compound 9 (15.0 mg, 0.05 mmol), aniline (0.05 mmol) were dissolved in 1 ml tert-butanol. To the solution was added trifluoroacetic acid (11 μL, 0.15 mmol). The resulting reaction liquid was heated in 110° C. oil bath with stirring, reacted for 24 hours. The reaction was stopped. The reaction solution was concentrated, purified by reversed-phase preparative HPLC (with 0.35% trifluoroacetic acid aqueous solution and methanol as mobile phase), and concentrated in vacuum to yield compound IV.

TABLE 6

Structure and identification of compound IV

| ID | Structure | NMR and/or MS data |
|---|---|---|
| IV-1 | 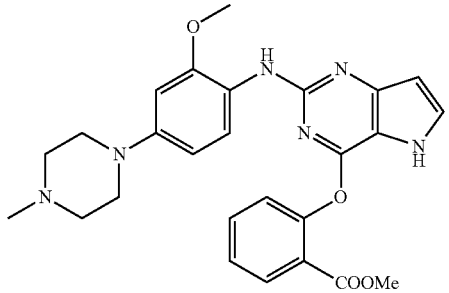<br>TFA salt | $^1$H-NMR (600 MHz; Methanol-d$_4$): δ 8.12 (dd, J = 7.8, 1.4 Hz, 1H), 7.79-7.77 (m, 1H), 7.73 (d, J = 2.7 Hz, 1H), 7.53 (dd, J = 7.6, 0.9 Hz, 1H), 7.47-7.45 (m, 1H), 7.15 (d, J = 8.7 Hz, 1H), 6.72 (s, 1H), 6.46 (d, J = 2.6 Hz, 2H), 3.95-3.88 (m, 2H), 3.84 (s, 3H), 3.72 (s, 3H), 3.66-3.59 (m, 2H), 3.31-3.27 (m, 2H), 3.15-3.11 (m, 2H), 3.00 (s, 3H). MS (ESI) m/z: 489 [M + H]$^+$. |
| IV-2 | 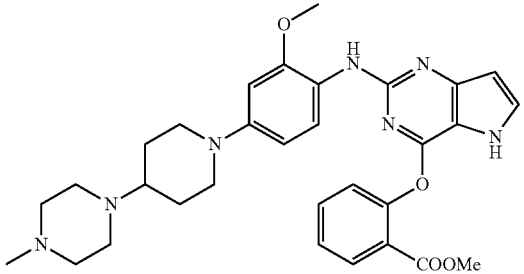<br>TFA salt | $^1$H-NMR (600 MHz; Methanol-d$_4$): δ 8.13 (dd, J = 7.8, 1.4 Hz, 1H), 7.80-7.75 (m, 2H), 7.55 (d, J = 6.9 Hz, 1H), 7.53-7.47 (m, 1H), 7.19 (t, J = 4.3 Hz, 1H), 6.86 (s, 1H), 6.61-6.59 (m, 1H), 6.48 (d, J = 2.5 Hz, 1H), 3.96-3.86 (m, 6H), 3.72 (s, 3H), 3.44-3.43 (m, 4H), 3.11-3.04 (m, 4H), 2.92 (d, J = 3.5 Hz, 5H), 2.19 (d, J = 12.4 Hz, 2H), 1.91-1.89 (m, 2H). MS (ESI) m/z: 572 [M + H]$^+$. |
| IV-3 | 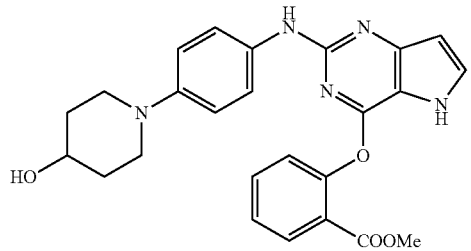<br>TFA salt | $^1$H-NMR (600 MHz; Methanol-d$_4$): δ 8.16-8.15 (m, 1H), 7.82 (t, J = 5.4 Hz, 2H), 7.60-7.57 (m, 1H), 7.49 (d, J = 8.1 Hz, 1H), 7.34-7.33 (m, 2H), 7.25 (d, J = 8.7 Hz, 2H), 6.58 (d, J = 2.1 Hz, 1H), 4.02 (s, 1H), 3.70 (d, J = 16.1 Hz, 5H), 3.38-3.35 (m, 2H), 2.19-2.16 (m, 2H), 1.93-1.92 (m, 2H). MS (ESI) m/z: 460 [M + H]$^+$. |
| IV-4 | 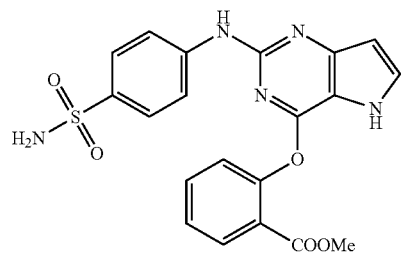<br>TFA salt | $^1$H-NMR (600 MHz; Methanol-d$_4$): δ 8.18-8.17 (m, 1H), 7.85 (s, 2H), 7.62-7.61 (m, 3H), 7.50-7.49 (m, 1H), 7.37 (d, J = 5.7 Hz, 2H), 6.61 (s, 1H), 3.68 (s, 3H). MS (ESI) m/z: 440 [M + H]$^+$. |

2. The formulas of compound II
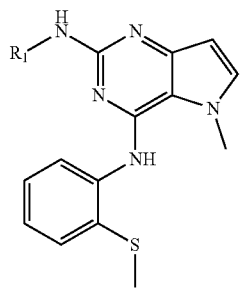 IIA
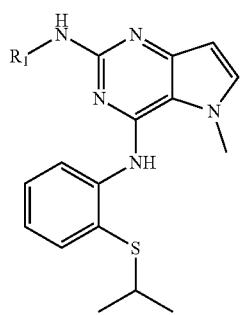 IIB
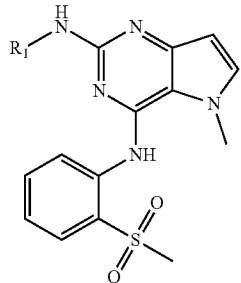 IIC
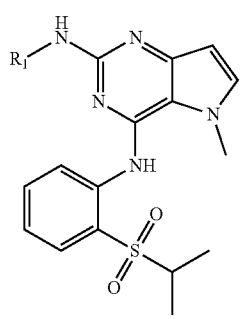 IID
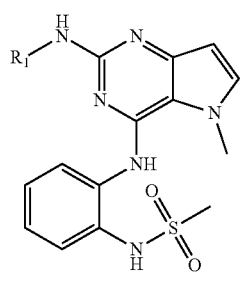 IIE
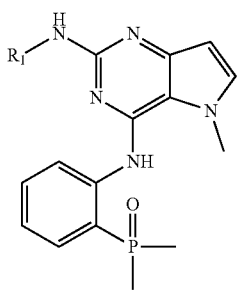 IIF
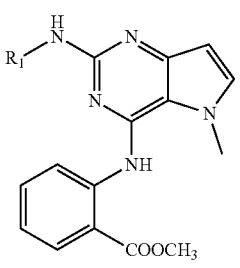 IIG
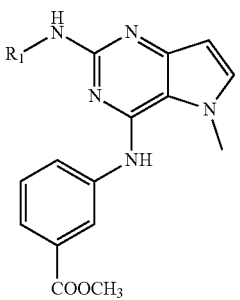 IIH
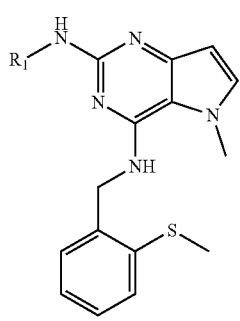 III
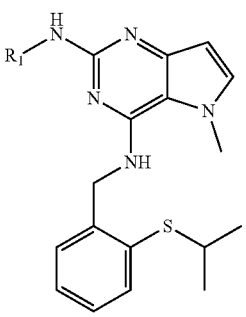 IIJ

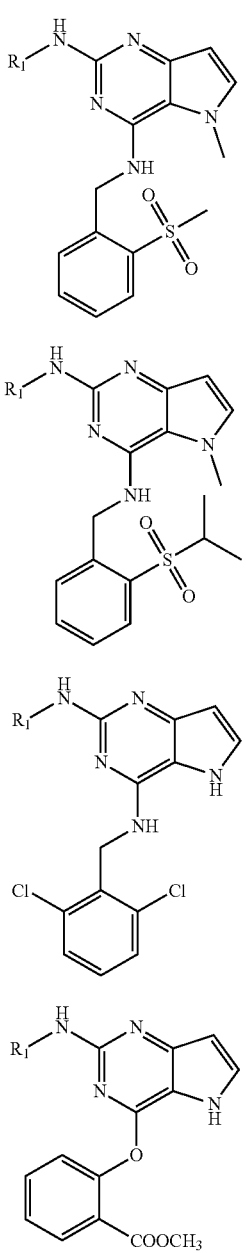

Example 7

Synthesis Scheme of Compound IIA

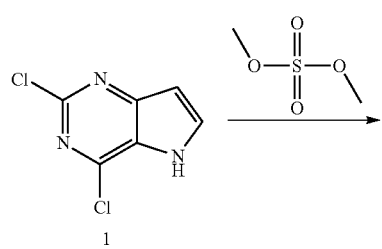

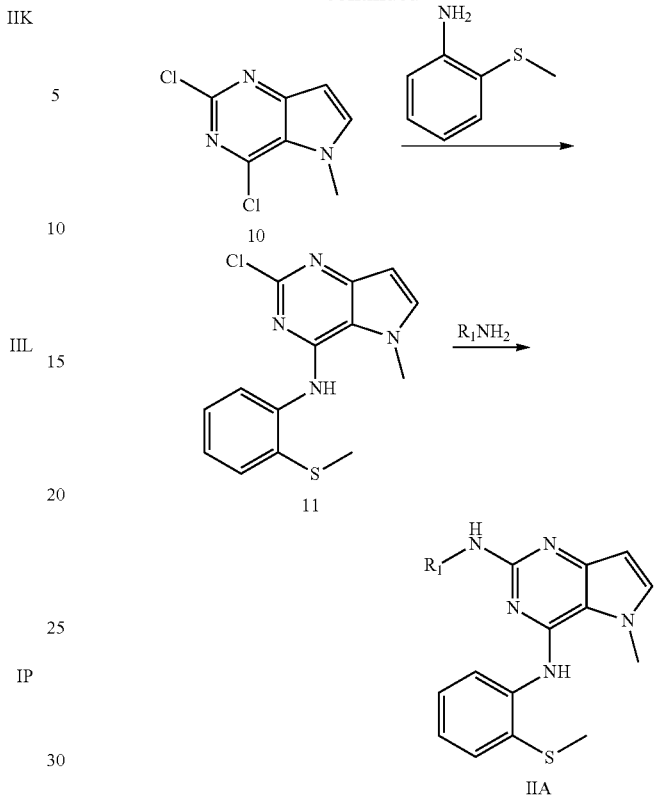

Preparation of Compound 10

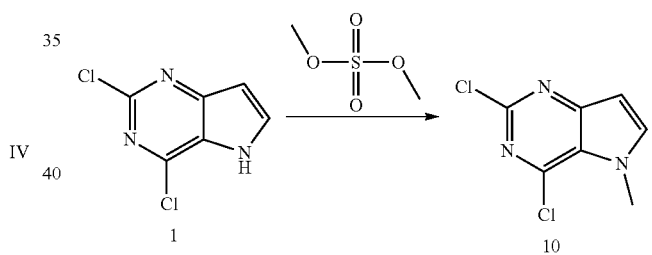

Compound 1 (100 mg, 0.53 mmol), cesium carbonate (350 mg, 1.06 mmol) were dissolved in 1 ml DMF. To the solution was added dimethyl sulfate (1 mL) in nitrogen atmosphere. The resulting reaction liquid was stirred at room temperature for 5 hours. The reaction was stopped. To the reaction liquid was added slowly 50 mL of water. After the system was cooled, added ethyl acetate, and the liquid was separated. The organic phase was washed twice with saturated sodium chloride solution, dried over anhydride sodium sulfate, concentrated and purified by silica-gel column chromatography (petroleum ether/ethyl acetate=2/1) to yield compound 10 (white solid, 76.3 mg, yield 70%), which was used directly for the reaction in next step.

MS (ESI) m/z: 203 [M+H]$^+$.

Preparation of Compound 11

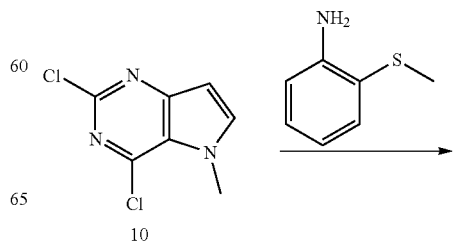

-continued

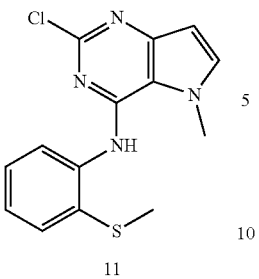

11

-continued

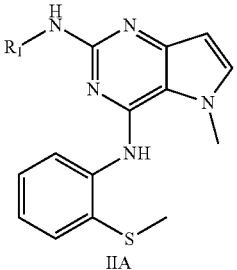

IIA

Compound 10 (101 mg. 0.5 mmol) was dissolved in N,N-dimethylformamide (4 mL), added NaH (60 mg, 2.5 mmol) in ice bath, stirred for 5-10 min, and then added 2-methylthioaniline (69.6 mg, 0.5 mmol), stirred at room temperature, reacted overnight until compound 10 was reacted completely (LC-MS tracking). The reaction was stopped. To the system was added ice to quench NaH, added ethyl acetate, and the liquid was separated. The organic phase was washed twice with saturated sodium chloride solution, dried over anhydride sodium sulfate, concentrated and purified by silica-gel column chromatography (petroleum ether/ethyl acetate=2/1) to yield compound 11 (solid, 64.7 mg, yield 42.5%), which was used directly for the reaction in next step.

MS (ESI) m/z: 305 [M+H]+.

Preparation of Compound IIA

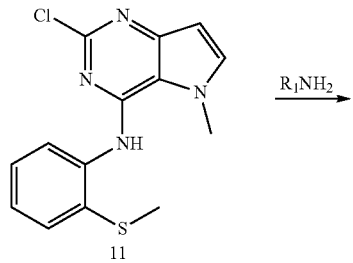

Process A:

Compound 11 (30.0 mg, 0.09 mmol), aniline (0.072 mmol) were dissolved in 1 mL tert-butanol. To the solution was added 2-dicyclohexylphosphino-2',4',6'-triisopropylbiphenyl (7.7 mg, 0.016 mmol), tris(dibenzylideneacetone)dipalladium (9.9 mg, 0.011 mmol), potassium carbonate (37 mg, 0.27 mmol). In nitrogen atmosphere, the resulting reaction liquid was heated in 120° C. oil bath with stirring until aniline was reacted completely (LC-MS and TLC tracking). The reaction was stopped. To the reaction liquid was added methanol and dichloromethane. The system was filtered, concentrated and purified by silica-gel column chromatography (dichloromethane/methanol) to yield compound IIA.

Process B:

Compound 11 (30.0 mg, 0.09 mmol), aniline (0.072 mmol) were dissolved in 1 mL tert-butanol. To the solution was added 2-dicyclohexylphosphino-2',4',6'-triisopropylbiphenyl (7.7 mg, 0.016 mmol), tris(dibenzylideneacetone)dipalladium (9.9 mg, 0.011 mmol), potassium carbonate (37 mg, 0.27 mmol). In nitrogen atmosphere, the resulting reaction liquid was heated in 120° C. oil bath with stirring until aniline was reacted completely (LC-MS and TLC tracking). The reaction was stopped. To the reaction liquid was added methanol and dichloromethane. The system was filtered, concentrated and purified by reversed-phase preparative HPLC (with 0.35% trifluoroacetic acid aqueous solution and methanol as mobile phase), and concentrated in vaccum to yield compound IIA.

Compounds IIB, IIC, IID', IIE, IIF were synthesized using similar processes.

TABLE 7

Structure and identification of compound IIA-IIF

| ID | Structure | NMR and/or MS data |
|---|---|---|
| IIA-1 | 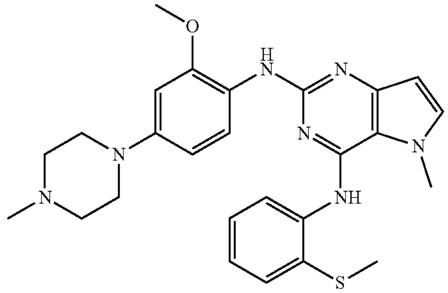 [SMILES: COc1cc(N2CCN(C)CC2)ccc1Nc1nc(Nc2ccccc2SC)c2c(ccn2C)n1] | $^{1}$H NMR (600 MHz, Chloroform-d) δ 8.58 (dd, J = 8.3, 1.3 Hz, 1H), 8.31 (d, J = 8.6 Hz, 1H), 8.18 (s, 1H), 7.53 (dd, J = 7.7, 1.5 Hz, 1H), 7.32 (ddd, J = 8.5, 7.3, 1.6 Hz, 1H), 7.17 (s, 1H), 7.03 (td, J = 7.5, 1.4 Hz, 1H), 7.01 (d, J = 3.0 Hz, 1H), 6.58-6.51 (m, 2H), 6.29 (d, J = 3.0 Hz, 1H), 4.13 (s, 3H), 3.86 (s, 3H), 3.19-3.13 (m, 4H), 2.61 (t, J = 4.9 Hz, 4H), 2.40 (s, 3H), 2.37 (s, 3H). MS (ESI) m/z: 490 [M + H]+. |

TABLE 7-continued

Structure and identification of compound IIA-IIF

| ID | Structure | NMR and/or MS data |
|---|---|---|
| IIA-2 | 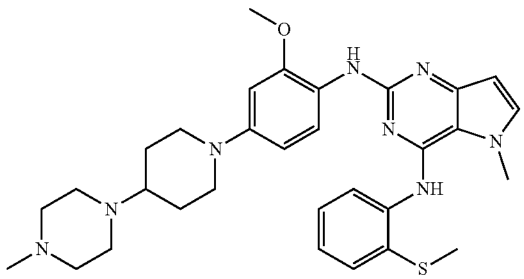 [SMILES: COc1cc(N2CCC(N3CCN(C)CC3)CC2)ccc1Nc1nc(Nc2ccccc2SC)c2c(ccn2C)n1] | $^1$H NMR (600 MHz, Chloroform-d) δ 8.57 (dd, J = 8.3, 1.3 Hz, 1H), 8.28 (d, J = 8.7 Hz, 1H), 8.18 (s, 1H), 7.53 (dd, J = 7.7, 1.5 Hz, 1H), 7.31 (ddd, J = 8.5, 7.4, 1.6 Hz, 1H), 7.21 (s, 1H), 7.03 (td, J = 7.5, 1.3 Hz, 1H), 7.00 (d, J = 3.0 Hz, 1H), 6.55 (d, J = 2.5 Hz, 1H), 6.52 (dd, J = 8.8, 2.5 Hz, 1H), 6.29 (d, J = 3.0 Hz, 1H), 4.13 (s, 3H), 3.86 (s, 3H), 3.65-3.59 (m, 2H), 2.68 (td, J = 12.3, 2.5 Hz, 6H), 2.56 (s, 2H), 2.45-2.41 (m, 1H), 2.39 (s, 3H), 2.34 (s, 3H), 1.98-1.92 (m, 2H), 1.78-1.68 (m, 2H), 1.25 (d, J = 1.4 Hz, 2H). MS (ESI) m/z: 573 [M + H]$^+$. |
| IIA-3 | 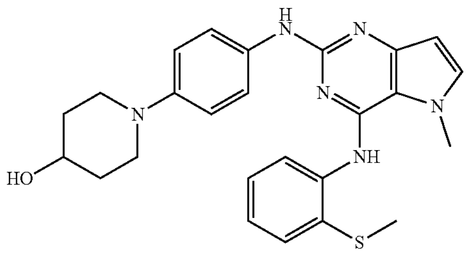 [SMILES: CSc1ccccc1Nc1nc(Nc2ccc(N3CCC(O)CC3)cc2)nc2ccn(C)c12] | $^1$H NMR (600 MHz, DMSO-d$_6$) δ 8.36 (s, 1H), 8.2454 (s, 1H), 8.12 (d, J = 8.0 Hz, 1H), 7.51-7.44 (m, 3H), 7.3433 (d, J = 3.0 Hz, 1H), 7.29 (td, J = 7.7, 1.6 Hz, 1H), 7.20 (td, J = 7.5, 1.4 Hz, 1H), 6.73 (d, J = 9.0 Hz, 2H), 6.12 (d, J = 2.9 Hz, 1H), 4.12 (s, 3H), 3.57 (tq, J = 8.6, 4.0 Hz, 1H), 3.37 (s, 2H), 2.69 (ddd, J = 12.6, 10.2, 2.9 Hz, 2H), 2.40 (s, 3H), 1.85-1.78 (m, 2H), 1.49 (dtd, J = 13.0, 9.6, 3.8 Hz, 2H). MS (ESI) m/z: 461 [M + H]$^+$. |
| IIA-4 | 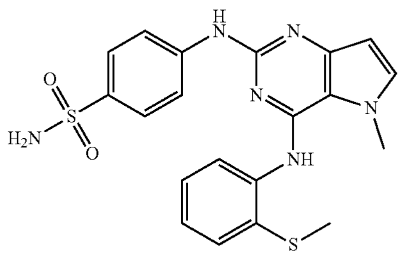 [SMILES: CSc1ccccc1Nc1nc(Nc2ccc(S(N)(=O)=O)cc2)nc2ccn(C)c12] | $^1$H NMR (600 MHz, DMSO-d$_6$) δ 9.16 (s, 1H), 8.37 (s, 1H), 7.84 (d, J = 7.3 Hz, 1H), 7.72-7.65 (m, 2H), 7.47 (dt, J = 7.9, 2.4 Hz, 3H), 7.42 (dd, J = 3.2, 1.6 Hz, 1H), 7.31 (tt, 5.2, 1.9 Hz, 2H), 7.06 (s, 2H), 6.20 (dd, J = 3.0, 1.6 Hz, 1H), 4.13 (d, J = 1.8 Hz, 3H), 2.39 (d, J = 1.6 Hz, 3H). MS (ESI) m/z: 441 [M + H]$^+$. |
| IIA-5 | 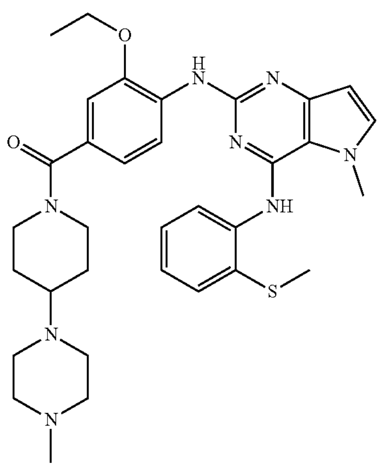 [SMILES: CCOc1cc(C(=O)N2CCC(N3CCN(C)CC3)CC2)ccc1Nc1nc(Nc2ccccc2SC)c2c(ccn2C)n1] | MS (ESI) m/z: 615 [M + H]$^+$. |
| IIA-6 | 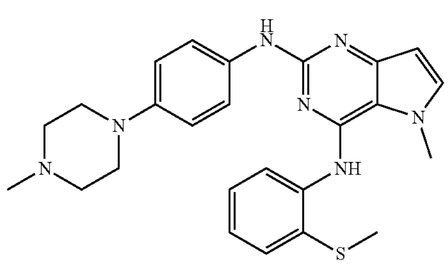 [SMILES: CSc1ccccc1Nc1nc(Nc2ccc(N3CCN(C)CC3)cc2)nc2ccn(C)c12] | $^1$H NMR (600 MHz, Chloroform-d) δ 8.53 (d, J = 8.4 Hz, 1H), 8.27 (s, 1H), 7.53 (dt, J = 7.8, 1.5 Hz, 1H), 7.49 (dd, J = 8.8, 1.4 Hz, 2H), 7.30-7.25 (m, 1H), 7.24 (s, 1H), 7.06-6.99 (m, 2H), 6.93-6.88 (m, 2H), 6.29 (dd, J = 3.1, 1.3 Hz, 1H), 4.15 (d, J = 1.3 Hz, 3H), 3.18 (t, J = 4.9 Hz, 4H), 2.63 (t, J = 4.8 Hz, 4H), 2.40 (d, J = 1.3 Hz, 3H), 2.38 (d, J = 1.2 Hz, 3H). MS (ESI) m/z: 460 [M + H]$^+$. |

TABLE 7-continued

Structure and identification of compound IIA-IIF

| ID | Structure | NMR and/or MS data |
| --- | --- | --- |
| IIB-1 | 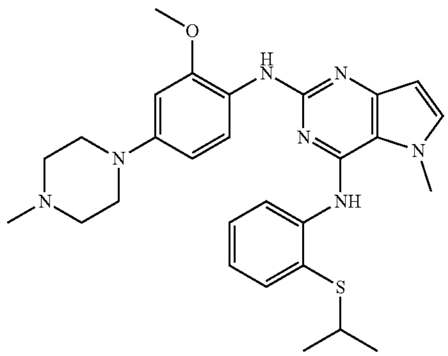 [SMILES: COc1cc(N2CCN(C)CC2)ccc1Nc1nc(Nc2ccccc2SC(C)C)c2c(ccn2C)n1] | ¹H NMR (600 MHz, Chloroform-d) δ 8.65 (dd, J = 8.4, 1.3 Hz, 1H), 8.61 (s, 1H), 8.20 (d, J = 8.5 Hz, 1H), 7.58 (s, 1H), 7.54 (dd, J = 7.7, 1.6 Hz, 1H), 7.31 (ddd, J = 8.6, 7.3, 1.6 Hz, 1H), 7.03-6.97 (m, 2H), 6.58-6.51 (m, 2H), 6.30 (d, J = 3.0 Hz, 1H), 4.17 (s, 3H), 3.85 (s, 3H), 3.19 (q, J = 6.2, 5.6 Hz, 4H), 3.20-3.13 (m, 1H), 2.71-2.66 (m, 4H), 2.40 (s, 3H), 1.24 (d, J = 6.7 Hz, 6H). MS (ESI) m/z: 518 [M + H]⁺. |
| IIB-2 | 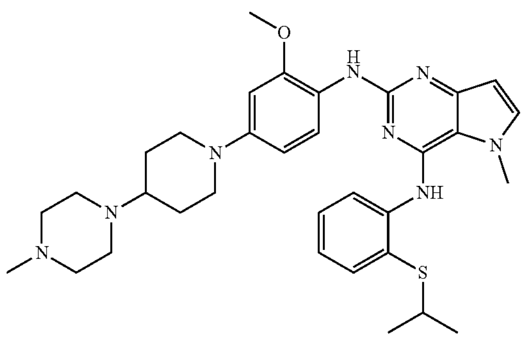 [SMILES: COc1cc(N2CCC(N3CCN(C)CC3)CC2)ccc1Nc1nc(Nc2ccccc2SC(C)C)c2c(ccn2C)n1] | ¹H NMR (600 MHz, Chloroform-d) δ 8.69 (dd, J = 8.5, 1.3 Hz, 1H), 8.57 (s, 1H), 8.28 (d, J = 8.6 Hz, 1H), 7.55 (dd, J = 7.6, 1.6 Hz, 1H), 7.35 (td, J = 8.3, 7.9, 1.6 Hz, 1H), 7.24 (s, 1H), 7.03-6.99 (m, 2H), 6.57-6.52 (m, 2H), 6.30 (dd, J = 3.0, 0.9 Hz, 1H), 4.17 (s, 3H), 3.86 (s, 3H), 3.63 (d, J = 11.9 Hz, 2H), 3.18 (hept, J = 6.8 Hz, 1H), 2.78-2.59 (m, 10H), 2.48-2.41 (m, 1H), 2.37 (s, 3H), 1.97 (d, J = 11.8 Hz, 2H), 1.74 (qd, J = 12.1, 3.9 Hz, 2H), 1.25 (d, J = 6.7, 0.9 Hz, 6H). MS (ESI) m/z: 601 [M + H]⁺. |
| IIB-3 | 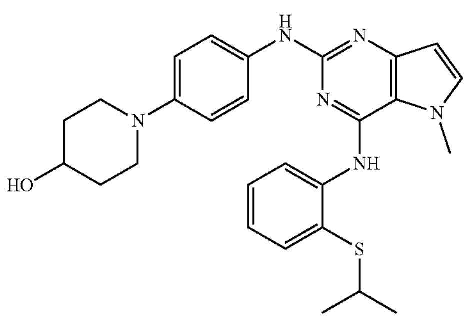 | ¹H NMR (600 MHz, Chloroform-d) δ 8.66-8.61 (m, 2H), 7.53 (dd, J = 7.5, 1.7 Hz, 1H), 7.46 (d, J = 8.3 Hz, 2H), 7.31-7.24 (m, 2H), 7.03-6.97 (m, 2H), 6.90 (d, J = 8.4 Hz, 2H), 6.28 (dd, J = 3.1, 1.3 Hz, 1H), 4.16 (s, 3H), 3.82 (dt, J = 9.1, 4.7 Hz, 1H), 3.47 (dt, J = 10.2, 4.6 Hz, 2H), 3.16 (hept, J = 6.6 Hz, 1H), 2.84 (ddd, J = 12.6, 10.1, 3.3 Hz, 2H), 2.01 (dq, J = 11.9, 3.7 Hz, 2H), 1.76-1.68 (m, 2H), 1.24 (d, J = 6.7 Hz, 6H). MS (ESI) m/z: 489 [M + H]⁺. |
| IIB-4<br>TFA salt | | ¹H NMR (600 MHz, DMSO-d₆) δ 10.45 (s, 1H), 9.52 (s, 1H), 7.73 (s, 1H), 7.65 (dd, J = 8.1, 3.3 Hz, 2H), 7.50 (d, J = 8.8 Hz, 2H), 7.48-7.40 (m, 4H), 7.23 (s, 2H), 6.34 (d, J = 2.9 Hz, 1H), 4.18 (s, 3H), 3.46 (s, 1H), 1.16 (d, J = 6.6 Hz, 6H). MS (ESI) m/z: 469 [M + H]⁺. |

TABLE 7-continued

Structure and identification of compound IIA-IIF

| ID | Structure | NMR and/or MS data |
| --- | --- | --- |
| IIB-5 | 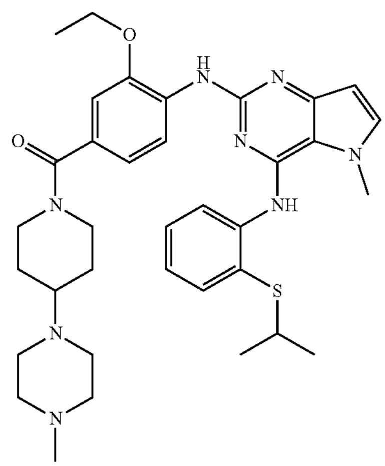 [SMILES: CCOc1cc(C(=O)N2CCC(N3CCN(C)CC3)CC2)ccc1Nc1nc(Nc2ccccc2SC(C)C)c2c(ccn2C)n1] | ¹H NMR (600 MHz, Chloroform-d) δ 8.33 (dd, J = 8.3, 1.3 Hz, 1H), 8.28 (d, J = 8.1 Hz, 1H), 8.24 (s, 1H), 7.24 (dd, J = 7.7, 1.5 Hz, 1H), 7.07-7.03 (m, 1H), 6.94 (s, 1H), 6.74 (d, J = 3.0 Hz, 1H), 6.71 (td, J = 7.4, 1.3 Hz, 1H), 6.65-6.62 (m, 2H), 6.02 (d, J = 2.9 Hz, 1H), 3.87 (s, 3H), 3.81 (q, J = 7.0 Hz, 2H), 2.87 (hept, J = 6.6 Hz, 1H), 2.56 (dd, J = 39.1, 28.5 Hz, 2H), 2.31 (s, 4H), 2.23-2.12 (m, 5H), 1.99 (s, 3H), 1.74 (d, J = 13.7 Hz, 4H), 1.56 (s, 2H), 1.17 (t, J = 6.9 Hz, 3H), 0.93 (d, J = 6.7 Hz, 6H). MS (ESI) m/z: 643 [M + H]⁺. |
| IIC-1 | 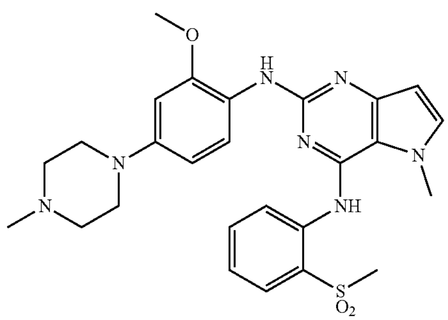 [SMILES: COc1cc(N2CCN(C)CC2)ccc1Nc1nc(Nc2ccccc2S(C)(=O)=O)c2c(ccn2C)n1] | ¹H NMR (600 MHz, Chloroform-d) δ 9.04 (s, 1H), 8.42 (d, J = 8.4 Hz, 1H), 8.27 (d, J = 8.7 Hz, 1H), 7.95 (dd, J = 8.0, 1.6 Hz, 1H), 7.63 (td, J = 7.9, 1.6 Hz, 1H), 7.25-7.21 (m, 2H), 7.07 (d, J = 2.9 Hz, 1H), 6.54 (d, J = 2.5 Hz, 1H), 6.45 (dd, J = 8.7, 2.5 Hz, 1H), 6.31 (d, J = 2.9 Hz, 1H), 4.05 (s, 3H), 3.85 (s, 3H), 3.15 (t, J = 5.0 Hz, 4H), 3.08 (s, 3H), 2.62 (t, J = 4.8 Hz, 4H), 2.37 (s, 3H). MS (ESI) m/z 522 [M + H]⁺. |
| IIC-2 | 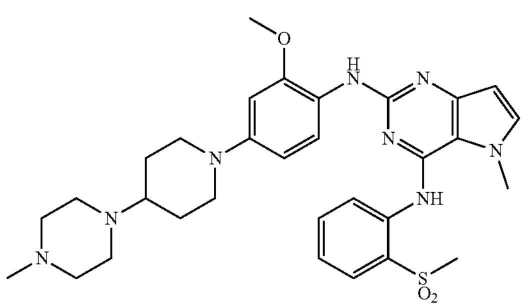 [SMILES: COc1cc(N2CCC(N3CCN(C)CC3)CC2)ccc1Nc1nc(Nc2ccccc2S(C)(=O)=O)c2c(ccn2C)n1] | ¹H NMR (600 MHz, Chloroform-d) δ 9.03 (s, 1H), 8.42 (dd, J = 8.4, 1.1 Hz, 1H), 8.26 (d, J = 8.8 Hz, 1H), 7.96 (dd, J = 8.1, 1.6 Hz, 1H), 7.63 (ddd, J = 8.7, 7.3, 1.6 Hz, 1H), 7.25-7.21 (m, 2H), 7.07 (d, J = 3.0 Hz, 1H), 6.54 (d, J = 2.5 Hz, 1H), 6.44 (dd, J = 8.8, 2.5 Hz, 1H), 6.31 (d, J = 3.0 Hz, 1H), 4.06 (s, 3H), 3.85 (s, 3H), 3.64-3.56 (m, 2H), 3.08 (s, 3H), 2.74-2.63 (m, 8H), 2.59 (s, 3H), 2.42 (ddd, J = 11.5, 7.9, 3.6 Hz, 1H), 2.35 (s, 3H), 1.97-1.94 (m, 2H), 1.72 (qd, J = 12.1, 3.9 Hz, 2H). MS (ESI) m/z: 605 [M + H]⁺. |
| IIC-3 | 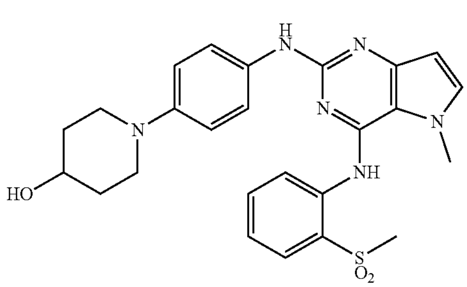 | ¹H NMR (600 MHz, Chloroform-d) δ 9.07 (s, 1H), 8.41 (dd, J = 8.4, 1.1 Hz, 1H), 7.94 (dd, J = 8.0, 1.6 Hz, 1H), 7.59 (ddd, J = 8.6, 7.3, 1.7 Hz, 1H), 7.49-7.40 (m, 2H), 7.25-7.18 (m, 1H), 7.07 (d, J = 3.0 Hz, 1H), 6.91-6.80 (m, 3H), 6.29 (d, J = 3.0 Hz, 1H), 4.05 (s, 3H), 3.80 (hept, J = 8.8, 4.1 Hz, 1H), 3.47-3.38 (m, 2H), 3.07 (s, 3H), 2.82 (ddd, J = 12.6, 9.1, 3.0 Hz, 2H), 2.03-1.95 (m, 2H), 1.70 (dtd, J = 13.1, 9.5, 3.8 Hz, 2H). MS (ESI) m/z: 493 [M + H]⁺. |

TABLE 7-continued

Structure and identification of compound IIA-IIF

| ID | Structure | NMR and/or MS data |
| --- | --- | --- |
| IIC-4 | 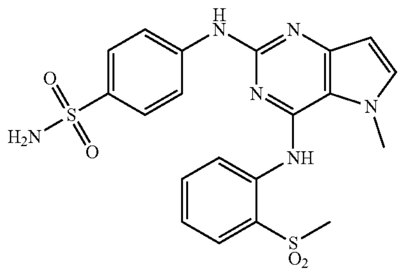 | $^1$H NMR (600 MHz, DMSO-d$_6$) δ 9.33 (s, 1H), 9.03 (s, 1H), 8.48 (d, J = 8.3 Hz, 1H), 7.93 (dd, J = 8.1, 1.6 Hz, 1H), 7.88 (d, J = 8.7 Hz, 2H), 7.79-7.75 (m, 1H), 7.63-7.59 (m, 2H), 7.52 (d, J = 3.0 Hz, 1H), 7.38 (t, J = 7.4 Hz, 1H), 7.10 (s, 2H), 6.30 (d, J = 3.0 Hz, 1H), 4.09 (s, 3H), 3.29 (s, 3H). MS (ESI) m/z: 473 [M + H]$^+$. |
| IIC-5 | 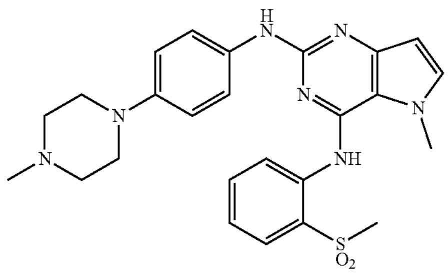 [SMILES: CN1CCN(c2ccc(Nc3nc(Nc4ccccc4S(C)(=O)=O)c4c(ccn4C)n3)cc2)CC1] | $^1$H NMR (600 MHz, Chloroform-d) δ 9.06 (s, 1H), 8.44-8.37 (m, 1H), 7.96-7.90 (m, 1H), 7.57 (t, J = 8.6 Hz, 1H), 7.45 (dd, J = 8.9, 2.8 Hz, 2H), 7.20 (td, J = 7.7, 2.7 Hz, 1H), 7.06 (d, J = 3.1 Hz, 1H), 6.94- 6.82 (m, 3H), 6.28 (t, J = 2.9 Hz, 1H), 4.05-4.01 (m, 3H), 3.13 (dd, J = 6.0, 3.1 Hz, 4H), 3.08-3.00 (m, 3H), 2.59 (dd, J = 7.1, 3.4 Hz, 4H), 2.42-2.30 (m, 3H). MS (ESI) m/z: 492 [M + H]$^+$. |
| IIC-6 | 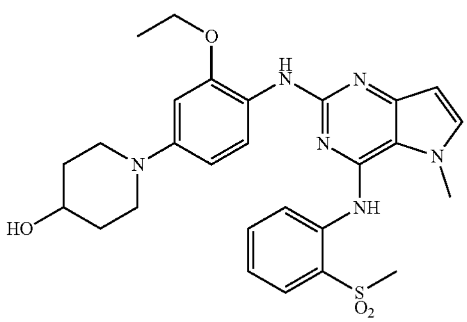 [SMILES: CCOc1cc(N2CCC(O)CC2)ccc1Nc1nc(Nc2ccccc2S(C)(=O)=O)c2c(ccn2C)n1] | $^1$H NMR (600 MHz, Chloroform-d) δ 9.06 (s, 1H), 8.43 (dd, J = 8.4, 1.1 Hz, 1H), 8.22 (d, J = 8.7 Hz, 1H), 7.96 (dd, J = 8.0, 1.6 Hz, 1H), 7.62 (ddd, J = 8.6, 7.3, 1.6 Hz, 1H), 7.34 (s, 1H), 7.26-7.21 (m, 1H), 7.08 (d, J = 3.0 Hz, 1H), 6.56 (d, J = 2.5 Hz, 1H), 6.43 (dd, J = 8.8, 2.6 Hz, 1H), 6.32 (d, J = 3.0 Hz, 1H), 4.09 (t, J = 6.9 Hz, 2H), 4.06 (s, 3H), 3.82 (hept, J = 8.7, 4.1 Hz, 1H), 3.41 (dt, J = 10.6, 4.7 Hz, 2H), 3.09 (s, 3H), 2.87-2.79 (m, 2H), 2.04-1.98 (m, 2H), 1.73 (dtd, J = 13.0, 9.3, 3.7 Hz, 2H), 1.44 (t, J = 6.9 Hz, 3H). MS (ESI) m/z: 537 [M + H]$^+$. |
| IID-1 | 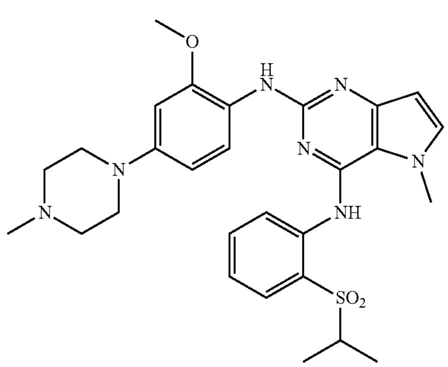 [SMILES: COc1cc(N2CCN(C)CC2)ccc1Nc1nc(Nc2ccccc2S(=O)(=O)C(C)C)c2c(ccn2C)n1] | $^1$H NMR (600 MHz, Chloroform-d) δ 9.27 (s, 1H), 8.42 (dd, J = 8.5, 1.1 Hz, 1H), 8.26 (d, J = 8.8 Hz, 1H), 7.88 (dd, J = 8.0, 1.6 Hz, 1H), 7.61 (ddd, J = 8.6, 7.3, 1.6 Hz, 1H), 7.27-7.19 (m, 2H), 7.07 (d, J = 3.0 Hz, 1H), 6.54 (d, J = 2.5 Hz, 1H), 6.43 (dd, J = 8.8, 2.5 Hz, 1H), 6.31 (d, J = 3.0 Hz, 1H), 4.07 (s, 3H), 3.86 (s, 3H), 3.24 (hept, J = 7.0 Hz, 1H), 3.20-3.15 (m, 4H), 2.68-2.63 (m, 4H), 2.40 (s, 3H), 1.29 (d, J = 6.8 Hz, 6H). MS (ESI) m/z: 550 [M + H]$^+$. |

TABLE 7-continued

Structure and identification of compound IIA-IIF

| ID | Structure | NMR and/or MS data |
| --- | --- | --- |
| IID-2 | 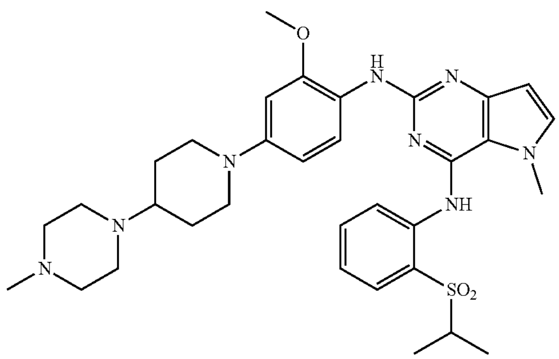 [SMILES: COc1cc(N2CCC(N3CCN(C)CC3)CC2)ccc1Nc1nc(Nc2ccccc2S(=O)(=O)C(C)C)c2c(ccn2C)n1] | $^1$H NMR (600 MHz, Chloroform-d) δ 9.27 (s, 1H), 8.42 (dd, J = 8.4, 1.1 Hz, 1H), 8.25 (d, J = 8.8 Hz, 1H), 7.87 (dd, J = 8.0, 1.6 Hz, 1H), 7.62 (ddd, J = 8.6, 7.3, 1.7 Hz, 1H), 7.23-7.20 (m, 2H), 7.06 (d, J = 3.0 Hz, 1H), 6.55 (d, J = 2.5 Hz, 1H), 6.43 (dd, J = 8.8, 2.6 Hz, 1H), 6.30 (d, J = 3.0 Hz, 1H), 4.07 (s, 3H), 3.86 (s, 3H), 3.62-3.58 (m, 2H), 3.24 (h, 1H), 2.73-2.62 (m, 6H), 2.54 (s, 2H), 2.43-2.36 (m, 1H), 2.32 (s, 3H), 2.20 (s, 2H), 1.95 (d, J = 12.3 Hz, 2H), 1.72 (qd, J = 12.1, 3.9 Hz, 2H), 1.28 (d, J = 6.8 Hz, 6H). MS (ESI) m/z: 633 [M + H]$^+$. |
| IID-3 | 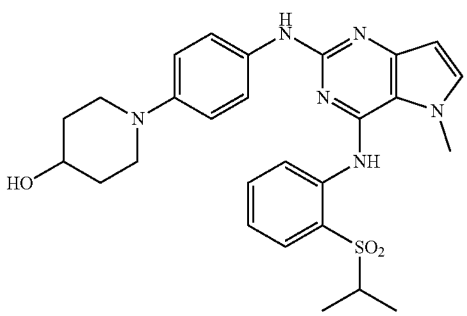 | $^1$H NMR (600 MHz, Chloroform-d) δ 9.31 (s, 1H), 8.41 (d, J = 8.4 Hz, 1H), 7.87 (dd, J = 8.0, 1.6 Hz, 1H), 7.61-7.55 (m, 1H), 7.45 (d, J = 8.9 Hz, 2H), 7.21 (t, J = 7.6 Hz, 1H), 7.07 (d, J = 3.0 Hz, 1H), 6.90-6.84 (m, 2H), 6.82 (d, J = 9.6 Hz, 1H), 6.29 (d, J = 2.9 Hz, 1H), 4.07 (s, 3H), 3.81 (hept, J = 8.7, 4.0 Hz, 1H), 3.46-3.42 (m, 2H), 3.23 (hept, J = 6.9 Hz, 1H), 2.83 (td, J = 10.9, 9.7, 2.9 Hz, 2H), 2.01 (dd, J = 12.9, 4.3 Hz, 2H), 1.72 (dtd, J = 13.0, 9.4, 3.7 Hz, 2H), 1.28 (d, J = 6.8 Hz, 6H). MS (ESI) m/z: 521 [M + H]$^+$. |
| IID-4 | 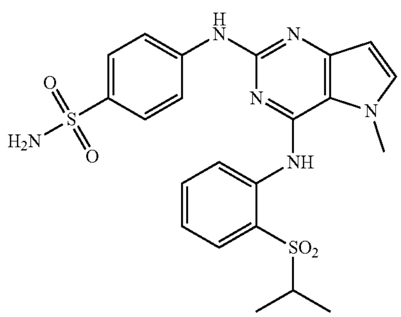 [SMILES: CC(C)S(=O)(=O)c1ccccc1Nc1nc(Nc2ccc(S(N)(=O)=O)cc2)nc2ccn(C)c12] | $^1$H NMR (600 MHz, DMSO-d$_6$) δ 9.35 (s, 1H), 9.16 (s, 1H), 8.45 (dd, J = 8.4, 1.1 Hz, 1H), 7.90 (d, J = 1.9 Hz, 1H), 7.88 (d, J = 2.0 Hz, 1H), 7.86 (dd, J = 8.0, 1.6 Hz, 1H), 7.78 (ddd, J = 8.6, 7.3, 1.6 Hz, 1H), 7.61-7.58 (m, 2H), 7.53 (d, J= 3.0 Hz, 1H), 7.38 (ddd, J = 8.2, 7.3, 1.1 Hz, 1H), 7.10 (s, 2H), 6.30 (d, J = 3.0 Hz, 1H), 4.10 (s, 3H), 3.51 (hept, J = 7.0 Hz, 1H), 1.17 (d, J = 6.7 Hz, 6H). MS (ESI) m/z: 501 [M + H]$^+$. |
| IID-5 | 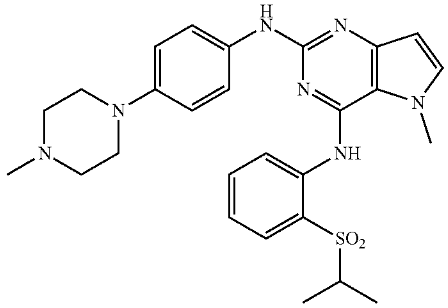 [SMILES: CC(C)S(=O)(=O)c1ccccc1Nc1nc(Nc2ccc(N3CCN(C)CC3)cc2)nc2ccn(C)c12] | $^1$H NMR (600 MHz, Chloroform-d) δ 9.30 (s, 1H), 8.41 (dd, J = 8.5, 1.1 Hz, 1H), 7.86 (dd, J = 8.0, 1.6 Hz, 1H), 7.60-7.52 (m, 1H), 7.49-7.43 (m, 2H), 7.20 (ddt, J = 8.2, 7.2, 1.0 Hz, 1H), 7.06 (d, J = 3.0 Hz, 1H), 6.90-6.79 (m, 3H), 6.28 (dd, J = 3.1, 0.8 Hz, 1H), 4.06 (s, 3H), 3.23 (hept, J = 6.9 Hz, 1H), 3.16-3.11 (m, 4H), 2.61-2.58 (m, 4H), 2.35 (s, 3H), 1.28 (d, J = 6.9 Hz, 6H). MS (ESI) m/z: 520 [M + H]$^+$. |

TABLE 7-continued

Structure and identification of compound IIA-IIF

| ID | Structure | NMR and/or MS data |
|---|---|---|
| IID-6 | 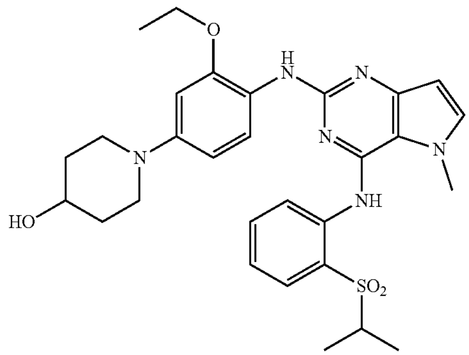 [SMILES: CCOc1cc(N2CCC(O)CC2)ccc1Nc1nc(Nc2ccccc2S(=O)(=O)C(C)C)c2c(ccn2C)n1] | ¹H NMR (600 MHz, Chloroform-d) δ 9.29 (s, 1H), 8.42 (d, J = 8.4 Hz, 1H), 8.20 (d, J = 8.7 Hz, 1H), 7.88 (d, J = 7.9, 1.7 Hz, 1H), 7.60 (t, 1H), 7.34 (s, 1H), 7.23 (t, J = 7.6 Hz, 1H), 7.07 (d, J = 3.0 Hz, 1H), 6.56 (s, 1H), 6.4369-6.37 (m, 1H), 6.31 (d, J = 3.0 Hz, 1H), 4.08-4.07 (m, 5H), 3.83 (dq, J = 8.9, 4.7 Hz, 1H), 3.46-3.39 (m, 2H), 3.24 (hept, J = 6.8 Hz, 1H), 2.82 (d, J = 12.1 Hz, 2H), 2.04-2.01 (m, 2H), 1.77-1.70 (m, 2H), 1.45 (t, J = 7.0 Hz, 3H), 1.28 (d, J = 7.0 Hz, 6H). MS (ESI) m/z: 565 [M + H]⁺. |
| IID-7 | 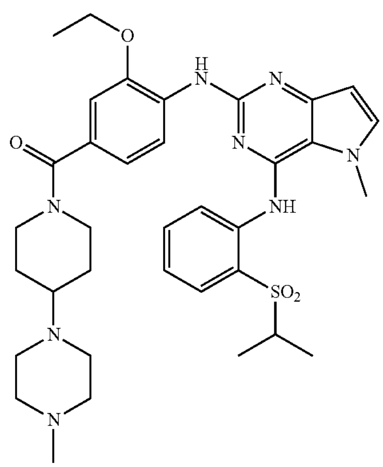 [SMILES: CCOc1cc(C(=O)N2CCC(N3CCN(C)CC3)CC2)ccc1Nc1nc(Nc2ccccc2S(=O)(=O)C(C)C)c2c(ccn2C)n1] | ¹H NMR (600 MHz, Chloroform-d) δ 9.35 (s, 1H), 8.50 (d, J = 8.3 Hz, 1H), 8.39 (dd, J = 8.5, 1.1 Hz, 1H), 7.90 (dd, J = 8.0, 1.6 Hz, 1H), 7.67-7.57 (m, 2H), 7.25-7.23 (m, 1H), 7.12 (d, J = 3.1 Hz, 1H), 6.94 (d, J = 1.8 Hz, 1H), 6.86 (dd, J = 8.3, 1.8 Hz, 1H), 6.36 (d, J = 3.0 Hz, 1H), 4.16-4.11 (m, 2H), 4.11 (s, 3H), 3.24 (h, J = 6.9 Hz, 1H), 2.96-2.81 (m, 2H), 2.68 (s, 6H), 2.54-2.49 (m, 1H), 2.38 (s, 3H), 2.09-1.97 (m, 6H), 1.90 (s, 2H), 1.47 (t, J = 6.9 Hz, 3H), 1.29 (d, J = 6.8 Hz, 6H). MS (ESI) m/z: 675 [M + H]⁺. |
| IID-8 | TFA salt | ¹H NMR (600 MHz, Methanol-d₄) δ 8.22 (d, J = 8.2 Hz, 1H), 7.98 (dd, J = 7.9, 1.6 Hz, 1H), 7.73-7.67 (m, 1H), 7.53 (d, J = 2.9 Hz, 1H), 7.54-7.48 (m, 1H), 7.35 (s, 1H), 6.90 (s, 1H), 6.32 (d, J = 3.0 Hz, 1H), 4.63 (hept, J = 6.1 Hz, 1H), 4.22 (s, 3H), 3.90-3.85 (m, 2H), 3.64 (d, J = 12.3 Hz, 2H), 3.37 (hept, J = 13.8, 6.9 Hz, 1H), 3.10 (q, J = 7.8, 6.4 Hz, 1H), 2.93 (s, 3H), 2.17 (s, 3H), 2.01 (td, J = 11.1, 10.0, 3.4 Hz, 4H), 1.26 (d, J = 6.0 Hz, 6H), 1.24 (d, J = 6.8 Hz, 6H). MS (ESI) m/z: 591 [M + H]⁺. |

TABLE 7-continued

Structure and identification of compound IIA-IIF

| ID | Structure | NMR and/or MS data |
| --- | --- | --- |
| IID-9 | 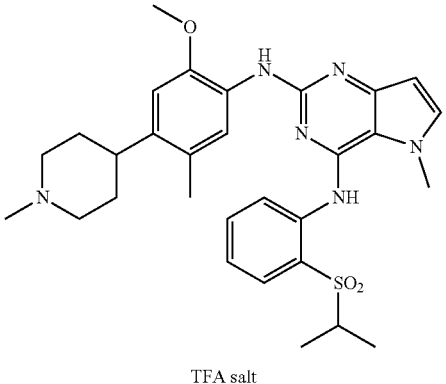 [SMILES: COc1cc(C2CCN(C)CC2)c(C)cc1Nc1nc(Nc2ccccc2S(=O)(=O)C(C)C)c2c(ccn2C)n1] TFA salt | $^1$H NMR (600 MHz, Methanol-d$_4$) δ 8.22-8.17 (m, 1H), 7.98 (dd, J = 7.9, 1.5 Hz, 1H), 7.69 (dd, J = 9.0, 7.3 Hz, 1H), 7.53 (d, J = 3.0 Hz, 1H), 7.50 (t, J = 7.8 Hz, 1H), 7.32 (s, 1H), 6.91 (s, 1H), 6.32 (d, J = 2.9 Hz, 1H), 4.22 (s, 3H), 3.86 (s, 3H), 3.65 (d, J = 12.4 Hz, 2H), 3.41-3.33 (m, 1H), 3.21 (ddd, J = 15.8, 10.1, 3.3 Hz, 2H), 3.17-3.10 (m, 1H), 2.94 (s, 3H), 2.18 (s, 3H), 2.05 (dt, J = 15.5, 11.6 Hz, 4H), 1.23 (d, J = 6.8 Hz, 6H). MS (ESI) m/z: 563 [M + H]$^+$. |
| IIE-1 | 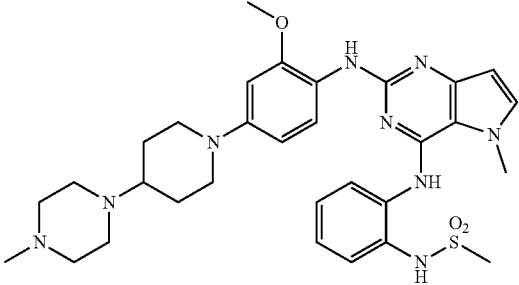 [SMILES: COc1cc(N2CCC(N3CCN(C)CC3)CC2)ccc1Nc1nc(Nc2ccccc2NS(C)(=O)=O)c2c(ccn2C)n1] | MS (ESI) m/z: 620[M + H]$^+$. |
| IIF-1 | 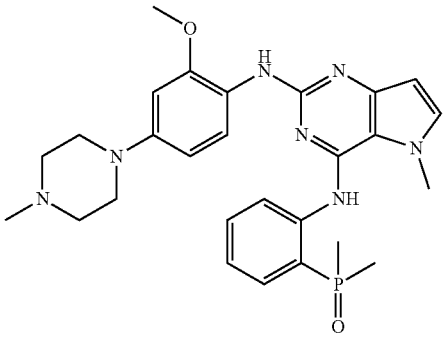 [SMILES: COc1cc(N2CCN(C)CC2)ccc1Nc1nc(Nc2ccccc2P(C)(C)=O)c2c(ccn2C)n1] | $^1$H NMR (600 MHz, DMSO-d$_6$) δ 10.82 (s, 1H), 8.31 (dd, J = 8.6, 4.0 Hz, 1H), 8.10 (d, J = 8.7 Hz, 1H), 7.56 (ddd, J = 14.0, 7.6, 1.6 Hz, 1H), 7.51 (td, J = 7.4, 1.4 Hz, 1H), 7.36 (d, J = 2.9 Hz, 1H), 7.15-7.09 (m, 1H), 7.08 (s, 1H), 6.62 (d, J = 2.5 Hz, 1H), 6.43 (dd, J = 8.8, 2.5 Hz, 1H), 6.15 (d, J = 2.9 Hz, 1H), 4.07 (s, 3H), 3.82 (s, 3H), 3.55-3.27 (m, 2H), 3.16-2.99 (m, 4H), 2.48 (s, 2H), 2.25 (s, 3H), 1.80 (d, J = 13.5 Hz, 6H). MS (ESI) m/z: 520[M + H]$^+$. |
| IIF-2 | 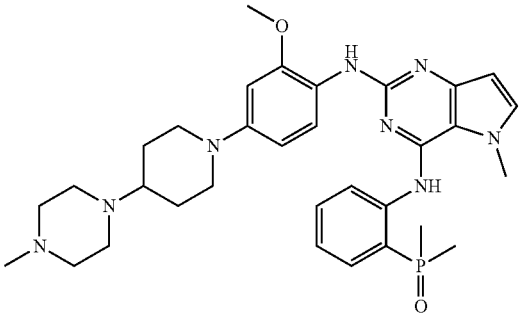 [SMILES: COc1cc(N2CCC(N3CCN(C)CC3)CC2)ccc1Nc1nc(Nc2ccccc2P(C)(C)=O)c2c(ccn2C)n1] | $^1$H NMR (600 MHz, DMSO-d$_6$) δ 10.87 (s, 1H), 8.29 (dd, J = 8.4, 4.1 Hz, 1H), 8.02 (s, 1H), 7.57 (ddd, J = 14.0, 7.8, 1.6 Hz, 1H), 7.50 (td, J = 8.0, 1.6 Hz, 1H), 7.39 (d, J = 3.0 Hz, 1H), 7.23 (s, 1H), 7.13 (td, J = 7.9, 7.3, 1.8 Hz, 1H), 6.62 (d, J = 2.5 Hz, 1H), 6.45 (dd, J = 8.8, 2.6 Hz, 1H), 6.15 (d, J = 2.9 Hz, 1H), 4.07 (s, 3H), 3.81 (s, 3H), 3.77 (td, J = 6.1, 3.2 Hz, 1H), 3.67 (d, J = 12.5 Hz, 2H), 2.88 (s, 6H), 2.62 (td, J = 12.1, 2.4 Hz, 3H), 1.91 (s, 2H), 1.80 (d, J = 13.4 Hz, 6H), 1.59 (s, 2H), 1.04 (d, J = 6.1 Hz, 4H). MS (ESI) m/z: 603[M + H]$^+$. |

TABLE 7-continued

Structure and identification of compound IIA-IIF

| ID | Structure | NMR and/or MS data |
|---|---|---|
| IIF-3 | 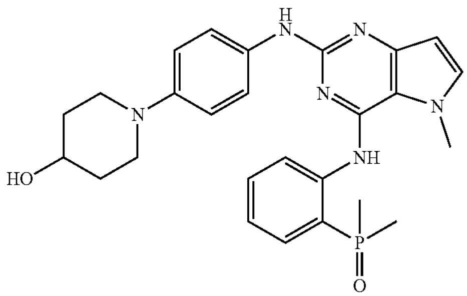 [SMILES: Cn1ccc2nc(Nc3ccc(N4CCC(O)CC4)cc3)nc(Nc3ccccc3P(C)(C)=O)c21] | ¹H NMR (600 MHz, DMSO-d₆) δ 10.78 (s, 1H), 8.42 (d, J = 9.3 Hz, 2H), 7.61-7.48 (m, 4H), 7.35 (d, J = 3.0 Hz, 1H), 7.16-7.08 (m, 1H), 6.85-6.79 (m, 2H), 6.15 (d, J = 3.0 Hz, 1H), 4.07 (s, 3H), 3.57 (dt, J = 9.0, 4.8 Hz, 1H), 3.38 (dq, J = 11.5, 7.1, 5.8 Hz, 4H), 2.72 (ddd, J = 12.6, 10.3, 3.0 Hz, 2H), 1.80 (d, J = 13.5 Hz, 6H), 1.51 (dtd, J = 13.0, 9.6, 3.8 Hz, 2H). MS (ESI) m/z: 491[M + H]⁺. |
| IIF-4 | 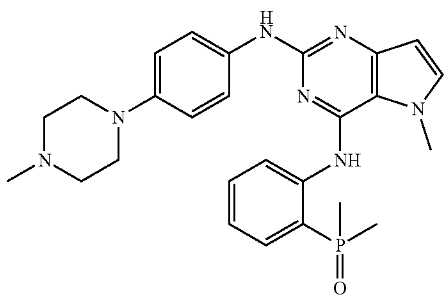 [SMILES: CN1CCN(c2ccc(Nc3nc(Nc4ccccc4P(C)(C)=O)c4c(ccn4C)n3)cc2)CC1] | ¹H NMR (600 MHz, DMSO-d₆) δ 10.77 (s, 1H), 8.42 (d, J = 5.4 Hz, 2H), 7.63-7.58 (m, 2H), 7.58-7.49 (m, 2H), 7.35 (d, J = 3.0 Hz, 1H), 7.12 (tdd, J = 7.4, 2.1, 1.0 Hz, 1H), 6.84-6.79 (m, 2H), 6.14 (d, J = 3.0 Hz, 1H), 4.07 (s, 3H), 3.12-2.97 (m, 4H), 2.47 (t, J = 5.0 Hz, 4H), 2.23 (s, 3H), 1.80 (d, J = 13.5 Hz, 6H). MS (ESI) m/z: 490[M + H]⁺. |
| IIF-5 | 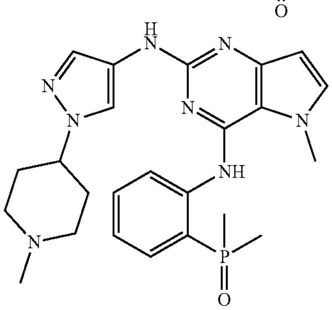 | ¹H NMR (600 MHz, DMSO-d₆) δ 10.69 (s, 1H), 8.46 (s, 1H), 8.34(s, 1H), 7.87 (s, 1H), 7.61-7.49 (m, 2H), 7.42 (s, 1H), 7.34 (d, J = 3.0 Hz, 1H), 7.13 (tt, J = 7.6, 1.3 Hz, 1H), 6.13 (d, J = 2.9 Hz, 1H), 4.05 (s, 3H), 3.98 (s, 1H), 2.88 (d, J = 11.3 Hz, 2H), 2.24 (s, 3H), 2.09 (d, J = 9.2 Hz, 2H), 1.94-1.87 (m, 4H), 1.79 (d, J = 13.5 Hz, 6H). MS (ESI) m/z: 479[M + H]⁺. |

Example 8

Synthesis Scheme of Compound IIG

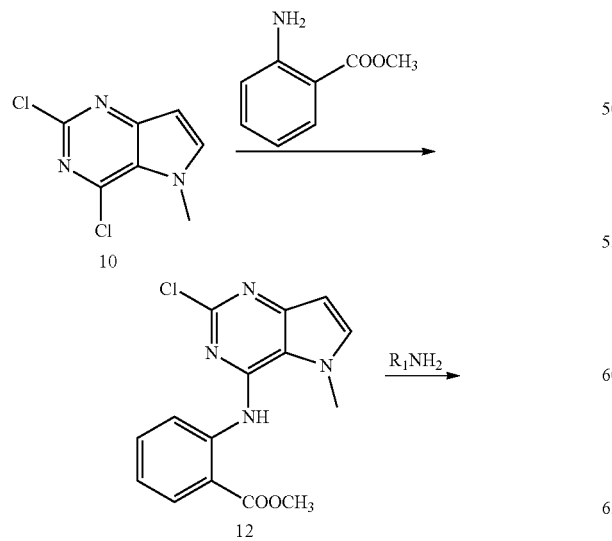

Preparation of Compound 12

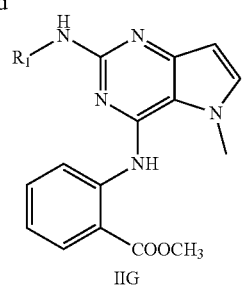

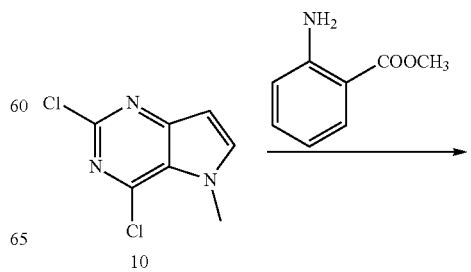

-continued

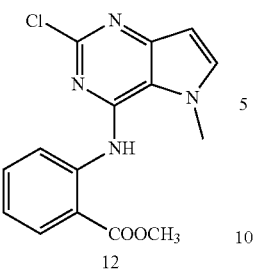
12

Compound 10 (76.3 mg, 0.38 mmol), methyl o-aminobenzoate (62.7 mg, 0.42 mmol) were dissolved in 3 ml tert-butanol. To the solution was added trifluoroacetic acid (0.085 mL, 1.14 mmol). The resulting reaction liquid was heated in 85° C. oil bath with stirring until compound 10 was reacted completely (LC-MS tracking). The reaction was stopped. To the reaction liquid was added 40 mL of saturated sodium bicarbonate, and the liquid was separated. The organic phase was washed twice with saturated sodium chloride solution, dried over anhydride sodium sulfate, concentrated and purified by silica-gel column chromatography (dichloromethane/methanol=1/25) to yield compound 12 (white solid, 43.2 mg, yield 56.2%), which was used directly for the reaction in next step.

MS (ESI) m/z: 317 [M+H]$^+$.

Preparation of Compound IIG

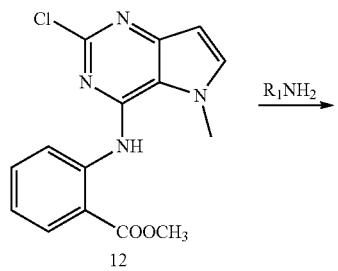

-continued

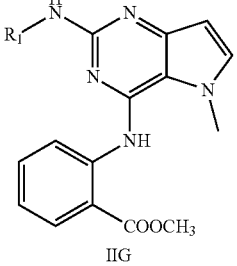
IIG

Process A:

Compound 12 (20.0 mg, 0.06 mmol), aniline (0.06 mmol) were dissolved in 1 mL tert-butanol. To the solution was added trifluoroacetic acid (28 μL, 0.36 mmol). The resulting reaction liquid was heated in 110° C. oil bath with stirring until aniline was reacted completely (LC-MS tracking). The reaction was stopped. To the reaction liquid was added 10 mL of saturated sodium bicarbonate solution, and the liquid was separated. The organic phase was washed twice with saturated sodium chloride solution, dried over anhydride sodium sulfate, concentrated and purified by silica-gel column chromatography (dichloromethane/methanol) to yield compound IIG.

Process B:

Compound 12 (20.0 mg, 0.06 mmol), aniline (0.06 mmol) were dissolved in 1 mL tert-butanol. To the solution was added trifluoroacetic acid (28 μL, 0.36 mmol). The resulting reaction liquid was heated in 110° C. oil bath with stirring until aniline was reacted completely (LC-MS tracking). The reaction was stopped. The reaction solution was concentrated, purified by reversed-phase preparative HPLC (with 0.35% trifluoroacetic acid aqueous solution and methanol as mobile phase), and concentrated in vaccum to yield compound IIG.

Compound IIH was synthesized using similar processes.

TABLE 8

Structure and identification of compounds IIG and IIH

| ID | Structure | NMR and/or MS data |
|---|---|---|
| IIG-1 | 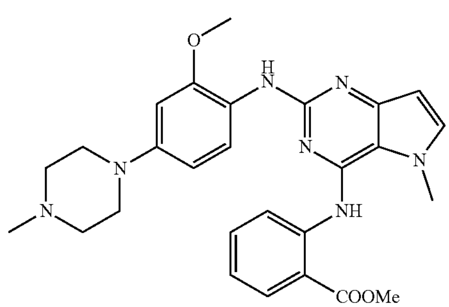 [SMILES: COC(=O)c1ccccc1Nc1nc(Nc2ccc(N3CCN(C)CC3)cc2OC)nc2ccn(C)c12] | $^1$H-NMR (600 MHz; Methanol-d$_4$): δ 8.74-8.73 (m, 1H), 8.10-8.08 (m, 1H), 7.89 (d, J = 8.7 Hz, 1H), 7.50 (td, J = 7.8, 1.6 Hz, 1H), 7.30 (d, J = 3.1 Hz, 1H), 7.10 (td, J = 7.6, 0.8 Hz, 1H), 6.71 (d, J = 2.5 Hz, 1H), 6.55 (dd, J = 8.8, 2.5 Hz, 1H), 6.21 (d, J = 3.0 Hz, 1H), 4.24 (s, 3H), 3.98 (s, 3H), 3.90 (s, 3H), 3.37 (s, 3H), 3.24-3.23 (m, 2H), 2.72-2.71 (m, 2H), 2.42 (s, 2H). MS (ESI) m/z: 502 [M + H]$^+$. |

TABLE 8-continued

Structure and identification of compounds IIG and IIH

| ID | Structure | NMR and/or MS data |
|---|---|---|
| IIG-2 | 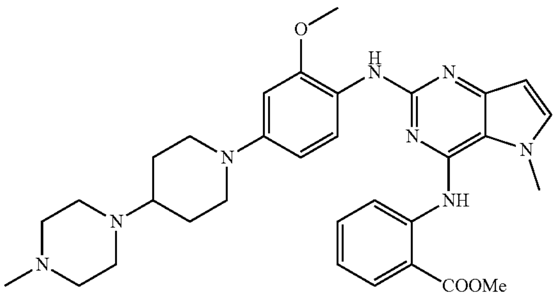 [SMILES: COC(=O)c1ccccc1Nc1nc(Nc2ccc(N3CCC(N4CCN(C)CC4)CC3)cc2OC)nc2ccn(C)c12] | ¹H-NMR (600 MHz; Methanol-d₄): δ 8.75-8.74 (m, 1H), 8.10-8.09 (m, 1H), 7.79-7.78 (m, 1H), 7.52-7.49 (m, 1H), 7.33-7.32 (m, 1H), 7.13-7.10 (m, 1H), 6.72-6.71 (m, 1H), 6.58-6.56 (m, 1H), 6.22 (d, J = 2.7 Hz, 1H), 4.24 (s, 3H), 3.98 (s, 3H), 3.89-3.88 (m, 3H), 3.76-3.73 (m, 2H), 2.78-2.75 (m, 8H), 2.49 (d, J = 4.0 Hz, 4H), 2.07-2.04 (m, 6H). MS (ESI) m/z: 585 [M + H]⁺. |
| IIG-3 | 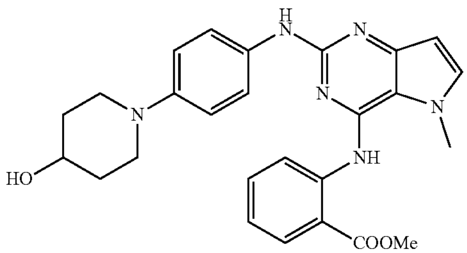 [SMILES: COC(=O)c1ccccc1Nc1nc(Nc2ccc(N3CCC(O)CC3)cc2)nc2ccn(C)c12] | ¹H-NMR (600 MHz; Methanol-d₄): δ 8.88 (dd, J = 8.6, 0.8 Hz, 1H), 8.09 (dd, J = 8.0, 1.5 Hz, 1H), 7.50 (ddd, J = 8.7, 7.1, 1.6 Hz, 1H), 7.45-7.44 (m, 1H), 7.26 (dd, J = 26.7, 2.7 Hz, 1H), 7.09 (td, J = 7.6, 1.0 Hz, 1H), 7.01-7.00 (m, 2H), 6.21 (d, J = 3.0 Hz, 1H), 4.24 (s, 3H), 3.98 (s, 3H), 3.78 (dd, J = 4.5, 0.5 Hz, 1H), 3.52-3.49 (m, 2H), 2.90-2.86 (m, 2H), 2.04-2.00 (m, 2H), 1.74-1.71 (m, 2H). MS (ESI) m/z: 473 [M + H]⁺. |
| IIG-4 | TFA salt | ¹H-NMR (600 MHz; Methanol-d₄): δ 8.49 (d, J = 8.3 Hz, 1H), 8.13 (dd, J = 8.0, 1.5 Hz, 1H), 7.74 (d, J = 8.0 Hz, 1H), 7.58-7.54 (m, 2H), 7.30-7.27 (m, 1H), 7.19 (d, J = 1.5 Hz, 1H), 7.00 (dd, J = 8.0, 1.7 Hz, 1H), 6.36 (d, J = 3.0 Hz, 1H), 4.32 (s, 3H), 3.98 (s, 3H), 3.92 (s, 3H), 3.38-3.35 (m, 2H), 3.24-3.21 (m, 2H), 3.12-3.10 (m, 2H), 2.99 (d, J = 3.1 Hz, 2H), 2.90 (s, 3H), 2.10-1.95 (m, 2H), 1.63-1.62 (m, 2H). MS (ESI) m/z: 613 [M + H]⁺. |
| IIH-1 | TFA salt | ¹H-NMR (600 MHz; Methanol-d₄): δ 8.18 (t, J = 0.3 Hz, 1H), 7.95-7.94 (m, 1H), 7.83-7.81 (m, 1H), 7.55-7.52 (m, 1H), 7.47 (d, J = 1.0 Hz, 1H), 7.32-7.30 (m, 1H), 6.71 (s, 1H), 6.38-6.36 (m, 1H), 6.29 (t, J = 1.3 Hz, 1H), 4.21 (s, 3H), 3.92 (d, J = 1.1 Hz, 3H), 3.85 (s, 3H), 3.68-3.63 (m, 2H), 3.13-3.07 (m, 2H), 3.01 (s, 3H). MS (ESI) m/z: 502 [M + H]⁺. |
| IIH-2 | TFA salt | ¹H-NMR (600 MHz; Methanol-d₄): δ 8.17 (t, J = 1.6 Hz, 1H), 8.06-8.04 (m, 1H), 7.80-7.79 (m, 1H), 7.63 (t, J = 7.9 Hz, 1H), 7.55 (d, J = 2.9 Hz, 1H), 7.50 (d, J = 9.0 Hz, 2H), 7.31 (d, J = 9.0 Hz, 2H), 6.40 (d, J = 3.0 Hz, 1H), 4.24 (s, 3H), 4.09-4.08 (m, 1H), 3.93 (s, 3H), 3.77-3.73 (m, 2H), 3.49-3.45 (m, 2H), 2.24-2.20 (m, 2H), 2.01-1.98 (m, 2H). MS (ESI) m/z: 473 [M + H]⁺. |

Example 9

Synthesis Scheme of Compound III

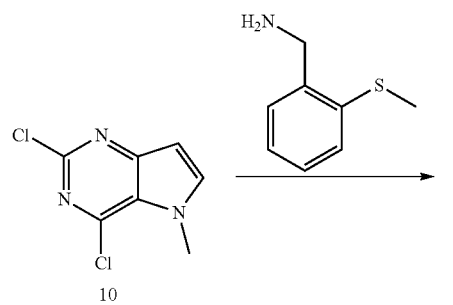

10

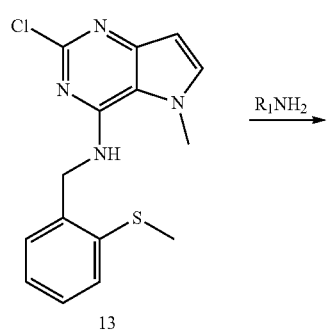

13

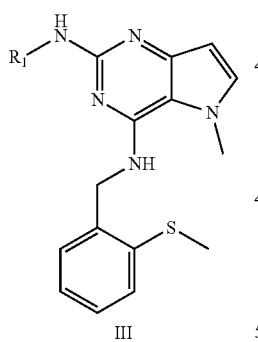

III

Preparation of Compound 13

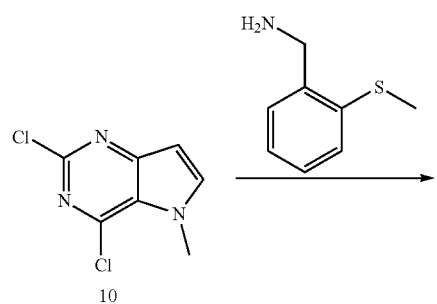

10

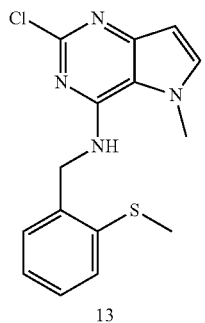

13

Compound 10 (66 mg, 0.33 mmol), 2-methylthiobenzylamine (50 mg, 0.33 mmol) were dissolved in 2 mL tert-butanol. To the solution was added N,N-diisopropylethylamine (0.74 mL, 4.47 mmol). The resulting reaction liquid was heated in 120° C. oil bath with stirring until compound 10 was reacted completely (LC-MS tracking). The reaction was stopped. The reaction liquid was concentrated and purified by silica-gel column chromatography (ethyl acetate/petroleum ether=1/1) to yield compound 13 (white solid, 60 mg, yield 57%), which was used directly for the reaction in next step.

MS (ESI) m/z: 319 [M+H]$^+$.

Preparation of Compound III

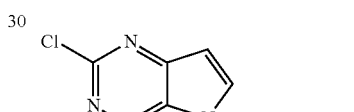

13

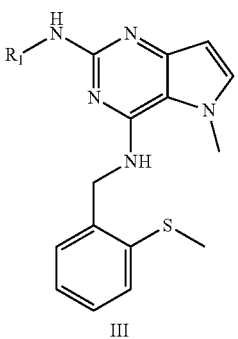

III

Process A:

Compound 13 (20 mg, 0.06 mmol), aniline (0.05 mmol) were dissolved in 2 mL tert-butanol. To the solution was added 2-dicyclohexylphosphino-2',4',6'-triisopropylbiphenyl (9.6 mg, 0.05 mmol), tris(dibenzylideneacetone)dipalladium (5.1 mg, 0.01 mmol), potassium carbonate (24.8 mg, 0.18 mmol). In nitrogen atmosphere, the resulting reaction liquid was heated in 120° C. oil bath with stirring until compound 13 was reacted completely (LC-MS tracking). The reaction was stopped. The reaction liquid was filtered by one-section silica gel column, concentrated and purified by silica-gel column chromatography (dichloromethane/methanol=20/3) to yield compound III.

Process B:

Compound 13 (20 mg, 0.06 mmol), aniline (0.05 mmol) were dissolved in 2 mL tert-butanol. To the solution was added 2-dicyclohexylphosphino-2',4',6'-triisopropylbiphenyl (9.6 mg, 0.05 mmol), tris(dibenzylideneacetone)dipalladium (5.1 mg, 0.01 mmol), potassium carbonate (24.8 mg, 0.18 mmol). In nitrogen atmosphere, the resulting reaction liquid was heated in 120° C. oil bath with stirring until compound 13 was reacted completely (LC-MS tracking). The reaction was stopped. The reaction liquid was filtered by one-section silica gel column, concentrated and purified by reversed-phase preparative HPLC (with 0.35% trifluoroacetic acid aqueous solution and methanol as mobile phase), and concentrated in vaccum to yield compound III.

Compounds IIJ, IIK, IIL were synthesized using similar processes.

TABLE 9

Structure and identification of compounds III-IIL

| ID | Structure | NMR and/or MS data |
|---|---|---|
| III-1 | 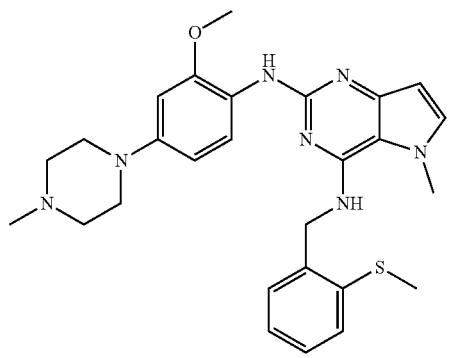 [SMILES: COc1cc(N2CCN(C)CC2)ccc1Nc1nc(NCc2ccccc2SC)c2c(ccn2C)n1] | $^1$H NMR (600 MHz, DMSO-d$_6$) δ 7.96 (d, J = 8.8 Hz, 1H), 7.36-7.29 (m, 3H), 7.28-7.26 (m, 1H), 7.26-7.23 (m, 1H), 7.22-7.13 (m, 1H), 7.12-7.08 (m, 1H), 6.58 (d, J = 2.5 Hz, 1H), 6.08 (t, J = 3.9 Hz, 1H), 4.68 (d, J = 5.6 Hz, 2H), 4.04 (s, 3H), 3.80 (d, J = 6.4 Hz, 3H), 3.10 (t, J = 4.8 Hz, 4H), 2.62 (t, J = 4.9 Hz, 4H), 2.55 (s, 3H), 2.34 (s, 3H). MS (ESI) m/z: 504 [M + H]$^+$. |
| III-2 | 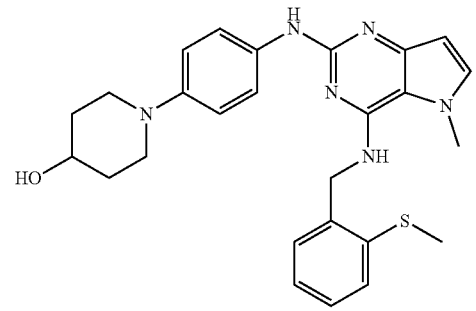<br>TFA salt | $^1$H NMR (600 MHz, DMSO-d$_6$) δ 8.47 (t, J = 5.6 Hz, 1H), 8.47 (t, J = 5.6 Hz, 1H), 7.54 (d, J = 2.9 Hz, 1H), 7.40-7.36 (m, 1H), 7.31 (t, J = 7.6 Hz, 1H), 7.25 (d, J = 7.6 Hz, 1H), 7.17 (d, J = 8.5 Hz, 2H), 7.13 (td, J = 7.4, 1.3 Hz, 1H), 7.01 (s, 2H), 6.23 (d, J = 2.9 Hz, 1H), 4.70 (d, J = 5.6 Hz, 2H), 4.11 (s, 2H), 3.74 (s, 1H), 3.52-3.45 (m, 2H), 3.06 (s, 2H), 2.55 (d, J = 7.2 Hz, 6H), 1.92 (d, J = 13.1 Hz, 2H), 1.67-1.56 (m, 2H). MS (ESI) m/z: 475 [M+H]$^+$. |
| III-3 | 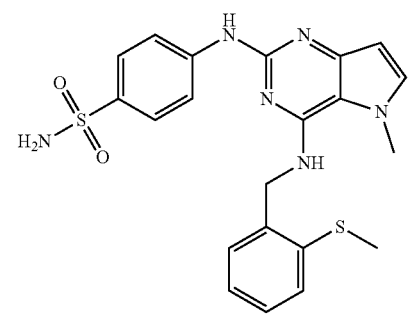 | $^1$H NMR (600 MHz, DMSO-d$_6$) δ 9.06 (s, 1H), 7.71-7.68 (m, 2H), 7.51-7.47 (m, 2H), 7.37-7.31 (m, 3H), 7.28 (dd, J = 11.1, 4.5 Hz, 1H), 7.24 (t, J = 6.0 Hz, 1H), 7.12 (td, J = 7.4, 1.2 Hz, 1H), 7.05 (s, 2H), 6.15 (d, J = 2.9 Hz, 1H), 4.74 (d, J = 5.7 Hz, 2H), 4.07 (s, 3H), 2.58 (s, 3H). MS (ESI) m/z: 455 [M + H]$^+$. |

TABLE 9-continued

Structure and identification of compounds III-IIL

| ID | Structure | NMR and/or MS data |
| --- | --- | --- |
| III-4 | 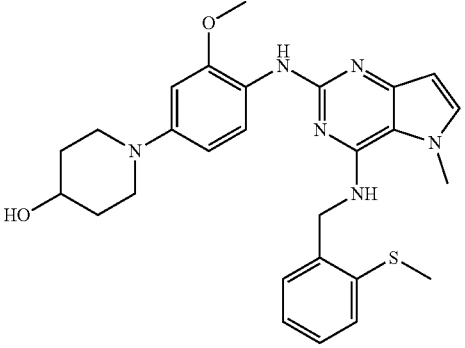<br>TFA salt | $^1$H NMR (600 MHz, DMSO-$d_6$) δ 9.09 (s, 1H), 8.33 (s, 1H), 7.51 (d, J = 3.0 Hz, 1H), 7.35 (dd, J = 8.0, 1.3 Hz, 1H), 7.30 (td, J = 7.6, 1.4 Hz, 1H), 7.25-7.21 (m, 1H), 7.19-7.15 (m, 1H), 7.12 (ddd, J = 7.4, 6.0, 1.3 Hz, 1H), 6.76 (s, 1H), 6.46 (d, J = 8.4 Hz, 1H), 6.22 (d, J = 2.9 Hz, 1H), 4.72 (d, J = 5.7 Hz, 2H), 4.09 (s, 3H), 4.03 (q, J = 7.0 Hz, 2H), 3.54-3.51 (m, 2H), 2.99 (s, 2H), 2.54 (s, 3H), 1.91-1.84 (m, 2H), 1.55 (d, J = 10.9 Hz, 2H), 1.21 (t, J = 6.9 Hz, 3H). MS (ESI) m/z: 519 [M + H]$^+$. |
| IIJ-1 | 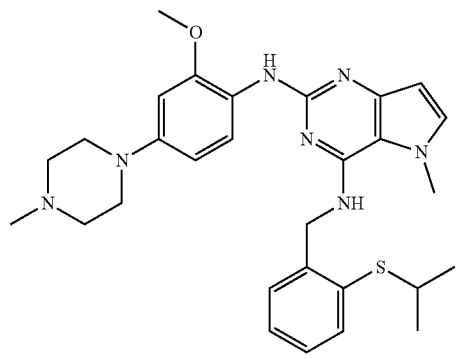 [SMILES: COc1cc(N2CCN(C)CC2)ccc1Nc1nc(NCc2ccccc2SC(C)C)c2c(ccn2C)n1] | $^1$H NMR (600 MHz, Chloroform-d) δ 8.31 (d, J = 8.6 Hz, 1H), 7.43 (dd, J = 7.9, 1.3 Hz, 1H), 7.40 (dd, J = 7.7, 1.6 Hz, 1H), 7.32 (s, 1H), 7.23 (td, J = 7.6, 1.6 Hz, 1H), 7.19-7.13 (m, 1H), 6.84 (d, J = 3.0 Hz, 1H), 6.56-6.49 (m, 2H), 6.17 (d, J = 3.0 Hz, 1H), 5.67-5.62 (m, 1H), 4.90 (d, J = 5.8 Hz, 2H), 3.92 (s, 3H), 3.85 (s, 3H), 3.44 (hept, J = 6.7 Hz, 1H), 3.14 (t, J = 5.0 Hz, 4H), 2.60 (d, J = 4.9 Hz, 4H), 2.35 (s, 3H), 1.33 (s, 3H), 1.32 (s, 3H). MS (ESI) m/z: 532 [M + H]$^+$. |
| IIJ-2 | 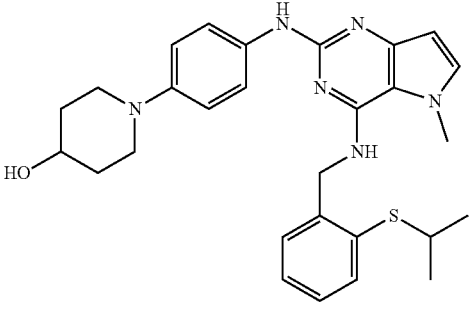 [SMILES: CC(C)Sc1ccccc1CNc1nc(Nc2ccc(N3CCC(O)CC3)cc2)nc2ccn(C)c12] | $^1$H NMR (600 MHz, Chloroform-d) δ 7.5159-7.4561 (m, 2H), 7.4310 (dd, J = 7.8, 1.3 Hz, 1H), 7.3607 (dd, J = 7.6, 1.5 Hz, 1H), 7.2340 (td, J = 7.6, 1.5 Hz, 1H), 7.1533 (td, J = 7.5, 1.3 Hz, 1H), 6.9567 (s, H), 6.9303-6.8705 (m, 2H), 6.8482 (d, J = 2.9 Hz, 1H), 6.1661 (d, J = 3.0 Hz, 1H), 5.6661 (t, J = 5.7 Hz, 1H), 4.8590 (d, J = 5.8 Hz, 2H), 3.9275 (s, 3H), 3.7948 (hept, J = 8.8, 4.1 Hz, 1H), 3.4661-3.4135 (m, 3H), 2.8242 (ddd, J = 12.6, 10.1, 3.0 Hz, 2H), 1.9955 (dqd, J = 12.6, 3.7, 1.8 Hz, 2H), 1.7077 (dtd, J = 13.1, 9.4, 3.8 Hz, 2H), 1.3208 (d, J = 6.7 Hz, 6H). MS (ESI) m/z: 503 [M + H]$^+$. |
| IIJ-3 | 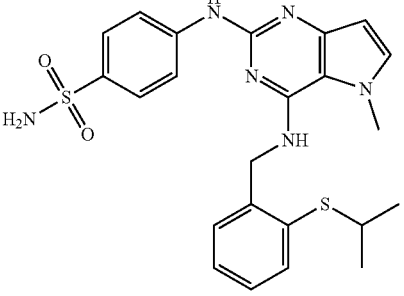 | $^1$H NMR (600 MHz, DMSO-$d_6$) δ 10.42 (s, 1H), 8.45 (s, 1H), 7.59-7.55 (m, 3H), 7.52 (d, J = 7.8 Hz, 1H), 7.44 (d, J = 8.4 Hz, 2H), 7.35-7.28 (m, 2H), 7.23 (d, J = 6.6 Hz, 3H), 6.30 (d, J = 2.9 Hz, 1H), 4.85 (d, J = 5.6 Hz, 2H), 4.12 (s, 3H), 3.54 (h, J = 6.8 Hz, 1H), 1.29 (d, J = 6.6 Hz, 6H). MS (ESI) m/z: 483 [M + H]$^+$. |

TABLE 9-continued

Structure and identification of compounds III-IIL

| ID | Structure | NMR and/or MS data |
|---|---|---|
| IIK-1 | 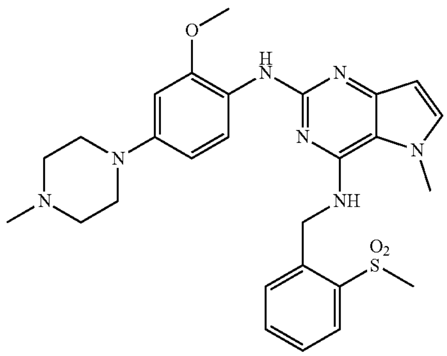 [SMILES: COc1cc(N2CCN(C)CC2)ccc1Nc1nc(NCc2ccccc2S(C)(=O)=O)c2c(ccn2C)n1] | ¹H NMR (600 MHz, DMSO-d₆) δ 7.98 (dd, J = 11.6, 10.3 Hz, 2H), 7.72-7.63 (m, 2H), 7.53 (t, J = 7.6 Hz, 1H), 7.26 (d, J = 2.8 Hz, 2H), 6.55 (d, J = 2.5 Hz, 1H), 6.28 (dd, J = 9.0, 2.5 Hz, 1H), 6.08 (d, J = 2.9 Hz, 1H), 5.02 (d, J = 5.7 Hz, 2H), 4.04 (s, 3H), 3.78 (s, 3H), 3.39 (s, 4H), 3.17 (d, J = 5.0 Hz, 3H), 3.05-3.01 (m, 4H), 2.23 (s, 3H). MS (ESI) m/z: 536 [M + H]⁺. |
| IIK-2 | 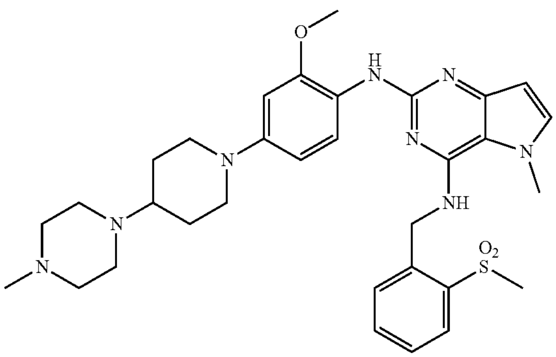 [SMILES: COc1cc(N2CCC(N3CCN(C)CC3)CC2)ccc1Nc1nc(NCc2ccccc2S(C)(=O)=O)c2c(ccn2C)n1] | ¹H NMR (600 MHz, DMSO-d₆) δ 7.98 (dd, J = 17.1, 8.3 Hz, 2H), 7.71-7.63 (m, 2H), 7.53 (t, J = 7.6 Hz, 1H), 7.25 (dd, J = 12.2, 4.5 Hz, 2H), 6.76 (s, 1H), 6.54 (d, J = 2.5 Hz, 1H), 6.29 (d, J = 8.8 Hz, 1H), 6.08 (d, J = 2.9 Hz, 1H), 5.02 (d, J = 5.7 Hz, 2H), 4.11 (q, J = 5.3 Hz, 1H), 4.04 (s, 3H), 3.77 (s, 3H), 3.55 (d, J = 12.1 Hz, 2H), 3.39 (s, 3H), 3.17 (d, J = 4.6 Hz, 4H), 2.41-2.20 (m, 6H), 2.15 (s, 3H), 1.82 (d, J = 12.2 Hz, 2H), 1.49 (qd, J = 12.0, 3.9 Hz, 2H). MS (ESI) m/z: 619 [M + H]⁺. |
| IIK-3 | 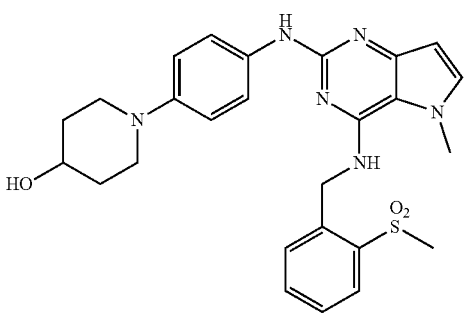 [SMILES: Cn1ccc2nc(Nc3ccc(N4CCC(O)CC4)cc3)nc(NCc3ccccc3S(C)(=O)=O)c21] | ¹H NMR (600 MHz, DMSO-d₆) δ 8.26 (s, 1H), 7.97 (dd, J = 7.7, 1.2 Hz, 1H), 7.72-7.63 (m, 2H), 7.57-7.51 (m, 1H), 7.28 (t, J = 6.0 Hz, 3H), 7.21 (s, 1H), 6.71-6.62 (m, 2H), 6.07 (d, J = 3.0 Hz, 1H), 5.08 (d, J = 5.8 Hz, 2H), 4.65 (d, J = 4.2 Hz, 1H), 4.10 (q, J = 5.3 Hz, 1H), 4.02 (s, 3H), 3.24 (s, 3H), 3.17 (d, J = 4.9 Hz, 4H), 2.73-2.64 (m, 2H), 1.80 (dq, J = 13.1, 3.9 Hz, 2H). MS (ESI) m/z: 507 [M + H]⁺. |
| IIK-4 | 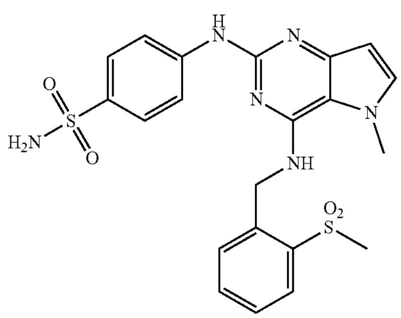 [SMILES: Cn1ccc2nc(Nc3ccc(S(N)(=O)=O)cc3)nc(NCc3ccccc3S(C)(=O)=O)c21] | ¹H NMR (600 MHz, DMSO-d₆) δ 8.97 (s, 1H), 7.99 (d, J = 7.8 Hz, 1H), 7.72-7.66 (m, 4H), 7.55 (t, J = 6.8 Hz, 1H), 7.48 (d, J = 8.9 Hz, 2H), 7.34 (d, J = 3.0 Hz, 1H), 7.19 (s, 1H), 7.05 (s, 2H), 6.16 (d, J = 2.9 Hz, 1H), 5.15 (d, J = 5.6 Hz, 2H), 4.05 (s, 3H), 3.31 (s, 3H). MS (ESI) m/z: 487 [M + H]⁺. |

TABLE 9-continued

Structure and identification of compounds III-IIL

| ID | Structure | NMR and/or MS data |
|---|---|---|
| IIK-5 | 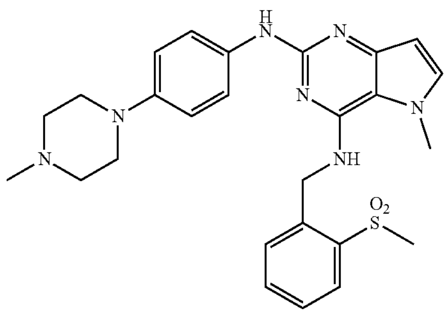 [SMILES: CN1CCN(c2ccc(Nc3nc(NCc4ccccc4S(C)(=O)=O)c4c(ccn4C)n3)cc2)CC1] | $^1$H NMR (600 MHz, DMSO-d$_6$) δ 8.16 (s, 1H), 7.97 (d, J = 8.0 Hz, 1H), 7.71-7.65 (m, 2H), 7.55 (t, J = 7.2 Hz, 1H), 7.35 (d, J = 9.0 Hz, 2H), 7.25 (d, J = 2.9 Hz, 1H), 7.10 (s, 1H), 6.67 (d, J = 8.9 Hz, 2H), 6.05 (d, J = 3.0 Hz, 1H), 5.08 (d, J = 5.5 Hz, 2H), 4.02 (s, 3H), 3.25 (s, 3H), 3.02 (s, 4H), 2.61 (s, 4H), 2.32 (s, 3H). MS (ESI) m/z: 506 [M + H]$^+$. |
| IIK-6 | 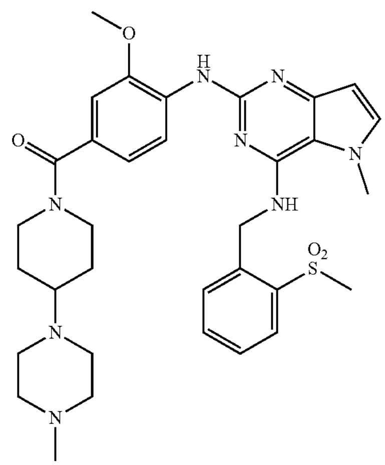 [SMILES: COc1cc(C(=O)N2CCC(N3CCN(C)CC3)CC2)ccc1Nc1nc(NCc2ccccc2S(C)(=O)=O)c2c(ccn2C)n1] | $^1$H NMR (600 MHz, DMSO-d$_6$) δ 8.37 (d, J = 8.3 Hz, 1H), 7.98 (dd, J = 7.9, 1.2 Hz, 1H), 7.72 (d, J = 7.6 Hz, 1H), 7.66 (td, J = 7.7, 1.2 Hz, 1H), 7.53 (t, J = 7.3 Hz, 1H), 7.40 (t, J = 5.9 Hz, 1H), 7.33 (d, J = 3.0 Hz, 1H), 7.15 (s, 1H), 6.92 (d, J = 1.7 Hz, 1H), 6.78 (dd, J = 8.3, 1.6 Hz, 1H), 6.16 (d, J = 3.0 Hz, 1H), 5.08 (d, J = 5.7 Hz, 2H), 4.08 (s, 3H), 3.84 (s, 3H), 3.42 (d, J = 10.1 Hz, 4H), 3.17 (s, 3H), 2.86 (s, 2H), 2.48-2.24 (m, 6H), 2.17 (s, 3H), 1.76 (s, 2H), 1.34 (qd, J = 12.3, 4.1 Hz, 2H). MS (ESI) m/z: 647 [M + H]$^+$. |
| IIK-7 | 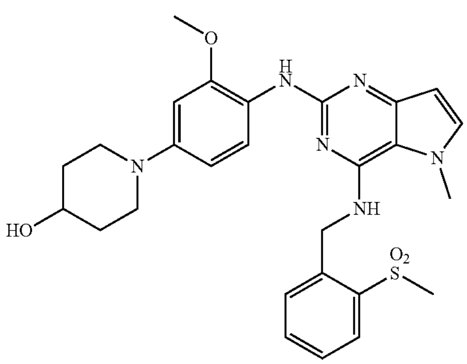 | $^1$H NMR (600 MHz, DMSO) δ 9.11 (s, 1H), 8.22 (d, J = 7.3 Hz, 1H), 7.99 (dd, J = 7.9, 1.4 Hz, 1H), 7.67 (tt, J = 5.0, 2.5 Hz, 1H), 7.58 (dd, J = 9.1, 6.6 Hz, 2H), 7.51 (d, J = 2.9 Hz, 1H), 7.07 (d, J = 8.7 Hz, 1H), 6.70 (s, 1H), 6.42 (s, 1H), 6.21 (d, J = 2.9 Hz, 1H), 5.15 (dd, J = 15.2, 5.7 Hz, 2H), 4.09 (s, 3H), 4.02 (p, J = 7.2 Hz, 2H), 3.52 (s, 2H), 3.24 (s, 3H), 2.95 (s, 2H), 1.85 (d, J = 12.6 Hz, 2H), 1.57-1.47 (m, 2H), 1.18 (t, J = 7.0 Hz, 3H). MS (ESI) m/z: 551 [M + H]$^+$. |
| IIL-1 | 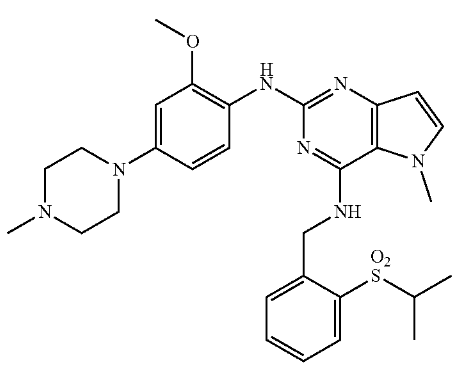 | $^1$H NMR (600 MHz, DMSO-d$_6$) δ 8.12 (d, J = 8.8 Hz, 1H), 7.90 (dd, J = 7.7, 1.1 Hz, 1H), 7.70-7.63 (m, 2H), 7.52 (ddd, J = 8.3, 6.4, 2.2 Hz, 1H), 7.32-7.25 (m, 2H), 6.86 (s, 1H), 6.57 (d, J = 2.5 Hz, 1H), 6.35 (dd, J = 8.9, 2.6 Hz, 1H), 6.10 (d, J = 2.9 Hz, 1H), 5.03 (d, J = 5.8 Hz, 2H), 4.05 (s, 3H), 3.78 (s, 3H), 3.69 (hept, J = 7.0 Hz, 1H), 3.11-3.02 (m, 4H), 2.61-2.56 (m, 4H), 2.31 (s, 3H), 1.29 (d, J = 6.8 Hz, 6H). MS (ESI) m/z: 564 [M + H]$^+$ |

TABLE 9-continued

Structure and identification of compounds III-IIL

| ID | Structure | NMR and/or MS data |
| --- | --- | --- |
| IIL-2 | 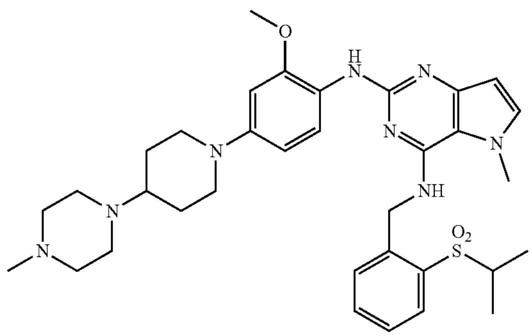 [SMILES: COc1cc(N2CCC(N3CCN(C)CC3)CC2)ccc1Nc1nc(NCc2ccccc2S(=O)(=O)C(C)C)c2c(ccn2C)n1] | $^1$H NMR (600 MHz, Methanol-d$_4$) δ 8.01 (dd, J = 7.9, 1.3 Hz, 1H), 7.69-7.63 (m, 1H), 7.57 (ddd, J = 10.0, 7.7, 1.8 Hz, 2H), 7.48 (t, J = 4.4 Hz, 1H), 7.36 (d, J = 2.9 Hz, 1H), 6.98 (s, 1H), 6.78 (dd, J = 8.8, 2.5 Hz, 1H), 6.23 (d, J = 3.0 Hz, 1H), 5.21 (s, 2H), 4.12 (s, 3H), 4.08 (s, 1H), 3.89 (s, 3H), 3.86 (d, J = 13.3 Hz, 2H), 3.49 (h, J = 6.8 Hz, 5H), 3.31 (s, 2H), 3.17 (dtd, J = 26.3, 11.8, 11.2, 4.9 Hz, 4H), 2.95 (s, 3H), 2.26-2.20 (m, 2H), 1.99 (qd, J = 11.8, 3.8 Hz, 2H), 1.33 (d, J = 6.8 Hz, 6H). MS (ESI) m/z: 647 [M + H]$^+$ |
| IIL-3 | 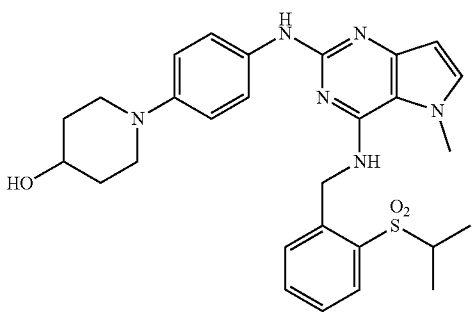 [SMILES: CC(C)S(=O)(=O)c1ccccc1CNc1nc(Nc2ccc(N3CCC(O)CC3)cc2)nc2ccn(C)c12] | $^1$H NMR (600 MHz, Chloroform-d) δ 7.93-7.88 (m, 1H), 7.57 (dd, J = 7.4, 1.6 Hz, 1H), 7.53-7.47 (m, 2H), 7.47-7.38 (m, 2H), 6.98-6.92 (m, 3H), 6.83 (d, J = 2.9 Hz, 1H), 6.51 (t, J = 6.5 Hz, 1H), 6.12 (d, J = 3.0 Hz, 1H), 4.94 (d, J = 6.4 Hz, 2H), 3.89 (s, 3H), 3.80 (hept, J = 8.6, 4.0 Hz, 1H), 3.49-3.42 (m, 2H), 3.29 (hept, J = 6.8 Hz, 1H), 2.84 (ddd, J = 12.7, 10.0, 3.0 Hz, 2H), 1.99 (dtd, J = 11.2, 3.7, 1.9 Hz, 2H), 1.76-1.64 (m, 2H), 1.33 (d, J = 6.8 Hz, 6H). MS (ESI) m/z: 535 [M + H]$^+$ |
| IIL-4 | 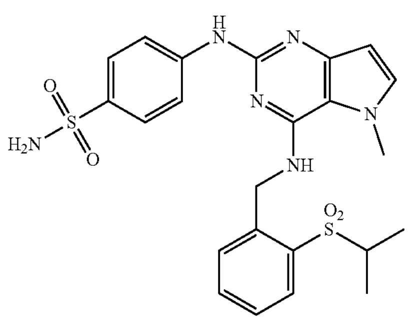 [SMILES: CC(C)S(=O)(=O)c1ccccc1CNc1nc(Nc2ccc(S(N)(=O)=O)cc2)nc2ccn(C)c12] | $^1$H NMR (600 MHz, DMSO-d$_6$) δ 7.94 (d, J = 7.6 Hz, 1H), 7.70 (t, J = 7.6 Hz. 1H), 7.64 (d, J = 7.8 Hz, 1H), 7.59 (t, J = 7.6 Hz, 1H), 7.53 (t, J = 10.1 Hz, 4H), 7.18 (m, 3H), 6.29 (d, J = 2.9 Hz, 1H), 5.21 (d, J = 5.8 Hz, 2H), 4.10 (s, 2H), 2.52 (s, 3H), 1.17 (d, J = 6.7 Hz, 6H). MS (ESI) m/z. 515 [M + H]$^+$ |
| IIL-5 | 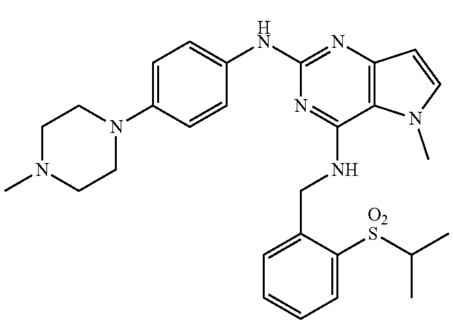 [SMILES: CC(C)S(=O)(=O)c1ccccc1CNc1nc(Nc2ccc(N3CCN(C)CC3)cc2)nc2ccn(C)c12] | $^1$H NMR (600 MHz, Methanol-d$_4$) δ 7.95 (dd, J = 7.9, 1.3 Hz, 1H), 7.61 (dd, J = 7.7, 1.7 Hz, 1H), 7.57 (td, J = 7.5, 1.4 Hz, 1H), 7.50 (td, J = 7.6, 1.5 Hz, 1H), 7.29 (d, J = 8.9 Hz, 2H), 7.13 (d, J = 3.0 Hz, 1H), 6.88 (d, J = 8.9 Hz, 2H), 6.08 (d, J = 3.0 Hz, 1H), 5.10 (s, 2H), 4.00 (s, 3H), 3.51-3.41 (m, 1H), 3.14 (t, J = 4.9 Hz, 4H), 2.64 (t, J = 5.1 Hz, 4H), 2.36 (s, 3H), 1.27 (s, 3H), 1.26 (s, 3H). MS (ESI) m/z: 534 [M + H]$^+$ |

Example 10

Synthesis Scheme of Compound IIM

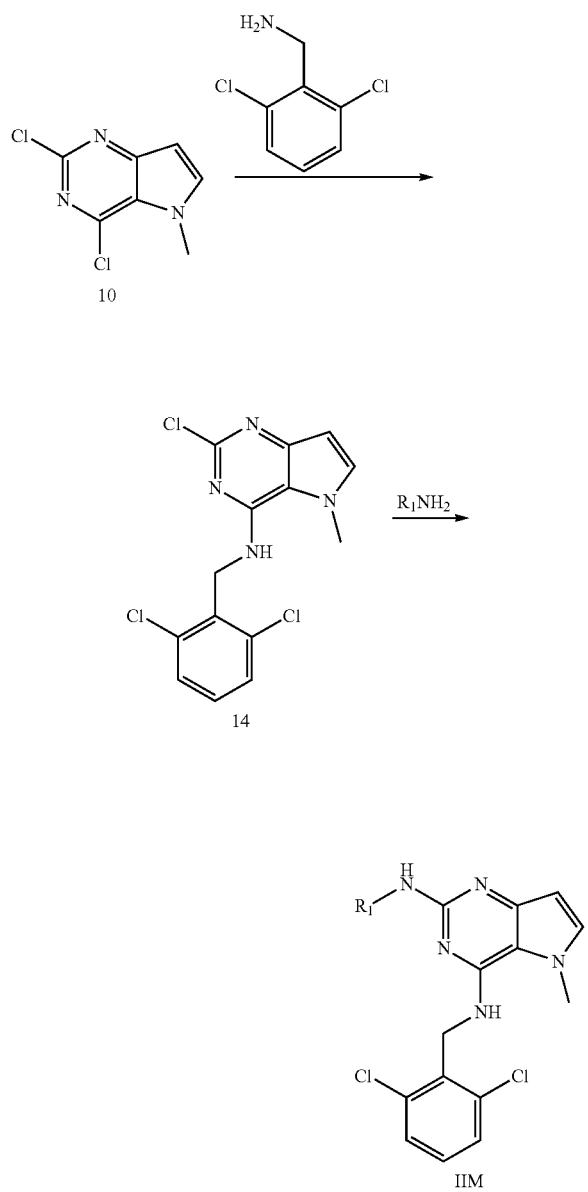

Preparation of Compound 14

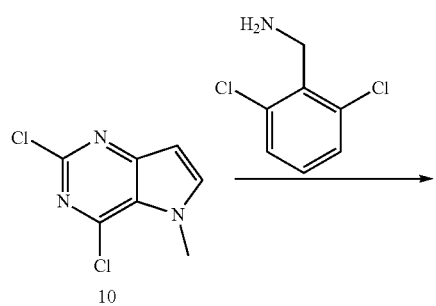

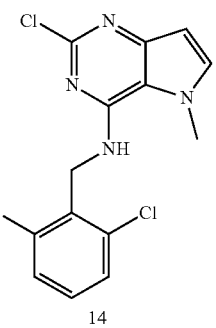

Compound 10 (150 mg, 0.74 mmol), 2,6-dichlorobenzylamine (130 mg, 0.74 mmol) were dissolved in 5 mL DMF. To the solution was added potassium carbonate (308 mg, 2.23 mmol). The resulting reaction liquid was heated in 60° C. oil bath with stirring, reacted for 16 hours. The reaction was stopped. To the reaction liquid was added saturated 40 mL of sodium chloride solution, 20 mL of ethyl acetate, and the liquid was separated. The organic phase was washed twice with saturated sodium chloride solution, dried over anhydride sodium sulfate, concentrated to yield compound 14 (yellow solid, 175.3 mg, yield 74.3%), which was used directly for the reaction in next step.

MS (ESI) m/z: 318 [M+H]$^+$.

Preparation of Compound IIM

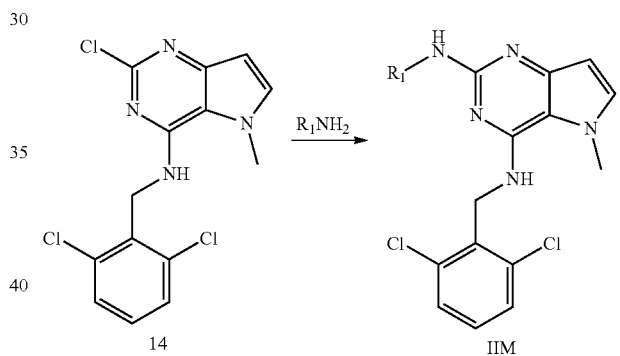

Process A:

Compound 14 (25.0 mg, 0.08 mmol), aniline (0.08 mmol) were dissolved in 1 mL tert-butanol. To the solution was added trifluoroacetic acid (35 µL, 0.47 mmol). The resulting reaction liquid was heated in 110° C. oil bath with stirring until aniline was reacted completely (LC-MS tracking). The reaction was stopped. To the reaction liquid was added 40 mL of saturated of sodium chloride and 20 mL of ethyl acetate, and the liquid was separated. The organic phase was washed twice with saturated sodium chloride solution, dried over anhydride sodium sulfate, concentrated and purified by silica-gel column chromatography (dichloromethane/methanol=40/1) to yield compound IIM.

Process B:

Compound 14 (25.0 mg, 0.08 mmol), aniline (0.08 mmol) were dissolved in 1 mL tert-butanol. To the solution was added trifluoroacetic acid (35 µL, 0.47 mmol). The resulting reaction liquid was heated in 110° C. oil bath with stirring until aniline was reacted completely (LC-MS tracking). The reaction was stopped. The reaction solution was concentrated and purified by reversed-phase preparative HPLC (with 0.35% trifluoroacetic acid aqueous solution and methanol as mobile phase), and concentrated in vaccum to yield compound IIM.

Compounds IIN were synthesized using similar processes.

TABLE 10

Structure and identification of compounds IIM-IIN

| ID | Structure | NMR and/or MS data |
|---|---|---|
| IIM-1 | 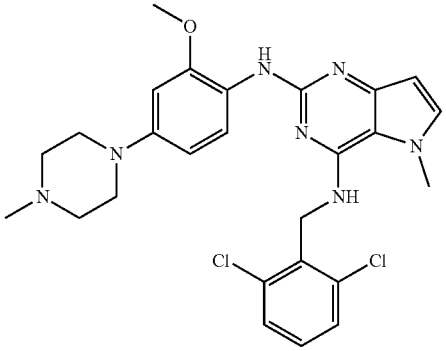 [SMILES: COc1cc(N2CCN(C)CC2)ccc1Nc1nc(NCc2c(Cl)cccc2Cl)c2c(ccn2C)n1] | ¹H NMR (600 MHz, DMSO-d$_6$) δ 8.30 (d, J = 7.1 Hz, 1H), 7.48 (d, J = 8.1 Hz, 2H), 7.41 (s, 1H), 7.33 (t, J = 8.1 Hz, 1H), 7.24 (d, J = 2.7 Hz, 1H), 7.06 (s, 1H), 6.66 (d, J = 2.2 Hz, 1H), 6.50 (dd, J = 8.8, 2.2 Hz, 1H), 6.10 (d, J = 2.9 Hz, 1H), 4.85 (d, J = 4.7 Hz, 2H), 3.94 (s, 3H), 3.89 (s, 3H), 3.17 (s, 4H), 2.78 (s, 4H), 2.46 (s, 3H). MS (ESI) m/z: 527[M + H]$^+$ |
| IIM-2 | 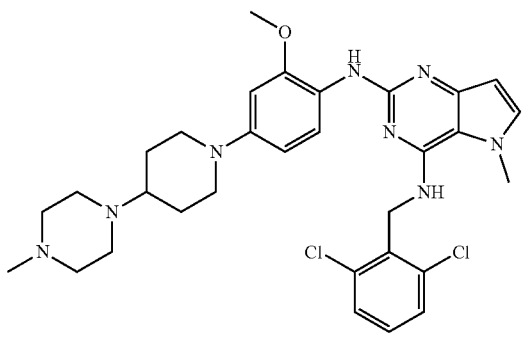 [SMILES: COc1cc(N2CCC(N3CCN(C)CC3)CC2)ccc1Nc1nc(NCc2c(Cl)cccc2Cl)c2c(ccn2C)n1] | ¹H NMR (600 MHz, DMSO-d$_6$) δ 8.38 (d, J = 8.8 Hz, 1H), 7.47 (d, J = 8.1 Hz, 2H), 7.35-7.27 (m, 1H), 7.21 (d, J = 2.9 Hz, 1H), 7.15 (s, 1H), 6.94 (t, J = 5.0 Hz, 1H), 6.62 (d, J = 2.5 Hz, 1H), 6.47 (dd, J = 8.9, 2.5 Hz, 1H), 6.09 (d, J = 2.9 Hz, 1H), 4.82 (d, J = 4.9 Hz, 2H), 4.60 (s, 1H), 3.94 (s, 3H), 3.89 (s, 3H), 3.60 (d, J = 12.2 Hz, 2H), 3.50 (t, J = 5.2 Hz, 4H), 2.57 (dd, J = 11.9, 10.3 Hz, 4H), 2.29 (s, 2H), 1.84 (d, J = 12.3 Hz, 2H), 1.52 (qd, J = 12.0, 3.6 Hz, 2H). MS (ESI) m/z: 610[M + H]$^+$ |
| IIM-3 | 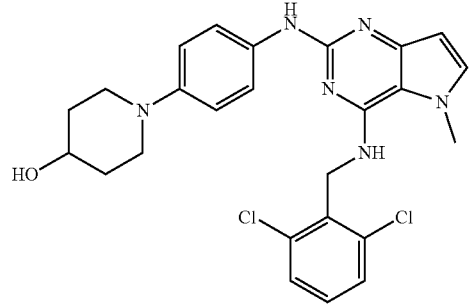 [SMILES: Cn1ccc2nc(Nc3ccc(N4CCC(O)CC4)cc3)nc(NCc3c(Cl)cccc3Cl)c21] | ¹H NMR (600 MHz, DMSO-d$_6$) δ 10.62 (s, 1H), 8.45 (s, 1H), 7.73 (d, J = 9.1 Hz, 2H), 7.59 (d, J = 8.1 Hz, 2H), 7.54-7.39 (m, 1H), 7.31 (t, J = 2.8 Hz, 1H), 7.09 (t, J = 4.0 Hz, 1H), 6.87 (d, J = 9.1 Hz, 2H), 6.26-5.96 (m, 1H), 4.92 (d, J = 4.2 Hz, 2H), 3.13-2.96 (m, 4H), 2.58-2.54 (m, 4H), 2.29 (s, 3H). MS (ESI) m/z: 498[M + H]$^+$ |
| IIM-4 | 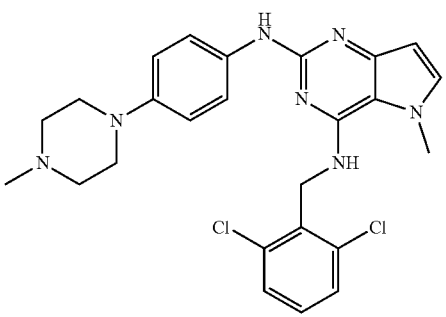 [SMILES: CN1CCN(c2ccc(Nc3nc(NCc4c(Cl)cccc4Cl)c4c(ccn4C)n3)cc2)CC1] | ¹H NMR (600 MHz, DMSO-d$_6$) δ 8.52 (s, 1H), 7.68 (d, J = 9.1 Hz, 2H), 7.52 (d, J = 8.1 Hz, 2H), 7.39 (dd, J = 8.5, 7.7 Hz, 1H), 7.25 (d, J = 2.9 Hz, 1H), 6.96-6.85 (m, 2H), 6.70 (s, 1H), 6.09 (d, J = 2.9 Hz, 1H), 4.95 (d, J = 4.7 Hz, 2H), 3.89 (s, 3H), 3.18 (d, J = 6.0 Hz, 4H), 2.91 (s, 4H), 2.55 (s, 3H). MS (ESI) m/z: 497[M + H]$^+$ |

TABLE 10-continued

Structure and identification of compounds IIM-IIN

| ID | Structure | NMR and/or MS data |
|---|---|---|
| IIN-1 | 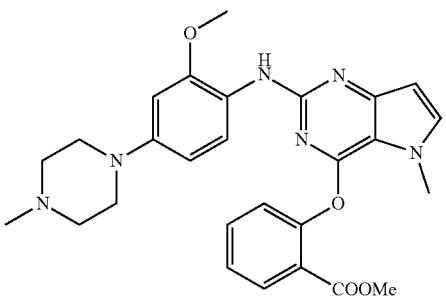 TFA salt | $^1$H-NMR (600 MHz; Methanol-$d_4$): δ 8.15 (dd, J = 7.9, 1.1 Hz, 1H), 7.80-7.77 (m, 1H), 7.67 (d, J = 2.7 Hz, 1H), 7.54-7.48 (m, 2H), 7.13-7.11 (m, 1H), 6.72-6.72 (m, 1H), 6.50-6.46 (m, 1H), 6.38 (d, J = 2.7 Hz, 1H), 4.18 (s, 3H), 3.89 (dd, J = 1.7, 0.6 Hz, 2H), 3.83-3.83 (m, 3H), 3.76-3.75 (m, 3H), 3.66-3.64 (m, 2H), 3.27-3.26 (m, 2H), 3.12-3.09 (m, 2H), 3.00 (s, 3H). MS (ESI) m/z: 503 [M + H]$^+$. |
| IIN-2 | 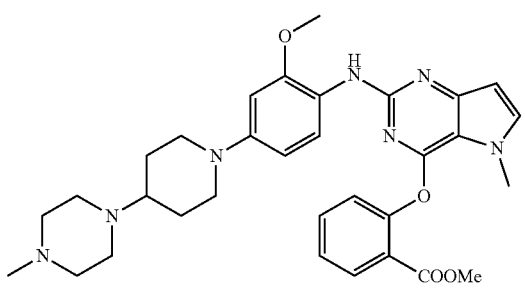 TFA salt | $^1$H-NMR (600 MHz; Methanol-$d_4$): δ 8.15 (d, J = 7.8 Hz, 1H), 7.80 (s, 1H), 7.70 (d, J = 2.5 Hz, 1H), 7.55 (s, 1H), 7.49 (d, J = 8.1 Hz, 1H), 7.18 (d, J = 8.7 Hz, 1H), 6.90 (s, 1H), 6.63-6.62 (m, 1H), 6.42 (d, J = 2.5 Hz, 1H), 4.18 (s, 3H), 3.86 (s, 5H), 3.76 (s, 3H), 3.54 (td, J = 1.3, 0.6 Hz, 4H), 3.42-3.40 (m, 3H), 3.25 (s, 1H), 3.14 (d, J = 0.2 Hz, 2H), 2.97 (s, 3H), 2.25-2.23 (m, 2H), 1.99-1.96 (m, 2H). MS (ESI) m/z: 586 [M + H]$^+$. |
| IIN-3 | 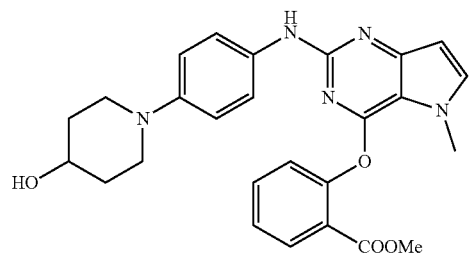 TFA salt | $^1$H-NMR (600 MHz; Methanol-$d_4$): δ 8.19-8.18 (m, 1H), 7.85-7.82 (m, 1H), 7.75 (d, J = 2.8 Hz, 1H), 7.60 (t, J = 7.7 Hz, 1H), 7.52 (d, J = 8.2 Hz, 1H), 7.34 (d, J = 9.0 Hz, 2H), 7.28 (d, J = 8.9 Hz, 2H), 6.51 (d, J = 2.9 Hz, 1H), 4.20 (s, 3H), 4.05 (s, 1H), 3.75-3.71 (m, 5H), 3.44-3.40 (m, 2H), 2.21-2.17 (m, 2H), 1.97-1.93 (m, 2H). MS (ESI) m/z: 474 [M + H]$^+$. |
| IIN-4 | 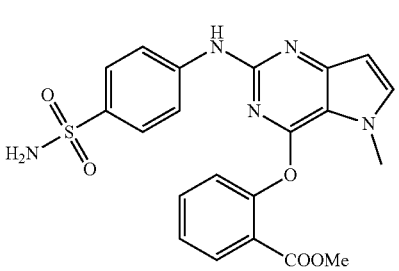 TFA salt | $^1$H-NMR (600 MHz; Methanol-$d_4$): δ 8.19 (dd, J = 7.9, 1.7 Hz, 1H), 7.84 (td, J = 7.8, 1.7 Hz, 1H), 7.74 (d, J = 3.0 Hz, 1H), 7.63-7.60 (m, 3H), 7.51 (dd, J = 8.1, 0.7 Hz, 1H), 7.37-7.36 (m, 2H), 6.51 (d, J = 3.0 Hz, 1H), 4.21 (s, 3H), 3.72 (s, 3H). MS (ESI) m/z: 454 [M + H]$^+$. |

Biological Examples

Test of Bioactivity

Activity of Compounds on Growth Inhibition of ALK Kinase Transformed Cell Lines

The activity of compounds against ALK kinase was evaluated by inhibiting the growth of cellular ALK kinase EML4-ALK-BaF3, EML4-ALK (L1196M)-BaF3, NPM-ALK-BaF3, and wild type BaF3 (Proc. Natl. Acad. Sci. USA., 2006, 103, 3153-8.) The growth of cellular ALK kinase EML4-ALK-BaF3, EML4-ALK(L1196M)-BaF3, and NPM-ALK-BaF3 depends on their kinase activity. If compounds can inhibit the activity of ALK kinase or the activity of ALK signaling pathway, they can inhibit the growth of ALK transformed Ba/F3 cells. The cell growth of wild type BaF3 does not depend on the activity of ALK and ALK signaling pathway. The broad-spectrum toxicity of compounds can be evaluated by determining the effect of the compounds on the growth of wild type BaF3 cells. Hence, the larger the ratio of IC$_{50}$ between wild-type BaF3 and transformed EML4-ALK-BaF3, EML4-ALK (L1196M)-BaF3 and NPM-ALK-BaF3, the better of the targeting of compounds.

Specific testing methods were as follows:

1) Medium: DMEM (Dulbecco's modified eagle medium) or RPMI1640 (containing 10% fetal bovine serum, 100 μg/mL ampicillin, 100 μg/mL streptomycin).)

Reagents: MTS solution (2 mg/mL MTS (3-(4,5-dimethylthiazol-2-yl)-5-(3-carboxymethoxyphenyl)-2-(4-sulfophenyl)-2H-tetrazolium, inner salt); 100 μg/mL PES (phenazine methosulfate)).

3) Test of compound: Transformed Ba/F3 cells (EML4-ALK-BaF3, EML4-ALK(L1196M)-BaF3, NPM-ALK-BaF3) (2×10$^4$/well) were distributed into 96-well plates, with volume of cell sap of 90 μL, 10 μL of compounds in gradient concentration (the highest concentration 10 was μM, followed by 1/3 step by step dilution, a total of 8 concentrations were set, the system contained 0.1% DMSO (dimethyl sulfoxide)). The cell plates mixed with compounds were cultured in a cell incubator (37° C.; 5% CO$_2$) for 48 hours, and the added 20 μL of MTS reaction solution, mixed and incubated in cell incubator (37° C.; 5% CO$_2$) for 1-4 hours. The OD value at a wavelength of 490 nm was measured using eliasa (VARIOSKAN FLASH, Thermo). Three parallels were set up for each group, with a final concentration of 0.1% DMSO as negative control, and with medium without cells and compounds as blank control. The inhibition rate of cell growth was calculated by the following formula:

Cell inhibition rate %=1−(OD experimental group−OD blank group)/(OD negative group−OD blank group)*100%

4) Calculation of IC$_{50}$ value: the semi inhibitory concentration of the compound acting on the cells was calculated using GradPad Prism 5 software according to the cell inhibitory rate measured.

TABLE 11

Activity of compounds of formula I on growth inhibition of ALK kinase transformed cell lines

| Cmpd ID | EML4-ALK (IC$_{50}$ nM) | EML4-ALK (L1196M) (IC$_{50}$ nM) | NPM-ALK (IC$_{50}$ nM) | BaF3 (IC$_{50}$ nM) |
|---|---|---|---|---|
| IA-1 | 1369 | 1804 | 703.4 | ~2788 |
| IA-2 | 648.7 | 760.6 | 1028 | 1523 |
| IA-3 | 2423 | 6632 | 12882 | 7712 |
| IB-1 | ~894.7 | ~2411 | 1447 | ~2799 |
| IB-2 | 785.6 | 1738 | 1768 | 1925 |
| IB-3 | 4220 | 8704 | 8833 | >10000 |
| IC-1 | 3927 | ~7247 | ~4557 | >10000 |
| IC-2 | 3678 | ~6859 | ~4913 | ~8766 |
| IC-3 | >10000 | >10000 | >10000 | >10000 |
| IC-4 | >10000 | >10000 | >10000 | >10000 |
| IC-5 | 4082 | ~3345 | 5258 | 4592 |
| ID-1 | 476.9 | 737.5 | 796 | ~8392 |
| ID-2 | 1171 | 2032 | ~2848 | ~8307 |
| ID-3 | 14.92 | 168 | 302.5 | 1013 |
| ID-4 | 2856 | 6151 | ~8935 | >10000 |
| ID-5 | >10000 | >10000 | >10000 | >10000 |
| ID-6 | 1505 | ~2649 | 1024 | ~2841 |
| ID-7 | 544.5 | ~1080 | ~1166 | ~2957 |
| ID-8 | 5173 | 5675 | >10000 | >10000 |
| IG-1 | 1467 | 1160 | 1797 | 2338 |
| IG-10 | 9798 | >10000 | 19612 | >10000 |
| IG-11 | 4674 | 5620 | >10000 | >10000 |
| IG-11 | 1505 | 1341 | 1686 | ~2787 |
| IG-12 | 6495 | 4128 | 4083 | ~7738 |
| IG-13 | >10000 | >10000 | >10000 | >10000 |
| IG-14 | ~1262 | 884.1 | 1393 | ~2548 |
| IG-15 | ~1127 | ~937.1 | ~1044 | ~2489 |
| IG-16 | 1371 | 1391 | 1738 | 2354 |
| IG-17 | 7613 | ~9462 | 7675 | 9387 |
| IG-18 | 4676 | 4366 | 8760 | >10000 |
| IG-2 | 1201 | 1191 | 1430 | 1804 |
| IG-3 | 2722 | 5043 | 6930 | 6866 |
| IG-4 | 5112 | 4940 | 6103 | 8512 |
| IG-5 | 7796 | >10000 | >10000 | >10000 |
| IG-6 | 1366 | 1521 | 1737 | ~3145 |
| IG-7 | 285.8 | 408.6 | 1206 | ~994.3 |
| IG-8 | 1831 | 1534 | 1673 | 3865 |
| IG-9 | >10000 | >10000 | >10000 | >10000 |
| IH-1 | 1118 | 915.5 | 1556 | 2066 |
| IH-2 | >10000 | 40377 | >10000 | >10000 |
| IH-3 | ~446.2 | 502.2 | ~858.5 | ~949.4 |
| IH-4 | ~1405 | ~974.5 | ~2762 | ~889.3 |
| II-1 | 1488 | ~2631 | 1640 | ~2713 |
| II-2 | 1813 | ~2563 | ~2598 | ~3033 |
| II-3 | 7474 | 6164 | 4909 | 9613 |
| II-4 | 1565 | 1675 | 1938 | ~2549 |
| II-5 | 237.8 | 488.5 | 1291 | 1055 |
| II-6 | 4959 | ~7403 | 6721 | ~8218 |
| IJ-1 | 4272 | 3936 | 4661 | 5009 |
| IJ-2 | ~8706 | 4112 | ~8358 | ~11667 |
| IJ-3 | >10000 | >10000 | >10000 | >10000 |
| IK-1 | ~2578 | 1548 | 1779 | 1825 |
| IK-2 | 668.5 | 451.3 | ~822.5 | ~912.8 |
| IL-1 | 1323 | 1615 | ~929.1 | ~2821 |
| IL-2 | ~2567 | 2002 | ~7724 | ~7842 |
| IL-3 | 3500 | 5024 | 5180 | 5184 |
| IL-4 | 9508 | >10000 | >10000 | >10000 |
| IM-1 | ~300.1 | 587.1 | 572.4 | ~866.7 |
| IM-2 | 1244 | 1310 | 1624 | 2899 |
| IM-3 | 7525 | >10000 | >10000 | >10000 |
| IN-1 | >10000 | >10000 | >10000 | >10000 |
| IN-2 | >10000 | >10000 | >10000 | >10000 |
| IN-3 | >10000 | >10000 | >10000 | >10000 |
| IN-4 | >10000 | >10000 | >10000 | >10000 |
| IN-5 | >10000 | >10000 | >10000 | 1206000 |
| IO-1 | 1719 | 3397 | 4828 | 4081 |
| IO-2 | 4423 | 5075 | 6634 | ~7813 |
| IO-3 | >10000 | >10000 | >10000 | >10000 |
| IO-4 | >10000 | >10000 | >10000 | >10000 |
| IO-5 | 4874 | 5205 | 5032 | 1912 |
| IQ-1 | >10000 | >10000 | >10000 | >10000 |
| IQ-2 | >10000 | >10000 | >10000 | >10000 |
| IQ-3 | >10000 | >10000 | >10000 | >10000 |
| IQ-4 | >10000 | >10000 | >10000 | >10000 |
| IQ-5 | >10000 | >10000 | >10000 | >10000 |
| IQ-6 | >10000 | >10000 | >10000 | >10000 |
| IR-1 | >10000 | >10000 | >10000 | >10000 |
| IR-2 | >10000 | >10000 | >10000 | >10000 |
| IR-3 | >10000 | >10000 | >10000 | >10000 |
| IS-1 | ~2552 | 1696 | 1790 | 5333 |
| IS-2 | >10000 | 5034 | >10000 | >10000 |
| IS-3 | 4485 | 9711 | >10000 | 11817 |
| IS-4 | >10000 | >10000 | >10000 | >10000 |
| IU-1 | >10000 | >10000 | >10000 | >10000 |
| IU-2 | 4578 | 2666 | 4905 | ~8339 |
| IU-3 | 4901 | 4183 | 8272 | 6518 |
| IU-4 | 9111 | 5987 | >10000 | >10000 |
| IU-5 | ~2877 | ~2512 | ~2850 | ~7724 |
| IV-1 | 6900 | 7306 | >10000 | >10000 |
| IV-2 | ~8984 | 3956 | ~9138 | ~8454 |
| IV-3 | 4553 | 4339 | 8153 | 8915 |
| IV-4 | >10000 | >10000 | >10000 | >10000 |
| Crizotinib | 54.92 | 741.73 | ND | 1077.33 |

* Crizotinib as positive control, ND means not detected.

TABLE 12

Activity of compounds of formula II on growth inhibition of ALK kinase transformed cell lines

| Cmpd ID | EML4-ALK ($IC_{50}$ nM) | L1196M ($IC_{50}$ nM) | NPM-ALK ($IC_{50}$ nM) | BaF3 ($IC_{50}$ nM) |
|---|---|---|---|---|
| IIA-1 | ~909.2 | ~2560 | 512.5 | 1547 |
| IIA-2 | ~1113 | 1620 | 1398 | ~883.2 |
| IIA-3 | 320.7 | 161.2 | 456.2 | 376.5 |
| IIA-4 | 1298 | 1320 | 2696 | 2572 |
| IIA-5 | ~876.8 | ~883.0 | 519.2 | ~336.5 |
| IIA-6 | 643.9 | 977.7 | 536.2 | 1372 |
| IIB-1 | 1719 | ~2796 | ~2509 | 1934 |
| IIB-2 | ~949.0 | ~852.9 | ~939.5 | 605.9 |
| IIB-3 | 488.9 | 916.8 | 653.4 | 1040 |
| IIB-4 | 3018 | 4207 | 4568 | 4876 |
| IIB-5 | ~2721 | ~2784 | ~1372 | ~2869 |
| IIC-1 | 3530 | ~5890 | 5122 | ~8674 |
| IIC-2 | 1510 | ~3512 | ~3462 | 5048 |
| IIC-3 | 8292 | 8994 | 11814 | ~10639 |
| IIC-4 | >10000 | 28193 | >10000 | >10000 |
| IIC-5 | ~3240 | 4410 | 3785 | ~7727 |
| IIC-6 | >10000 | >10000 | >10000 | >10000 |
| IID-1 | 546.2 | ~2955 | 2264 | ~8176 |
| IID-2 | 329.8 | 390.6 | 828.9 | 2907 |
| IID-3 | 2156 | 6647 | 6988 | >10000 |
| IID-4 | ~3286 | ~6442 | ~6354 | 7543 |
| IID-5 | ~1127 | ~1116 | ~2578 | ~7935 |
| IID-6 | 1599 | ~3004 | ~3130 | >10000 |
| IID-7 | 782.8 | ~2781 | ~981.7 | ~2580 |
| IID-8 | 1756 | 4770 | ~3464 | ~8378 |
| IID-9 | 2241 | ~2882 | 4736 | ~8299 |
| IIG-1 | 2372 | 3442 | 4871 | 5168 |
| IIG-2 | ~3882 | 3726 | 4894 | ~7941 |
| IIG-3 | 4255 | 2787 | 3180 | 5043 |
| IIG-4 | ~1333 | 3950 | 4211 | 4871 |
| IIH-1 | 1618 | 1844 | 1748 | 4941 |
| IIH-2 | 1972 | 1809 | 4469 | 2832 |
| III-1 | ~1359 | 1692 | ~2744 | ~2784 |
| III-2 | >10000 | >10000 | >10000 | >10000 |
| III-3 | 3202 | 4000 | 3711 | ~3335 |
| III-4 | >10000 | >10000 | >10000 | >10000 |
| IIJ-1 | ~865.4 | 544.4 | 626.6 | ~910.6 |
| IIJ-2 | 1710 | 1610 | 1609 | ~2865 |
| IIJ-3 | >10000 | 9697 | >10000 | >10000 |
| IIK-1 | ~2702 | 2098 | 1978 | 3275 |
| IIK-2 | ~3150 | ~2951 | ~3420 | ~2947 |
| IIK-3 | >10000 | >10000 | >10000 | >10000 |
| IIK-4 | >10000 | >10000 | 1777000 | >10000 |
| IIK-5 | 1429 | ~2559 | 1878 | ~2870 |
| IIK-6 | >10000 | >10000 | >10000 | >10000 |
| IIK-7 | >10000 | >10000 | >10000 | >10000 |
| IIL-1 | 1298 | 1595 | 1346 | ~2607 |
| IIL-2 | 627.3 | 1420 | 1823 | 2616 |
| IIL-3 | >10000 | >10000 | 7442 | >10000 |
| IIL-4 | >10000 | >10000 | >10000 | >10000 |
| IIL-5 | 1143 | 1531 | 847.6 | ~2761 |
| IIN-1 | ~5746 | 6467 | >10000 | ~9964 |
| IIN-2 | ~2593 | 2225 | 2327 | 5626 |
| IIN-3 | >10000 | >10000 | >10000 | >10000 |
| IIN-4 | >10000 | >10000 | >10000 | >10000 |
| Crizotinib | 54.92 | 741.73 | ND | 1077.33 |

* Crizotinib as positive control, ND means not detected.

It can be seen from the above activity data that compounds ID-3, II-5, IID-2 and IIL-2 having good activity exhibited good targeting selectivity.

Activity of Compounds on Growth Inhibition of Tumor Cells

If the tumor cells to be tested were suspension cells, the test was performed according to the method (1).

If the tumor cells to be tested were adherent cells, 1000-10000 cells/well were added to 96-well plates, incubated to adhere to the wall, and then added compounds. Other operations were conducted according to the method (1).

Compound ID-3 exhibited good growth inhibition on lung cancer cells H3122, A549, DFC1076 (crizotinib resistant tumor cell lines), melanoma A375, liver cancer HepG2, breast cancer MCF7, and were the most sensitive to ALK kinase-positive lung cancer cell lines H3122 and DFC1076.

TABLE 13

Growth inhibitory activity of compound ID-3 against tumor cells

| Cmpd ID | H3122 ($IC_{50}$ nM) | A549 ($IC_{50}$ nM) | A375 ($IC_{50}$ nM) | HepG2 ($IC_{50}$ nM) | MCF7 ($IC_{50}$ nM) |
|---|---|---|---|---|---|
| ID-3 | 61.14 | 2724 | 3758 | 3445 | 2835 |
| Crizotinib | 185.23 | 2404 | ND | ND | ND |

Above described are only some embodiments of the present invention. For those skilled in the art, some modifications and improvements can be made without departure of the inventive concept, all of which belong to the protection scope of the invention.

We claim:

1. A compound of formula I:

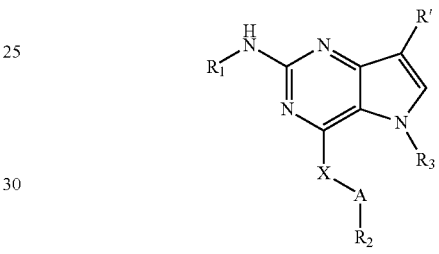

wherein
R' is H, Cl or Br;
$R_1$ is selected from the group consisting of:
2)

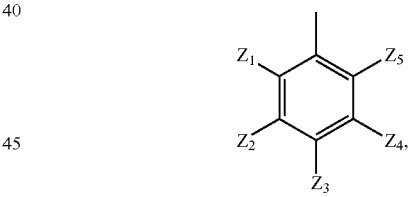

wherein $Z_1$, $Z_2$, $Z_3$, $Z_4$, $Z_5$ are independently selected from the group consisting of:
(1) H, F, Cl, Br, I, nitro, cyano;
(2) C1-C6 alkyl, C1-C6 alkoxy, C1-C6 oxyalkyl, C1-C6 fluoroalkyl, C1-C6 fluoroalkoxy, N-methyl-4-piperidyl;
(3) N,N-dimethylamino, N,N-diethylamino, N,N-diisopropylamino, 2-N,N-dimethylaminoethylamino, 2-morpholinoethylamino, 2-(4-N-methylpiperazinyl)ethylamino, 3-N,N-dimethylaminopropylamino, 3-N,N-diethylaminopropylamino, 3-N,N-diisopropylaminopropylamino, 3-morpholinopropylamino, 3-(4-N-methylpiperazinyl)propylamino, N-methylpiperid-4-ylamino, N-ethylpiperid-4-ylamino, N-isopropylpiperid-4-ylamino;
(4) 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinoethoxy, 2-thiomorpholinoethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinopropoxy, 3-thiomorpholinoethoxy, 3-piperidylpropoxy, 2-pyridylmethoxy, 3-pyridylmethoxy, 4-pyridylmethoxy, phenylmethoxy, monohalogen-substituted phenyl methoxy, gem-dihalogen substituted phenyl methoxy, hetero-dihalogen substituted phenyl methoxy;

(5) piperidyl, 4-N,N-dimethylaminopiperidyl, 4-N,N-diethylaminopiperidyl, 4-N,N-diisopropylaminopiperidyl, 4-hydroxypiperidyl, morpholino, 3,5-dimethylmorpholino, thiomorpholino, pyrrolidinyl, 3-N,N-dimethylpyrrolidinyl, 3-N,N-diethylpyrrolidinyl, N-methylpiperazinyl, N-ethylpiperazinyl, N-ispropylpiperazinyl, N-acetylpiperazinyl, N-tert-butoxyformylpiperazinyl, N-methylsulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, imidazolyl, 4-methylimidazolyl;

(6) 4-(N-methylpiperazinyl)piperidyl, 4-(N-ethylpiperazinyl)piperidyl, 4-(N-isopropylpiperazinyl)piperidyl, 4-(N-acetylpiperazinyl)piperidyl, 4-(N-tert-butoxyformyl)piperazinyl)piperidyl, 4-(N-methylsulfonylpiperazinyl)piperidyl, 4-(N-(2-hydroxyethyl)piperazinyl)piperidyl, 4-(N-(2-cyanoethyl)piperazinyl)piperidyl, 4-(N-(3-hydroxypropyl)piperazinyl)piperidyl, 4-(N-(2-N,N-dimethylethyl)piperazinyl)piperidyl, 4-(N-(2-N,N-diethylethyl)piperazinyl)piperidyl, 4-(N-(3-N,N-dimethylpropyl)piperazinyl)piperidyl, 4-(N-(3-N,N-diethylpropyl)piperazinyl)piperidyl, 4-(pyrrolidinyl)piperidyl, 4-(3-N,N-dimethylpyrrolidinyl)piperidyl, N—(N-methyl-4-piperidyl)piperazinyl, N—(N-ethyl-4-piperidyl)piperazinyl;

(7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylpiperidin-1-ylsulfonyl, 4-N,N-diethylpiperidin-1-ylsulfonyl, pyrrolidin-1-ylsulfonyl, 3-N,N-dimethylpyrrolidin-1-ylsulfonyl, 3-N,N-diethylpyrrolidin-1-ylsulfonyl, N-methylpiperazin-1-ylsulfonyl, N-ethylpiperazin-1-ylsulfonyl, N-acetylpiperazin-1-ylsulfonyl, N-tert-butoxyformylpiperazin-1-ylsulfonyl, N-(2-hydroxyethyl)piperazin-1-ylsulfonyl, N-(2-cyanoethyl)piperazin-1-ylsulfonyl, N-(2-N,N-dimethylethyl)piperazin-1-ylsulfonyl, N-(2-N,N-diethylethyl)piperazin-1-ylsulfonyl, N-(3-hydroxypropyl)piperazin-1-ylsulfonyl, N-(3-N,N-dimethylpropyl)piperazin-1-ylsulfonyl, N-(3-N,N-diethylpropyl)piperazin-1-ylsulfonyl, morpholino-1-sulfonyl, 3,5-dimethylmorpholino-1-sulfonyl, 4-(N-methyl-1-piperazinyl)piperidin-1-ylsulfonyl, 4-(N-ethyl-1-piperazinyl)piperidin-1-ylsulfonyl, 4-(N-acetyl-1-piperazinyl)piperidin-1-ylsulfonyl, N—(N-methyl-4-piperidyl)piperazin-1-ylsulfonyl;

(8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidin-1-ylcarbonyl, 4-hydroxypiperidin-1-ylcarbonyl, 4-N,N-dimethylpiperidin-1-ylcarbonyl, 4-N,N-diethylpiperidin-1-ylcarbonyl, pyrrolidin-1-ylcarbonyl, 3-N,N-dimethylpyrrolidin-1-ylcarbonyl, 3-N,N-diethylpyrrolidin-1-ylcarbonyl, N-methylpiperazin-1-ylcarbonyl, N-ethylpiperazin-1-ylcarbonyl, N-acetylpiperazin-1-ylcarbonyl, N-tert-butoxycarbonylpiperazin-1-ylcarbonyl, N-(2-hydroxyethyl)piperazin-1-ylcarbonyl, N-(2-cyanoethyl)piperazin-1-ylcarbonyl, N-(2-N,N-dimethylethyl)piperazin-1-ylcarbonyl, N-(2-N,N-diethylethyl)piperazin-1-ylcarbonyl, N-(3-hydroxypropyl)piperazin-1-ylcarbonyl, N-(3-N,N-dimethylpropyl)piperazin-1-ylcarbonyl, N-(3-N,N-diethylpropyl)piperazin-1-ylcarbonyl, morpholino-1-carbonyl, 3,5-dimethylmorpholino-1-carbonyl, 4-(N-methyl-1-piperazinyl)piperidin-1-ylcarbonyl, 4-(N-ethyl-1-piperazinyl)piperidin-1-ylcarbonyl, 4-(N-acetyl-1-piperazinyl)piperidin-1-ylcarbonyl, N—(N-methyl-4-piperidyl)piperazin-1-ylcarbonyl;

(9) methoxycarbonyl, ethoxycarbonyl, propoxycarbonyl, isopropoxycarbonyl, n-butoxycarbonyl, isobutoxycarbonyl, tert-butoxycarbonyl;

(10) aminoformamido, methylaminoformamido, ethylaminoformamido, propylaminoformamido, isopropylaminoformamido, cyclopropylaminoformamido, cyclobutylaminoformamido, cyclopentylaminoformamido, piperidin-1-ylformamido, 4-hydroxypiperidin-1-ylformamido, 4-N,N-dimethylpiperidin-1-ylformamido, 4-N,N-diethylpiperidin-1-ylformamido, pyrrolidin-1-ylformamido, 3-N,N-dimethylpyrrolidin-1-ylformamido, 3-N,N-diethylpyrrolidin-1-ylformamido, N-methylpiperazin-1-ylformamido, N-ethylpiperazin-1-ylformamido, N-acetylpiperazin-1-ylformamido, N-tert-butoxycarbonylpiperazin-1-ylformamido, N-(2-hydroxyethyl)piperazin-1-ylformamido, N-(2-cyanoethyl)piperazin-1-ylformamido, N-(2-N,N-dimethylethyl)piperazin-1-ylformamido, N-(2-N,N-diethylethyl)piperazin-1-ylformamido, N-(3-hydroxypropyl)piperazin-1-ylformamido, N-(3-N,N-dimethylpropyl)piperazin-1-ylformamido, N-(3-N,N-diethylpropyl)piperazin-1-ylformamido, morpholino-1-formamido, 3,5-dimethylmorpholino-1-formamido, 4-(N-methyl-1-piperazinyl)piperidin-1-ylformamido, 4-(N-ethyl-1-piperazinyl)piperidin-1-ylformamido, 4-(N-acetyl-1-piperazinyl)piperidin-1-ylformamido, N—(N-methyl-4-piperidyl)piperazin-1-ylformamido;

(11) aminoacetamido, N-tert-butoxycarbonylacetamido, N-acetylaminoacetamido, acrylamido, cyclopropionamido, chloroacetamido, piperidylacetamido, 4-hydroxypiperidylacetamido, 4-N,N-dimethylpiperidylacetamido, 4-N,N-diethylpiperidylacetamido, pyrrolidinylacetamido, 3-N,N-dimethylpyrrolidinylacetamido, 3-N,N-diethylpyrrolidinylacetamido, N-methylpiperazinylacetamido, N-ethylpiperazinylacetamido, N-acetylpiperazinylacetamido, N-tert-butoxycarbonylpiperazinylacetamido, N-(2-hydroxyethyl)piperazinylacetamido, N-(2-cyanoethyl)piperazinylacetamido, N-(2-N,N-dimethylethyl)piperazinylacetamido, N-(2-N,N-diethylethyl)piperazinylacetamido, N-(3-hydroxypropyl)piperazinylacetamido, N-(3-N,N-dimethylpropyl)piperazinylacetamido, N-(3-N,N-diethylpropyl)piperazinylacetamido, morpholino-1-acetamido, 3,5-dimethylmorpholinoacetamido, 4-(N-methyl-1-piperazinyl)piperidylacetamido, 4-(N-ethyl-1-piperazinyl)piperidylacetamido, 4-(N-acetyl-1-piperazinyl)piperidylacetamido, N—(N-methyl-4-piperidyl)piperazinylacetamido; 4-(pyrrolidin-1-yl)

piperidylacetamido, 2-methylaminoacetamido, 2-(1-methylethyl)aminoacetamido; N-benzyloxycarbonyl-2-methylaminoacetamido;
(12) $Z_2$ and $Z_3$ can form substituted or unsubstituted 5- or 6-membered oxygen-containing ring; the substituents may be selected from the same substituents for $Z_1$;
(13) $Z_2$ and $Z_3$ can form substituted or unsubstituted 5- or 6-membered nitrogen-containing ring; the substituents may be selected from the same substituents for $Z_1$;
A is a direct bond;
X is a NH, S or O;
$R_2$ is selected from the group consisting of:
2)

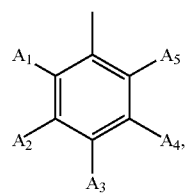

wherein $A_1$ is selected from the group consisting of:
(1) F, Cl, Br, I, cyano, trifluoromethyl, trifluoromethoxy, nitro;
(2) methylthio, ethylthio, isopropylthio, methylsulfinyl, ethylsulfinyl, isopropylsulfinyl, methylsulfonyl, ethylsulfonyl, isopropylsulfonyl, methylsulfonylamino, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl;
wherein $A_3$ is selected from the group consisting of:
(1) H, F, trifluoromethyl, trifluoromethoxy, nitro;
(2) methylthio, ethylthio, isopropylthio, methylsulfinyl, ethylsulfinyl, isopropylsulfinyl, methylsulfonyl, ethylsulfonyl, isopropylsulfonyl, methylsulfonylamino, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl;
wherein $A_2$, $A_4$ and $A_5$ are independently selected from the group consisting of:
(1) H, F, Cl, Br, I, cyano, trifluoromethyl, trifluoromethoxy, nitro;
(2) methylthio, ethylthio, isopropylthio, methylsulfinyl, ethylsulfinyl, isopropylsulfinyl, methylsulfonyl, ethylsulfonyl, isopropylsulfonyl, methylsulfonylamino, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl diethylphosphinyl, diisopropylphosphinyl;

3)

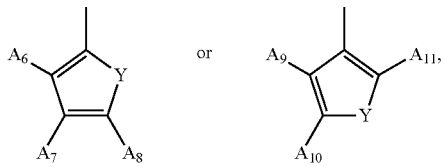

wherein Y is NH, S or O,
$A_6$, $A_7$, As, $A_9$, $A_{10}$, $A_{11}$ are independently selected from the group consisting of:
(1) H, F, Cl, Br, I, cyano, trifluoromethyl, trifluoromethoxy, nitro;
(2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl;
4)

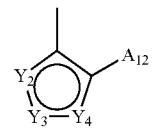

wherein $A_{12}$ is selected from the group consisting of:
(1) H, F, Cl, Br, I, cyano, trifluoromethyl, trifluoromethoxy, nitro,
(2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, methylsulfinyl, ethylsulfinyl, isopropylsulfinyl, methylsulfonyl, ethylsulfonyl, isopropylsulfonyl;
$Y_2$, $Y_3$, $Y_4$ are selected from the group consisting of:
$Y_2$ is N, $Y_3$ is N-$A_{13}$, $Y_4$ is CH or N;
$Y_2$ is N, $Y_3$ is C-$A_{13}$, $Y_4$ is N, O or S;
$Y_2$ is O or S, $Y_3$ is N-$A_{13}$, $Y_4$ is CH;
$Y_2$ is O or S, $Y_3$ is C-$A_{13}$, $Y_4$ is N; and
$Y_2$ is C, $Y_3$ is N-$A_{13}$, $Y_4$ is O or S;
wherein $A_{13}$ is H, C1-C6 alkyl, C2-C6 alkenyl, C2-C6 alkynyl, C3-C6 cycloalkyl;
$R_3$ is H, C1-C6 alkyl, C2-C6 alkenyl, C2-C6 alkynyl, C3-C6 cycloalkyl, or a stereoisomer, a pharmaceutically acceptable salt, or a pharmaceutically acceptable solvate thereof.
2. A compound of formula II:

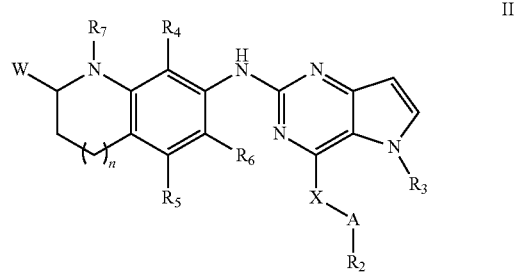

wherein

W is oxo, thio, or H;

n=0 or 1;

R₄, R₅, R₆ are independently selected from the group consisting of:
(1) H, F, Cl, Br, I, nitro, cyano;
(2) C1-C6 alkyl, C1-C6 alkoxy, C1-C6 oxyalkyl, C1-C6 fluoroalkyl, C1-C6 fluoroalkoxy;

R₇ is selected from the group consisting of:
(1) H, C1-C6 alkyl, acetyl, propionyl, n-butyryl, isobutyryl;
(2) glycyl, 2-N,N-dimethylacetyl, 2-N,N-diethylacetyl, 2-N,N-diisopropylacetyl, piperidylacetyl, 4-hydroxypiperidylacetyl, 4-N,N-dimethylpiperidylacetyl, 4-N,N-diethylpiperidylacetyl, pyrrolidinylacetyl, 3-N,N-dimethylpyrrolidinylacetyl, 3-N,N-diethylpyrrolidinylacetyl, N-methylpiperazinylacetyl, N-ethylpiperazinylacetyl, N-acetylpiperazinylacetyl, N-tert-butoxycarbonylpiperazinylacetyl, N-(2-hydroxyethyl)piperazinylacetyl, N-(2-cyanoethyl)piperazinylacetyl, N-(2-N,N-dimethylethyl)piperazinylacetyl, N-(2-N,N-diethylethyl)piperazinylacetyl, N-(3-hydroxypropyl)piperazinylacetyl, N-(3-N,N-dimethylpropyl)piperazinylacetyl, N-(3-N,N-diethylpropyl)piperazinylacetyl, morpholinoacetyl, 3,5-dimethylmorpholinoacetyl, 4-(N-methyl-1-piperazinyl)piperidylacetyl, 4-(N-ethyl-1-piperazinyl)piperidylacetyl, 4-(N-acetyl-1-piperazinyl)piperidylacetyl, N—(N-methyl-4-piperidyl)piperazinylacetyl;

A, X, R₂, R₃ are as defined in claim 1;

or a stereoisomer, a pharmaceutically acceptable salt, or a pharmaceutically acceptable solvate thereof.

3. A compound of formula III:

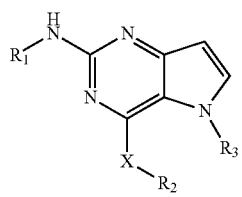

III wherein,
X, R₁, R₂, R₃ are as defined in claim 1,
or a stereoisomer, a pharmaceutically acceptable salt, or a pharmaceutically acceptable solvate thereof.

4. A compound of formula IV:

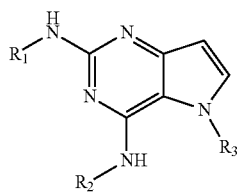

IV wherein,
R₁, R₃ are as defined in claim 1,
R₂ is selected from the group consisting of:
2)

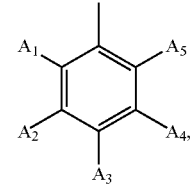

wherein A₁ is selected from the group consisting of:
(1) F, Cl, Br, I, cyano, trifluoromethyl, trifluoromethoxy, nitro;
(2) methylthio, ethylthio, isopropylthio, methylsulfinyl, ethylsulfinyl, isopropylsulfinyl, methylsulfonyl, ethylsulfonyl, isopropylsulfonyl, methylsulfonylamino, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl;

and wherein A₂, A₃, A₄ and A₅ are independently selected from the group consisting of:
(1) H, F, Cl, Br, I, cyano, trifluoromethyl, trifluoromethoxy, nitro;
(2) methylthio, ethylthio, isopropylthio, methylsulfinyl, ethylsulfinyl, isopropylsulfinyl, methylsulfonyl, ethylsulfonyl, isopropylsulfonyl, methylsulfonylamino, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl;

3)

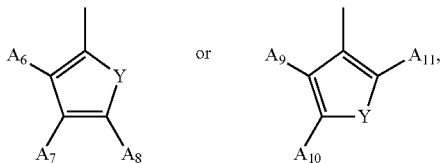

wherein
Y is NH, S or O, and
A₆, A₇, A₈, A₉, A₁₀, A₁₁ are independently selected from the group consisting of:
(1) H, F, Cl, Br, I, cyano, trifluormethyl, trifluoromethoxy, nitro;
(2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl;

or a stereoisomer, a pharmaceutically acceptable salt, or a pharmaceutically acceptable solvate thereof.

5. A compound according to claim 1, a stereoisomer, a pharmaceutically acceptable salt, or a pharmaceutically acceptable solvate thereof, which is selected from at least one of the group consisting of:

(1) in $R_1$, $Z_1$ is independently selected from methoxy, ethoxy, isopropoxy or trifluoromethoxy, and/or $Z_3$ is independently selected from 4-N,N-dimethylaminopiperidyl, 4-hydroxypiperidyl, morpholino, pyrrolidinyl, 3-N,N-dimethylpyrrolidyl, N-methylpiperazinyl, N-ethylpiperazinyl, N-acetylpiperazinyl, N-(2-hydroxyethyl)piperazinyl, N-(2-cyanoethyl)piperazinyl, N-(3-hydroxypropyl)piperazinyl, 4-(N-methylpiperazinyl)piperidyl, 4-(N-ethylpiperazinyl)piperidyl, 4-(N-acetylpiperazinyl)piperidyl, 4-(N-tert-butoxycarbonylpiperazinyl)piperidyl, 4-(N-(2-hydroxyethyl)piperazinyl)piperidyl, 4-(N-(2-cyanoethyl)piperazinyl)piperidyl, 4-pyrrolidylpiperidyl, N—(N-methyl-4-piperidyl)piperazinyl, N—(N-ethyl-4-piperidyl)piperazinyl, aminosulfonyl, methaminosulfonyl, cyclopropaminosulfonyl, piperidin-1-ylsulfonyl, 4-hydroxypiperidin-1-ylsulfonyl, 4-N,N-dimethylpiperidin-1-ylsulfonyl, pyrrolidin-1-ylsulfonyl, 3-N,N-dimethylpyrrolidin-1-ylsulfonyl, N-methylpiperazin-1-ylsulfonyl, N-ethylpiperazin-1-ylsulfonyl, morpholino-1-sulfonyl, hydroxycarbonyl, aminocarbonyl, methylaminocarbonyl, ethylaminocarbonyl, isopropylaminocarbonyl, cyclopropylaminocarbonyl, piperidin-1-ylcarbonyl, 4-hydroxypiperidin-1-ylcarbonyl, 4-N,N-dimethylpiperidin-1-ylcarbonyl, pyrrolidin-1-ylcarbonyl, 3-N,N-dimethylpyrrolidin-1-ylcarbonyl, N-methylpiperazin-1-ylcarbonyl, N-ethylpiperazin-1-ylcarbonyl, N-acetylpiperazin-1-ylcarbonyl, morpholino-1-carbonyl, 4-(N-methyl-1-piperazinyl)piperidin-1-ylcarbonyl, 4-(N-ethyl-1-piperazinyl)piperidin-1-ylcarbonyl, 4-(N-acetyl-1-piperazinyl)piperidin-1-ylcarbonyl, N—(N-methyl-4-piperidyl)piperazin-1-ylcarbonyl;

(2) $R_2$ is selected from 2-methylsulfonylphenyl, 2-ethylsulfonylphenyl, 2-isopropylsulfonylphenyl, 2-methylsulfoamidophenyl or 2-dimethylphosphinylphenyl;

(3) $R_3$ is selected from H or methyl;

(4) the compound is a pharmaceutically acceptable salt, wherein the pharmaceutically acceptable salt is a salt of an inorganic or organic acid, wherein the salt of inorganic acid is the salt of hydrochloric, hydrobromic, nitric, sulfuric and phosphoric acid; the salt of organic acid is the salt of formic acid, acetic acid, propionic acid, benzoic acid, maleic acid, fumaric acid, succinic acid, tartaric acid, citric acid, alkylsulfonic acid or arylsulfonic acid.

6. A compound selected from the following compounds:

$N^2$-(2-methoxy-4-(4-methylpiperazin-1-yl)phenyl)-$N^4$-(2-(methylthio)phenyl)-5H-pyrrolo[3,2-d]pyrimidine-2,4-diamine;

$N^2$-(4-(4-hydroxypiperidine-1-yl)phenyl)-$N^4$-(2-(methylthio)phenyl)-5H-pyrrolo[3,2-d]pyrimidine-2,4-diamine;

$N^2$-(4-amino sulfonylphenyl)-$N^4$-(2-(methylthio)phenyl)-5H-pyrrolo[3,2-d]pyrimidine-2,4-diamine;

$N^2$-(2-methoxy-4-(4-methylpiperazin-1-yl)phenyl)-$N^4$-(2-(ispropylthio)phenyl)-5H-pyrrolo[3,2-d]pyrimidine-2,4-diamine;

$N^2$-(4-(4-hydroxypiperidine-1-yl)phenyl)-$N^4$-(2-(isopropylthio)phenyl)-5H-pyrrolo[3,2-d]pyrimidine-2,4-diamine;

$N^2$-(4-amino sulfonylphenyl)-$N^4$-(2-(isopropylthio)phenyl)-5H-pyrrolo[3,2-d]pyrimidine-2,4-diamine;

$N^2$-(2-methoxy-4-(4-methylpiperazin-1-yl)phenyl)-$N^4$-(2-(methylsulfonyl)phenyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(methylsulfonyl)phenyl)-5H-pyrrolo[3,2-d]pyrimidine-2,4-diamine;

$N^2$-(4-(4-hydroxypiperidine-1-yl)phenyl)-$N^4$-(2-(methylsulfonyl)phenyl)-5H-pyrrolo[3,2-d]pyrimidine-2,4-diamine;

$N^2$-(4-amino sulfonylphenyl)-$N^4$-(2-(methylsulfonyl)phenyl)-5H-pyrrolo[3,2-d]pyrimidine-2,4-diamine;

$N^2$-(4-(4-methylpiperazin-1-yl)phenyl)-$N^4$-(2-(methylsulfonyl)phenyl)-5H-pyrrolo[3,2-d]pyrimidine-2,4-diamine;

$N^2$-(2-methoxy-4-(4-methylpiperazin-1-yl)phenyl)-$N^4$-(2-(isopropylsulfonyl)phenyl)-5H-pyrrolo[3,2-d]pyrimidine-2,4-diamine;

$N^2$-(4-(4-methylpiperazin-1-yl)phenyl)-$N^4$-(2-(isopropylsulfonyl)phenyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(isopropylsulfonyl)phenyl)-5H-pyrrolo[3,2-d]pyrimidine-2,4-diamine;

$N^2$-(4-(4-hydroxypiperidine-1-yl)phenyl)-$N^4$-(2-(isopropylsulfonyl)phenyl)-5H-pyrrolo[3,2-d]pyrimidine-2,4-diamine;

$N^2$-(4-amino sulfonylphenyl)-$N^4$-(2-(isopropylsulfonyl)phenyl)-5H-pyrrolo[3,2-d]pyrimidine-2,4-diamine;

$N^2$-(2-isopropoxy-5-methyl-(4-(1-methylpiperidin-4-yl)phenyl-$N^4$-(2-(isopropylsulfonyl)phenyl)-5H-pyrrolo[3,2-d]pyrimidine-2,4-diamine;

$N^2$-(2-methoxy-5-methyl-(4-(1-methylpiperidin-4-yl)phenyl-$N^4$-(2-(isopropylsulfonyl)phenyl)-5H-pyrrolo[3,2-d]pyrimidine-2,4-diamine;

$N^2$-(1-(1-methylpiperidin-4-yl)-1H-pyrazolyl-4-yl-$N^4$-(2-(isopropylsulfonyl)phenyl)-5H-pyrrolo[3,2-d]pyrimidine-2,4-diamine;

$N^2$-(2-methoxy-4-(4-pyrrolidin-1-yl)piperidin-1-yl)phenyl)-$N^4$-(2-(isopropylsulfonyl)phenyl)-5H-pyrrolo[3,2-d]pyrimidine-2,4-diamine;

$N^2$-(4-(pyridine-2-methoxy)phenyl-$N^4$-(2-(isopropylsulfonyl)phenyl)-5H-pyrrolo[3,2-d]pyrimidine-2,4-diamine;

$N^2$-(2-methoxy-4-(4-(N,N-dimethylamino)piperidin-1-yl)phenyl)-$N^4$-(2-(isopropylsulfonyl)phenyl)-5H-pyrrolo[3,2-d]pyrimidine-2,4-diamine;

$N^2$-(6-(4-hydroxypiperdin-1-yl)pyridine-3-yl)-$N^4$-(2-(isopropylsulfonyl)phenyl)-5H-pyrrolo[3,2-d]pyrimidine-2,4-diamine;

$N^2$-(6-morpholinopyridin-3-yl)-$N^4$-(2-(isopropylsulfonyl)phenyl)-5H-pyrrolo[3,2-d]pyrimidine-2,4-diamine;

$N^2$—(N-(2-N,N-dimethylaminoacetyl)-5-methoxyindolin-6-yl)-$N^4$-(2-(isopropylsulfonyl)phenyl)-5H-pyrrolo[3,2-d]pyrimidine-2,4-diamine;

$N^2$-(3,4-dihydroquinolin-2(1H)-one-6-yl)-$N^4$-(2-(isopropylsulfonyl)phenyl)-5H-pyrrolo[3,2-d]pyrimidine-2,4-diamine;

$N^2$-(2-methoxy-4-(4-(4-methylpiperazin-1-yl)piperidin-1-ylcarbonyl)phenyl)-$N^4$-(2-(isopropylsulfonyl)phenyl)-5H-pyrrolo[3,2-d]pyrimidine-2,4-diamine;

$N^2$-(2-trifluoromethoxy-4-(4-(4-methylpiperazin-1-yl)piperidin-1-yl)phenyl)-$N^4$-(2-(isopropylsulfonyl)phenyl)-5H-pyrrolo[3,2-d]pyrimidine-2,4-diamine;

N²-(3-acrylamidophenyl)-N⁴-(2-(isopropylsulfonyl)phenyl)-5H-pyrrolo[3,2-d]pyrimidine-2,4-diamine;
N²-(3-(2-morpholinoacetamido)phenyl)-N⁴-(2-(isopropylsulfonyl)phenyl)-5H-pyrrolo[3,2-d]pyrimidine-2,4-diamine;
N²-(3-(2-(4-methylpiperazin-1-yl)acetamido)phenyl)-N⁴-(2-(isopropylsulfonyl)phenyl)-5H-pyrrolo[3,2-d]pyrimidine-2,4-diamine;
N²-(3-(2-(4-(N,N-dimethylamino)piperidin-1-yl)acetamido)phenyl)-N⁴-(2-(isopropylsulfonyl)phenyl)-5H-pyrrolo[3,2-d]pyrimidine-2,4-diamine;
N²-(3-(2-(4-(pyrrolidin-1-yl)piperidin-1-yl)acetamido)phenyl)-N⁴-(2-(isopropylsulfonyl)phenyl)-5H-pyrrolo[3,2-d]pyrimidine-2,4-diamine;
N²-(3-(2-(4-(4-methylpiperazin-1-yl)piperidin-1-yl)acetamido)phenyl)-N⁴-(2-(isopropylsulfonyl)phenyl)-5H-pyrrolo[3,2-d]pyrimidine-2,4-diamine;
N²-(3-(cyclopropanecarboxamido)phenyl)-N⁴-(2-(isopropylsulfonyl)phenyl)-5H-pyrrolo[3,2-d]pyrimidine-2,4-diamine;
N²-(3-aminophenyl)-N⁴-(2-(isopropylsulfonyl)phenyl)-5H-pyrrolo[3,2-d]pyrimidine-2,4-diamin;
N²-(3-(2-tert-butoxyformamidoacetamido)phenyl)-N⁴-(2-(isopropylsulfonyl)phenyl)-5H-pyrrolo[3,2-d]pyrimidine-2,4-diamine;
N²-(3-(2-acetaminoacetamido)phenyl)-N⁴-(2-(isopropylsulfonyl)phenyl)-5H-pyrrolo[3,2-d]pyrimidine-2,4-diamine;
N²-(3-(2-aminoacetamido)phenyl)-N⁴-(2-(isopropylsulfonyl)phenyl)-5H-pyrrolo[3,2-d]pyrimidine-2,4-diamine;
(S)—N²-(3-(2-benzoxyformamido-2-methylacetamido)phenyl)-N⁴-(2-(isopropylsulfonyl)phenyl)-5H-pyrrolo[3,2-d]pyrimidine-2,4-diamine;
(S)—N²-(3-(2-methyl-2-aminoacetamido)phenyl)-N⁴-(2-(isopropylsulfonyl)phenyl)-5H-pyrrolo[3,2-d]pyrimidine-2,4-diamine;
(S)—N²-(3-(2-isopropyl-2-amino acetamido)phenyl)-N⁴-(2-(isopropylsulfonyl)phenyl)-5H-pyrrolo[3,2-d]pyrimidine-2,4-diamine;
N²-(2-methoxy-4-(4-(4-methylpiperazin-1-yl)piperidin-1-yl)phenyl)-N⁴-(2-(methylsulfonamido)phenyl)-5H-pyrrolo[3,2-d]pyrimidine-2,4-diamine;
N²-(4-(4-hydroxypiperidine-1-yl)phenyl)-N⁴-(2-(methylsulfonamido)phenyl)-5H-pyrrolo[3,2-d]pyrimidine-2,4-diamine;
N²-(1-(1-methylpiperidin-4-yl)-1H-pyrazol-4-yl)-N⁴-(2-(methylsulfonamido)phenyl)-5H-pyrrolo[3,2-d]pyrimidine-2,4-diamine;
N²-(4-(4-methylpiperazin-1-yl)phenyl)-N⁴-(2-(methylsulfonamido)phenyl)-5H-pyrrolo[3,2-d]pyrimidine-2,4-diamine;
N²-(4-morpholinophenyl)-N⁴-(2-(methylsulfonamido)phenyl)-5H-pyrrolo[3,2-d]pyrimidine-2,4-diamine;
N²-(2-methoxy-4-morpholinophenyl)-N⁴-(2-(methylsulfonamido)phenyl)-5H-pyrrolo[3,2-d]pyrimidine-2,4-diamine;
N²-(2-methoxy-4-(4-(4-methylpiperazin-1-yl)piperidin-1-yl)phenyl)-N⁴-(2-(dimethylphosphinyl)phenyl)-5H-pyrrolo[3,2-d]pyrimidine-2,4-diamine;
N²-(4-(4-hydroxypiperidine-1-yl)phenyl)-N⁴-(2-(dimethylphosphinyl)phenyl)-5H-pyrrolo[3,2-d]pyrimidine-2,4-diamine;
N²-(1-(1-methylpiperidin-4-yl)-1H-pyrazol-4-yl)-N⁴-(2-(dimethylphosphinyl)phenyl)-5H-pyrrolo[3,2-d]pyrimidine-2,4-diamine;
N²-(4-(4-methylpiperazin-1-yl)phenyl)-N⁴-(2-(dimethylphosphinyl)phenyl)-5H-pyrrolo[3,2-d]pyrimidine-2,4-diamine;
N²-(2-methoxy-4-(4-methylpiperazin-1-yl)phenyl)-N⁴-(2-(dimethylphosphinyl)phenyl)-5H-pyrrolo[3,2-d]pyrimidine-2,4-diamine;
N²-(2-methoxy-4-(4-(N,N-dimethylamino)piperidin-1-yl)phenyl-N⁴-(2-(dimethylphosphinyl)phenyl)-5H-pyrrolo[3,2-d]pyrimidine-2,4-diamine;
N²-(2-methoxy-4-(4-methylpiperazin-1-yl)phenyl)-N⁴-(2-methoxyformyl)phenyl-5H-pyrrolo[3,2-d]pyrimidine-2,4-diamine;
N²-(2-methoxy-4-(4-(4-methylpiperazin-1-yl)piperidin-1-yl)phenyl)-N⁴-(2-(methoxyformyl)phenyl)-5H-pyrrolo[3,2-d]pyrimidine-2,4-diamine;
N²-(4-(4-hydroxypiperidin-1-yl)phenyl)-N⁴-(2-(methoxyformyl)phenyl)-5H-pyrrolo[3,2-d]pyrimidine-2,4-diamine;
N²-(4-amino sulfonylphenyl)-N⁴-(2-(methoxyformyl)phenyl)-5H-pyrrolo[3,2-d]pyrimidine-2,4-diamine;
N²-(4-morpholinophenyl)-N⁴-(2-(methoxyformyl)phenyl)-5H-pyrrolo[3,2-d]pyrimidine-2,4-diamine;
N²-(4-(4-methylpiperazin-1-yl)phenyl)-N⁴-(2-(methoxyformyl)phenyl)-5H-pyrrolo[3,2-d]pyrimidine-2,4-diamine;
N²-(2-methoxy-4-(4-(pyrrolidin-1-yl)piperidin-1-yl)phenyl)-N⁴-(2-(methoxyformyl)phenyl)-5H-pyrrolo[3,2-d]pyrimidine-2,4-diamine;
N²-(4-(pyridin-2-ylmethoxy)phenyl)-N⁴-(2-(methoxyformyl)phenyl)-5H-pyrrolo[3,2-d]pyrimidine-2,4-diamine;
N²-(2-isopropoxy-4-(4-hydroxypiperidine-1-yl)phenyl)-N⁴-(2-(methoxyformyl)phenyl)-5H-pyrrolo[3,2-d]pyrimidine-2,4-diamine;
N²-(2-ethoxy-4-(4-hydroxypiperidine-1-yl)phenyl)-N⁴-(2-(methoxyformyl)phenyl)-5H-pyrrolo[3,2-d]pyrimidine-2,4-diamine;
N²-(4-(4-hydroxypiperidine-1-ylsulfonyl)phenyl)-N⁴-(2-(methoxyformyl)phenyl)-5H-pyrrolo[3,2-d]pyrimidine-2,4-diamine;
N²-(2-methoxy-4-(4-(4-methylpiperazin-1-yl)piperidin-1-ylformyl)phenyl)-N⁴-(2-(methoxyformyl)phenyl)-5H-pyrrolo[3,2-d]pyrimidine-2,4-diamine;
N²-(5-(4-methylpiperazin-1-yl)pyrid-2-yl)-N⁴-(2-(methoxyformyl)phenyl)-5H-pyrrolo[3,2-d]pyrimidine-2,4-diamine;
N²-(2-methoxy-5-methyl-4-(1-methylpiperidin-4-yl)phenyl)-N⁴-(2-(methoxyformyl)phenyl)-5H-pyrrolo[3,2-d]pyrimidine-2,4-diamine;
N²-(2-isopropoxy-5-methyl-4-(1-methylpiperidin-4-yl)phenyl)-N⁴-(2-(methoxyformyl)phenyl)-5H-pyrrolo[3,2-d]pyrimidine-2,4-diamine;
N²-(2-methoxy-4-morpholinophenyl)-N⁴-(2-(methoxyformyl)phenyl)-5H-pyrrolo[3,2-d]pyrimidine-2,4-diamine;
N²-(2-methoxy-4-morpholinoformylphenyl)-N⁴-(2-(methoxyformyl)phenyl)-5H-pyrrolo[3,2-d]pyrimidine-2,4-diamine;
N²-(6-(4-hydroxypiperidine-1-yl)pyridin-3-yl)-N⁴-(2-(methoxyformyl)phenyl)-5H-pyrrolo[3,2-d]pyrimidine-2,4-diamine;
N²-(2-ethoxy-4-(4-methylpiperazin-1-yl)phenyl)-N⁴-(2-(methoxyformyl)phenyl)-5H-pyrrolo[3,2-d]pyrimidine-2,4-diamine;
N²-(2-methoxy-4-(4-methylpiperazin-1-yl)phenyl)-N⁴-(2-(isobutoxyformyl)phenyl)-5H-pyrrolo[3,2-d]pyrimidine-2,4-diamine;

$N^2$-(4-(4-hydroxypiperidine-1-yl)phenyl)-$N^4$-(2-isobutoxyformyl)phenyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-isobutoxyformyl)phenyl)-5H-pyrrolo[3,2-d]pyrimidine-2,4-diamine;

$N^2$-(2-methoxy-4-(4-(pyrrolidin-1-yl)piperidin-1-yl)phenyl)-$N^4$-(2-isobutoxyformyl)phenyl)-5H-pyrrolo[3,2-d]pyrimidine-2,4-diamine;

$N^2$-(2-methoxy-4-(4-methylpiperazin-1-yl)phenyl)-$N^4$-(3-(methoxyformyl)phenyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(3-(methoxyformyl)phenyl)-5H-pyrrolo[3,2-d]pyrimidine-2,4-diamine;

$N^2$-(4-(4-hydroxypiperidine-1-yl)phenyl)-$N^4$-(3-(methoxyformyl)phenyl)-5H-pyrrolo[3,2-d]pyrimidine-2,4-diamine;

$N^2$-(4-(4-methylpiperazin-1-yl)phenyl)-$N^4$-(3-(methoxyformyl)phenyl)-5H-pyrrolo[3,2-d]pyrimidine-2,4-diamine;

$N^2$-(4-morpholinophenyl)-$N^4$-(3-(methoxyformyl)phenyl)-5H-pyrrolo[3,2-d]pyrimidine-2,4-diamine;

$N^2$-(2-methoxy-4-(4-(pyrrolidin-1-yl)piperidin-1-yl)phenyl)-$N^4$-(3-(methoxyformyl)phenyl)-5H-pyrrolo[3,2-d]pyrimidine-2,4-diamine;

$N^2$-(2-morpholino-5-pyridyl)-$N^4$-(3-(methoxyformyl)phenyl)-5H-pyrrolo[3,2-d]pyrimidine-2,4-diamine;

$N^2$-(2-methoxy-(4-morpholin-1-yl)phenyl)-$N^4$-(3-(methoxyformyl)phenyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(N-methylaminoformyl)phenyl)-5H-pyrrolo[3,2-d]pyrimidine-2,4-diamine;

$N^2$-(2-methoxy-4-(4-(pyrrolidin-1-yl)piperidin-1-yl)phenyl)-$N^4$-(2-(N-methylaminoformyl)phenyl)-5H-pyrrolo[3,2-d]pyrimidine-2,4-diamine;

$N^2$-(4-amino sulfonylphenyl)-$N^4$-(2-(N-methylaminoformyl)phenyl)-5H-pyrrolo[3,2-d]pyrimidine-2,4-diamine;

$N^2$-(2-methoxy-4-(4-methylpiperazin-1-yl)phenyl)-$N^4$-(2-(methoxyformyl)thien-3-yl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(methoxyformyl)thien-3-yl)-5H-pyrrolo[3,2-d]pyrimidine-2,4-diamine;

$N^2$-(4-(4-hydroxypiperidine-1-yl)phenyl)-$N^4$-(2-(methoxyformyl)thien-3-yl)-5H-pyrrolo[3,2-d]pyrimidine-2,4-diamine;

$N^2$-(4-morpholinophenyl)-$N^4$-(2-(methoxyformyl)thien-3-yl)-5H-pyrrolo[3,2-d]pyrimidine-2,4-diamine;

$N^2$-(2-methoxy-4-morpholinophenyl)-$N^4$-(2-(methoxyformyl)thien-3-yl)-5H-pyrrolo[3,2-d]pyrimidine-2,4-diamine;

$N^2$-(4-(4-(4-methylpiperazin-1-yl)piperidin-1-yl)phenyl)-$N^4$-(2-(methoxyformyl)thien-3-yl)-5H-pyrrolo[3,2-d]pyrimidine-2,4-diamine;

$N^2$-(2-ethoxy-4-(4-methylpiperazin-1-yl)phenyl)-$N^4$-(2-(methoxyformyl)thien-3-yl)-5H-pyrrolo[3,2-d]pyrimidine-2,4-diamine;

$N^2$-(2-methoxy-4-(4-(pyrrolidin-1-yl)piperidin-1-yl)phenyl)-$N^4$-(2-(methoxyformyl)thien-3-yl)-5H-pyrrolo[3,2-d]pyrimidine-2,4-diamine;

$N^2$-(2-methoxy-4-(4-(N,N-dimethylamino)piperidin-1-yl)phenyl-$N^4$-(2-(methoxyformyl)thien-3-yl)-5H-pyrrolo[3,2-d]pyrimidine-2,4-diamine;

$N^2$-(2-methoxy-5-methyl-4-(1-methylpiperidin-4-yl)phenyl)-$N^4$-(2-(methoxyformyl)thien-3-yl)-5H-pyrrolo[3,2-d]pyrimidine-2,4-diamine;

$N^2$-(2-isopropoxy-5-methyl-(4-(1-methylpiperidin-4-yl)phenyl)-$N^4$-(2-(methoxyformyl)thien-3-yl)-5H-pyrrolo[3,2-d]pyrimidine-2,4-diamine;

$N^2$—(N-(2-N,N-dimethylaminoacetyl)-5-methoxyindolin-6-yl)-$N^4$-(2-(methoxyformyl)thien-3-yl)-5H-pyrrolo[3,2-d]pyrimidine-2,4-diamine;

$N^2$-(2-methoxy-4-)4-(4-methylpiperazin-1-yl)piperidin-1-yl)phenyl-$N^4$-(3-isopropylsulfon-1-ylmethyl-1H-pyrazol-1-yl)-5H-pyrrolo[3,2-d]pyrimidine-2,4-diamine;

$N^2$—(N-(2-N,N-dimethylamino acetyl)-5-methoxyindolin-6-yl)-$N^4$-(3-isopropylsulfon-1-ylmethyl-1H-pyrazol-1-yl)-5H-pyrrolo[3,2-d]pyrimidine-2,4-diamine;

$N^2$-(2-methoxy-4-(4-(4-methylpiperazin-1-yl)phenyl-$N^4$-(3-isopropylsulfon-1-ylmethyl-1H-pyrazol-1-yl)-5H-pyrrolo[3,2-d]pyrimidine-2,4-diamine;

$N^2$-(4-(4-hydroxypiperidin-1-yl)phenyl)-$N^4$-(3-isopropylsulfon-1-ylmethyl-1H-pyrazol-1-yl)-5H-pyrrolo[3,2-d]pyrimidine-2,4-diamine;

$N^2$-(2-methoxy-4-(4-methylpiperazin-1-yl)phenyl-$N^4$-(2-(methylthio)benzyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(methylthio)benzyl)-5H-pyrrolo[3,2-d]pyrimidine-2,4-diamine;

$N^2$-(4-(4-hydroxypiperidin-1-yl)phenyl-$N^4$-(2-(methylthio)benzyl)-5H-pyrrolo[3,2-d]pyrimidine-2,4-diamine;

$N^2$-(4-amino sulfonylphenyl)-$N^4$-(2-(methoxyformyl)phenyl-5H-pyrrolo[3,2-d]pyrimidine-2,4-diamine;

$N^2$-(2-methoxy-4-(4-methylpiperazin-1-yl)phenyl)-$N^4$-(2-(isopropylthio)benzyl)-5H-pyrrolo[3,2-d]pyrimidine-2,4-diamine;

$N^2$-(4-(4-hydroxypiperidine-1-yl)phenyl)-$N^4$-(2-(isopropylthio)benzyl)-5H-pyrrolo[3,2-d]pyrimidine-2,4-diamine;

$N^2$-(4-amino sulfonylphenyl)-$N^4$-(2-(isopropylthio)benzyl)-5H-pyrrolo[3,2-d]pyrimidine-2,4-diamine;

$N^2$-(2-methoxy-4-(4-methylpiperazin-1-yl)phenyl)-$N^4$-(2-(methylsulfonyl)benzyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(methylsulfonyl)benzyl)-5H-pyrrolo[3,2-d]pyrimidine-2,4-diamine;

$N^2$-(4-(4-hydroxypiperidine-1-yl)phenyl)-$N^4$-(2-(methylsulfonyl)benzyl)-5H-pyrrolo[3,2-d]pyrimidine-2,4-diamine;

$N^2$-(4-amino sulfonylphenyl)-$N^4$-(2-(methylsulfonyl)benzyl)-5H-pyrrolo[3,2-d]pyrimidine-2,4-diamine;

$N^2$-(4-(4-methylpiperazin-1-yl)phenyl)-$N^4$-(2-(methylsulfonyl)benzyl)-5H-pyrrolo[3,2-d]pyrimidine-2,4-diamine;

$N^2$-(2-methoxy-4-(4-methylpiperazin-1-yl)phenyl)-$N^4$-(2-(isopropylsulfonyl)benzyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(isopropylsulfonyl)benzyl)-5H-pyrrolo[3,2-d]pyrimidine-2,4-diamine;

$N^2$-(4-(4-hydroxypiperidine-1-yl)phenyl)-$N^4$-(2-(isopropylsulfonyl)benzyl)-5H-pyrrolo[3,2-d]pyrimidine-2,4-diamine;

$N^2$-(4-amino sulfonylphenyl)-$N^4$-(2-(isopropylsulfonyl)benzyl)-5H-pyrrolo[3,2-d]pyrimidine-2,4-diamine;

$N^2$-(4-(4-methylpiperazin-1-yl)phenyl)-$N^4$-(2-(isopropylsulfonyl)benzyl)-5H-pyrrolo[3,2-d]pyrimidine-2,4-diamine;

$N^2$-(2-methoxy-4-(4-methylpiperazin-1-yl)phenyl)-$N^4$-(2,6-dichlorobenzyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2,6-dichlorobenzyl)-5H-pyrrolo[3,2-d]pyrimidine-2,4-diamine;

$N^2$-(4-(4-hydroxypiperidine-1-yl)phenyl)-$N^4$-(2,6-dichlorobenzyl)-5H-pyrrolo[3,2-d]pyrimidine-2,4-diamine;

$N^2$-(4-(4-methylpiperazin-1-yl)phenyl)-$N^4$-(2,6-dichlorobenzyl)-5H-pyrrolo[3,2-d]pyrimidine-2,4-diamine;

$N^2$-(2-methoxy-4-(4-methylpiperazin-1-yl)phenyl)-$N^4$-methyl-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-methyl-5H-pyrrolo[3,2-d]pyrimidine-2,4-diamine;

$N^2$-(4-(4-hydroxypiperidin-1-yl)phenyl)-$N^4$-methyl-5H-pyrrolo[3,2-d]pyrimidine-2,4-diamine;

$N^2$-(4-aminosulfonylphenyl)-$N^4$-methyl-5H-pyrrolo[3,2-d]pyrimidine-2,4-diamine;

$N^2$-(2-methoxy-4-morpholinoformylphenyl)-$N^4$-methyl-5H-pyrrolo[3,2-d]pyrimidine-2,4-diamine;

$N^2$-(2-methoxy-4-(4-methylpiperazin-1-ylformyl)phenyl)-$N^4$-methyl-5H-pyrrolo[3,2-d]pyrimidine-2,4-diamine;

7-chloro-$N^2$-(2-methoxy-4-(4-methylpiperazin-1-yl)phenyl)-$N^4$-methyl-5H-pyrrolo[3,2-d]pyrimidine-2,4-diamine;

7-chloro-$N^2$-(2-methoxy-4-morpholinoformylphenyl)-$N^4$-methyl-5H-pyrrolo[3,2-d]pyrimidine-2,4-diamine;

$N^2$-(2-methoxy-4-(4-methylpiperazin-1-ylformyl)phenyl)-$N^4$-ethyl-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-ethyl-5H-pyrrolo[3,2-d]pyrimidine-2,4-diamine;

$N^2$-(4-(4-hydroxypiperidine-1-yl)phenyl)-$N^4$-ethyl-5H-pyrrolo[3,2-d]pyrimidine-2,4-diamine;

7-bromo-$N^2$-(2-methoxy-4-(4-methylpiperazin-1-ylformyl)phenyl)-$N^4$-ethyl-5H-pyrrolo[3,2-d]pyrimidine-2,4-diamine;

7-bromo-$N^2$-(2-methoxy-4-(4-(4-methylpiperazin-1-yl)piperidin-1-yl)phenyl)-$N^4$-ethyl 5H-pyrrolo[3,2-d]pyrimidine-2,4-diamine;

7-bromo-$N^2$-(4-(4-hydroxypiperidine-1-yl)phenyl)-$N^4$-ethyl-5H-pyrrolo[3,2-d]pyrimidine-2,4-diamine;

7-chloro-$N^2$-(2-methoxy-4-(4-methylpiperazin-1-ylformyl)phenyl)-$N^4$-ethyl-5H-pyrrolo[3,2-d]pyrimidine-2,4-diamine;

7-chloro-$N^2$-(2-methoxy-4-(4-(4-methylpiperazin-1-yl)piperidin-1-yl)phenyl)-$N^4$-ethyl-5H-pyrrolo[3,2-d]pyrimidine-2,4-diamine;

7-chloro-$N^2$-(4-(4-hydroxypiperidine-1-yl)phenyl)-$N^4$-ethyl-5H-pyrrolo[3,2-d]pyrimidine-2,4-diamine;

$N^2$-(2-methoxy-4-(4-methylpiperazin-1-ylformyl)phenyl)-$N^4$-cyclopropyl-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-cyclopropyl-5H-pyrrolo[3,2-d]pyrimidine-2,4-diamine;

$N^2$-(4-(4-hydroxypiperidine-1-yl)phenyl)-$N^4$-cyclopropyl-5H-pyrrolo[3,2-d]pyrimidine-2,4-diamine;

$N^2$-(4-aminosulfonylphenyl)-$N^4$-cyclopropyl-5H-pyrrolo[3,2-d]pyrimidine-2,4-diamine;

7-bromo-$N^2$-(2-methoxy-4-(4-methylpiperazin-1-ylformyl)phenyl)-$N^4$-cyclopropyl-5H-pyrrolo[3,2-d]pyrimidine-2,4-diamine;

7-bromo-$N^2$-(2-methoxy-4-(4-(4-methylpiperazin-1-yl)piperidin-1-yl)phenyl)-$N^4$-cyclopropyl-5H-pyrrolo[3,2-d]pyrimidine-2,4-diamine;

7-bromo-$N^2$-(4-(4-hydroxypiperidine-1-yl)phenyl)-$N^4$-cyclopropyl 5H-pyrrolo[3,2-d]pyrimidine-2,4-diamine;

7-chloro-$N^2$-(2-methoxy-4-(4-methylpiperazin-1-ylformyl)phenyl)-$N^4$-cyclopropyl-5H-pyrrolo[3,2-d]pyrimidine-2,4-diamine;

7-chloro-$N^2$-(2-methoxy-4-(4-(4-methylpiperazin-1-yl)piperidin-1-yl)phenyl)-$N^4$-cyclopropyl-5H-pyrrolo[3,2-d]pyrimidine-2,4-diamine;

7-chloro-$N^2$-(4-(4-hydroxypiperidine-1-yl)phenyl)-$N^4$-cyclopropyl-5H-pyrrolo[3,2-d]pyrimidine-2,4-diamine;

$N^2$-(4-(4-hydroxypiperidine-1-yl)phenyl)-4-morpholino-5H-pyrrolo[3,2-d]pyrimidine-2-amine;

4-((2-(methoxyformyl)phenyl)thio)-N-(2-methoxy-4-(4-methylpiperazin-1-yl)phenyl)-5H-pyrrolo[3,2-d]pyrimidine-2-amine;

4-((2-(methoxyformyl)phenyl)thio)-$N^2$-(2-methoxy-4-(4-(4-methylpiperazin-1-yl)piperidin-1-yl)phenyl)-5H-pyrrolo[3,2-d]pyrimidine-2-amine;

4-((2-(methoxyformyl)phenyl)thio)-$N^2$-(4-(4-hydroxypiperidine-1-yl)phenyl)-5H-pyrrolo[3,2-d]pyrimidine-2-amine;

4-((2-(methoxyformyl)phenyl)thio)-$N^2$-(4-aminosulfonylphenyl)-5H-pyrrolo[32-d]pyrimidine-2-amine;

4-((2-(methoxyformyl)phenyl)thio)-$N^2$-(2-methoxy-4-(4-(pyrrolidin-1-yl)piperidin-1-yl)phenyl)-5H-pyrrolo[3,2-d]pyrimidine-2-amine;

4-((2-(methoxyformyl)phenyl)oxy)-$N^2$-(2-methoxy-4-(4-methylpiperazin-1-yl)phenyl)-5H-pyrrolo[3,2-d]pyrimidine-2-amine;

4-((2-(methoxyformyl)phenyl)oxy)-$N^2$-(2-methoxy-4-(4-(4-methylpiperazin-1-yl)piperidin-1-yl)phenyl)-5H-pyrrolo[3,2-d]pyrimidine-2-amine;

4-((2-(methoxyformyl)phenyl)oxy)-$N^2$-(4-(4-hydroxypiperazin-1-yl)phenyl)-5H-pyrrolo[3,2-d]pyrimidine-2-amine;

4-((2-(methoxyformyl)phenyl)oxy)-$N^2$-(4-amino sulfonylphenyl-5H-pyrrolo[3,2-d]pyrimidine-2-amine;

5-methyl-$N^2$-(2-methoxy-4-(4-methylpiperazin-1-yl)phenyl)-$N^4$-(2-(methylthio)phenyl)-5H-pyrrolo[3,2-d]pyrimidine-2,4-diamine;

5-methyl-$N^2$-(2-methoxy-4-(4-(4-methylpiperazin-1-yl)piperidin-1-yl)phenyl)-$N^4$-(2-(methylthio)phenyl)-5H-pyrrolo[3,2-d]pyrimidine-2,4-diamine;

5-methyl-$N^2$-(4-(4-hydroxypiperidine-1-yl)phenyl)-$N^4$-(2-(methylthio)phenyl)-5H-pyrrolo[3,2-d]pyrimidine-2,4-diamine;

5-methyl-$N^2$-(4-amino sulfonylphenyl)-$N^4$-(2-(methylthio)phenyl)-5H-pyrrolo[3,2-d]pyrimidine-2,4-diamine;

5-methyl-$N^2$-(2-ethoxy-4-(4-(4-methylpiperazin-1-yl)piperidin-1-ylformyl)phenyl)-$N^4$-(2-(methylthio)phenyl)-5H-pyrrolo[3,2-d]pyrimidine-2,4-diamine;

5-methyl-$N^2$-(4-(4-methylpiperazin-1-yl)phenyl)-$N^4$-(2-(methylthio)phenyl)-5H-pyrrolo[3,2-d]pyrimidine-2,4-diamine;

5-methyl-$N^2$-(2-methoxy-4-(4-methylpiperazin-1-yl)phenyl)-$N^4$-(2-(isopropylthio)phenyl)-5H-pyrrolo[3,2-d]pyrimidine-2,4-diamine;

5-methyl-N$^2$-(2-methoxy-4-(4-(4-methylpiperazin-1-yl)piperidin-1-yl)phenyl)-N$^4$-(2-(isopropylthio)phenyl)-5H-pyrrolo[3,2-d]pyrimidine-2,4-diamine;

5-methyl-N$^2$-(4-(4-hydroxypiperidine-1-yl)phenyl)-N$^4$-(2-(isopropylthio)phenyl)-5H-pyrrolo[3,2-d]pyrimidine-2,4-diamine;

5-methyl-N$^2$-(4-amino sulfonylphenyl)-N$^4$-(2-(methylthio)phenyl)-5H-pyrrolo[3,2-d]pyrimidine-2,4-diamine;

5-methyl-N$^2$-(2-ethoxy-4-(4-(4-methylpiperazin-1-ylformyl)piperidin-1-yl)phenyl)-N$^4$-(2-(methyl thio)phenyl)-5H-pyrrolo[3,2-d]pyrimidine-2,4-diamine;

5-methyl-N$^2$-(2-methoxy-4-(4-(4-methylpiperazin-1-yl)phenyl)-N$^4$-(2-(methylsulfonyl)phenyl)-5H-pyrrolo[3,2-d]pyrimidine-2,4-diamine;

5-methyl-N$^2$-(2-methoxy-4-(4-(4-methylpiperazin-1-yl)piperidin-1-yl)phenyl)-N$^4$-(2-(methylsulfonyl)phenyl)-5H-pyrrolo[3,2-d]pyrimidine-2,4-diamine;

5-methyl-N$^2$-(4-(4-hydroxypiperidine-1-yl)phenyl)-N$^4$-(2-(methylsulfonyl)phenyl)-5H-pyrrolo[3,2-d]pyrimidine-2,4-diamine;

5-methyl-N$^2$-(4-amino sulfonylphenyl)-N$^4$-(2-(methylsulfonyl)phenyl)-5H-pyrrolo[3,2-d]pyrimidine-2,4-diamine;

5-methyl-N$^2$-(4-(4-methylpiperazin-1-yl)phenyl)-N$^4$-(2-(methylsulfonyl)phenyl)-5H-pyrrolo[3,2-d]pyrimidine-2,4-diamine;

5-methyl-N$^2$-(2-ethoxy-4-(4-hydroxypiperidine-1-yl)phenyl)-N$^4$-(2-(methylsulfonyl)phenyl)-5H-pyrrolo[3,2-d]pyrimidine-2,4-diamine;

5-methyl-N$^2$-(2-methoxy-4-(4-(4-methylpiperazin-1-yl)phenyl)-N$^4$-(2-(isopropylsulfonyl)phenyl)-5H-pyrrolo[3,2-d]pyrimidine-2,4-diamine;

5-methyl-N$^2$-(2-methoxy-4-(4-(4-methylpiperazin-1-yl)piperidin-1-yl)phenyl)-N$^4$-(2-(isopropylsulfonyl)phenyl)-5H-pyrrolo[3,2-d]pyrimidine-2,4-diamine;

5-methyl-N$^2$-(4-(4-hydroxypiperidine-1-yl)phenyl)-N$^4$-(2-(isopropylsulfonyl)phenyl)-5H-pyrrolo[3,2-d]pyrimidine-2,4-diamine;

5-methyl-N$^2$-(4-amino sulfonylphenyl)-N$^4$-(2-(isopropylsulfonyl)phenyl)-5H-pyrrolo[3,2-d]pyrimidine-2,4-diamine;

5-methyl-N$^2$-(4-(4-methylpiperazin-1-yl)phenyl)-N$^4$-(2-(isopropylsulfonyl)phenyl)-5H-pyrrolo[3,2-d]pyrimidine-2,4-diamine;

5-methyl-N$^2$-(2-ethoxy-4-(4-hydroxypiperidine-1-yl)phenyl)-N$^4$-(2-(isopropylsulfonyl)phenyl)-5H-pyrrolo[3,2-d]pyrimidine-2,4-diamine;

5-methyl-N$^2$-(2-ethoxy-4-(4-(4-methylpiperazin-1-ylformyl)piperidin-1-yl)phenyl)-N$^4$-(2-(isopropylsulfonyl)phenyl)-5H-pyrrolo[3,2-d]pyrimidine-2,4-diamine;

5-methyl-N$^2$-(2-isopropoxy-5-methyl-4-(1-methylpiperidin-4-yl)phenyl)-N$^4$-(2-(isopropylsulfonyl phenyl)-5H-pyrrolo[3,2-d]pyrimidine-2,4-diamine;

5-methyl-N$^2$-(2-methoxy-5-methyl-4-(1-methylpiperidin-4-yl)phenyl)-N$^4$-(2-(isopropylsulfonyl phenyl)-5H-pyrrolo[3,2-d]pyrimidine-2,4-diamine;

5-methyl-N$^2$-(2-methoxy-4-(4-(4-methylpiperazin-1-yl)piperidin-1-yl)phenyl)-N$^4$-(2-(methylsulfonamido)phenyl)-5H-pyrrolo[3,2-d]pyrimidine-2,4-diamine;

5-methyl-N$^2$-(2-methoxy-4-(4-methylpiperazin-1-yl)phenyl)-N$^4$-(2-(dimethylphosphinyl)phenyl)-5H-pyrrolo[3,2-d]pyrimidine-2,4-diamine;

5-methyl-N$^2$-(2-methoxy-4-(4-(4-methylpiperazin-1-yl)piperidin-1-yl)phenyl)-N$^4$-(2-(dimethylphosphinyl)phenyl)-5H-pyrrolo[3,2-d]pyrimidine-2,4-diamine;

5-methyl-N$^2$-(4-(4-hydroxypiperidine-1-yl)phenyl)-N$^4$-(2-(dimethylphosphinyl)phenyl)-5H-pyrrolo[3,2-d]pyrimidine-2,4-diamine;

5-methyl-N$^2$-(4-(4-methylpiperazin-1-yl)phenyl)-N$^4$-(2-(dimethylphosphinyl)phenyl)-5H-pyrrolo[3,2-d]pyrimidine-2,4-diamine;

5-methyl-N$^2$-(1-(1-methylpiperidin-4-yl)-1H-pyrazol-4-yl)-N$^4$-(2-(dimethylphosphinyl)phenyl)-5H-pyrrolo[3,2-d]pyrimidine-2,4-diamine;

5-methyl-N$^2$-(2-methoxy-4-(4-methylpiperazin-1-yl)phenyl)-N$^4$-(2-(methoxyformyl)phenyl)-5H-pyrrolo[3,2-d]pyrimidine-2,4-diamine;

5-methyl-N$^2$-(2-methoxy-4-(4-(4-methylpiperazin-1-yl)piperidin-1-yl)phenyl)-N$^4$-(2-(methoxyformyl)phenyl)-5H-pyrrolo[3,2-d]pyrimidine-2,4-diamine;

5-methyl-N$^2$-(4-(4-hydroxypiperidine-1-yl)phenyl)-N$^4$-(2-(methoxyformyl)phenyl)-5H-pyrrolo[3,2-d]pyrimidine-2,4-diamine;

5-methyl-N$^2$-(2-methoxy-4-(4-(4-methylpiperazin-1-yl)piperidin-1-ylformyl)phenyl)-N$^4$-(2-(methoxyformyl)phenyl)-5H-pyrrolo[3,2-d]pyrimidine-2,4-diamine;

5-methyl-N$^2$-(2-methoxy-4-(4-(4-methylpiperazin-1-yl)phenyl)-N$^4$-(3-(methoxyformyl)phenyl)-5H-pyrrolo[3,2-d]pyrimidine-2,4-diamine;

5-methyl-N$^2$-(4-(4-hydroxypiperidine-1-yl)phenyl)-N$^4$-(3-(methoxyformyl)phenyl)-5H-pyrrolo[3,2-d]pyrimidine-2,4-diamine;

5-methyl-N$^2$-(2-methoxy-4-(4-(4-methylpiperazin-1-yl)phenyl)-N$^4$-(2-(methylthio)benzyl)-5H-pyrrolo[3,2-d]pyrimidine-2,4-diamine;

5-methyl-N$^2$-(4-(4-hydroxypiperidine-1-yl)phenyl)-N$^4$-(2-(methylthio)benzyl)-5H-pyrrolo[3,2-d]pyrimidine-2,4-diamine;

5-methyl-N$^2$-(4-amino sulfonylphenyl)-N$^4$-(2-(methylthio)benzyl)-5H-pyrrolo[3,2-d]pyrimidine-2,4-diamine;

5-methyl-N$^2$-(2-ethoxy-4-(4-hydroxypiperidine-1-yl)phenyl)-N$^4$-(2-(methylthio)benzyl)-5H-pyrrolo[3,2-d]pyrimidine-2,4-diamine;

5-methyl-N$^2$-(2-methoxy-4-(4-(4-methylpiperazin-1-yl)phenyl)-N$^4$-(2-(isopropylthio)benzyl)-5H-pyrrolo[3,2-d]pyrimidine-2,4-diamine;

5-methyl-N$^2$-(4-(4-hydroxypiperidine-1-yl)phenyl)-N$^4$-(2-(isopropylthio)benzyl)-5H-pyrrolo[3,2-d]pyrimidine-2,4-diamine;

5-methyl-N$^2$-(4-amino sulfonylphenyl)-N$^4$-(2-(isopropylthio)benzyl)-5H-pyrrolo[3,2-d]pyrimidine-2,4-diamine;

5-methyl-N$^2$-(2-methoxy-4-(4-(4-methylpiperazin-1-yl)phenyl)-N$^4$-(2-(methylsulfonyl)benzyl)-5H-pyrrolo[3,2-d]pyrimidine-2,4-diamine;

5-methyl-N$^2$-(2-methoxy-4-(4-(4-methylpiperazin-1-yl)piperidin-1-yl)phenyl)-N$^4$-(2-(methylsulfonyl)benzyl)-5H-pyrrolo[3,2-d]pyrimidine-2,4-diamine;

5-methyl-N$^2$-(4-(4-hydroxypiperidine-1-yl)phenyl)-N$^4$-(2-(methylsulfonyl)benzyl)-5H-pyrrolo[3,2-d]pyrimidine-2,4-diamine;

5-methyl-N$^2$-(4-amino sulfonylphenyl)-N$^4$-(2-(methylsulfonyl)benzyl)-5H-pyrrolo[3,2-d]pyrimidine-2,4-diamine;

5-methyl-N$^2$-(4-(4-methylpiperazin-1-yl)phenyl)-N$^4$-(2-(methylsulfonyl)benzyl)-5H-pyrrolo[3,2-d]pyrimidine-2,4-diamine;

5-methyl-N$^2$-(2-methoxy-4-(4-(4-methylpiperazin-1-yl)piperidin-1-ylformyl)phenyl)-N$^4$-(2-(methylsulfonyl)benzyl)-5H-pyrrolo[3,2-d]pyrimidine-2,4-diamine;

5-methyl-N²-(2-ethoxy-4-(4-hydroxypiperidine-1-yl)
 phenyl)-N⁴-(2-(methylsulfonyl)benzyl)-5H-pyrrolo[3,
 2-d]pyrimidine-2,4-diamine;
5-methyl-N²-(2-methoxy-4-(4-methylpiperazin-1-yl)phe-
 nyl)-N⁴-(2-(isopropylsulfonyl)benzyl)-5H-pyrrolo[3,
 2-d]pyrimidine-2,4-diamine;
5-methyl-N²-(2-methoxy-4-(4-(4-methylpiperazin-1-yl)
 piperidin-1-yl)phenyl)-N⁴-(2-(isopropylsulfonyl)ben-
 zyl)-5H-pyrrolo[3,2-d]pyrimidine-2,4-diamine;
5-methyl-N²-(4-(4-hydroxypiperidine-1-yl)phenyl)-N⁴-
 (2-(isopropylsulfonyl)benzyl)-5H-pyrrolo[3,2-d]py-
 rimidine-2,4-diamine;
5-methyl-N²-(4-amino sulfonylphenyl)-N⁴-(2-(isopropyl-
 sulfonyl)benzyl)-5H-pyrrolo[3,2-d]pyrimidine-2,4-di-
 amine;
5-methyl-N²-(4-(4-methylpiperazin-1-yl)phenyl)-N⁴-(2-
 (isopropylsulfonyl)benzyl)-5H-pyrrolo[3,2-d]pyrimi-
 dine-2,4-diamine;
5-methyl-N²-(2-methoxy-4-(4-methylpiperazin-1-yl)phe-
 nyl)-N⁴-(2,6-dichlorobenzyl)-5H-pyrrolo[3,2-d]py-
 rimidine-2,4-diamine;
5-methyl-N²-(2-methoxy-4-(4-(4-methylpiperazin-1-yl)
 piperidin-1-yl)phenyl)-N⁴-(2,6-dichlorobenzyl)-5H-
 pyrrolo[3,2-d]pyrimidine-2,4-diamine;
5-methyl-N²-(4-(4-hydroxypiperidine-1-yl)phenyl)-N⁴-
 (2,6-dichlorobenzyl)-5H-pyrrolo[3,2-d]pyrimidine-2,
 4-diamine;
5-methyl-N²-(4-(4-methylpiperazin-1-yl)phenyl)-N⁴-(2,
 6-dichlorobenzyl)-5H-pyrrolo[3,2-d]pyrimidine-2,4-
 diamine;
4-((2-(methoxyformyl)phenyl)oxy)-5-methyl-N²-(2-
 methoxy-4-(4-methylpiperazin-1-yl)phenyl)-5H-pyr-
 rolo[3,2-d]pyrimidine-2-amine;
4-((2-(methoxyformyl)phenyl)oxy)-5-methyl-N²-(2-
 methoxy-4-(4-(4-methylpiperazin-1-yl)piperidin-1-yl)
 phenyl)-5H-pyrrolo[3,2-d]pyrimidine-2-amine;
4-((2-(methoxyformyl)phenyl)oxy)-5-methyl-N²-(4-(4-
 hydroxypiperidine-1-yl)phenyl)-5H-pyrrolo[3,2-d]py-
 rimidine-2-amine; or
4-((2-(methoxyformyl)phenyl)oxy)-5-methyl-N²-(4-
 amino sulfonylphenyl)-5H-pyrrolo[3,2-d]pyrimidine-
 2-amine;
or a stereoisomer thereof, or a pharmaceutically accept-
 able salt thereof, or a pharmaceutically acceptable
 solvate thereof.

7. A pharmaceutical composition comprising a compound according to claim 1, a stereoisomer, a pharmaceutically acceptable salt, or a pharmaceutically acceptable solvate thereof, and a pharmaceutically acceptable carrier, diluent or excipient.

8. A process for preparing a compound according to claim 1, comprising the steps of:

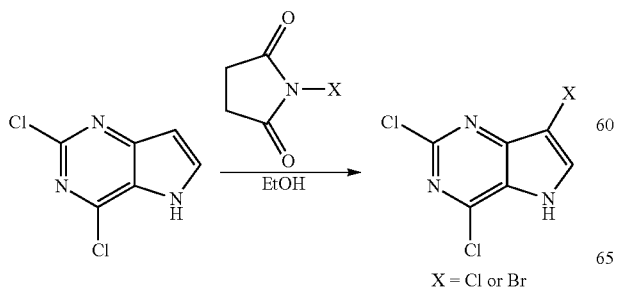

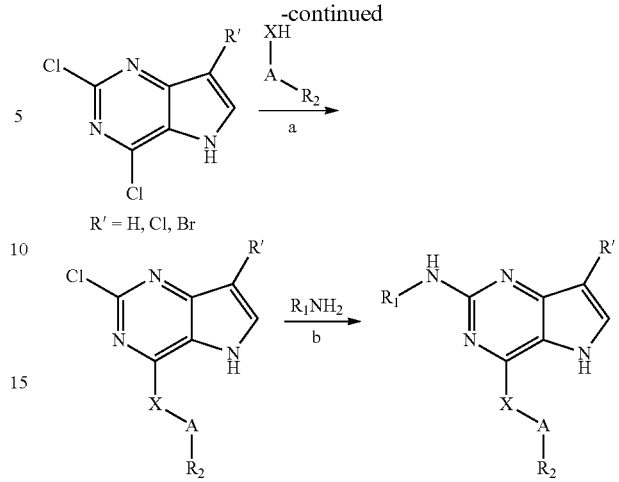

wherein
(a) is substitution reaction under basic conditions, option-
 ally comprising diisopropylethylamine, trimethylam-
 ine, or potassium carbonate; or substitution under
 acidic conditions, optionally comprising trifluoroacetic
 acid, or hydrochloric acid;
(b) is amination reaction under acidic conditions, option-
 ally comprising trifluoroacetic acid, or hydrochloric
 acid; or amination in the presence of palladium cata-
 lyst;
or

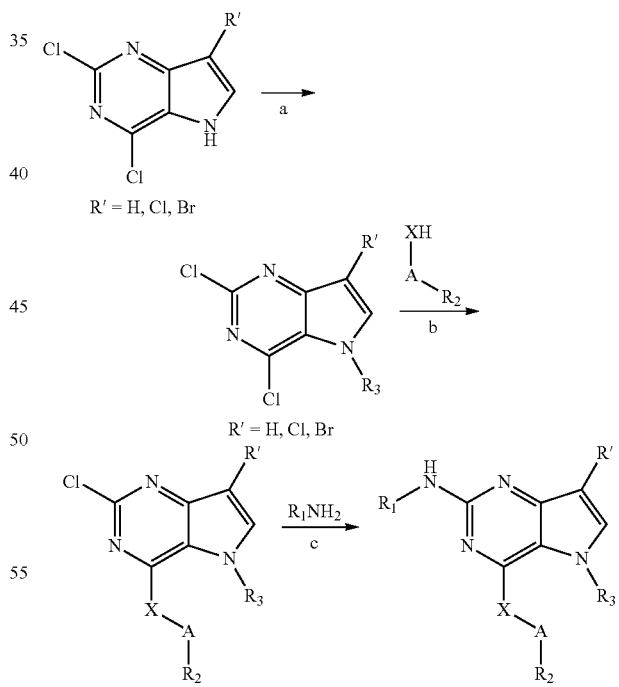

wherein
(a) is substitution reaction with alkyl halide under basic
 condition s, optionally comprising NaH; or methyl-
 ation, optionally with dimethyl sulfate;
(b) is substitution reaction under basic conditions, option-
 ally comprising diisopropylethylamine, trimethylamine, or potassium carbonate; or substitution under acidic conditions, optionally comprising trifluoroacetic acid, or hydrochloric acid;

(c) is amination reaction under acidic conditions, optionally comprising trifluoroacetic acid, or hydrochloric acid; or amination in the presence of palladium catalyst.

9. A method of treating a tumor mediated by ALK kinase, comprising administering to a patient in need thereof a compound according to claim 1, a stereoisomer, or a pharmaceutically acceptable salt, or a pharmaceutically acceptable solvate thereof.

10. The method according to claim 9, wherein the tumor mediated by ALK kinase is any of anaplastic large cell lymphoma (ALCL), inflammatory myofibroblastic tumor (IMT), non-small cell lung cancer (NSCLC), or neuroblastoma.

11. The compound according to claim 5, further wherein the salt of alkylsulfonic acid is the salt of methylsulfonic acid or ethylsulfonic acid; and the salt of arylsulfonic acid is the salt of benzenesulfonic acid or p-methylbenzenesulfonic acid.

12. The compound according to claim 6, selected from the group consisting of:

$N^2$-(2-methoxy-4-(4-methylpiperazin-1-yl)phenyl)-$N^4$-(2-(methylthio)phenyl)-5H-pyrrolo[3,2-d]pyrimidine-2,4-diamine;

$N^2$-(4-(4-hydroxypiperidine-1-yl)phenyl)-$N^4$-(2-(methylthio)phenyl)-5H-pyrrolo[3,2-d]pyrimidine-2,4-diamine;

$N^2$-(4-aminosulfonylphenyl)-$N^4$-(2-(methylthio)phenyl)-5H-pyrrolo[3,2-d]pyrimidine-2,4-diamine;

$N^2$-(2-methoxy-4-(4-methylpiperazin-1-yl)phenyl)-$N^4$-(2-(ispropylthio)phenyl)-5H-pyrrolo[3,2-d]pyrimidine-2,4-diamine;

$N^2$-(4-(4-hydroxypiperidine-1-yl)phenyl)-$N^4$-(2-(isopropylthio)phenyl)-5H-pyrrolo[3,2-d]pyrimidine-2,4-diamine;

$N^2$-(4-aminosulfonylphenyl)-$N^4$-(2-(isopropylthio)phenyl)-5H-pyrrolo[3,2-d]pyrimidine-2,4-diamine;

$N^2$-(2-methoxy-4-(4-methylpiperazin-1-yl)phenyl)-$N^4$-(2-(methylsulfonyl)phenyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(methylsulfonyl)phenyl)-5H-pyrrolo[3,2-d]pyrimidine-2,4-diamine;

$N^2$-(4-(4-hydroxypiperidine-1-yl)phenyl)-$N^4$-(2-(methylsulfonyl)phenyl)-5H-pyrrolo[3,2-d]pyrimidine-2,4-diamine;

$N^2$-(4-amino sulfonylphenyl)-$N^4$-(2-(methylsulfonyl)phenyl)-5H-pyrrolo[3,2-d]pyrimidine-2,4-diamine;

$N^2$-(4-(4-methylpiperazin-1-yl)phenyl)-$N^4$-(2-(methylsulfonyl)phenyl)-5H-pyrrolo[3,2-d]pyrimidine-2,4-diamine;

$N^2$-(2-methoxy-4-(4-methylpiperazin-1-yl)phenyl)-$N^4$-(2-(isopropylsulfonyl)phenyl)-5H-pyrrolo[3,2-d]pyrimidine-2,4-diamine;

$N^2$-(4-(4-methylpiperazin-1-yl)phenyl)-$N^4$-(2-(isopropylsulfonyl)phenyl)-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(isopropylsulfonyl)phenyl)-5H-pyrrolo[3,2-d]pyrimidine-2,4-diamine;

$N^2$-(4-(4-hydroxypiperidine-1-yl)phenyl)-$N^4$-(2-(isopropylsulfonyl)phenyl)-5H-pyrrolo[3,2-d]pyrimidine-2,4-diamine;

$N^2$-(4-amino sulfonylphenyl)-$N^4$-(2-(isopropylsulfonyl)phenyl)-5H-pyrrolo[3,2-d]pyrimidine-2,4-diamine;

$N^2$-(2-isopropoxy-5-methyl-(4-(1-methylpiperidin-4-yl)phenyl-$N^4$-(2-(isopropylsulfonyl)phenyl)-5H-pyrrolo[3,2-d]pyrimidine-2,4-diamine;

$N^2$-(2-methoxy-5-methyl-(4-(1-methylpiperidin-4-yl)phenyl-$N^4$-(2-(isopropylsulfonyl)phenyl)-5H-pyrrolo[3,2-d]pyrimidine-2,4-diamine;

$N^2$-(1-(1-methylpiperidin-4-yl)-1H-pyrazolyl-4-yl-$N^4$-(2-(isopropylsulfonyl)phenyl)-5H-pyrrolo[3,2-d]pyrimidine-2,4-diamine;

$N^2$-(2-methoxy-4-(4-methylpiperazin-1-yl)phenyl)-$N^4$-(2-methoxyformyl)phenyl-5H-pyrrolo[3,2-d]pyrimidine-2,4-diamine;

$N^2$-(2-methoxy-4-(4-(4-methylpiperazin-1-yl)piperidin-1-yl)phenyl)-$N^4$-(2-(methoxyformyl)phenyl)-5H-pyrrolo[3,2-d]pyrimidine-2,4-diamine;

$N^2$-(4-(4-hydroxypiperidin-1-yl)phenyl)-$N^4$-(2-(methoxyformyl)phenyl)-5H-pyrrolo[3,2-d]pyrimidine-2,4-diamine;

$N^2$-(4-amino sulfonylphenyl)-$N^4$-(2-(methoxyformyl)phenyl)-5H-pyrrolo[3,2-d]pyrimidine-2,4-diamine;

$N^2$-(4-morpholinophenyl)-$N^4$-(2-(methoxyformyl)phenyl)-5H-pyrrolo[3,2-d]pyrimidine-2,4-diamine;

$N^2$-(4-(4-methylpiperazin-1-yl)phenyl)-$N^4$-(2-(methoxyformyl)phenyl)-5H-pyrrolo[3,2-d]pyrimidine-2,4-diamine;

$N^2$-(2-methoxy-4-(4-(pyrrolidin-1-yl)piperidin-1-yl)phenyl)-$N^4$-(2-(methoxyformyl)phenyl)-5H-pyrrolo[3,2-d]pyrimidine-2,4-diamine;

$N^2$-(4-(pyridin-2-ylmethoxy)phenyl)-$N^4$-(2-(methoxyformyl)phenyl)-5H-pyrrolo[3,2-d]pyrimidine-2,4-diamine;

$N^2$-(2-isopropoxy-4-(4-hydroxypiperidine-1-yl)phenyl)-$N^4$-(2-(methoxyformyl)phenyl)-5H-pyrrolo[3,2-d]pyrimidine-2,4-diamine;

$N^2$-(2-ethoxy-4-(4-hydroxypiperidine-1-yl)phenyl)-$N^4$-(2-(methoxyformyl)phenyl)-5H-pyrrolo[3,2-d]pyrimidine-2,4-diamine;

$N^2$-(4-(4-hydroxypiperidine-1-ylsulfonyl)phenyl)-$N^4$-(2-(methoxyformyl)phenyl)-5H-pyrrolo[3,2-d]pyrimidine-2,4-diamine;

$N^2$-(2-methoxy-4-(4-(4-methylpiperazin-1-yl)piperidin-1-ylformyl)phenyl)-$N^4$-(2-(methoxyformyl)phenyl)-5H-pyrrolo[3,2-d]pyrimidine-2,4-diamine;

$N^2$-(5-(4-methylpiperazin-1-yl)pyrid-2-yl)-$N^4$-(2-(methoxyformyl)phenyl)-5H-pyrrolo[3,2-d]pyrimidine-2,4-diamine;

$N^2$-(2-methoxy-5-methyl-4-(1-methylpiperidin-4-yl)phenyl)-$N^4$-(2-(methoxyformyl)phenyl)-5H-pyrrolo[3,2-d]pyrimidine-2,4-diamine;

$N^2$-(2-isopropoxy-5-methyl-4-(1-methylpiperidin-4-yl)phenyl)-$N^4$-(2-(methoxyformyl)phenyl)-5H-pyrrolo[3,2-d]pyrimidine-2,4-diamine;

$N^2$-(2-methoxy-4-morpholinophenyl)-$N^4$-(2-(methoxyformyl)phenyl)-5H-pyrrolo[3,2-d]pyrimidine-2,4-diamine;

$N^2$-(2-methoxy-4-morpholinoformylphenyl)-$N^4$-(2-(methoxyformyl)phenyl)-5H-pyrrolo[3,2-d]pyrimidine-2,4-diamine;

$N^2$-(6-(4-hydroxypiperidine-1-yl)pyridin-3-yl)-$N^4$-(2-(methoxyformyl)phenyl)-5H-pyrrolo[3,2-d]pyrimidine-2,4-diamine;

$N^2$-(2-methoxy-4-(4-methylpiperazin-1-yl)phenyl)-$N^4$-(2-(isobutoxyformyl)phenyl)-5H-pyrrolo[3,2-d]pyrimidine-2,4-diamine;

N²-(4-(4-hydroxypiperidine-1-yl)phenyl)-N⁴-(2-isobutoxyformyl)phenyl)-5H-pyrrolo[3,2-d]pyrimidine-2,4-diamine;

N²-(2-methoxy-4-(4-(4-methylpiperazin-1-yl)piperidin-1-yl)phenyl)-N⁴-(2-isobutoxyformyl)phenyl)-5H-pyrrolo[3,2-d]pyrimidine-2,4-diamine;

N²-(2-methoxy-4-(4-(pyrrolidin-1-yl)piperidin-1-yl)phenyl)-N⁴-(2-isobutoxyformyl)phenyl)-5H-pyrrolo[3,2-d]pyrimidine-2,4-diamine;

N²-(2-methoxy-4-(4-methylpiperazin-1-yl)phenyl)-N⁴-(3-(methoxyformyl)phenyl)-5H-pyrrolo[3,2-d]pyrimidine-2,4-diamine;

N²-(2-methoxy-4-(4-(4-methylpiperazin-1-yl)piperidin-1-yl)phenyl)-N⁴-(3-(methoxyformyl)phenyl)-5H-pyrrolo[3,2-d]pyrimidine-2,4-diamine;

N²-(4-(4-hydroxypiperidine-1-yl)phenyl)-N⁴-(3-(methoxyformyl)phenyl)-5H-pyrrolo[3,2-d]pyrimidine-2,4-diamine;

N²-(4-(4-methylpiperazin-1-yl)phenyl)-N⁴-(3-(methoxyformyl)phenyl)-5H-pyrrolo[3,2-d]pyrimidine-2,4-diamine;

N²-(4-morpholinophenyl)-N⁴-(3-(methoxyformyl)phenyl)-5H-pyrrolo[3,2-d]pyrimidine-2,4-diamine;

N²-(2-methoxy-4-(4-(pyrrolidin-1-yl)piperidin-1-yl)phenyl)-N⁴-(3-(methoxyformyl)phenyl)-5H-pyrrolo[3,2-d]pyrimidine-2,4-diamine;

N²-(2-methoxy-4-(4-(4-methylpiperazin-1-yl)piperidin-1-yl)phenyl)-N⁴-(2-(N-methylaminoformyl)phenyl)-5H-pyrrolo[3,2-d]pyrimidine-2,4-diamine;

N²-(2-methoxy-4-(4-(pyrrolidin-1-yl)piperidin-1-yl)phenyl)-N⁴-(2-(N-methylaminoformyl)phenyl)-5H-pyrrolo[3,2-d]pyrimidine-2,4-diamine;

N²-(4-amino sulfonylphenyl)-N⁴-(2-(N-methylaminoformyl)phenyl)-5H-pyrrolo[3,2-d]pyrimidine-2,4-diamine;

N²-(2-methoxy-4-(4-methylpiperazin-1-yl)phenyl)-N⁴-(2-(methoxyformyl)thien-3-yl)-5H-pyrrolo[3,2-d]pyrimidine-2,4-diamine;

N²-(2-methoxy-4-(4-(4-methylpiperazin-1-yl)piperidin-1-yl)phenyl)-N⁴-(2-(methoxyformyl)thien-3-yl)-5H-pyrrolo[3,2-d]pyrimidine-2,4-diamine;

N²-(2-methoxy-4-(4-methylpiperazin-1-yl)phenyl-N⁴-(2-(methylthio)benzyl)-5H-pyrrolo[3,2-d]pyrimidine-2,4-diamine;

N²-(2-methoxy-4-(4-(4-methylpiperazin-1-yl)piperidin-1-yl)-N⁴-(2-(methylthio)benzyl)-5H-pyrrolo[3,2-d]pyrimidine-2,4-diamine;

N²-(4-(4-hydroxypiperidin-1-yl)phenyl-N⁴-(2-(methylthio)benzyl)-5H-pyrrolo[3,2-d]pyrimidine-2,4-diamine;

N²-(4-amino sulfonylphenyl)-N⁴-(2-(methoxyformyl)phenyl-5H-pyrrolo[3,2-d]pyrimidine-2,4-diamine;

N²-(2-methoxy-4-(4-methylpiperazin-1-yl)phenyl)-N⁴-(2-(isopropylthio)benzyl)-5H-pyrrolo[3,2-d]pyrimidine-2,4-diamine;

N²-(4-(4-hydroxypiperidine-1-yl)phenyl)-N⁴-(2-(isopropylthio)benzyl)-5H-pyrrolo[3,2-d]pyrimidine-2,4-diamine;

N²-(4-amino sulfonylphenyl)-N⁴-(2-(isopropylthio)benzyl)-5H-pyrrolo[3,2-d]pyrimidine-2,4-diamine;

N²-(2-methoxy-4-(4-methylpiperazin-1-yl)phenyl)-N⁴-(2-(methylsulfonyl)benzyl)-5H-pyrrolo[3,2-d]pyrimidine-2,4-diamine;

N²-(2-methoxy-4-(4-(4-methylpiperazin-1-yl)piperidin-1-yl)phenyl)-N⁴-(2-(methylsulfonyl)benzyl)-5H-pyrrolo[3,2-d]pyrimidine-2,4-diamine;

N²-(4-(4-hydroxypiperidine-1-yl)phenyl)-N⁴-(2-(methylsulfonyl)benzyl)-5H-pyrrolo[3,2-d]pyrimidine-2,4-diamine;

N²-(4-amino sulfonylphenyl)-N⁴-(2-(methylsulfonyl)benzyl)-5H-pyrrolo[3,2-d]pyrimidine-2,4-diamine;

N²-(4-(4-methylpiperazin-1-yl)phenyl)-N⁴-(2-(methylsulfonyl)benzyl)-5H-pyrrolo[3,2-d]pyrimidine-2,4-diamine;

N²-(2-methoxy-4-(4-methylpiperazin-1-yl)phenyl)-N⁴-(2-(isopropylsulfonyl)benzyl)-5H-pyrrolo[3,2-d]pyrimidine-2,4-diamine;

N²-(2-methoxy-4-(4-(4-methylpiperazin-1-yl)piperidin-1-yl)phenyl)-N⁴-(2-(isopropylsulfonyl)benzyl)-5H-pyrrolo[3,2-d]pyrimidine-2,4-diamine;

N²-(4-(4-hydroxypiperidine-1-yl)phenyl)-N⁴-(2-(isopropylsulfonyl)benzyl)-5H-pyrrolo[3,2-d]pyrimidine-2,4-diamine;

N²-(4-amino sulfonylphenyl)-N⁴-(2-(isopropylsulfonyl)benzyl)-5H-pyrrolo[3,2-d]pyrimidine-2,4-diamine;

N²-(4-(4-methylpiperazin-1-yl)phenyl)-N⁴-(2-(isopropylsulfonyl)benzyl)-5H-pyrrolo[3,2-d]pyrimidine-2,4-diamine;

N²-(2-methoxy-4-(4-methylpiperazin-1-yl)phenyl)-N⁴-methyl-5H-pyrrolo[3,2-d]pyrimidine-2,4-diamine;

N²-(2-methoxy-4-(4-(4-methylpiperazin-1-yl)piperidin-1-yl)phenyl)-N⁴-methyl-5H-pyrrolo[3,2-d]pyrimidine-2,4-diamine;

N²-(4-(4-hydroxypiperidine-1-yl)phenyl)-N⁴-methyl-5H-pyrrolo[3,2-d]pyrimidine-2,4-diamine;

N²-(4-aminosulfonylphenyl)-N⁴-methyl-5H-pyrrolo[3,2-d]pyrimidine-2,4-diamine;

N²-(2-methoxy-4-morpholinoformylphenyl)-N⁴-methyl-5H-pyrrolo[3,2-d]pyrimidine-2,4-diamine;

N²-(2-methoxy-4-(4-methylpiperazin-1-ylformyl)phenyl)-N⁴-methyl-5H-pyrrolo[3,2-d]pyrimidine-2,4-diamine;

N²-(2-methoxy-4-(4-methylpiperazin-1-ylformyl)phenyl)-N⁴-ethyl-5H-pyrrolo[3,2-d]pyrimidine-2,4-diamine;

N²-(2-methoxy-4-(4-(4-methylpiperazin-1-yl)piperidin-1-yl)phenyl)-N⁴-ethyl-5H-pyrrolo[3,2-d]pyrimidine-2,4-diamine;

N²-(4-(4-hydroxypiperidin-1-yl)phenyl)-N⁴-ethyl-5H-pyrrolo[3,2-d]pyrimidine-2,4-diamine;

N²-(2-methoxy-4-(4-methylpiperazin-1-ylformyl)phenyl)-N⁴-cyclopropyl-5H-pyrrolo[3,2-d]pyrimidine-2,4-diamine;

N²-(2-methoxy-4-(4-(4-methylpiperazin-1-yl)piperidin-1-yl)phenyl)-N⁴-cyclopropyl-5H-pyrrolo[3,2-d]pyrimidine-2,4-diamine;

N²-(4-(4-hydroxypiperidine-1-yl)phenyl)-N⁴-cyclopropyl-5H-pyrrolo[3,2-d]pyrimidine-2,4-diamine;

N²-(4-aminosulfonylphenyl)-N⁴-cyclopropyl-5H-pyrrolo[3,2-d]pyrimidine-2,4-diamine;

4-((2-(methoxyformyl)phenyl)thio)-N-(2-methoxy-4-(4-methylpiperazin-1-yl)phenyl)-5H-pyrrolo[3,2-d]pyrimidine-2-amine;

4-((2-(methoxyformyl)phenyl)thio)-N²-(2-methoxy-4-(4-(4-methylpiperazin-1-yl)piperidin-1-yl)phenyl)-5H-pyrrolo[3,2-d]pyrimidine-2-amine;

4-((2-(methoxyformyl)phenyl)thio)-N²-(4-(4-hydroxypiperidine-1-yl)phenyl)-5H-pyrrolo[3,2-d]pyrimidine-2-amine;

4-((2-(methoxyformyl)phenyl)thio)-N²-(4-aminosulfonylphenyl)-5H-pyrrolo[3,2-d]pyrimidine-2-amine;

4-((2-(methoxyformyl)phenyl)thio)-$N^2$-(2-methoxy-4-(4-(pyrrolidin-1-yl)piperidin-1-yl)phenyl)-5H-pyrrolo[3,2-d]pyrimidine-2-amine;

4-((2-(methoxyformyl)phenyl)oxy)-$N^2$-(2-methoxy-4-(4-methylpiperazin-1-yl)phenyl)-5H-pyrrolo[3,2-d]pyrimidine-2-amine;

4-((2-(methoxyformyl)phenyl)oxy)-$N^2$-(2-methoxy-4-(4-(4-methylpiperazin-1-yl)piperidin-1-yl)phenyl)-5H-pyrrolo[3,2-d]pyrimidine-2-amine;

4-((2-(methoxyformyl)phenyl)oxy)-$N^2$-(4-(4-hydroxypiperazin-1-yl)phenyl)-5H-pyrrolo[3,2-d]pyrimidine-2-amine;

4-((2-(methoxyformyl)phenyl)oxy)-$N^2$-(4-amino sulfonylphenyl-5H-pyrrolo[3,2-d]pyrimidine-2-amine;

5-methyl-$N^2$-(2-methoxy-4-(4-methylpiperazin-1-yl)phenyl)-$N^4$-(2-(methylthio)phenyl)-5H-pyrrolo[3,2-d]pyrimidine-2,4-diamine;

5-methyl-$N^2$-(2-methoxy-4-(4-(4-methylpiperazin-1-yl)piperidin-1-yl)phenyl)-$N^4$-(2-(methylthio)phenyl)-5H-pyrrolo[3,2-d]pyrimidine-2,4-diamine;

5-methyl-$N^2$-(4-(4-hydroxypiperidine-1-yl)phenyl)-$N^4$-(2-(methylthio)phenyl)-5H-pyrrolo[3,2-d]pyrimidine-2,4-diamine;

5-methyl-$N^2$-(4-amino sulfonylphenyl)-$N^4$-(2-(methylthio)phenyl)-5H-pyrrolo[3,2-d]pyrimidine-2,4-diamine;

5-methyl-$N^2$-(2-ethoxy-4-(4-(4-methylpiperazin-1-yl)piperidin-1-ylformyl)phenyl)-$N^4$-(2-(methylthio)phenyl)-5H-pyrrolo[3,2-d]pyrimidine-2,4-diamine;

5-methyl-$N^2$-(4-(4-methylpiperazin-1-yl)phenyl)-$N^4$-(2-(methylthio)phenyl)-5H-pyrrolo[3,2-d]pyrimidine-2,4-diamine;

5-methyl-$N^2$-(2-methoxy-4-(4-methylpiperazin-1-yl)phenyl)-$N^4$-(2-(isopropylthio)phenyl)-5H-pyrrolo[3,2-d]pyrimidine-2,4-diamine;

5-methyl-$N^2$-(2-methoxy-4-(4-(4-methylpiperazin-1-yl)piperidin-1-yl)phenyl)-$N^4$-(2-(isopropylthio)phenyl)-5H-pyrrolo[3,2-d]pyrimidine-2,4-diamine;

5-methyl-$N^2$-(4-(4-hydroxypiperidine-1-yl)phenyl)-$N^4$-(2-(methylthio)phenyl)-5H-pyrrolo[3,2-d]pyrimidine-2,4-diamine;

5-methyl-$N^2$-(4-amino sulfonylphenyl)-$N^4$-(2-(methylthio)phenyl)-5H-pyrrolo[3,2-d]pyrimidine-2,4-diamine;

5-methyl-$N^2$-(2-ethoxy-4-(4-(4-methylpiperazin-1-yl)piperidin-1-ylformyl)phenyl)-$N^4$-(2-(isopropylthio)phenyl)-5H-pyrrolo[3,2-d]pyrimidine-2,4-diamine;

5-methyl-$N^2$-(2-methoxy-4-(4-methylpiperazin-1-yl)phenyl)-$N^4$-(2-(methylsulfonyl)phenyl)-5H-pyrrolo[3,2-d]pyrimidine-2,4-diamine;

5-methyl-$N^2$-(2-methoxy-4-(4-(4-methylpiperazin-1-yl)piperidin-1-yl)phenyl)-$N^4$-(2-(methylsulfonyl)phenyl)-5H-pyrrolo[3,2-d]pyrimidine-2,4-diamine;

5-methyl-$N^2$-(4-(4-hydroxypiperidine-1-yl)phenyl)-$N^4$-(2-(methylsulfonyl)phenyl)-5H-pyrrolo[3,2-d]pyrimidine-2,4-diamine;

5-methyl-$N^2$-(4-aminosulfonylphenyl)-$N^4$-(2-(methylsulfonyl)phenyl)-5H-pyrrolo[3,2-d]pyrimidine-2,4-diamine;

5-methyl-$N^2$-(4-(4-methylpiperazin-1-yl)phenyl)-$N^4$-(2-(methylsulfonyl)phenyl)-5H-pyrrolo[3,2-d]pyrimidine-2,4-diamine;

5-methyl-$N^2$-(2-ethoxy-4-(4-hydroxypiperidine-1-yl)phenyl)-$N^4$-(2-(methylsulfonyl)phenyl)-5H-pyrrolo[3,2-d]pyrimidine-2,4-diamine;

5-methyl-$N^2$-(2-methoxy-4-(4-methylpiperazin-1-yl)phenyl)-$N^4$-(2-(isopropylsulfonyl)phenyl)-5H-pyrrolo[3,2-d]pyrimidine-2,4-diamine;

5-methyl-$N^2$-(2-methoxy-4-(4-(4-methylpiperazin-1-yl)piperidin-1-yl)phenyl)-$N^4$-(2-(isopropylsulfonyl)phenyl)-5H-pyrrolo[3,2-d]pyrimidine-2,4-diamine;

5-methyl-$N^2$-(4-(4-hydroxypiperidine-1-yl)phenyl)-$N^4$-(2-(isopropylsulfonyl)phenyl)-5H-pyrrolo[3,2-d]pyrimidine-2,4-diamine;

5-methyl-$N^2$-(4-amino sulfonylphenyl)-$N^4$-(2-(isopropylsulfonyl)phenyl)-5H-pyrrolo[3,2-d]pyrimidine-2,4-diamine;

5-methyl-$N^2$-(4-(4-methylpiperazin-1-yl)phenyl)-$N^4$-(2-(isopropylsulfonyl)phenyl)-5H-pyrrolo[3,2-d]pyrimidine-2,4-diamine;

5-methyl-$N^2$-(2-ethoxy-4-(4-hydroxypiperidine-1-yl)phenyl)-$N^4$-(2-(isopropylsulfonyl)phenyl)-5H-pyrrolo[3,2-d]pyrimidine-2,4-diamine;

5-methyl-$N^2$-(2-ethoxy-4-(4-(4-methylpiperazin-1-yl)piperidin-1-ylformyl)phenyl)-$N^4$-(2-(isopropylsulfonyl)phenyl)-5H-pyrrolo[3,2-d]pyrimidine-2,4-diamine;

5-methyl-$N^2$-(2-isopropoxy-5-methyl-4-(1-methylpiperidin-4-yl)phenyl)-$N^4$-(2-(isopropylsulfonyl) phenyl)-5H-pyrrolo[3,2-d]pyrimidine-2,4-diamine;

5-methyl-$N^2$-(2-methoxy-5-methyl-4-(1-methylpiperidin-4-yl)phenyl)-$N^4$-(2-(isopropylsulfonyl) phenyl)-5H-pyrrolo[3,2-d]pyrimidine-2,4-diamine;

5-methyl-$N^2$-(2-methoxy-4-(4-methylpiperazin-1-yl)phenyl)-$N^4$-(2-(methoxyformyl)phenyl)-5H-pyrrolo[3,2-d]pyrimidine-2,4-diamine;

5-methyl-$N^2$-(2-methoxy-4-(4-(4-methylpiperazin-1-yl)piperidin-1-ylformyl)phenyl)-$N^4$-(2-(methoxyformyl)phenyl)-5H-pyrrolo[3,2-d]pyrimidine-2,4-diamine;

5-methyl-$N^2$-(2-methoxy-4-(4-methylpiperazin-1-yl)phenyl)-$N^4$-(3-(methoxyformyl)phenyl)-5H-pyrrolo[3,2-d]pyrimidine-2,4-diamine;

5-methyl-$N^2$-(4-(4-hydroxypiperidine-1-yl)phenyl)-$N^4$-(3-(methoxyformyl)phenyl)-5H-pyrrolo[3,2-d]pyrimidine-2,4-diamine;

5-methyl-$N^2$-(2-methoxy-4-(4-methylpiperazin-1-yl)phenyl)-$N^4$-(2-(methylthio)benzyl)-5H-pyrrolo[3,2-d]pyrimidine-2,4-diamine;

5-methyl-$N^2$-(4-(4-hydroxypiperidine-1-yl)phenyl)-$N^4$-(2-(methylthio)benzyl)-5H-pyrrolo[3,2-d]pyrimidine-2,4-diamine;

5-methyl-$N^2$-(4-amino sulfonylphenyl)-$N^4$-(2-(methylthio)benzyl)-5H-pyrrolo[3,2-d]pyrimidine-2,4-diamine;

5-methyl-$N^2$-(2-ethoxy-4-(4-hydroxypiperidine-1-yl)phenyl)-$N^4$-(2-(methylthio)benzyl)-5H-pyrrolo[3,2-d]pyrimidine-2,4-diamine;

5-methyl-$N^2$-(2-methoxy-4-(4-methylpiperazin-1-yl)phenyl)-$N^4$-(2-(isopropylthio)benzyl)-5H-pyrrolo[3,2-d]pyrimidine-2,4-diamine;

5-methyl-$N^2$-(4-(4-hydroxypiperidine-1-yl)phenyl)-$N^4$-(2-(isopropylthio)benzyl)-5H-pyrrolo[3,2-d]pyrimidine-2,4-diamine;

5-methyl-$N^2$-(4-amino sulfonylphenyl)-$N^4$-(2-(isopropylthio)benzyl)-5H-pyrrolo[3,2-d]pyrimidine-2,4-diamine;

5-methyl-$N^2$-(2-methoxy-4-(4-methylpiperazin-1-yl)phenyl)-$N^4$-(2-(methylsulfonyl)benzyl)-5H-pyrrolo[3,2-d]pyrimidine-2,4-diamine;

5-methyl-$N^2$-(2-methoxy-4-(4-(4-methylpiperazin-1-yl)piperidin-1-yl)phenyl)-$N^4$-(2-(methylsulfonyl)benzyl)-5H-pyrrolo[3,2-d]pyrimidine-2,4-diamine;

5-methyl-N²-(4-(4-hydroxypiperidine-1-yl)phenyl)-N⁴-(2-(methylsulfonyl)benzyl)-5H-pyrrolo[3,2-d]pyrimidine-2,4-diamine;

5-methyl-N²-(4-amino sulfonylphenyl)-N⁴-(2-(methylsulfonyl)benzyl)-5H-pyrrolo[3,2-d]pyrimidine-2,4-diamine;

5-methyl-N²-(4-(4-methylpiperazin-1-yl)phenyl)-N⁴-(2-(methylsulfonyl)benzyl)-5H-pyrrolo[3,2-d]pyrimidine-2,4-diamine;

5-methyl-N²-(2-methoxy-4-(4-(4-methylpiperazin-1-yl)piperidin-1-ylformyl)phenyl)-N⁴-(2-(methylsulfonyl)benzyl)-5H-pyrrolo[3,2-d]pyrimidine-2,4-diamine;

5-methyl-N²-(2-ethoxy-4-(4-hydroxypiperidine-1-yl)phenyl)-N⁴-(2-(methylsulfonyl)benzyl)-5H-pyrrolo[3,2-d]pyrimidine-2,4-diamine;

5-methyl-N²-(2-methoxy-4-(4-methylpiperazin-1-yl)phenyl)-N⁴-(2-(isopropylsulfonyl)benzyl)-5H-pyrrolo[3,2-d]pyrimidine-2,4-diamine;

5-methyl-N²-(2-methoxy-4-(4-(4-methylpiperazin-1-yl)piperidin-1-yl)phenyl)-N⁴-(2-(isopropylsulfonyl)benzyl)-5H-pyrrolo[3,2-d]pyrimidine-2,4-diamine;

5-methyl-N²-(4-(4-hydroxypiperidine-1-yl)phenyl)-N⁴-(2-(isopropylsulfonyl)benzyl)-5H-pyrrolo[3,2-d]pyrimidine-2,4-diamine;

5-methyl-N²-(4-aminosulfonylphenyl)-N⁴-(2-(isopropylsulfonyl)benzyl)-5H-pyrrolo[3,2-d]pyrimidine-2,4-diamine;

4-((2-(methoxyformyl)phenyl)oxy)-5-methyl-N²-(4-(4-hydroxypiperidin-1-yl)phenyl)-5H-pyrrolo[3,2-d]pyrimidine-2-amine; and 4-((2-(methoxyformyl)phenyl)oxy)-5-methyl-N²-(4-amino sulfonylphenyl-5H-pyrrolo[3,2-d]pyrimidine-2-amine.

13. The compound of claim 1, wherein X is NH and A is a direct bond.

14. The compound of claim 13, wherein:

$R_1$ is

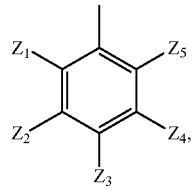

where $Z_1$ is $C_1$-$C_6$ alkoxy and $Z_3$ is 4-(N-methylpiperazinyl)piperidyl; and $R_2$

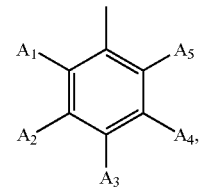

where $A_1$ is isopropylsulfonyl; so that the structure is represented by the following subgeneric formula

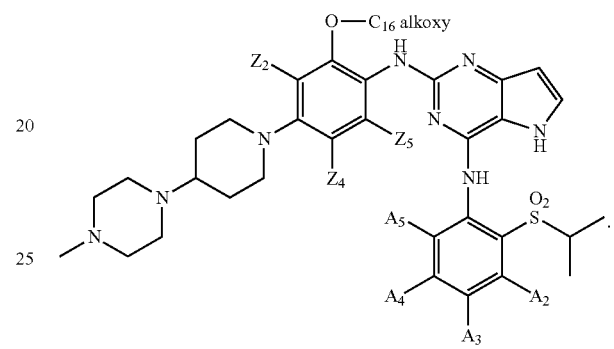

15. The compound of claim 14, wherein $Z_1$ is methoxy and $Z_2$, $Z_4$, $Z_5$, $A_2$, $A_3$, $A_4$, and $A_5$ are all hydrogen, so that the compound is N²-(2-methoxy-4-(4-(4-methylpiperazin-1-yl)piperidin-1-yl)phenyl)-N⁴-(2-(isopropylsulfonyl)phenyl)-5H-pyrrolo[3,2-d]pyrimidine-2,4-diamine, having the structure

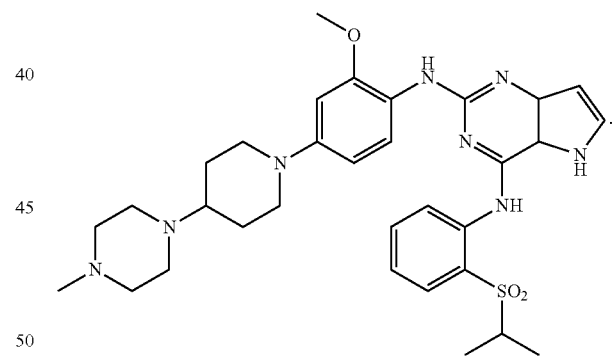

* * * * *